(12) United States Patent
Abbott et al.

(10) Patent No.: US 11,812,952 B2
(45) Date of Patent: Nov. 14, 2023

(54) SURGICAL IMPLANT AND METHOD AND INSTRUMENT FOR INSTALLING THE SAME

(71) Applicant: MAQUET CARDIOVASCULAR LLC, Mahwah, NJ (US)

(72) Inventors: Ryan Abbott, San Jose, CA (US); Robert Pearson, San Jose, CA (US); Monroe C. Stewart, Jr., Campbell, CA (US)

(73) Assignee: MAQUET CARDIOVASCULAR LLC, Wayne, NJ (US)

( * ) Notice: Subject to any disclaimer, the term of this patent is extended or adjusted under 35 U.S.C. 154(b) by 666 days.

(21) Appl. No.: 16/666,004

(22) Filed: Oct. 28, 2019

(65) Prior Publication Data

US 2020/0129174 A1      Apr. 30, 2020

Related U.S. Application Data

(60) Division of application No. 15/257,908, filed on Sep. 6, 2016, now Pat. No. 10,499,908, which is a
(Continued)

(51) Int. Cl.
*A61B 17/064* (2006.01)
*A61B 17/072* (2006.01)
(Continued)

(52) U.S. Cl.
CPC .... *A61B 17/0643* (2013.01); *A61B 17/07207* (2013.01); *A61B 17/11* (2013.01); *A61B 17/1222* (2013.01); *A61B 17/07292* (2013.01); *A61B 17/1114* (2013.01); *A61B 2017/0053* (2013.01); *A61B 2017/00327* (2013.01); *A61B 2017/00526* (2013.01); *A61B 2017/00853* (2013.01); *A61B 2017/0641* (2013.01); *A61B 2017/0648* (2013.01); *A61B 2017/0649* (2013.01); *A61B 2017/07271* (2013.01); *A61B 2017/07278* (2013.01);
(Continued)

(58) Field of Classification Search
CPC .......... A61B 17/07292; A61B 17/0643; A61B 17/07207; A61B 2017/00004; A61B 17/0644; A61B 17/068; A61B 17/072; A61B 17/064; A61B 17/08; A61B 17/105
See application file for complete search history.

(56) References Cited

U.S. PATENT DOCUMENTS 274,481 A    3/1883   Frost
352,000 A   11/1886   Penfold
(Continued)

OTHER PUBLICATIONS

International Preliminary Report on Patentability issued in PCT Application No. PCT/US2015/018839, dated Sep. 6, 2016.
(Continued)

*Primary Examiner* — Katherine M Shi

(57) ABSTRACT

A surgical implant comprising a receiver member and deployment member for clamping and sealing tissue of variable thickness, a corresponding applicator tool and surgical system for connecting, sealing, fastening and/or attaching tissue to itself, to other tissue and/or to non-tissue structures, and/or sealing the flow of fluid at and/or between structures such as tissue and vessel structures.

4 Claims, 119 Drawing Sheets

Related U.S. Application Data continuation-in-part of application No. PCT/US2015/018839, filed on Mar. 4, 2015, said application No. 15/257,908 is a continuation-in-part of application No. 14/641,136, filed on Mar. 6, 2015, now Pat. No. 9,795,385, which is a continuation of application No. PCT/US2015/018839, filed on Mar. 4, 2015, said application No. 15/257,908 is a continuation-in-part of application No. 14/639,113, filed on Mar. 4, 2015, now abandoned, which is a continuation of application No. PCT/US2015/018839, filed on Mar. 4, 2015.

(60) Provisional application No. 61/947,956, filed on Mar. 4, 2014, provisional application No. 62/214,190, filed on Sep. 3, 2015.

(51) Int. Cl.
*A61B 17/11* (2006.01)
*A61B 17/122* (2006.01)
*A61B 17/29* (2006.01)
*A61B 17/00* (2006.01)

(52) U.S. Cl.
CPC ............... *A61B 2017/07285* (2013.01); *A61B 2017/2923* (2013.01); *A61B 2017/2927* (2013.01); *A61B 2017/2939* (2013.01)

(56) References Cited

U.S. PATENT DOCUMENTS

| | | |
|---|---|---|
| 1,438,575 A | 12/1922 | Brown |
| 2,283,814 A | 5/1942 | Place |
| 2,476,506 A | 7/1949 | Olsen |
| 3,542,900 A | 11/1970 | Lammers |
| 3,618,447 A | 11/1971 | Goins |
| 3,757,629 A | 9/1973 | Schneider |
| 3,969,975 A | 7/1976 | Krol |
| 4,090,337 A | 5/1978 | Szekeres |
| 4,220,070 A | 9/1980 | Anstett |
| 4,534,352 A | 8/1985 | Korthoff |
| 4,548,202 A | 10/1985 | Duncan ............... A61B 17/0643 606/220 |
| 4,570,623 A | 2/1986 | Ellison et al. |
| D284,509 S | 7/1986 | Johnson |
| D286,180 S | 10/1986 | Korthoff |
| D286,441 S | 10/1986 | Korthoff et al. |
| D286,442 S | 10/1986 | Korthoff et al. |
| 4,728,237 A | 3/1988 | Lorincz et al. |
| 4,752,024 A | 6/1988 | Green et al. |
| 5,149,027 A | 9/1992 | Weber |
| 5,189,766 A | 3/1993 | Weber |
| 5,223,675 A | 6/1993 | Taft |
| 5,253,965 A | 10/1993 | Angel |
| 5,258,012 A | 11/1993 | Luscombe et al. |
| 5,263,629 A | 11/1993 | Trumbull et al. |
| 5,312,456 A | 5/1994 | Reed et al. |
| 5,344,060 A | 9/1994 | Gravener et al. |
| 5,397,324 A | 3/1995 | Carroll et al. |
| 5,441,193 A | 8/1995 | Gravener |
| 5,443,193 A | 8/1995 | Lenard |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,630,540 A | 5/1997 | Blewett |
| 5,653,373 A | 8/1997 | Green et al. |
| 5,720,755 A | 2/1998 | Dakov |
| 5,728,110 A | 3/1998 | Vidal et al. |
| 5,730,758 A | 3/1998 | Allgeyer |
| 5,738,474 A | 4/1998 | Blewett |
| 5,752,965 A | 5/1998 | Francis et al. |
| 5,779,130 A | 7/1998 | Alesi et al. |
| 5,797,538 A | 8/1998 | Heaton et al. |
| 5,908,427 A | 6/1999 | McKean et al. |
| 5,911,353 A | 6/1999 | Bolanos et al. |
| 5,919,198 A | 7/1999 | Graves et al. |
| 5,964,774 A | 10/1999 | McKean et al. |
| 5,993,064 A | 11/1999 | Teramachi et al. |
| 5,993,464 A | 11/1999 | Knodel |
| 6,045,560 A | 4/2000 | McKean et al. |
| 6,066,144 A | 5/2000 | Wolf et al. |
| 6,162,233 A | 12/2000 | Williamson et al. |
| 6,273,897 B1 | 8/2001 | Dalessandro et al. |
| RE37,814 E | 8/2002 | Allgeyer |
| 6,447,524 B1 | 9/2002 | Knodel et al. |
| 6,551,333 B2 | 4/2003 | Kuhns et al. |
| 6,572,626 B1 | 6/2003 | Knodel et al. |
| 6,644,532 B2 | 11/2003 | Green et al. |
| 6,656,193 B2 | 12/2003 | Grant et al. |
| 6,716,232 B1 | 4/2004 | Vidal et al. |
| 6,773,437 B2 | 8/2004 | Ogilvie et al. |
| 6,783,531 B2 | 8/2004 | Allen |
| RE38,708 E | 3/2005 | Bolanos et al. |
| D509,297 S | 9/2005 | Wells |
| 6,978,921 B2 | 12/2005 | Shelton et al. |
| 6,986,451 B1 | 1/2006 | Mastri et al. |
| 7,000,818 B2 | 2/2006 | Shelton et al. |
| 7,044,353 B2 | 5/2006 | Mastri et al. |
| 7,056,330 B2 | 6/2006 | Gayton |
| 7,074,294 B2 | 7/2006 | Dubrow |
| 7,128,253 B2 | 10/2006 | Mastri et al. |
| 7,225,964 B2 | 6/2007 | Mastri et al. |
| 7,258,262 B2 | 8/2007 | Mastri et al. |
| 7,278,562 B2 | 10/2007 | Mastri et al. |
| 7,296,722 B2 | 11/2007 | Ivanko |
| 7,296,724 B2 | 11/2007 | Green et al. |
| 7,303,108 B2 | 12/2007 | Shelton et al. |
| 7,308,998 B2 | 12/2007 | Mastri et al. |
| 7,380,696 B2 | 6/2008 | Shelton et al. |
| D574,956 S | 8/2008 | Grim |
| 7,407,078 B2 | 8/2008 | Shelton et al. |
| RE40,514 E | 9/2008 | Mastri et al. |
| 7,438,209 B1 | 10/2008 | Hess et al. |
| 7,462,185 B1 | 12/2008 | Knodel |
| 7,467,740 B2 | 12/2008 | Shelton et al. |
| 7,472,815 B2 | 1/2009 | Shelton et al. |
| D586,915 S | 2/2009 | Grim |
| 7,490,749 B2 | 2/2009 | Schall et al. |
| 7,499,742 B2 | 3/2009 | Bolea et al. |
| 7,559,937 B2 | 7/2009 | de la Torre et al. |
| 7,588,177 B2 | 9/2009 | Racenet |
| 7,604,151 B2 | 10/2009 | Hess et al. |
| 7,635,074 B2 | 12/2009 | Olson et al. |
| 7,637,410 B2 | 12/2009 | Marczyk |
| 7,641,091 B2 | 1/2010 | Olson et al. |
| 7,665,646 B2 | 2/2010 | Prommersberger |
| 7,669,746 B2 | 3/2010 | Shelton |
| 7,678,121 B1 | 3/2010 | Knodel |
| 7,690,547 B2 | 4/2010 | Racenet et al. |
| 7,699,205 B2 | 4/2010 | Ivanko |
| 7,721,934 B2 | 5/2010 | Shelton et al. |
| 7,722,528 B2 | 5/2010 | Arnal et al. |
| 7,722,642 B2 | 5/2010 | Williamson et al. |
| 7,726,537 B2 | 6/2010 | Olson et al. |
| 7,727,246 B2 | 6/2010 | Sixto et al. |
| 7,735,703 B2 | 6/2010 | Morgan et al. |
| 7,770,774 B2 | 8/2010 | Mastri et al. |
| 7,793,477 B1 | 9/2010 | Potts |
| 7,819,297 B2 | 10/2010 | Doll et al. |
| 7,819,896 B2 | 10/2010 | Racenet |
| 7,845,533 B2 | 12/2010 | Marczyk et al. |
| 7,845,535 B2 | 12/2010 | Scircia |
| 7,861,906 B2 | 1/2011 | Doll et al. |
| 7,861,907 B2 | 1/2011 | Green et al. |
| 7,866,525 B2 | 1/2011 | Scirica |
| 7,866,528 B2 | 1/2011 | Olson et al. |
| 7,891,532 B2 | 2/2011 | Mastri et al. |
| 7,891,533 B2 | 2/2011 | Green et al. |
| 7,905,893 B2 | 3/2011 | Kuhns et al. |
| 7,909,220 B2 | 3/2011 | Viola |
| 7,909,224 B2 | 3/2011 | Prommersberger |
| 7,913,893 B2 | 3/2011 | Mastri et al. |

(56) References Cited

U.S. PATENT DOCUMENTS

| | | |
|---|---|---|
| 7,942,301 B2 | 5/2011 | Sater |
| 7,950,561 B2 | 5/2011 | Aranyi |
| 7,959,051 B2 | 6/2011 | Smith et al. |
| 7,980,443 B2 | 7/2011 | Scheib et al. |
| 7,988,027 B2 | 8/2011 | Olson et al. |
| 7,988,028 B2 | 8/2011 | Farascioni |
| 7,997,468 B2 | 8/2011 | Farascioni |
| 7,997,469 B2 | 8/2011 | Olson et al. |
| 8,011,550 B2 | 9/2011 | Aranyi |
| 8,011,552 B2 | 9/2011 | Ivanko |
| 8,016,177 B2 | 9/2011 | Bettuchi |
| 8,016,178 B2 | 9/2011 | Olson et al. |
| 8,033,442 B2 | 10/2011 | Racenet |
| 8,038,045 B2 | 10/2011 | Bettuchi |
| 8,061,577 B2 | 11/2011 | Racenet et al. |
| 8,062,330 B2 | 11/2011 | Prommersberger et al. |
| 8,066,168 B2 | 11/2011 | Vidal et al. |
| 8,066,721 B2 | 11/2011 | Kortenbach et al. |
| 8,067,577 B2 | 11/2011 | Jiménez et al. |
| 8,070,033 B2 | 12/2011 | Milliman et al. |
| 8,074,859 B2 | 12/2011 | Kostrzewski |
| 8,087,563 B2 | 1/2012 | Milliman et al. |
| 8,096,459 B2 | 1/2012 | Ortiz et al. |
| 8,097,017 B2 | 1/2012 | Viola |
| 8,113,409 B2 | 2/2012 | Cohen et al. |
| 8,123,765 B2 | 2/2012 | Deem et al. |
| 8,127,975 B2 | 3/2012 | Olson et al. |
| 8,127,976 B2 | 3/2012 | Scirica |
| 8,157,149 B2 | 4/2012 | Olson et al. |
| 8,157,151 B2 | 4/2012 | Ingmanson et al. |
| 8,162,197 B2 | 4/2012 | Mastri et al. |
| 8,186,556 B2 | 5/2012 | Viola |
| 8,186,558 B2 | 5/2012 | Sapienza |
| 8,186,560 B2 | 5/2012 | Hess et al. |
| 8,191,752 B2 | 6/2012 | Scirica |
| 8,211,109 B2 | 7/2012 | Groiso |
| 8,220,690 B2 | 7/2012 | Hess et al. |
| 8,231,043 B2 | 7/2012 | Tarinelli et al. |
| 8,235,995 B2 | 8/2012 | Focht et al. |
| 8,245,901 B2 | 8/2012 | Stopek |
| 8,256,654 B2 | 9/2012 | Bettuchi et al. |
| 8,257,365 B2 | 9/2012 | Demarais et al. |
| 8,257,634 B2 | 9/2012 | Scirica |
| 8,267,302 B2 | 9/2012 | Farascioni et al. |
| 8,272,553 B2 | 9/2012 | Mastri et al. |
| 8,292,151 B2 | 10/2012 | Viola |
| 8,292,154 B2 | 10/2012 | Marczyk |
| 8,308,042 B2 | 11/2012 | Aranyi |
| 8,308,046 B2 | 11/2012 | Prommersberger |
| 8,336,753 B2 | 12/2012 | Olson et al. |
| 8,342,378 B2 | 1/2013 | Marczyk et al. |
| 8,342,380 B2 | 1/2013 | Viola |
| 8,348,123 B2 | 1/2013 | Scirica |
| 8,348,126 B2 | 1/2013 | Olson et al. |
| 8,348,130 B2 | 1/2013 | Shah et al. |
| 8,348,972 B2 | 1/2013 | Soltz et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,961 B2 | 2/2013 | Holsten et al. |
| 8,393,513 B2 | 3/2013 | Jankowski |
| 8,393,514 B2 | 3/2013 | Shelton et al. |
| 8,408,440 B2 | 4/2013 | Olson et al. |
| 8,408,442 B2 | 4/2013 | Racenet et al. |
| 8,413,871 B2 | 4/2013 | Racenet et al. |
| 8,418,907 B2 | 4/2013 | Johnson et al. |
| 8,435,263 B2 | 5/2013 | Viola |
| 8,439,244 B2 | 5/2013 | Holcomb et al. |
| 8,453,909 B2 | 6/2013 | Olson et al. |
| 8,453,912 B2 | 6/2013 | Mastri et al. |
| 8,464,922 B2 | 6/2013 | Marczyk |
| 8,464,923 B2 | 6/2013 | Shelton |
| 8,474,677 B2 | 7/2013 | Woodard, Jr. et al. |
| 8,475,457 B2 | 7/2013 | Shano |
| 8,475,491 B2 | 7/2013 | Milo |
| 8,479,968 B2 | 7/2013 | Hodgkinson et al. |
| 8,485,412 B2 | 7/2013 | Shelton et al. |
| 8,489,169 B2 | 7/2013 | Skubitz et al. |
| 8,496,154 B2 | 7/2013 | Marczyk et al. |
| 8,496,683 B2 | 7/2013 | Prommersberger et al. |
| 8,499,993 B2 | 8/2013 | Shelton et al. |
| 8,512,402 B2 | 8/2013 | Marczyk et al. |
| 8,529,600 B2 | 9/2013 | Woodard et al. |
| 2004/0138683 A1 | 7/2004 | Shelton et al. |
| 2004/0138705 A1 | 7/2004 | Heino et al. |
| 2006/0015144 A1 | 1/2006 | Burbank et al. |
| 2006/0235469 A1* | 10/2006 | Viola ............... A61B 17/0643 606/219 |
| 2007/0045379 A1 | 3/2007 | Shelton |
| 2008/0140095 A1 | 6/2008 | Smith ............... A61B 17/00234 606/151 |
| 2009/0020584 A1 | 1/2009 | Soltz ............... A61B 17/0644 227/175.1 |
| 2009/0030434 A1 | 1/2009 | Paz et al. |
| 2009/0177201 A1 | 7/2009 | Soltz et al. |
| 2010/0137904 A1 | 6/2010 | Wenchell |
| 2010/0234861 A1 | 9/2010 | Oray et al. |
| 2010/0243709 A1 | 9/2010 | Hess et al. |
| 2010/0256675 A1 | 10/2010 | Romans |
| 2012/0168486 A1 | 7/2012 | Ingmanson et al. |
| 2012/0221019 A1 | 8/2012 | Hart et al. |
| 2012/0325891 A1 | 12/2012 | Farascioni et al. |
| 2013/0037598 A1 | 2/2013 | Marczyk |
| 2013/0068816 A1 | 3/2013 | Mandakolathur et al. |
| 2013/0096584 A1 | 4/2013 | Kirsch |
| 2013/0105548 A1 | 5/2013 | Hodgkinson et al. |
| 2013/0105553 A1 | 5/2013 | Racenet et al. |
| 2013/0146641 A1 | 6/2013 | Shelton et al. |
| 2013/0153627 A1 | 6/2013 | Euteneuer et al. |
| 2013/0153632 A1 | 6/2013 | Hartoumbekis |
| 2013/0153635 A1 | 6/2013 | Hodgkinson |
| 2013/0153636 A1 | 6/2013 | Shelton et al. |
| 2013/0153641 A1 | 6/2013 | Shelton et al. |
| 2013/0161374 A1 | 6/2013 | Swayze et al. |
| 2013/0175321 A1 | 7/2013 | Shelton et al. |
| 2013/0181031 A1 | 7/2013 | Olson et al. |
| 2013/0193186 A1 | 8/2013 | Racenet et al. |
| 2013/0218177 A1 | 8/2013 | Miksza et al. |
| 2013/0221062 A1 | 8/2013 | Hodgkinson |
| 2013/0256366 A1 | 10/2013 | Shelton et al. |
| 2013/0261661 A1 | 10/2013 | Piraka |
| 2013/0334287 A1 | 12/2013 | Shelton et al. |
| 2015/0250474 A1 | 9/2015 | Abbott et al. |

OTHER PUBLICATIONS

Non-Final Office Action issued in U.S. Appl. No. 14/639,113, dated Oct. 12, 2016.
International Search Report and Written Opinion dated Aug. 12, 2015 for International Application No. PCT/US2015/018839 filed Mar. 4, 2015, 14 pages.
Notice of Allowance dated Jun. 15, 2017 for U.S. Appl. No. 14/641,136, which shares priority with this application.

* cited by examiner

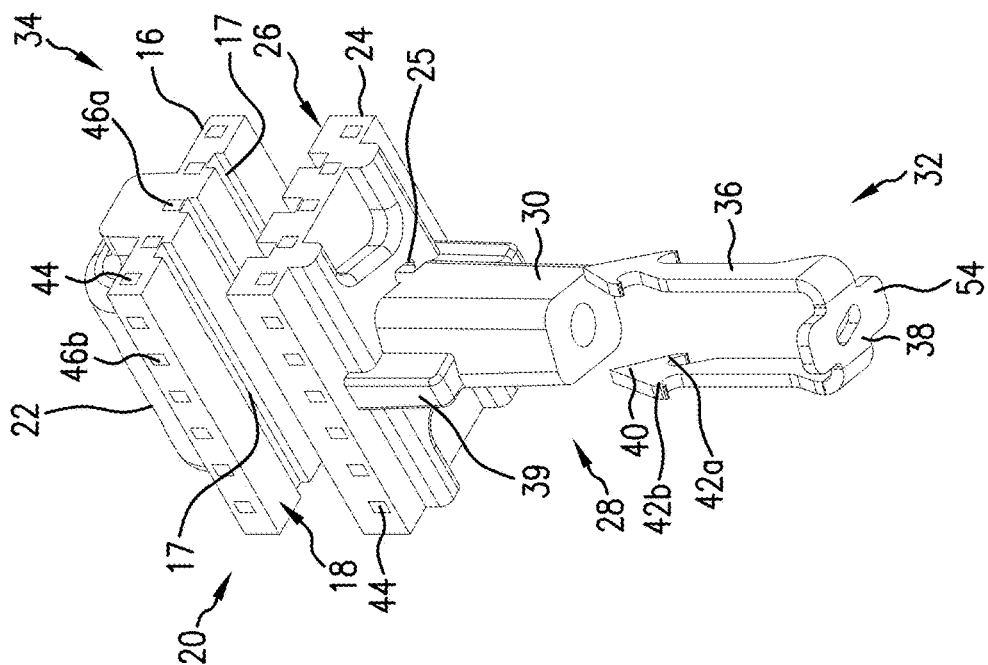
FIG.5
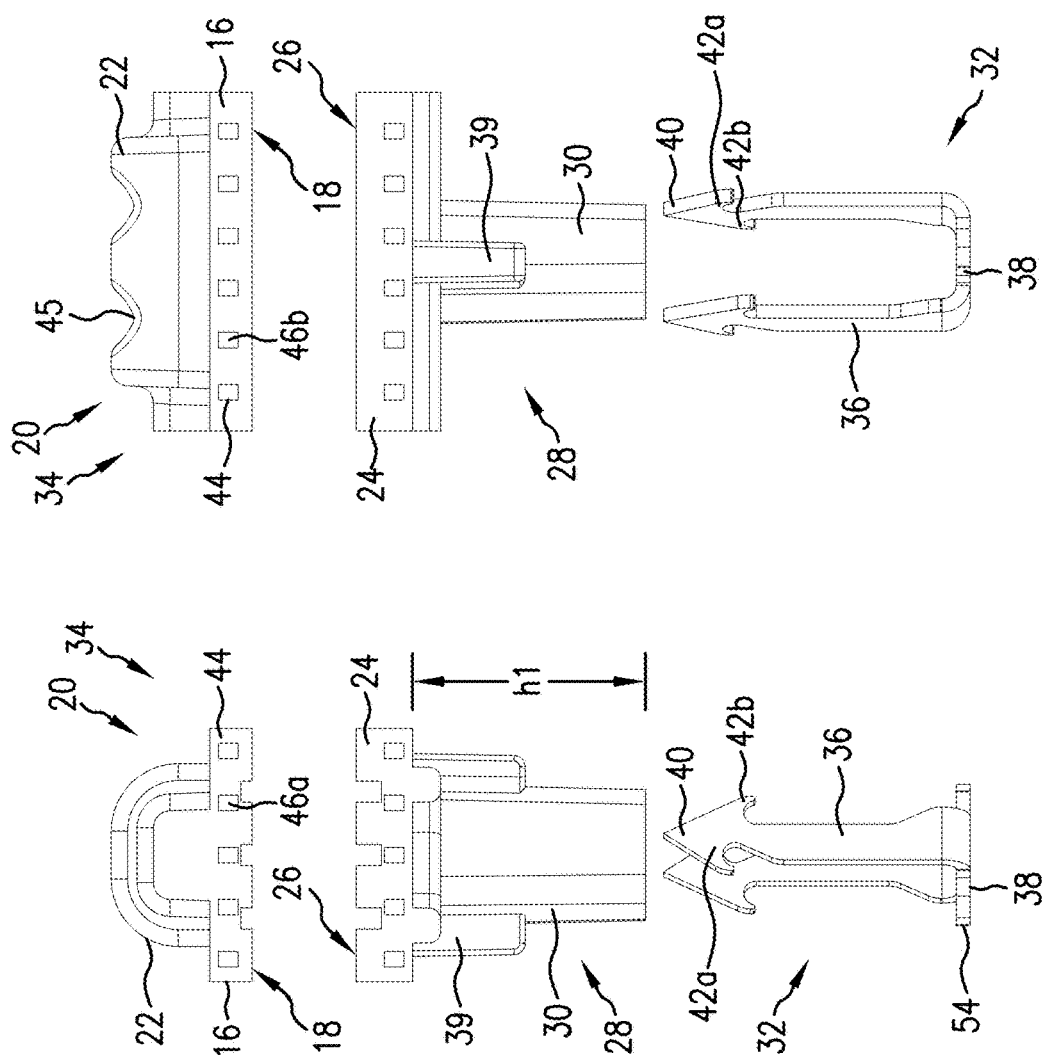
FIG.4
FIG.3

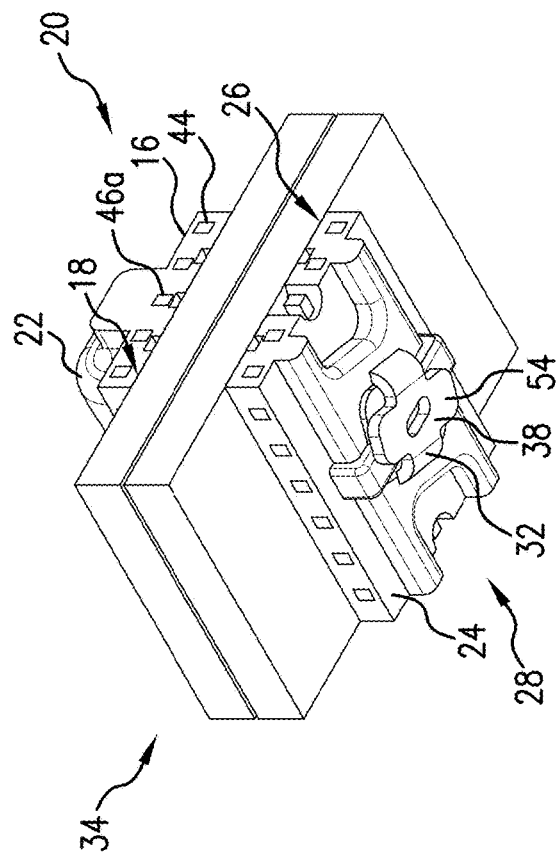
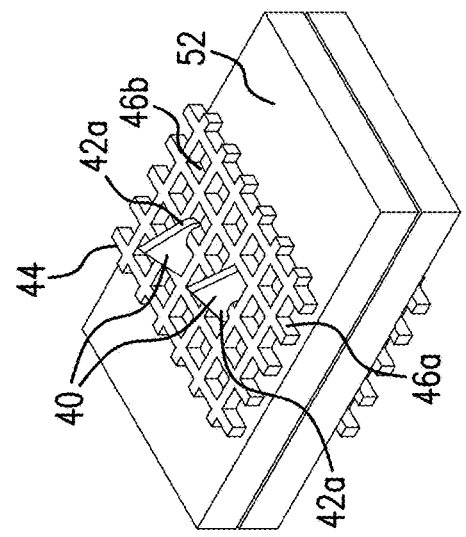
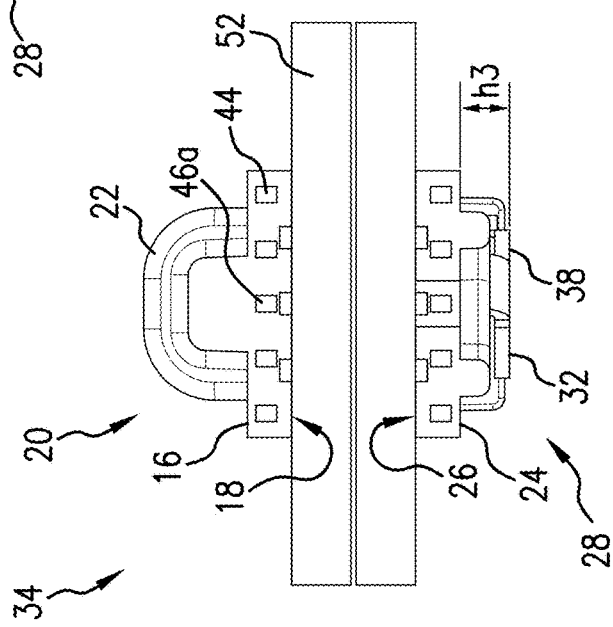

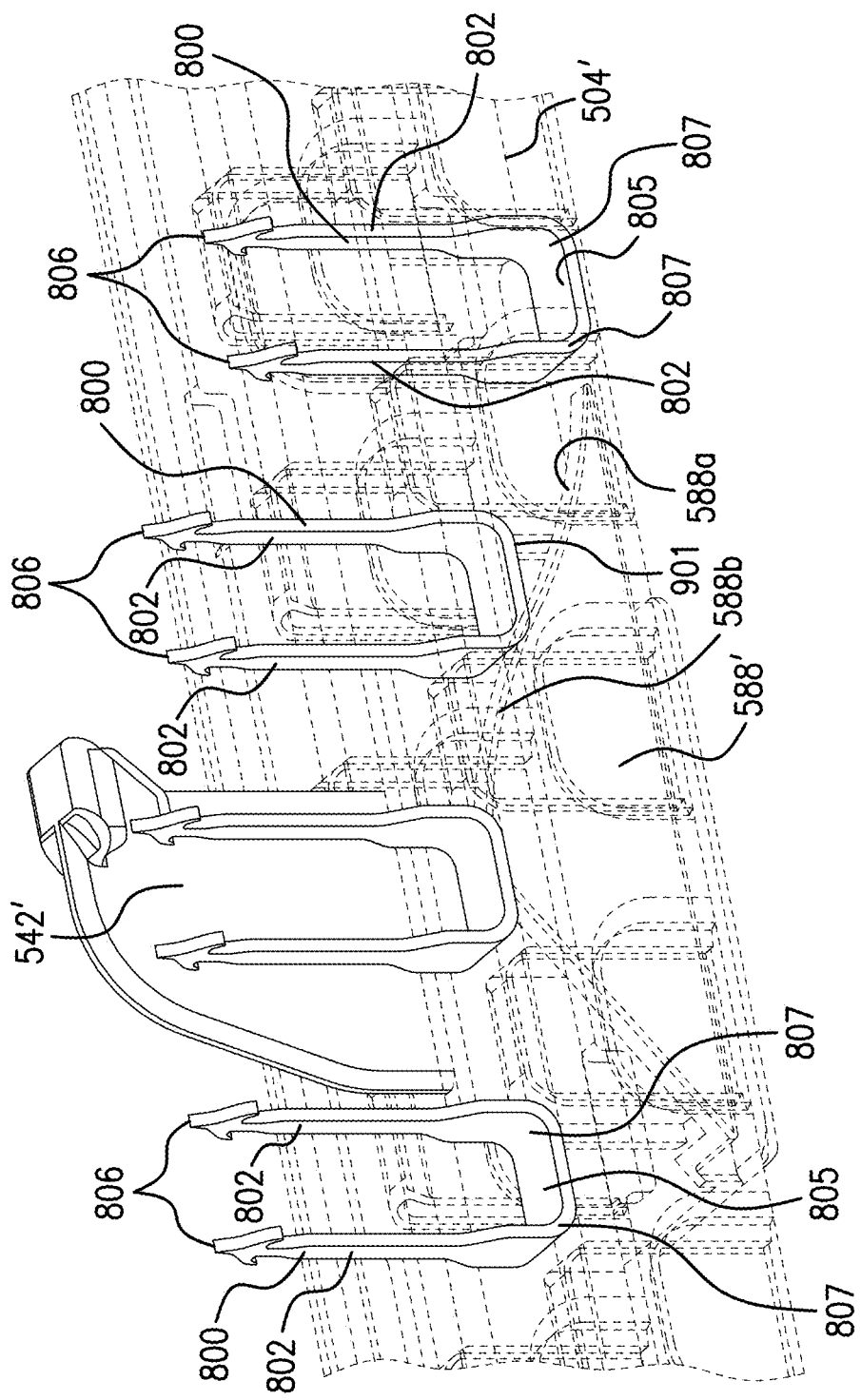

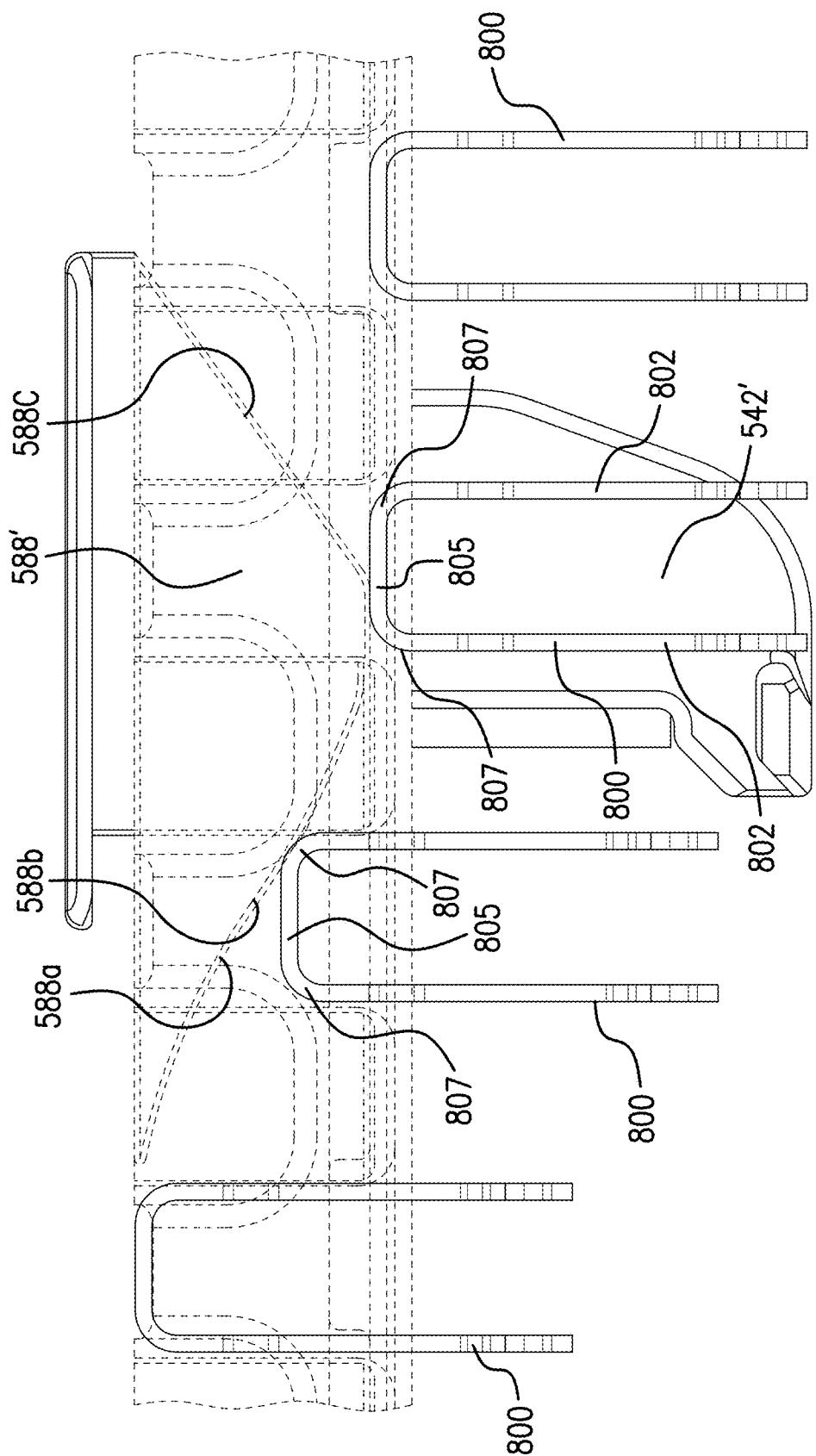

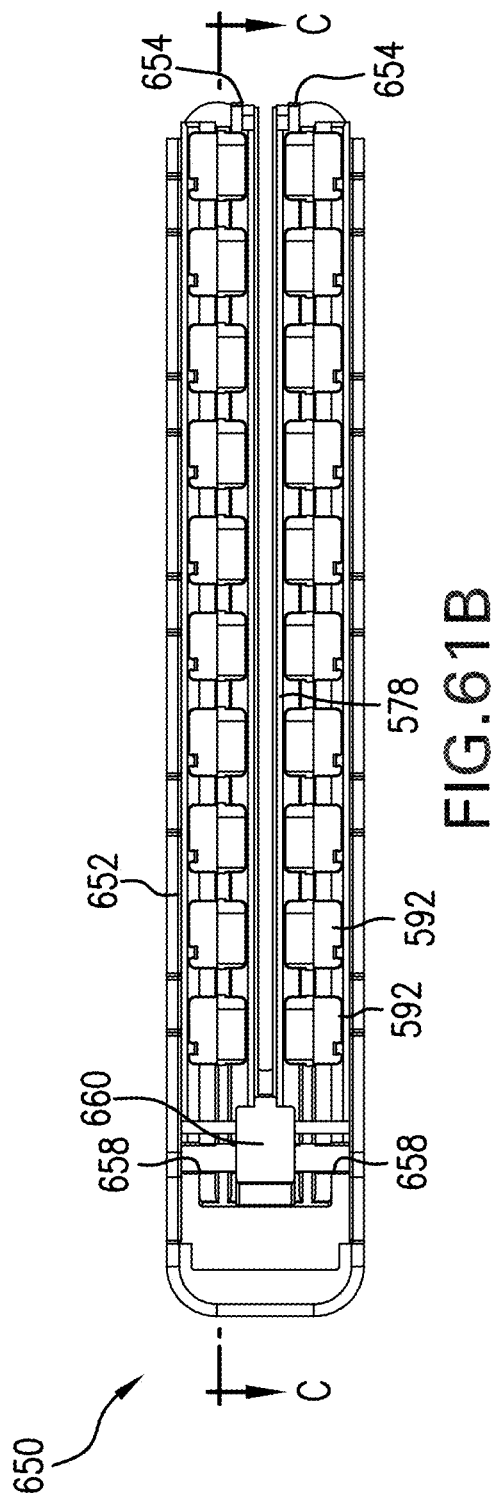
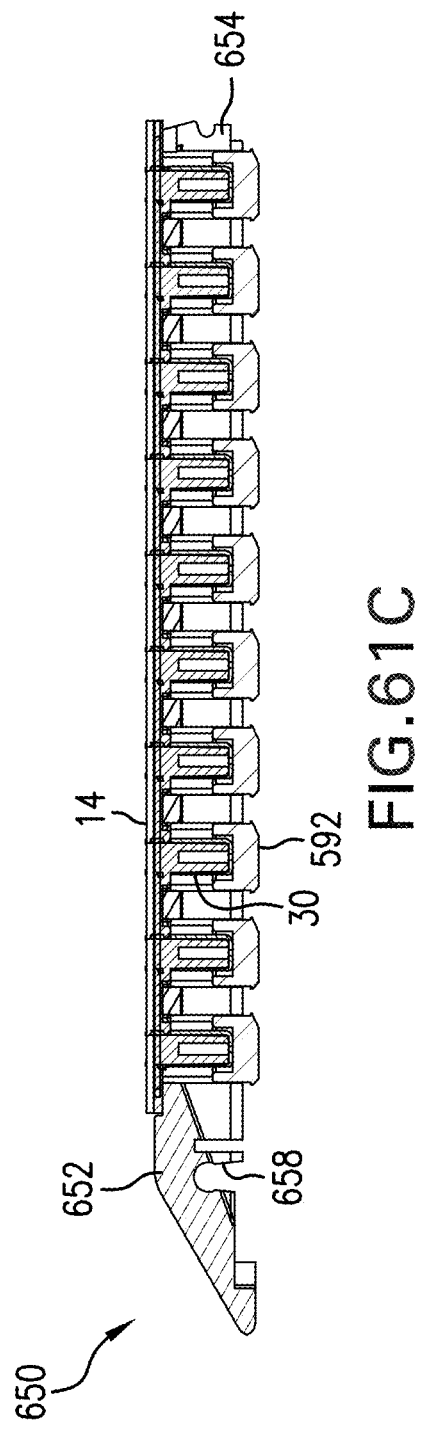

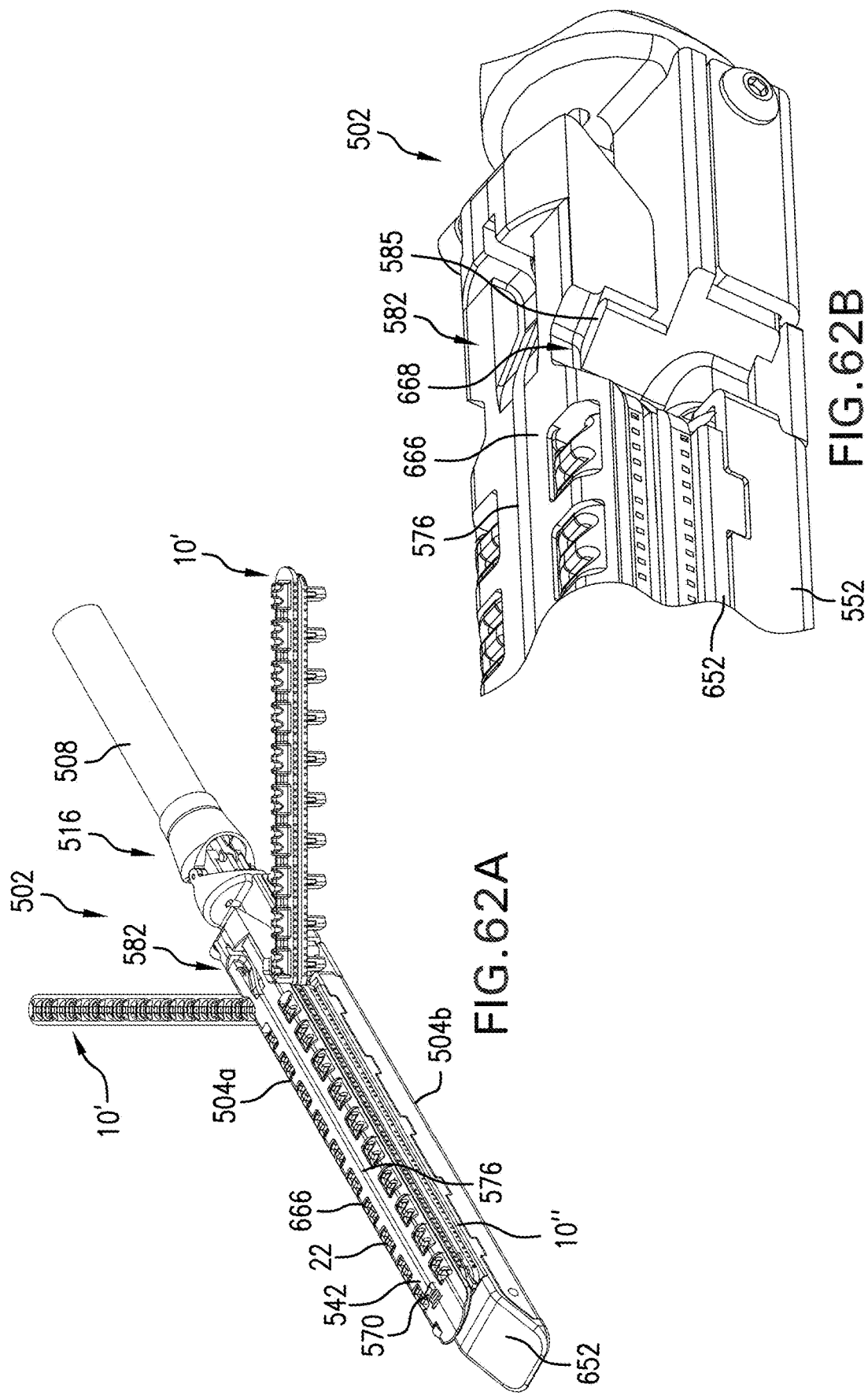

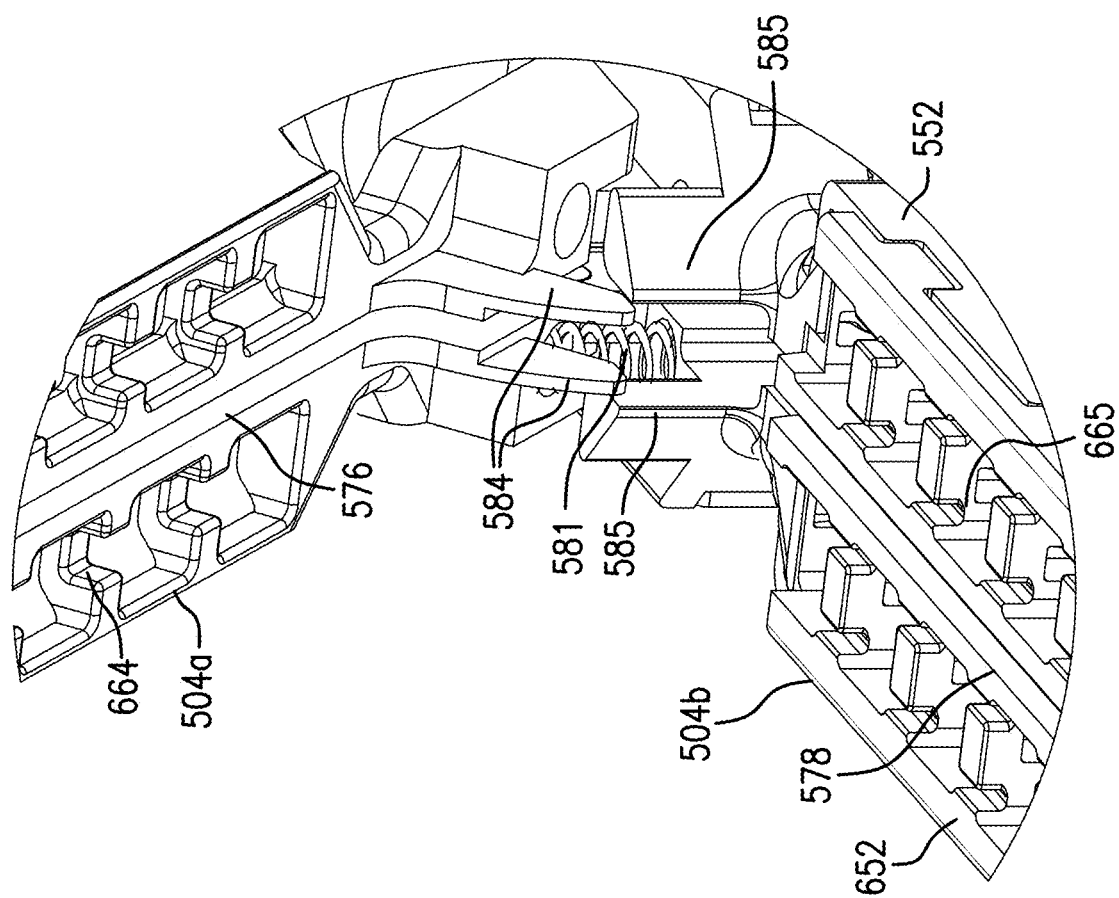
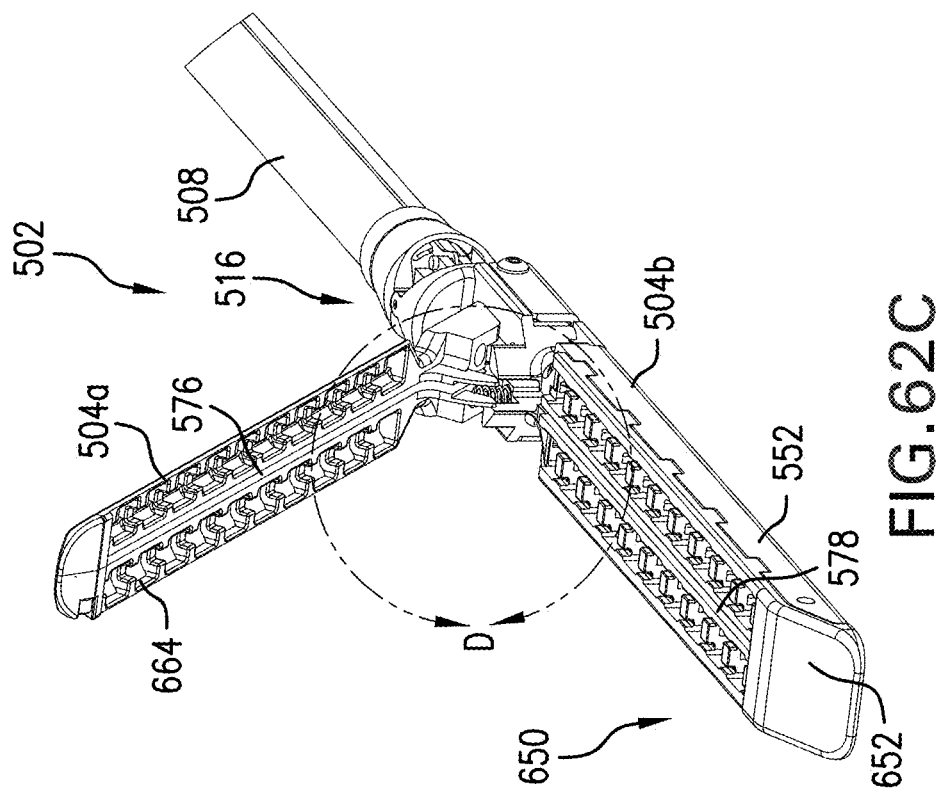

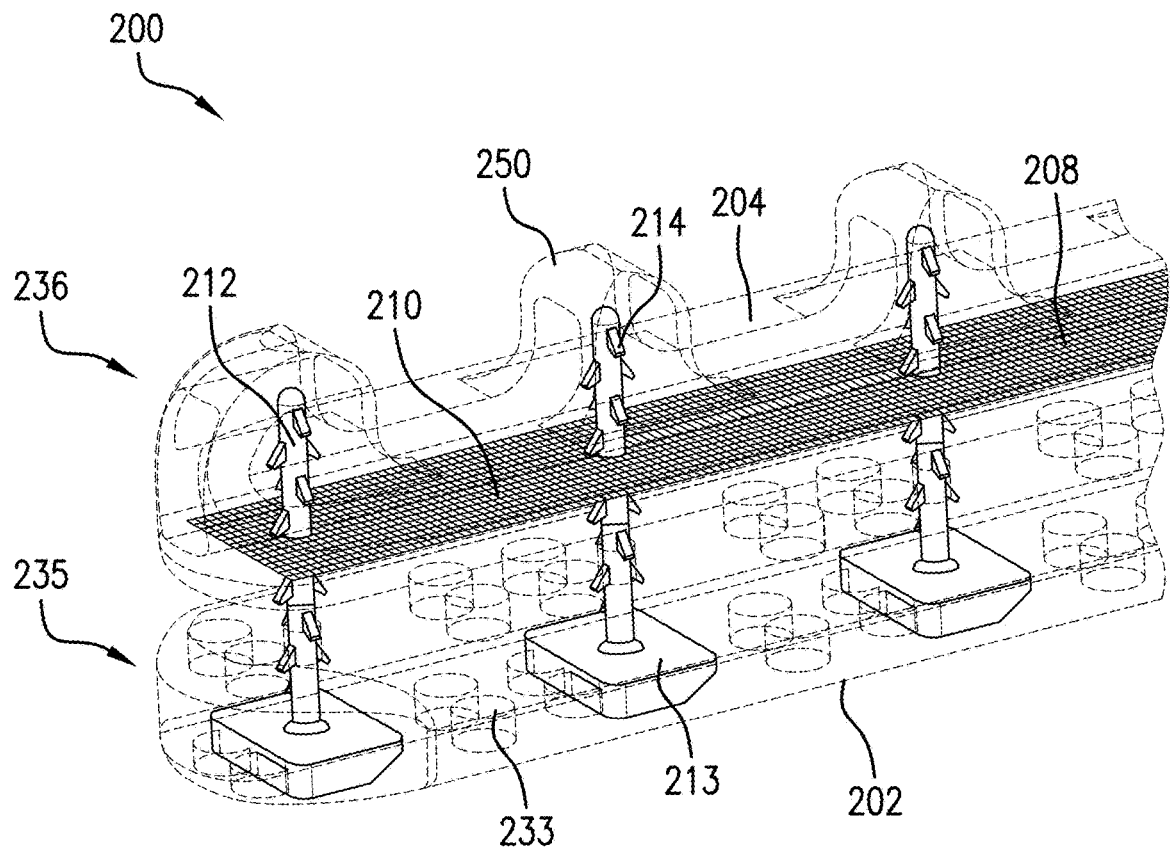
FIG.66
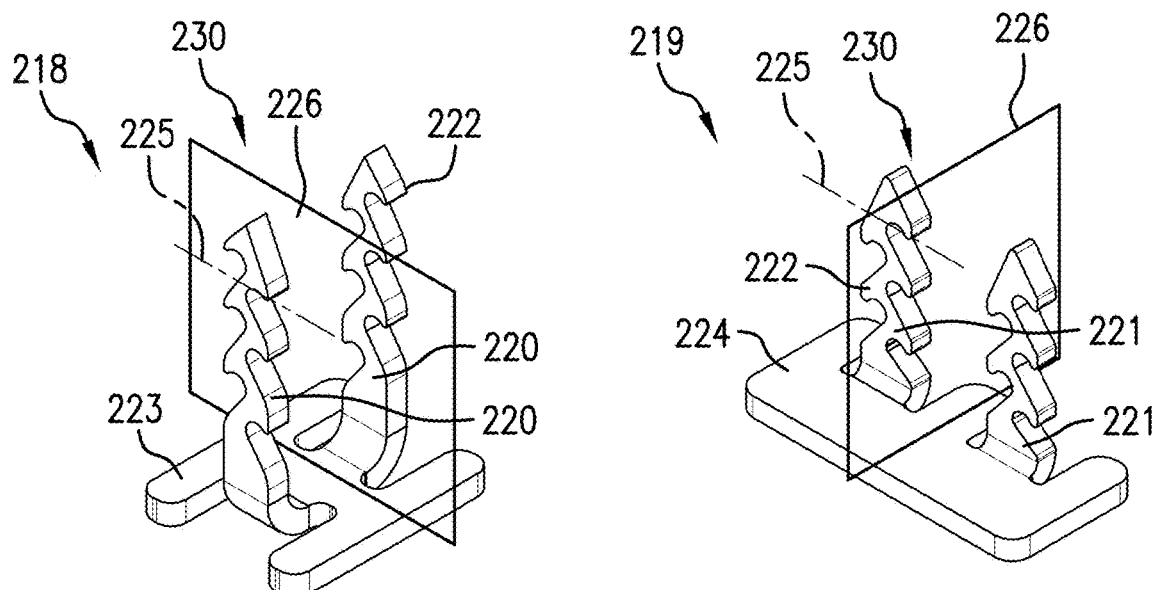
FIG.67
FIG.68

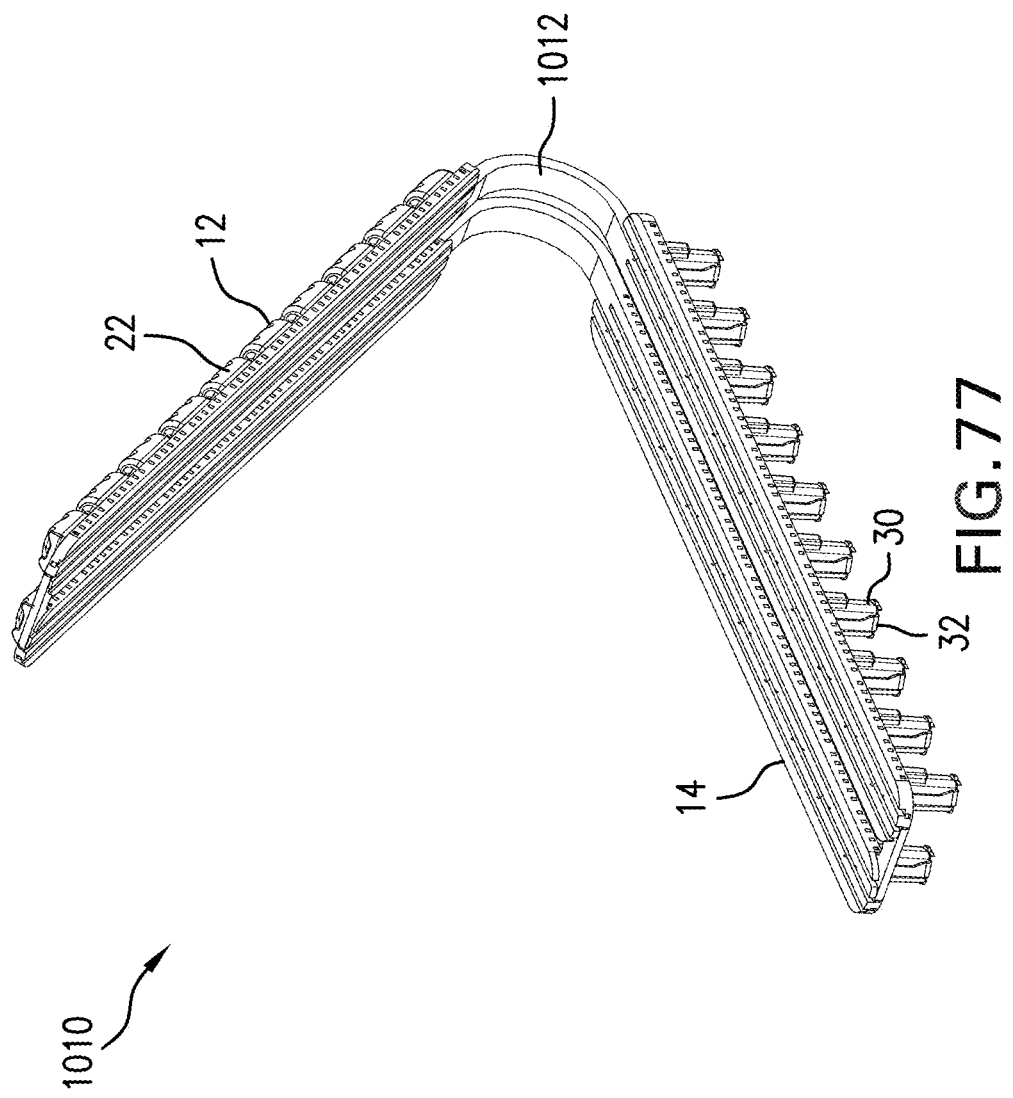

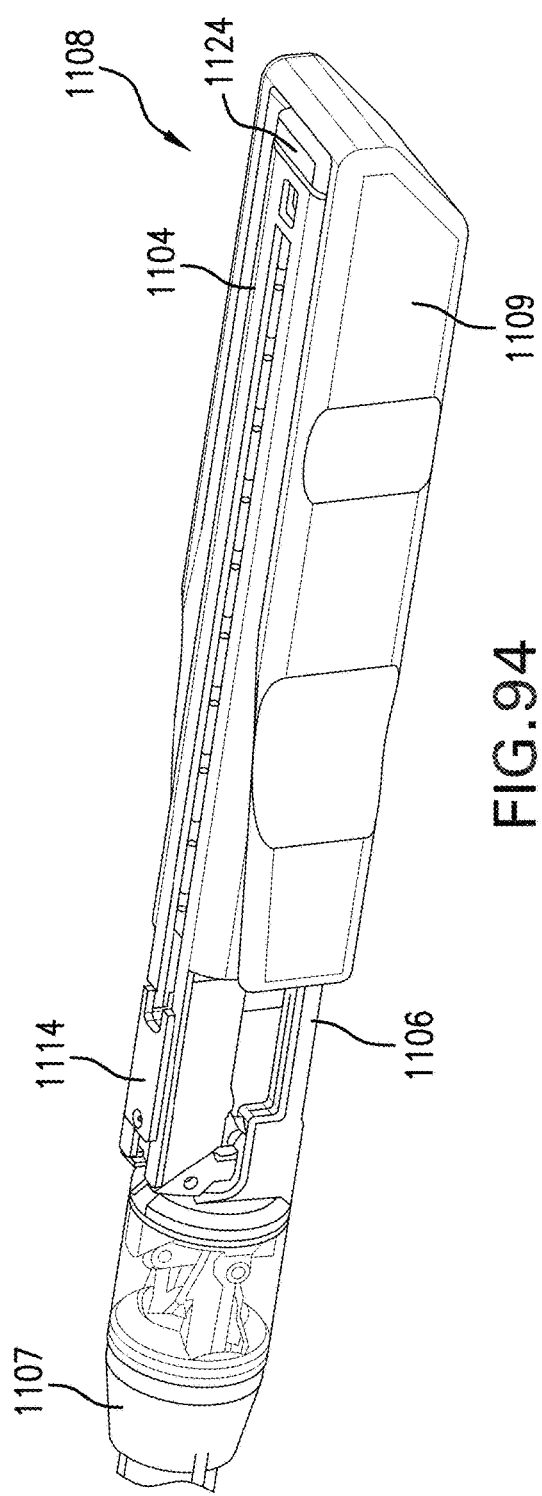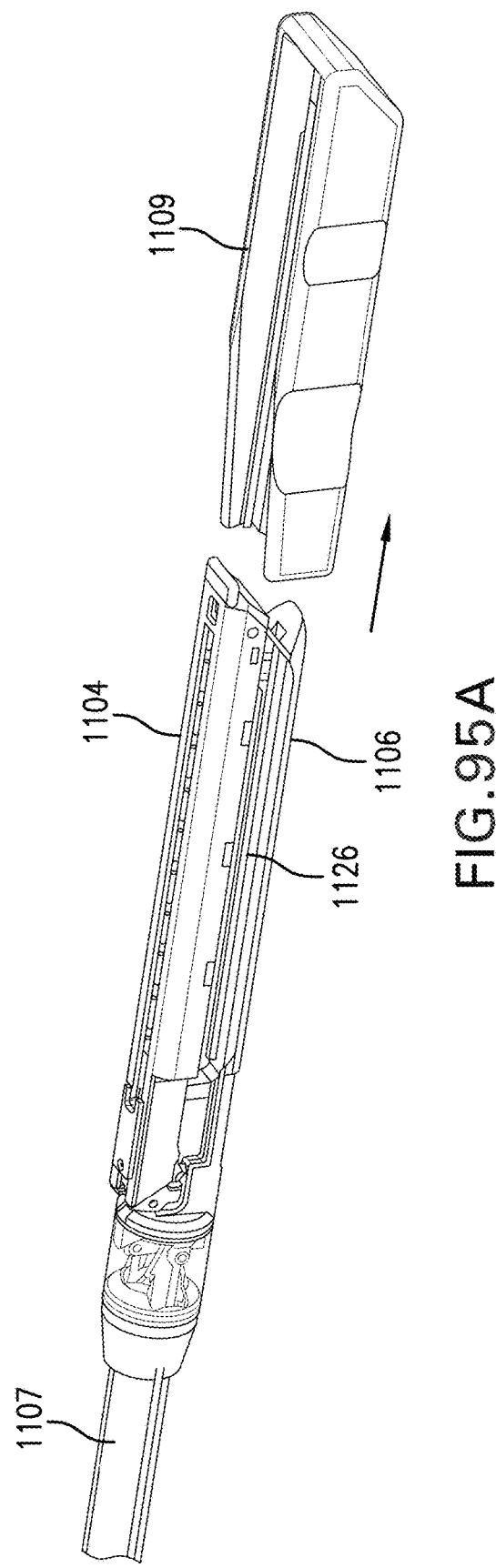

SURGICAL IMPLANT AND METHOD AND INSTRUMENT FOR INSTALLING THE SAME

CROSS-REFERENCES TO RELATED APPLICATIONS

This application is a divisional application of U.S. patent application Ser. No. 15/257,908, filed Sep. 6, 2016, which is a continuation-in-part of International Patent Application No. PCT/US15/18839, filed on Mar. 4, 2015, pursuant to 35 USC § 365(c), which in turn claims benefit of priority to U.S. Provisional Application No. 61/947,956, filed on Mar. 4, 2014. U.S. patent application Ser. No. 15/257,908 is also a continuation-in-part of U.S. patent application Ser. No. 14/641,136, filed Mar. 6, 2015 (now U.S. Pat. No. 9,795,385), pursuant to 35 USC § 120, which is a continuation of International Patent Application No. PCT/US15/18839, filed on Mar. 4, 2015, pursuant to 35 USC § 363, which in turn claims benefit of priority to U.S. Provisional Application No. 61/947,956, filed on Mar. 4, 2014. U.S. patent application Ser. No. 15/257,908 is also a continuation-in-part application of U.S. patent application Ser. No. 14/639,113, filed Mar. 4, 2015, pursuant to 35 USC § 120, which is a continuation of International Patent Application No. PCT/US15/18839, filed on Mar. 4, 2015, pursuant to 35 USC § 363, which in turn claims benefit of priority to U.S. Provisional Application No. 61/947,956, filed on Mar. 4, 2014. U.S. patent application Ser. No. 15/257,908 also claims the benefit of priority to U.S. Provisional Application No. 62/214,190, filed on Sep. 3, 2015 pursuant to 35 USC § 119. The entire disclosures of the afore-listed applications are expressly incorporated by reference herein. U.S. patent application Ser. No. 15/257,908 was published on Dec. 29, 2016 as US 2016/0374685 A1, which is incorporated herein by reference in its entirety.

TECHNICAL FIELD AND INDUSTRIAL APPLICABILITY

The present disclosure relates to devices, systems, tools, and/or methods useful for connecting, sealing, fastening, and/or attaching to itself or other tissue and/or non-tissue structures, and/or sealing the flow of fluid at and/or between structures such as tissue and vessel structures of a human or non-human mammal.

BACKGROUND

In the discussion of the background that follows, reference is made to certain structures and/or methods. However, the following references should not be construed as an admission that these structures and/or methods constitute prior art. Applicant expressly reserves the right to demonstrate that such structures and/or methods do not qualify as prior art.

Various devices and tools are known in the medical arts for sealing the flow of fluid through tissue structures in a patient. Common examples include bipolar, monopolar, and other radiofrequency (RF) and thermal energy sealers, staplers, and two-part fasteners. While these devices generally work for their intended uses, each solution is not without its tradeoffs. For example, RF and thermal energy sealers require the availability of a source of energy as well as high power requirements and can scorch or burn tissue due to overheating. Medical staplers and two-part fastener appliers must be accurately and precisely toleranced during manufacture and aligned during use in order to ensure proper engagement and functioning with respect to the tissue chosen for stapling. Medical staplers and two-part fastener appliers are also generally configured for certain tissue sizes and thicknesses and do not accommodate easily various tissue thicknesses. In view of these and other tradeoffs, there is the ever-present desire for new and alternate devices and tools for connecting tissue to itself or other tissue and non-tissue structures, and/or sealing the flow of fluid at and/or between tissue structures of a patient.

SUMMARY

A surgical implant according to an example embodiment of the present disclosure comprises a deployment member having a first base with a first tissue contacting surface. At least one fastener is disposed within the deployment member. A receiver member has a second base with a second tissue contacting surface facing the first tissue contacting surface of the deployment member. A retainer is embedded within the second base of the receiver member. The fastener is movable with respect to and penetrable through the deployment member, receiver member and any tissue located therebetween to engage the retainer, and wherein engagement of fastener and the retainer couples the deployment and receiver members together.

A surgical implant according to another example embodiment of the present disclosure comprises a base having a tissue contacting surface and a first thickness. A suspension having a second thickness extends from the base opposite to the tissue contacting surface. A fastener, movable with respect to the base, is coupled to the suspension to compress the suspension as the fastener is inserted into the base.

According to the example embodiment, the suspension can be a resilient, compressible member configured as a tower.

A surgical apparatus according to another example embodiment of the present disclosure comprises a body and a shaft extending distally from the body. An end effector disposed at a distal end of the shaft includes a first jaw and a second jaw. The first jaw is receivable of a first portion of a surgical implant, and the second jaw is receivable of a second portion of a surgical implant. The first and second jaws are relatively movable with respect to one another between an open position wherein the first and second jaws are spaced apart and a closed position wherein the first and second jaws are proximate to one another. A driver for transitioning the first and second jaws to the closed position engages the first and second jaws, wherein moving the driver distally with respect to the first and second jaws compresses the first and second jaws with respect to one another. An actuator coupled to the driver transfers an actuation force to the driver to transition the first and second jaws to the closed position via tension.

A surgical implant applicator according to another example embodiment of the present disclosure comprises a main body and a shaft extending distally from the main body. First and second jaws disposed at a distal end of the shaft are relatively movable with respect to one another. A driver is movably mounted to the first and second jaws for closing the jaws and deploying tissue fasteners of a surgical implant positionable within the first and second jaws. A trigger is operatively associated with the driver, wherein actuation of the trigger closes the jaws as well as advances the driver towards a distal end of the first and second jaws. Subsequent actuation of the trigger after the driver has reached the distal end of the first and second jaws induces movement of the driver towards a proximal end of the first and second jaws.

According to an example embodiment, the driver can further include a blade positioned to engage and sever tissue as the driver is moved along the first and second jaws.

According to an example embodiment, the applicator can further include a safety mechanism comprising a user actuation rod. When oriented in a first safety position, the rod inhibits movement of the driver until the first and second jaws are closed.

According to an example embodiment, the rod is spring biased to assume the first position.

According to an example embodiment, the rod is locked in a second position to allow the driver to advance from the proximal end to the distal end of the first and second jaws.

According to an example embodiment, the applicator further includes a drive mechanism operatively associated with the trigger, driver and safety mechanism. The drive mechanism comprises a flange having a shoulder that abuts the rod when the rod is oriented in the first position. The drive mechanism further includes two ratchet gears coupled to the trigger and positioned on opposite sides of the flange that induces rotation of the flange upon actuation of the trigger. Cables operatively associated with the ratchet gears and operatively associated with the driver and/or one of the first and second jaws transmit force between therebetween.

According to an example embodiment, the rod has a variable diameter along its length to selectively impede the rotation of the flange.

According to an example embodiment, the applicator can further comprise a quarter gear positioned between the two ratchet gears.

A method for using a surgical implant applicator according to another example embodiment of the present disclosure comprises the steps of actuating a trigger to (i) advance a driver towards a distal end of first and second jaws of the applicator and (ii) deploy tissue fasteners of a surgical implant positioned within the first and second jaws, wherein the driver is movably mounted to the first and second jaws. The method further includes subsequently actuating the trigger after the driver has reached the distal end of the first and second jaws to move the driver towards a proximal end of the first and second jaws.

According to an example embodiment, the method can further include orienting a rod of a safety mechanism in a first safety position to prevent movement of the driver until the first and second jaws axe closed.

According to an example embodiment, the method can further comprise positioning the rod in a second position to allow the driver to advance from the proximal end to the distal end of the first and second jaws.

According to an example embodiment, the method can further include actuating a blade along a slot of the first and second jaws and severing tissue as the driver is advanced towards a distal end of the first and second jaws.

According to an example embodiment, the blade is actuated after the tissue fasteners on opposite sides of the blade have been deployed and secure the tissue.

According to an example embodiment, the method can further comprise severing a portion of the surgical implant upon actuation of the blade.

According to an example embodiment, the method can further comprise compressing the surgical implant between the first and second jaws upon closure of the jaws and subsequently further compressing the surgical implant between the closed first and second jaws upon advancing the driver towards the distal end the jaws.

According to another embodiment, a surgical implant is provided including a fastener supporting member having a first surface. At least one fastener is supported by the fastener supporting member. A receiver member has a second surface facing the first surface of the fastener supporting member. A retainer is positioned within the receiver member. At least one fastener is deployable from the fastener supporting member toward the receiver member to engage the retainer within the receiver member. Engagement of the retainer by the at least one fastener couples the fastener supporting member and the receiver member together.

According to another embodiment, a surgical implant is provided including a fastener carrying member supporting a plurality of fasteners having penetrating tips, the fastener carrying member having a first tissue contacting surface. A receiver member has a second tissue contacting surface. The first and second tissue contacting surfaces are positionable opposite each other so that tissue to receive the plurality of fasteners is positionable between the first and second tissue contacting surfaces. Deployment of the fasteners moves the penetrating tips of the fasteners through the fastener carrying member and through the tissue between the first and second tissue contacting surfaces and into the receiver member to couple the receiver member and fastener carrying member.

According to another embodiment, a surgical implant is provided including a fastener supporting member having a first surface. At least one fastener is supported by the fastener supporting member. At least one compressible member extends from the fastener supporting member. A receiver member has a second surface facing the first surface of the fastener supporting member. Deployment of the at least one fastener toward the receiver member compresses the at least one compressible member.

According to another embodiment, a surgical implant is provided comprising a fastener carrying member supporting a plurality of fasteners and a plurality of compressible members, each of the fasteners engageable with one of the compressible members. The plurality of fasteners are deployable through the fastener carrying member, wherein deployment of the plurality of fasteners compresses the compressible members.

According to another embodiment, a surgical implant is provided including a fastener supporting member and a plurality of fasteners arranged along a longitudinally extending row substantially parallel to a longitudinal axis of the implant. A retainer is positioned in the fastener supporting member and has a plurality of openings. The plurality of fasteners are retained by engagement with the plurality of openings in the retainer. A plurality of compressible members are engageable by the plurality of fasteners, and the plurality of compressible members are compressed by the plurality of fasteners.

According to another embodiment, a surgical implant is provided configured to accommodate a range of tissue thicknesses, the implant including first and second fasteners and first and second compressible members. The first fastener is engageable with the first compressible member and the second fastener is engageable with the second compressible member. The first compressible member is compressible in accordance with a distance of advancement of the first fastener and the second compressible member is compressible in accordance with a distance of advancement of the second fastener. The distances of advancement of the first and second fasteners are dependent on a tissue thickness through which the fasteners advance.

According to another embodiment, a surgical implant is provided including a fastener supporting member having a first surface. A plurality of fasteners are supported by the fastener supporting member. The plurality of fasteners have a penetrating tip and are deployable in a first direction. A receiver member is configured to receive the plurality of fasteners. A plurality of counterforce members extend from the fastener supporting member to apply a counterforce on the plurality of fasteners when the plurality of fasteners have been deployed. The counterforce members apply a force against the plurality of fasteners in a second direction opposite a first direction of deployment of the plurality of fasteners.

According to another embodiment, a surgical implant is provided including a receiver member, a fastener supporting member and a plurality of fasteners supported on the fastener supporting member and arranged along a longitudinally extending row substantially parallel to a longitudinal axis of the fastener supporting member. The fasteners are engageable with the receiver member. The fastener supporting member and the receiver member have a width and length exceeding the width, and the fasteners couple the fastener supporting member and the receiver member together and pull the receiver member toward the fastener supporting member after coupling the fastener supporting member and receiver member.

According to another embodiment, a surgical method of sealing tissue is provided including providing a fastener supporting member supporting a plurality of fasteners and having a plurality of compressible members. The method further includes providing a receiver member and clamping tissue between a first surface on the fastener supporting member and a second surface on the receiver member. The fasteners are advanced into the receiver member and compress the compressible members in accordance with a distance of advancement of the fasteners, the distance relating to a thickness of tissue between the first and second surfaces.

According to another embodiment, a surgical method of fastening parenchyma is provided including providing a fastener supporting member supporting a plurality of fasteners and a receiver member to receive the plurality of fasteners when advanced from the fastener supporting member. Parenchyma is clamped between a first surface on the fastener supporting member and a second surface on the receiver member. The fasteners are advanced in a first direction from the fastener supporting member into the receiver member to couple the fastener supporting member and the receiver member, wherein a counterforce is applied to each of the fasteners in a direction opposite to the first direction of advancement of the plurality of fasteners thereby accommodating for variations in tissue thickness.

According to another embodiment, a surgical method of forming an anastomosis between a first structure and a second structure within a body of a patient is provided, the method including providing a fastener supporting member supporting a plurality of fasteners, positioning the fastener supporting member adjacent the first structure, providing a receiver member and positioning the receiver member adjacent the second structure. The fasteners are advanced through the fastener supporting member and into the receiver member to couple together the fastener supporting member and the receiver member.

According to another embodiment, an end effector assembly of a surgical device is provided, the end effector assembly including a first jaw and a second jaw. At least one of the first and second jaws is movable toward the other jaw to transition the first and second jaws between an open configuration and a closed configuration. The first jaw and the second jaw are arranged to receive tissue therebetween when in the open configuration and to clamp the tissue when in the closed configuration. A fastener supporting member is supported by the first jaw. A plurality of fasteners is supported by the fastener supporting member and a receiver member supported by the second jaw. A retainer is positioned in the second jaw. A drive assembly is movable with respect to the first jaw to advance the plurality of fasteners toward the receiver member and into engagement with the retainer to couple together the fastener supporting member and the receiver member.

According to another embodiment, an end effector assembly of a surgical device is provided. The end effector assembly includes a first jaw and a second jaw. At least one of the first and second jaws is movable toward the other jaw to transition the first and second jaws between an open configuration and a closed configuration. The first jaw and the second jaw are arranged to receive tissue therebetween when in the open configuration and to clamp tissue when in the closed configuration. A fastener supporting member is supported by the first jaw. A plurality of fasteners is supported by the fastener supporting member. A plurality of compressible members is supported by the first jaw and engageable by the fasteners. A receiver member is supported by the second jaw. A drive assembly is movable with respect to the first jaw to advance the plurality of fasteners toward the receiver member. The plurality of fasteners compress the plurality of compressible members in accordance with a thickness of tissue clamped between the first and second jaws.

According to another embodiment, an end effector assembly of a surgical device is provided. The end effector assembly includes a first jaw and a second jaw. At least one of the first and second jaws is movable toward the other jaw to transition the first and second jaws between an open configuration and a closed configuration. The first jaw and the second jaw are arranged to receive tissue therebetween when in the open configuration and to clamp tissue when in the closed configuration. A fastener supporting member is supported by the first jaw, a plurality of fasteners is supported by the fastener supporting member, and a receiver member is supported by the second jaw. A drive assembly is movable with respect to the first jaw to advance the plurality of fasteners in a first direction toward the receiver member against a counterforce applied to the plurality of fasteners. The fasteners are engageable with the receiver member and the counterforce applies a force to the fasteners in a second direction opposite the first direction when the fasteners are engaged with the receiver member.

According to another embodiment, a surgical device is provided including a handle portion at a proximal portion of the device. An elongated portion extends distally from the handle portion. A first jaw and a second jaw are at the distal portion of the device. A fastener supporting member of a surgical implant is supported in the first jaw, the fastener supporting member supporting a plurality of surgical fasteners. A fastener receiver member of the surgical implant is supported in the second jaw. A drive assembly is actuable from the handle portion to advance the plurality of fasteners. The fasteners are advanced in a first direction toward the receiver member and engageable therewith to couple the fastener supporting member and receiver member and to exert a force to pull the receiver member toward the fastener supporting member after engagement of the plurality of fasteners with the receiver member.

According to another embodiment, a surgical device is provided including a handle portion at a proximal portion of the device. An elongated portion extends distally from the handle portion. A first jaw and a second jaw are at a distal portion of the device. A fastener supporting member of a surgical implant is supported in the first jaw, the fastener supporting member supporting a plurality of surgical fasteners. A fastener receiver member of the surgical implant is supported in the second jaw. A plurality of compressible members interact with the plurality of fasteners. The compressible members have a first configuration prior to advancement of the plurality of fasteners and a second configuration subsequent to advancement of the plurality of fasteners. A drive assembly is actuable from the handle portion to sequentially advance the plurality of fasteners against the plurality of compressible members. The plurality of fasteners moves at least some of the plurality of compressible members to the second configuration.

According to another embodiment, a surgical device is provided including a handle portion at a proximal portion of the device. An elongated portion extends distally from the handle portion. A first jaw and a second jaw are at the distal portion of the device. A fastener supporting member of a surgical implant is supported in the first jaw. A plurality of fasteners is supported by the fastener supporting member, and a fastener receiver member of the surgical implant is supported in the second jaw. A retainer is included, and a drive assembly actuable from the handle portion advances the plurality of fasteners toward and into engagement with the retainer. The fasteners are engageable with the retainer to couple the fastener supporting member and receiver member.

According to another embodiment, a surgical device is provided including a handle portion at a proximal portion of the device and an actuator. An elongated portion extends distally from the handle portion. A first jaw and a second jaw are at the distal portion of the device. At least one of the first jaw and the second jaw is movable to transition the first and second jaws between an open position and a closed position. The first jaw and the second jaw are arranged to receive tissue therebetween when in the open position and to clamp tissue when in the closed position. A plurality of fasteners is supported by the first jaw. A drive assembly is operably connected to the actuator and actuable by the actuator to advance the plurality of fasteners from the first jaw toward the second jaw. The drive assembly includes a drive member movable with respect to the first jaw. The drive member is movable in a first direction to advance the plurality of fasteners and movable in a second direction opposite the first direction after movement in the first direction to further advance at least one of the plurality of fasteners.

According to another embodiment, a surgical device is provided including a handle portion at a proximal portion of the device. The handle portion includes a movable handle member and an elongated portion extends distally from the handle portion. A first jaw and a second jaw are at the distal portion of the device. At least one of the first jaw and the second jaw is movable to transition the first and second jaws between an open position and a closed position. The first jaw and the second jaw are arranged to receive tissue therebetween when in the open position and to clamp tissue when in the closed position. A plurality of fasteners is supported by the first jaw. First and second rotatable spools are included for moving a drive member. A first gear is operably connected to the handle member and operably connected to at least one of the first and second rotatable spools. Movement of the handle member rotates the first gear which rotates at least one of the first and second rotatable spools to move the drive member to advance the plurality of fasteners into tissue.

According to another embodiment, a surgical device is provided for applying fasteners including a handle portion at a proximal portion of the device and including an actuator. An elongated portion extends distally from the handle portion. A first jaw and a second jaw are at the distal portion of the device. At least one of the first jaw and the second jaw is movable to transition the first and second jaws between an open position and a closed position. The first jaw and the second jaw are arranged to receive tissue therebetween when in the open position and to clamp tissue when in the closed position. A plurality of fasteners is supported by the first jaw. A drive assembly is operably connected to the actuator and actuable by the actuator to advance the plurality of fasteners from the first jaw toward the second jaw. The drive assembly includes a first tensioning member, a second tensioning member and a pulley. The first tensioning member interacts with the pulley to effect advancement of the plurality of fasteners toward the second jaw.

According to another embodiment, a surgical implant is provided comprising a fastener supporting member having a first surface and at least one fastener supported by the fastener supporting member. A receiver member has a second surface facing the first surface of the fastener supporting member. A retainer is positioned within the receiver member. A flexible flap extends from one or both of the fastener supporting member and the receiver member, wherein the at least one fastener is deployable from the fastener supporting member toward the receiver member to engage the retainer within the receiver member, wherein engagement of the retainer by the at least one fastener couples the fastener supporting member and the receiver member together.

In some embodiments, the flap extends radially from both sides of the receiver member and the fastener supporting member. In some embodiments, the flap is formed integrally with the fastener supporting member and receiver member. In some embodiments, the receiver member is formed of a first material and the retainer is formed of a more rigid material than the first material of the receiver member, and the retainer extends into the flap.

In some embodiments, the at least one fastener is deployable through the fastener supporting member and the retainer restricts movement of the least one fastener in a direction opposite to a direction of deployment of the at least one fastener after the at least one fastener engages the retainer. The retainer can include a mesh having a plurality of openings, wherein the at least one fastener is receivable within one of the openings. In some embodiments, the at least one fastener is deployed in a first direction toward the receiver member and is biased in a second direction opposite the first direction.

In accordance with another embodiment, a surgical implant is provided comprising a fastener carrying member supporting a plurality of fasteners having penetrating tips and having a first tissue contacting surface and a first radially extending flexible flap extending from opposing sides of the fastener carrying member. A receiver member has a second tissue contacting surface and a second radially extending flexible flap extending from opposing sides of the receiver member. The first and second tissue contacting surfaces are positionable opposite each other so that tissue to receive the plurality of fasteners is positionable between the first and second tissue contacting surfaces, wherein deployment of the plurality of fasteners moves the penetrating tips of the fasteners through the fastener carrying member and through the tissue between the first and second tissue contacting surfaces and into the receiver member to couple the receiver member and fastener carrying member.

In some embodiments, a first retainer is positioned within the receiver member and/or a second retainer is positioned in the fastener carrying member, and the penetrating tips of the fasteners extend through the retainers. The fastener carrying member can further include a plurality of compressible members compressed by the plurality of fasteners when the fasteners are deployed.

In some embodiments, the first and second retainers extend into the flaps. The first flap in some embodiments can be formed of the same material as the fastener carrying member and/or the second flap can be formed of the same material as the receiver member.

In accordance with another embodiment, an end effector assembly of a surgical device is provided comprising a first jaw, a second jaw, at least one of the first and second jaws movable toward the other jaw to transition the first and second jaws between an open configuration and a closed configuration. The first jaw and the second jaw are arranged to receive tissue therebetween when in the open configuration and to clamp the tissue when in the closed configuration. A fastener supporting member is supported by the first jaw, a plurality of fasteners are supported by the fastener supporting member, and a receiver member is supported by the second jaw. A retainer is positioned in the second jaw and a drive assembly is movable with respect to the first jaw to advance the plurality of fasteners toward the receiver member and into engagement with the retainer to couple together the fastener supporting member and the receiver member. The drive assembly includes a driver having a camming surface directly engageable with the fasteners during distal movement thereof to advance the plurality of fasteners toward the receiver member.

In some embodiments, the plurality of fasteners have a base and a pair of legs extending from the base, and the base is aligned substantially parallel to a longitudinal axis of the fastener supporting member.

In some embodiments, the plurality of fasteners have a curved surface directly engageable by the driver. A plurality of compressible members can be provided in some embodiments positioned in the first jaw, wherein advancement of the plurality of fasteners compresses the plurality of compressible members.

In some embodiments, the plurality of fasteners are arranged in at least two rows substantially parallel to a longitudinal axis of the fastener supporting member, and a cutting blade is movable between the rows of fasteners to sever tissue.

In some embodiments, a first cable and a second cable are provided, wherein the first cable effects movement of the driver in a distal direction and the second cable effects movement of the driver in a proximal direction.

According to another embodiment, an end effector assembly of a surgical device is provided comprising a first jaw, a second jaw. At least one of the first and second jaws is movable toward the other jaw to transition the first and second jaws between an open configuration and a closed configuration. The first jaw and the second jaw are arranged to receive tissue therebetween when in the open configuration and to clamp the tissue when in the closed configuration. A fastener supporting member is supported by the first jaw and a plurality of fasteners are supported by the fastener supporting member. A receiver member is supported by the second jaw and a drive assembly is movable with respect to the first jaw to advance the plurality of fasteners into the receiver member to couple together the fastener supporting member and the receiver member. The drive assembly includes a driver having a distal camming surface and a proximal camming surface, the distal camming surface directly engageable with the plurality of fasteners during distal movement thereof to advance the plurality of fasteners and the proximal camming surface directly engageable with the plurality of fasteners during proximal movement thereof to further advance the plurality of fasteners.

In some embodiments, the plurality of fasteners have a base and a pair of legs extending from the base, the base aligned substantially parallel to a longitudinal axis of the fastener supporting member.

In some embodiments, the distal camming surface has a first region having a first curve and a second region having a second different curve. In some embodiments, the first curve reduces the firing force on initial advancement of the fastener and the second curve reduces the firing force on final advancement of the fastener.

In some embodiments, the fasteners have a curved surface directly engageable by the driver. In some embodiments, a plurality of compressible members are positioned in the first jaw, wherein advancement of the fasteners compresses the compressible members. The compressible members can in some embodiments be in the form of towers, the towers having a channel therein to decrease lateral expansion of the towers when compressed by the fasteners The end effector assembly can include guide surfaces which are in contact with a side of the fastener opposite a side of the fastener contacted by the distal camming surface.

The end effector assembly can further include a retainer positioned in the receiver member and the plurality of fasteners are advanced into engagement with the retainer. The retainer can, in some embodiments, restrict movement of the least one fastener in a direction opposite to a direction of deployment of the at least one fastener after the at least one fastener engages the retainer.

In some embodiments, the end effector assembly of includes a plurality of channels through which the distal and proximal camming surfaces travel.

A first cable and a second cable can be provided wherein the first cable effects movement of the driver in a distal direction and the second cable effects movement of the driver in a proximal direction.

In some embodiments, the fastener supporting member and receiver member each have a flap extending radially from each side of the receiver member and the fastener supporting member. In some embodiments, the fasteners are deployable through the fastener supporting member.

According to another embodiment, an end effector assembly of a surgical device is provided comprising a first jaw and a second jaw. At least one of the first and second jaws is movable toward the other jaw to transition the first and second jaws between an open configuration and a closed configuration, wherein the first jaw and the second jaw are arranged to receive tissue therebetween when in the open configuration and to clamp the tissue when in the closed configuration. A fastener supporting member is supported by the first jaw and a plurality of fasteners are supported by the fastener supporting member. A receiver member is supported by the second jaw. A drive assembly is movable with respect to the first jaw to advance the plurality of fasteners into the receiver member to couple together the fastener supporting member and the receiver member, the drive assembly including a driver having a camming surface having a first region having a first curve and a second region having a second different curve, wherein the first curve reduces a firing force on initial advancement of the fastener and the second curve reduces the firing force on final advancement of the fastener.

According another embodiment, a surgical implant is provided comprising a fastener supporting member having a first surface, a plurality of fasteners supported by the fastener supporting member, a receiver member having a second surface facing the first surface of the fastener supporting member, and a plurality of compressible members extending from the fastener supporting member. The compressible members have a solid region extending in a direction away from the receiver member and a channel formed within the solid region, wherein deployment of the at least one fastener toward the receiver member compresses the at least one compressible member.

In some embodiments, the surgical implant has a first tissue contacting surface on a first side of the fastener supporting member and the compressible members extend from a second opposite side of the fastener supporting member. In some embodiments, the compressible members are in the form of a tower having a base and fasteners have a base engageable with the base of the compressible members, the base of fasteners applying a force to the base of the compressible members to deform the at least one compressible member.

In some embodiments, the receiver member includes a plurality of shields arranged along a row substantially parallel to a longitudinal axis of the receiver, each of the plurality of shields being positioned opposite a fastener. The extent of compression of the compressible members in some embodiments is dependent on a thickness of tissue clamped between the fastener supporting member and the receiver member, and the compressible members apply a counter-force to the fasteners in a direction opposite a direction in which the fasteners are deployed.

According to another embodiment, an end effector assembly of a surgical device is provided comprising a first jaw and a second jaw movable toward the first jaw between an open configuration and a closed configuration, wherein the first jaw and the second jaw are arranged to receive tissue therebetween when in the open configuration and to clamp the tissue when in the closed configuration. A fastener supporting member is supported in the second jaw and a plurality of fasteners are supported by the fastener supporting member. A receiver member is supported by the first jaw and a drive assembly is movable with respect to the second jaw to advance the plurality of fasteners into the receiver member to couple together the fastener supporting member and the receiver member, In some embodiments, the drive assembly includes a driver having a distal camming surface and a proximal camming surface, the distal camming surface advancing the plurality of fasteners during distal movement and the proximal camming surface advancing the plurality of fasteners during proximal movement to further advance the plurality of fasteners. In some embodiments, the second jaw has first and second protrusions, the first protrusion engageable with a first opening in the first jaw and the second protrusion engageable with a second opening in the first jaw, wherein the first and second protrusions can be configured to snap over and into the first and second openings.

In some embodiments the end effector assembly further comprises a plurality of compressible members positioned in the second jaw, wherein advancement of the plurality of fasteners compresses the plurality of compressible members.

In some embodiments, the drive assembly is advanceable at an angle of up to about 90 degrees to advance the plurality of fasteners.

In some embodiments, the end effector assembly further comprises a retainer positioned in the receiver member and the plurality of fasteners are advanced into engagement with the retainer, wherein the retainer can be configured to restrict movement of the fasteners in a direction opposite to a direction of deployment of the fasteners after the fasteners engage the retainer. In some embodiments, the plurality of fasteners are deployable through the fastener supporting member.

In some embodiments, the drive system includes a first cable and a second cable, the first cable effects movement of the driver in a distal direction and the second cable effects movement of the driver in a proximal direction. In some embodiments, the drive system includes a driver, and a pull force that moves the driver proximally is on an opening side of a moving jaw pivot to create a jaw opening moment and a pull force that moves the driver distally is below the moving jaw pivot to create a jaw closing moment during advancement of the fasteners.

According to another embodiment, an end effector assembly of a surgical device is provided comprising a first jaw and a second jaw movable toward the first jaw between an open configuration and a closed configuration, wherein the first jaw and the second jaw are arranged to receive tissue therebetween when in the open configuration and to clamp the tissue when in the closed configuration. A plurality of fasteners are supported in the second jaw. A driver is movable with respect to the first and second jaws, the driver movable along a first plane in a distal direction to advance the plurality of fasteners toward the first jaw and subsequently movable in a second plane in a proximal direction to return to a proximal position, In some embodiments, the driver is operable to transition the first and second jaws between the open configuration and the closed configuration. In some embodiments, when the driver is moved to a distal position, the jaws can move to a slightly open position. In some embodiments, the driver can include a tab and the first jaw can include a first camming surface, the tab engaging the first camming surface to maintain the jaws in the closed configuration as the driver is advanced in the distal direction. In some embodiments, the first jaw has an opening at a distal portion to receive the tab so the driver can move from the first plane to the second plane.

In some embodiments, the driver advances the plurality of fasteners toward a receiver member in the first jaw and into engagement with a retainer in the receiver member, and the second jaw supports a plurality of compressible members, wherein advancement of the plurality of fasteners compresses the plurality of compressible members.

According to another embodiment an end effector assembly of a surgical device is provided comprising a first jaw and a second jaw movable toward the first jaw between an open configuration and a closed configuration, wherein the first jaw and the second jaw are arranged to receive tissue therebetween when in the open configuration and to clamp the tissue when in the closed configuration. A fastener supporting member is supported in the second jaw and a plurality of fasteners are supported in the fastener supporting member. A receiver member is supported by the first jaw. A driver is movable with respect to the first and second jaws to advance the plurality of fasteners into the receiver member to couple the fastener supporting member and the receiver member together, the driver engageable with the first and second jaws as it travels distally to hold the first and second jaws together and engageable with a surface of the first jaw to push the first jaw open as it moves proximally.

In some embodiments, when the driver moves to the distal position, the driver moves in a direction away from the second jaw to allow the first jaw to spring slightly open. In some embodiments, the driver includes a tab engageable with a camming surface of the first jaw to hold the jaws together.

In accordance with another embodiment, a loading assembly for a surgical applicator is provided having a first jaw and a second jaw. The loading assembly comprises a housing and an implant contained within the housing. The implant has a first portion and a second portion, the first portion having a fastener supporting member supporting a plurality fasteners and a plurality of compressible members. The second portion has a receiver member and a retainer positioned within the receiver member. The housing is positionable within the jaws of the applicator to transfer the first portion to the first jaw and the second portion to the second jaw.

In some embodiments, the housing is separable from the implant to leave the implant in the first and second jaws. In some embodiments, transitioning of the first and second jaws to the closed position transfers the implant to the first and second jaws.

In some embodiments, the plurality of fasteners are deployable from the fastener supporting member toward the receiver member to engage the retainer within the receiver member to couple the fastener supporting member and the receiver member together. The plurality of fasteners can include a plurality of fasteners arranged along at least one row substantially parallel to a longitudinal axis of the fastener supporting member. The receiver member can include a plurality of shields arranged along at least one row substantially parallel to a longitudinal axis of the receiver member with each shield positioned opposite one of the plurality of fasteners. In some embodiments, the retainer is embedded in the receiver member and includes a plurality of strands and a plurality of openings between the strands to receive the plurality of fasteners. In some embodiments, the receiver member is at least partially composed of silicone rubber In some embodiments, the loading assembly has a slot at a proximal portion to engage a tab of the first jaw and/or at least one protrusion to snap into a slot of the first jaw.

In accordance with another embodiment, a loading assembly for reloading an end effector of a surgical applicator is provided, the end effector having a first jaw movable toward the second jaw to transition the jaws from an open configuration to a closed configuration. The loading assembly comprises an implant having a first portion and a second portion, the first portion having a fastener supporting member supporting a plurality fasteners and the second portion having a receiver member. The implant is mountable within the first and second jaws of the applicator upon placement of the first portion in the first jaw and subsequent movement of the first jaw toward the second jaw.

In some embodiments, subsequent movement of the first jaw toward the second jaw transfers the first portion of the implant to the first jaw and the second portion of the implant to the second jaw.

In some embodiments, the fastener supporter member includes a plurality of compressible members compressible by the plurality of fasteners. A retainer can be positioned within the receiver member.

In some embodiments, the loading assembly includes a housing and the implant is removably positioned within the housing and transferable from the housing into the first and second jaws. In some embodiments, the loading assembly has at least one protrusion which snaps into a slot of the first jaw.

In accordance with another embodiment, a method of loading a surgical implant into a surgical applicator is provided comprising the steps of providing a housing having an implant including a plurality of fasteners and removably supported by the housing; placing the housing into a first jaw of the applicator; closing the first jaw of the applicator; and removing the housing from the implant to leave the implant within the first jaw of the surgical applicator.

In some embodiments the implant includes a receiver member, and the step of closing the first jaw transfers the receiver member to the second jaw. In some embodiments, the method further includes the steps of placing a proximal portion of the housing in engagement with a tab of the first jaw and subsequently rotating the housing toward the first jaw. In some embodiments, the receiver is frictionally retained in the second jaw upon closing of the first jaw.

In accordance with another embodiment, a surgical device is provided comprising a handle portion at a proximal portion of the device, an elongated portion extending distally from the handle portion, and an end effector connected to a distal portion of the elongated portion and having a first jaw and a second jaw. At least one of the jaws is movable toward the other jaw to effect transition of the jaws from an open to a closed configuration. The end effector is connected for articulation with respect to the elongated portion about a first axis and about a second axis, the first and second axes intersecting.

In some embodiments, the device includes a first pair of tension ribbons to effect articulation about the first axis and/or a second pair of tension ribbons to effect articulation about the second axis. In some embodiments, pulling a first ribbon of the first pair of ribbons in a proximal direction allows the second ribbon of the first pair of ribbons to extend articulating the end effector in a first direction and pulling the second ribbon of the first pair of ribbons in a proximal direction allows the first ribbon of the first pair of ribbons to extend articulating the end effector in a second direction opposite the first direction. In some embodiments, pulling a first ribbon of the second pair of ribbons in a proximal direction allows the second ribbon of the second pair of ribbons to extend articulating the end effector in a third direction different than the first and second directions and pulling the second ribbon of the second pair of ribbons in a proximal direction allows the first ribbon of the second pair of ribbons to extend articulating the end effector in a fourth direction opposite the third direction. In some embodiments, the first axis is a yaw axis and the second axis is a pitch axis and the yaw and pitch axes intersect at a central point. In some embodiments, the first and second axes are substantially orthogonal to each other. In some embodiments, a rotatable joint is connected to the first and second jaws and the first pair of ribbons attach to the rotatable joint in line with the second axis.

In some embodiments, the device includes a driver movable within the jaws to advance fasteners supported in one of the jaws, a first cable and a second cable, wherein the first cable effects movement of the driver in a distal direction and the second cable effects movement of the driver in the proximal direction, and the first and second cables. In some embodiments, the first and second cables are contained in a tube which extends through the intersection of the first and second axes.

In some embodiments, the handle portion includes a movable handle, and initial movement of the movable handle moves the drive assembly to transition the first and second jaws to a closed configuration and further movement of the movable handle advances fasteners in the first jaw toward a receiver member in the second jaw.

In some embodiments, a fastener supporting member of a surgical implant is supported in the first jaw and supports a plurality of fasteners, and a fastener receiver member of the surgical implant is supported in the second jaw. In some embodiments a plurality of compressible members interact with the plurality of fasteners, the plurality of compressible members having a first configuration prior to advancement of the plurality of fasteners and a second deformed configuration subsequent to advancement of the plurality of fasteners.

In accordance with another embodiment, a surgical device is provided comprising a handle portion at a proximal portion of the device, an elongated portion extending distally from the handle portion, and an end effector connected to a distal portion of the elongated portion and having a first jaw and a second jaw, at least one of the jaws movable toward the other jaw to effect transition of the jaws from an open to a closed configuration. A fastener supporting member of a surgical implant is supported in the first jaw and supports a plurality of fasteners. A fastener receiver member of the surgical implant is supported in the second jaw. The end effector is articulatable with respect to the elongated portion for movement in first and second opposite directions and third and fourth opposite directions.

In some embodiments, a first pair of tension ribbons and/or a second pair of tension ribbons are provided, wherein the first pair of tension ribbons are positioned on opposing sides of a longitudinal axis of the elongated portion and the second pair of tension ribbons are positioned on opposing sides of the longitudinal axis. In some embodiments, a) pulling a first ribbon of the first pair of ribbons in a proximal direction allows the second ribbon of the first pair of ribbons to extend articulating the end effector in a first direction, b) pulling the second ribbon of the first pair of ribbons in a proximal direction allows the first ribbon of the first pair of ribbons to extend articulating the end effector in a second direction opposite the first direction, c) pulling a first ribbon of the second pair of ribbons in a proximal direction allows the second ribbon of the second pair of ribbons to extend articulating the end effector in a third direction different than the first and second directions and/or d) pulling the second ribbon of the second pair of ribbons in a proximal direction allows the first ribbon of the second pair of ribbons to extend articulating the end effector in a fourth direction opposite the third direction.

In some embodiments, a plurality of compressible members interacting with the plurality of fasteners are provided, the plurality of compressible members having a first configuration prior to advancement of the plurality of fasteners and a second configuration subsequent to advancement of the plurality of fasteners.

In accordance with another embodiment, an articulation mechanism for an end effector of a surgical device is provided. The articulation mechanism comprises a pivot, first and second pitch ribbons connected to first and second portions of the pivot and third and fourth yaw ribbons connected to third and fourth portions of the pivot. The first and second ribbons are selectively tensionable to effect articulation of the end effector about a pitch axis and the third and fourth ribbons are selectively tensionable to effect articulation of the end effector about a pitch axis.

In some embodiments, the pitch and yaw axis intersect at a central point. In some embodiments, the third and fourth ribbons attach to the pivot in line with the pitch axis.

In accordance with another embodiment, a surgical device is provided comprising a handle portion at a proximal portion of the device including a movable handle, an elongated portion extending distally from the handle portion, and a first jaw and a second jaw at a distal portion of the device. At least one of the jaws is movable toward the other jaw to transition the first and second jaws from an open configuration to a closed configuration. A fastener supporting member of a surgical implant is supported in the first jaw and supports a plurality of surgical fasteners. A fastener receiver member of the surgical implant is supported in the second jaw. A drive assembly is actuable by the movable handle to transition the first and second jaws between the open and closed configurations and to advance the plurality of fasteners in a first direction into engagement with the fastener receiver member to couple the fastener supporting member and receiver member. A release is operatively associated with the movable handle, the release movable from a first position to a second position to enable the movable handle to actuate the drive assembly to advance the plurality of fasteners.

In some embodiments, the release is movable to a third position, the third position being between the first and second positions, wherein in the third position the movable handle can be returned to an initial position to transition the first and second jaws from the closed configuration back to the open configuration. In some embodiments, the movable handle is movable from an initial position to a second position to effect transition of the first and second jaws to the closed configuration, and the movable handle can have a hook engageable with a hook receiving member to retain the movable handle in the second position. In some embodiments, movement of the release to the third position releases engagement of the hook with the hook receiving member but prevents movement of the movable handle to actuate the drive assembly. In some embodiments, upon movement of the release to the second position, the first and second jaws cannot be transitioned to the open configuration until the plurality of fasteners are advanced into the receiver member.

In some embodiments, the movable handle is pivotable toward a stationary handle and the hook is positioned between the movable handle and the stationary handle. In some embodiments, the release is actuable by a button positioned on the movable handle. The button can be biased in a counterclockwise direction.

The device can further include a ratchet wheel, and the ratchet wheel can include a ridge to disengage a handle catch from the ratchet wheel. In some embodiments, the handle catch is biased against the ratchet wheel.

In some embodiments, a plurality of counterforce members are supported within the first jaw, the plurality of fasteners engageable with the plurality of counterforce members, and the plurality of counterforce members biasing the plurality of fasteners in a second direction opposite the first direction. In some embodiments, the fasteners exert a force to pull the receiver member toward the fastener supporting member after engagement of the plurality fasteners with the receiver member.

In some embodiments, the drive assembly is movable in a distal direction to advance the plurality of fasteners and movable in a proximal direction to further advance at least one of the plurality of fasteners in the first direction. The device can include a first cable and a second cable, the first cable effecting movement of the drive assembly in a distal direction and the second cable effecting movement of the drive assembly in the proximal direction.

According to another embodiment, a surgical device is provided comprising a handle portion at a proximal portion of the device including a movable handle, an elongated portion extending distally from the handle portion, a first jaw and a second jaw at a distal portion of the device. At least one of the jaws is movable toward the other jaw to transition the first and second jaws from an open configuration to a closed configuration. A fastener supporting member of a surgical implant is supported in the first jaw and the fastener supporting member supports a plurality of fasteners. A fastener receiver member of the surgical implant is supported in the second jaw. A drive assembly is actuable by the movable handle to transition the first and second jaws between the open and closed configurations and to advance the plurality of fasteners in a first direction into engagement with the fastener receiver member to couple the fastener supporting member and fastener receiver member. A release is operatively associated with the movable handle. The movable handle is movable from a first position to a second position to transition the jaws to the closed configuration, the movable handle locked in the second position and the release actuable to release the movable handle to enable movement back to the first position.

According to another embodiment, a surgical device is provided comprising a handle portion at a proximal portion of the device including a movable handle, an elongated portion extending distally from the handle portion, and a first jaw and a second jaw at a distal portion of the device. At least one of the jaws is movable toward the other jaw to transition the first and second jaws from an open configuration to a closed configuration. A plurality of surgical fasteners are supported in the first jaw. A drive assembly is movable from a proximal position to a distal position to advance the plurality of fasteners from the first jaw toward the second jaw, the movable handle operatively associated with the drive assembly, wherein the movable handle is actuable to transition the first and second jaws from the open configuration to the closed configuration and to advance the driver to advance the plurality of fasteners. A release is operatively associated with the movable handle and has a first release position enabling movement of the movable handle to transition the jaws from the closed configuration back to the open configuration and has a second release position enabling the movable handle to effect advancement of the drive assembly to advance the plurality of fasteners.

In some embodiments, the drive assembly is movable in distal and proximal directions, wherein distal movement of the drive assembly advances the plurality of fasteners and proximal movement of the drive assembly further advances at least one of the plurality of fasteners. The device may further include a first tensioning member connected to the drive assembly and a second tensioning member connected to the drive assembly, wherein the first tensioning member moves the drive member distally in the first direction and the second tensioning member moves the drive member proximally in the second direction, and the first tensioning member extends from a first drive spool and the second tensioning member extends from a second drive spool.

In some embodiments, upon movement of the release to the first position, further actuation of the movable handle to effect advancement of the drive assembly is blocked. In some embodiments, wherein upon movement of the release to the second position, the jaws cannot be transitioned to the open configuration until the plurality of fasteners are advanced. In some embodiments, the movable handle is pivotable toward a stationary handle and a hook is positioned between the movable handle and the stationary handle which locks the movable handle. In some embodiments, the release is actuable by a button positioned on the movable handle.

BRIEF DESCRIPTION OF THE DRAWINGS

The following descriptions should not be considered limiting in any way. With reference to the accompanying drawings, like elements are numbered alike:

FIG. 3 is a sectional exploded view of a segment of the implant of FIG. 1,

FIG. 4 is a side elevation view of the exploded section shown in FIG. 3;

FIG. 5 is a perspective view of the exploded section shown in FIGS. 3 and 4;

FIG. 12 is a perspective view of a section of the implant of FIG. 1 engaging a relatively thick structure;

FIG. 13A is a side view of the implant of FIG. 9 engaging the relatively thick structure.

FIG. 14 is a perspective view showing the tips of the legs of the implant illustrated in FIG. 9 catching on or otherwise engaging the retainer, with portions of the implant removed for clarity, the view rotated with respect to the orientation of FIG. 9;

FIG. 27B is a cut-away perspective view of the implant of FIG. 27C;

FIG. 55J is a perspective view of a portion of the stationary jaw of FIG. 55D showing the driver partially advanced to deploy some of the fasteners;

FIG. 55K is a side view in the orientation opposite FIG. 55J showing the driver partially advanced to deploy some of the fasteners;

FIG. 60H is a side view similar to FIG. 60G showing the handle in the jaws closed position and the safety button fully pressed;

FIG. 60I is a side view similar to FIG. 60H showing the handle sprung to the jaws open position for commencement of the ratcheting cycle to fire the fasteners;

FIG. 60J is a side view similar to FIG. 60I showing the handle pulled to commence the cycle to fire the fasteners;

FIG. 60K is an enlarged perspective view of a portion of the handle of FIG. 60E showing the ratchet wheel engagement;

FIG. 60L is an enlarged perspective view of a portion of the handle of FIG. 60E showing the interaction of the handle catch and ratchet wheel ridge;

FIG. 61A is a perspective view of one embodiment of a loading assembly for the jaws of the applicator of FIG. 50;

FIG. 61B is a bottom view of the loading assembly of FIG. 61A;

FIG. 61C is a cross-sectional view of the loading assembly of FIG. 61B taken generally along line C-C;

FIG. 62A is a perspective view illustrating two implants being installed by the jaws of the applicator of FIG. 50 in a head-to-tail arrangement;

FIG. 62B is a perspective side view illustrating an angled gap for assisting in the head-to-tail arrangement of FIG. 62A;

FIG. 62C is a perspective view of the jaws of FIG. 50 in an open configuration;

FIG. 62D is an enlarged view of the portion of FIG. 62D within circle D;

Figure 64:
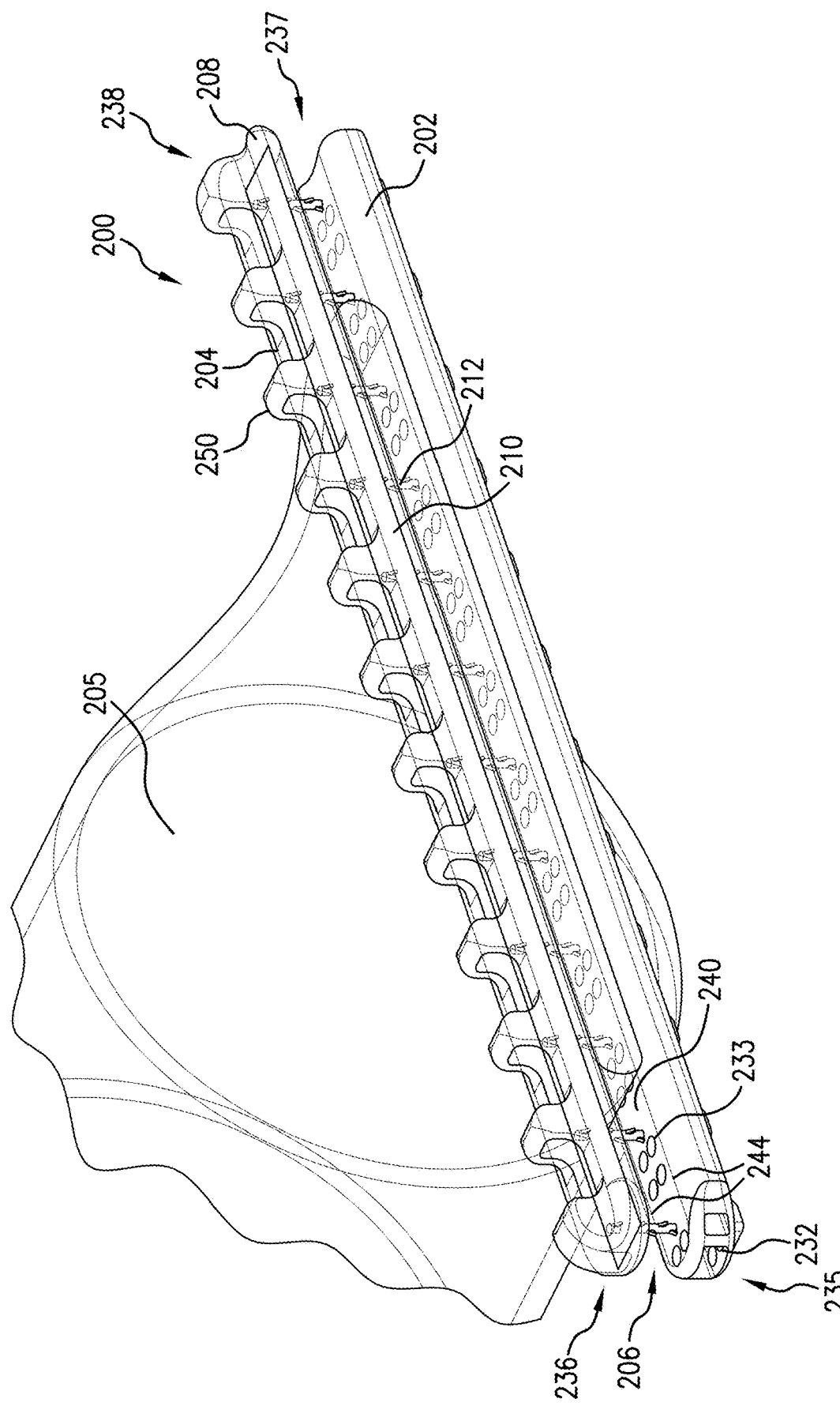
Figure 65:
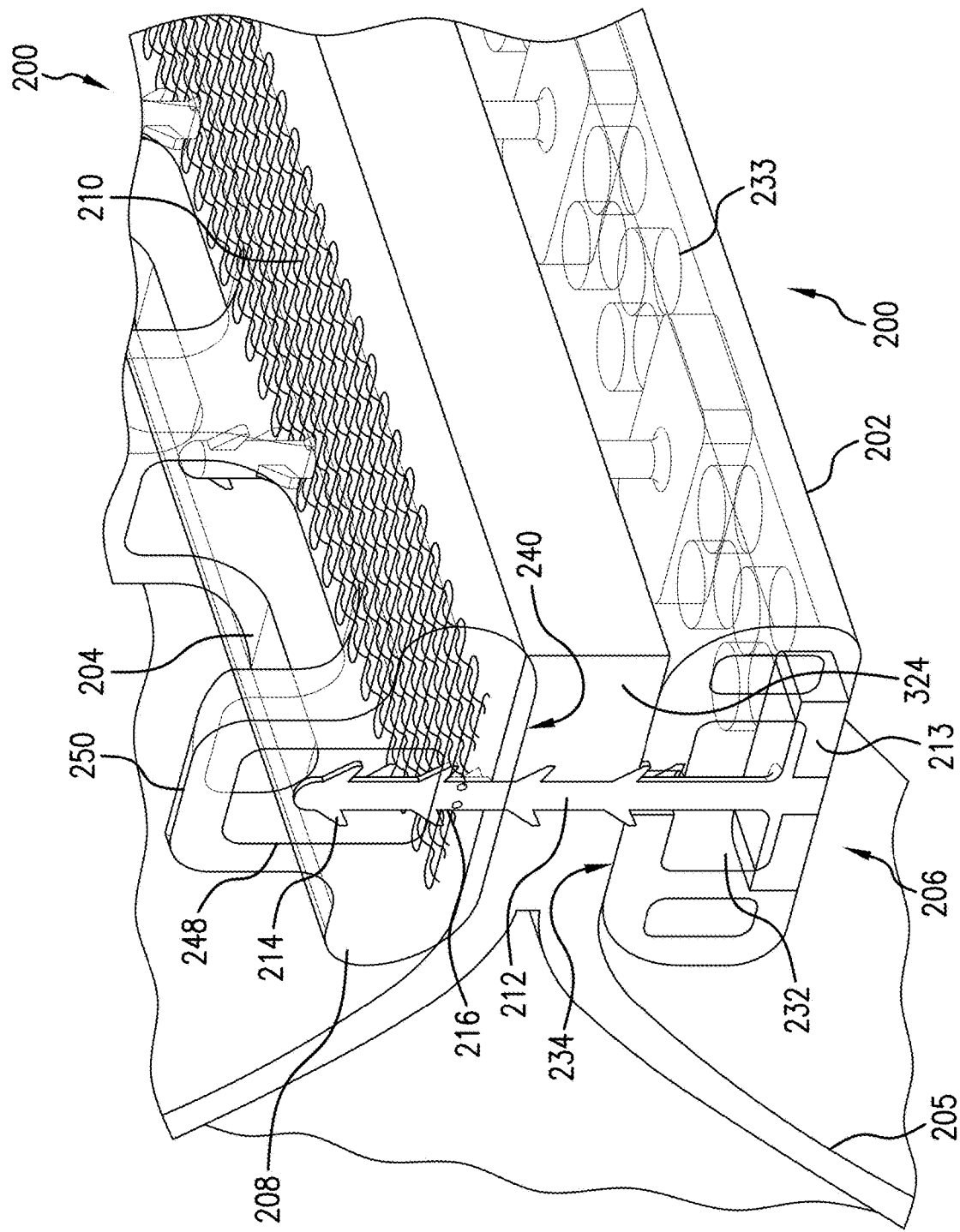
Figure 69:
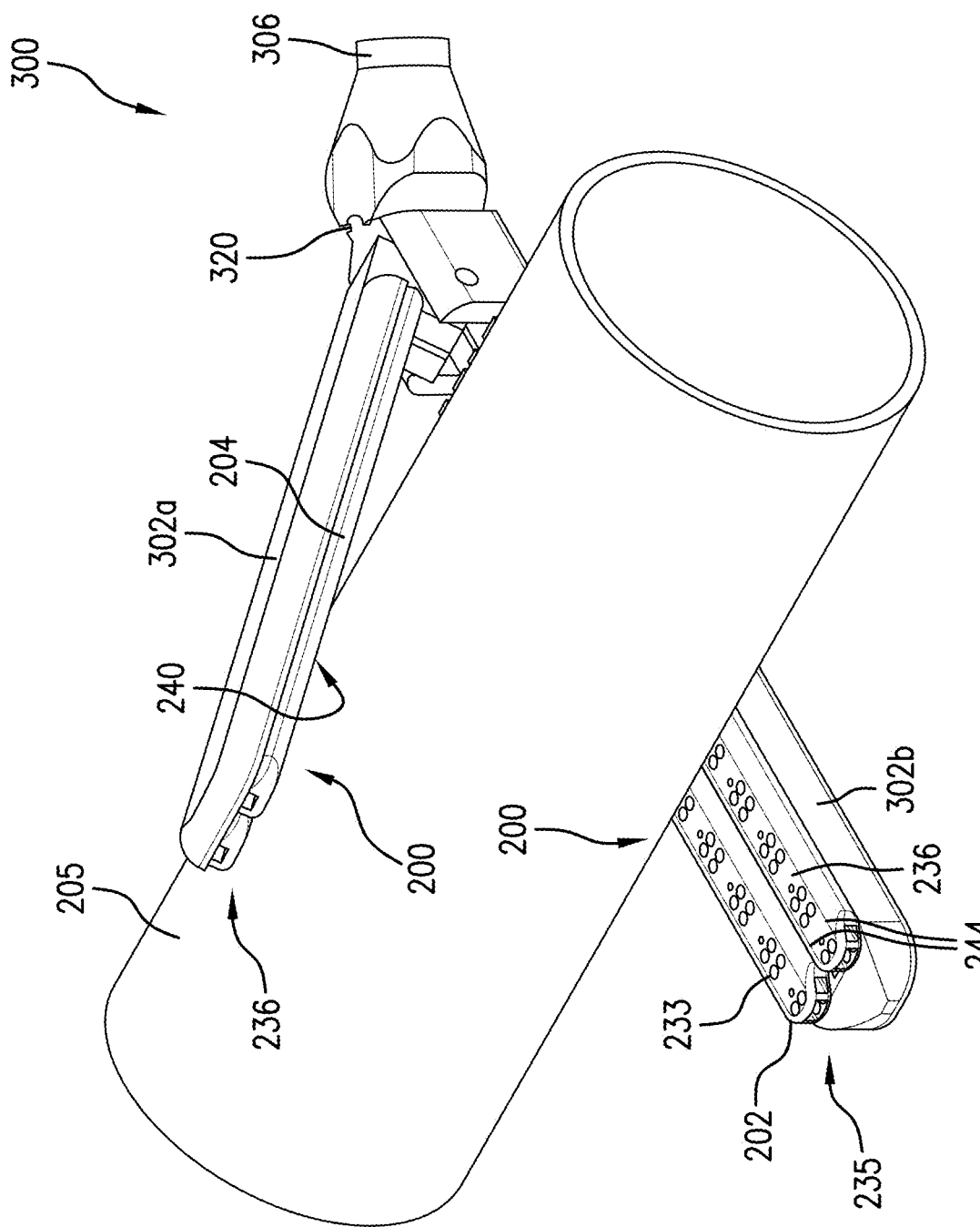
Figure 70:
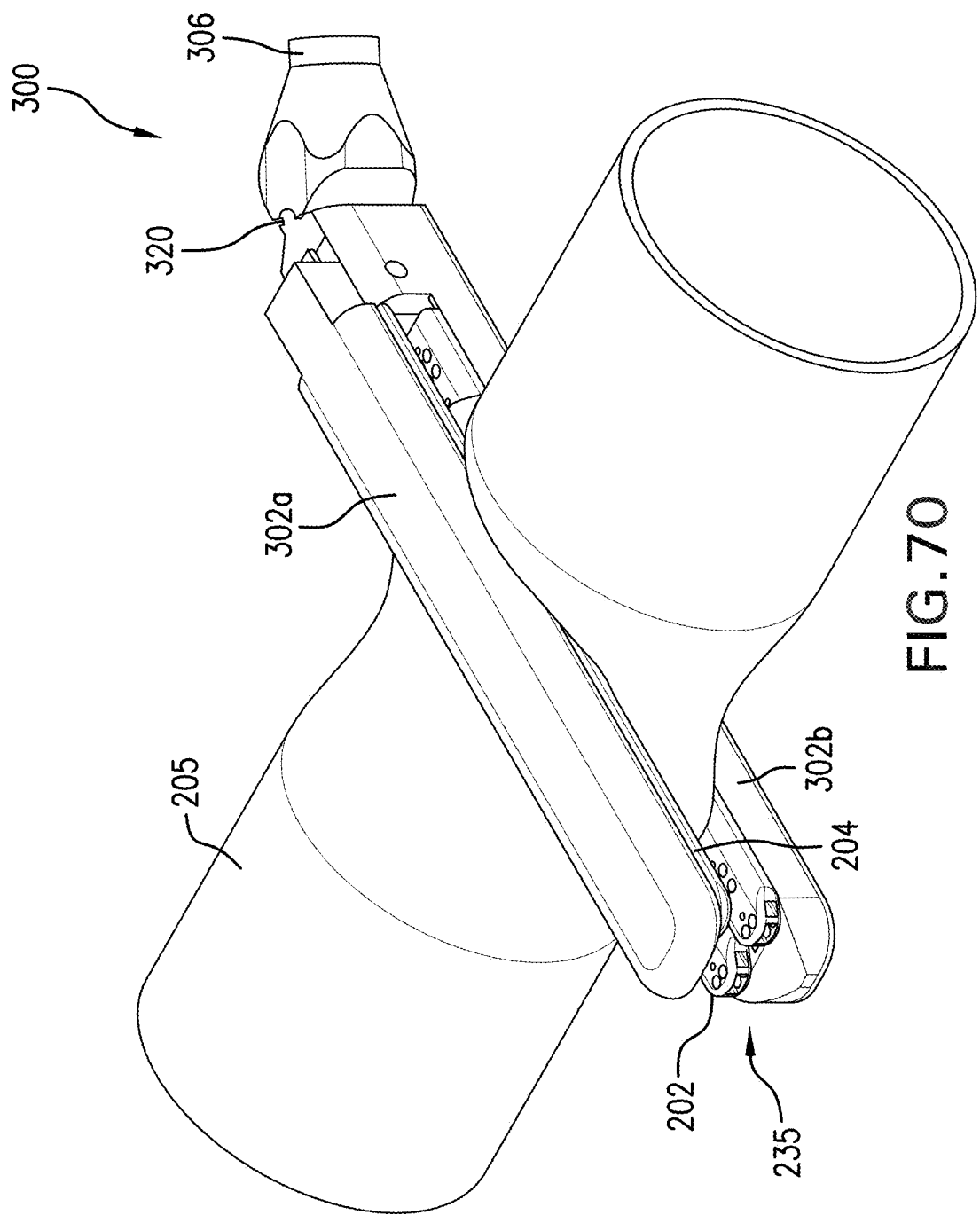
Figure 71:
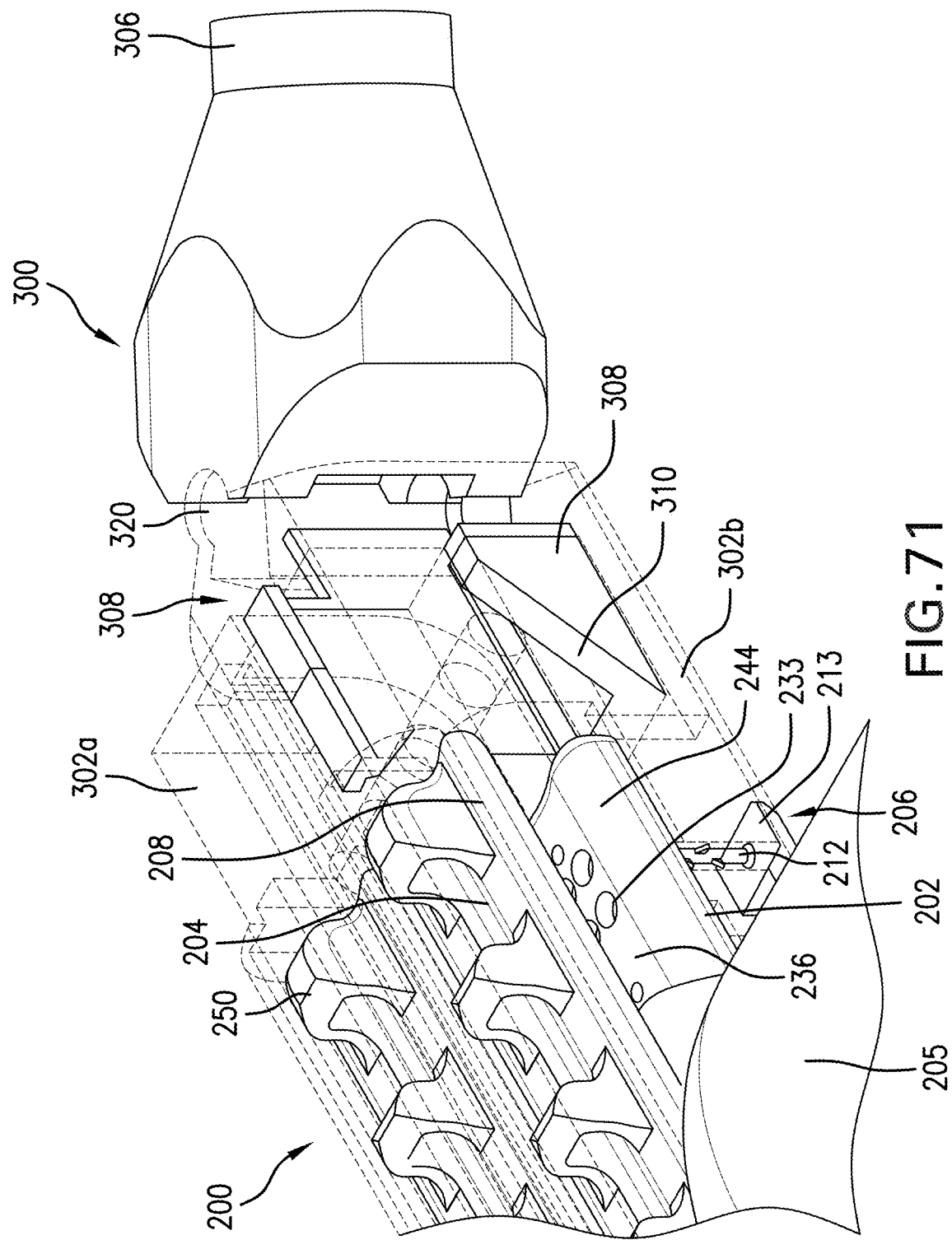
Figure 72:
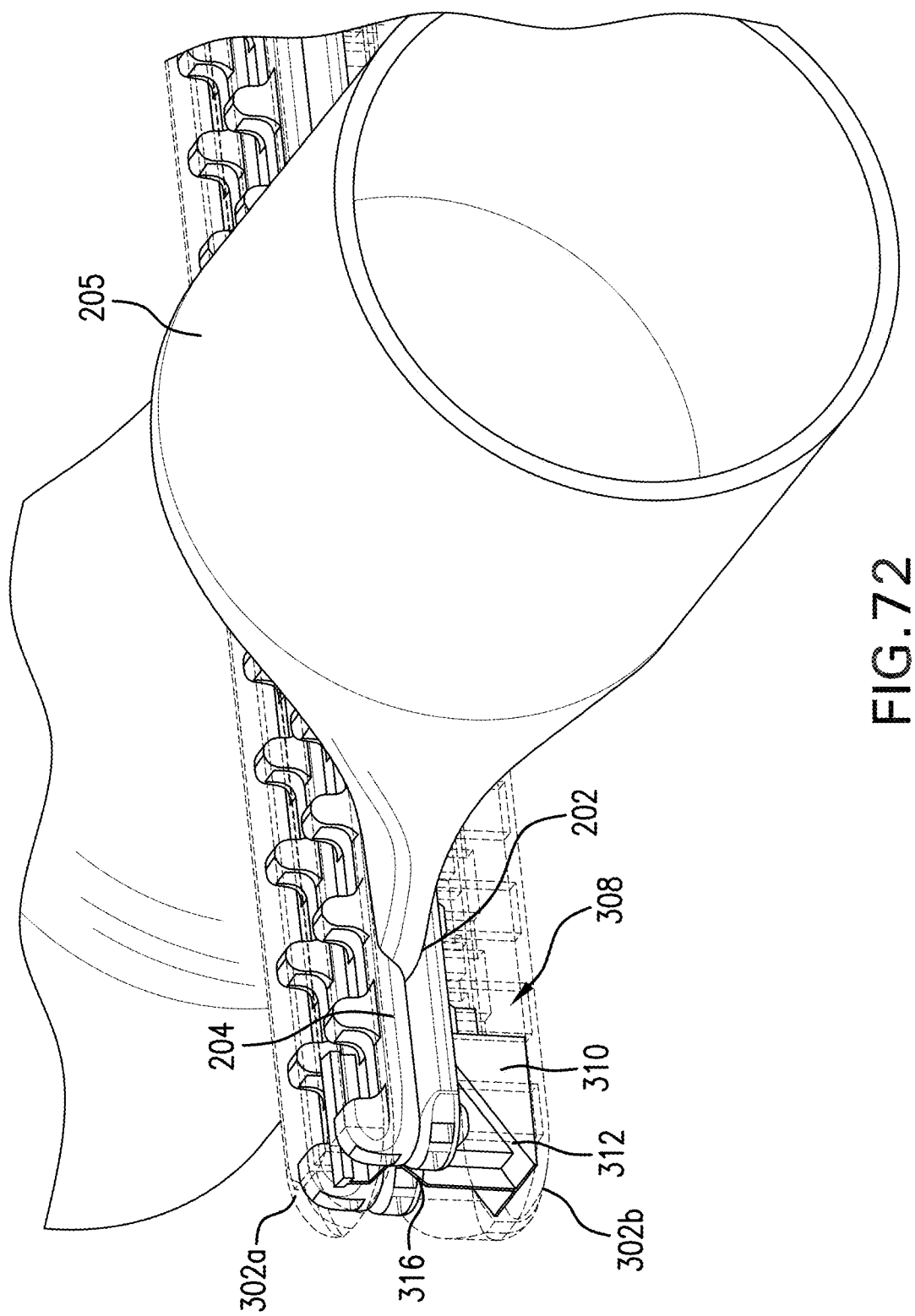
Figure 73:
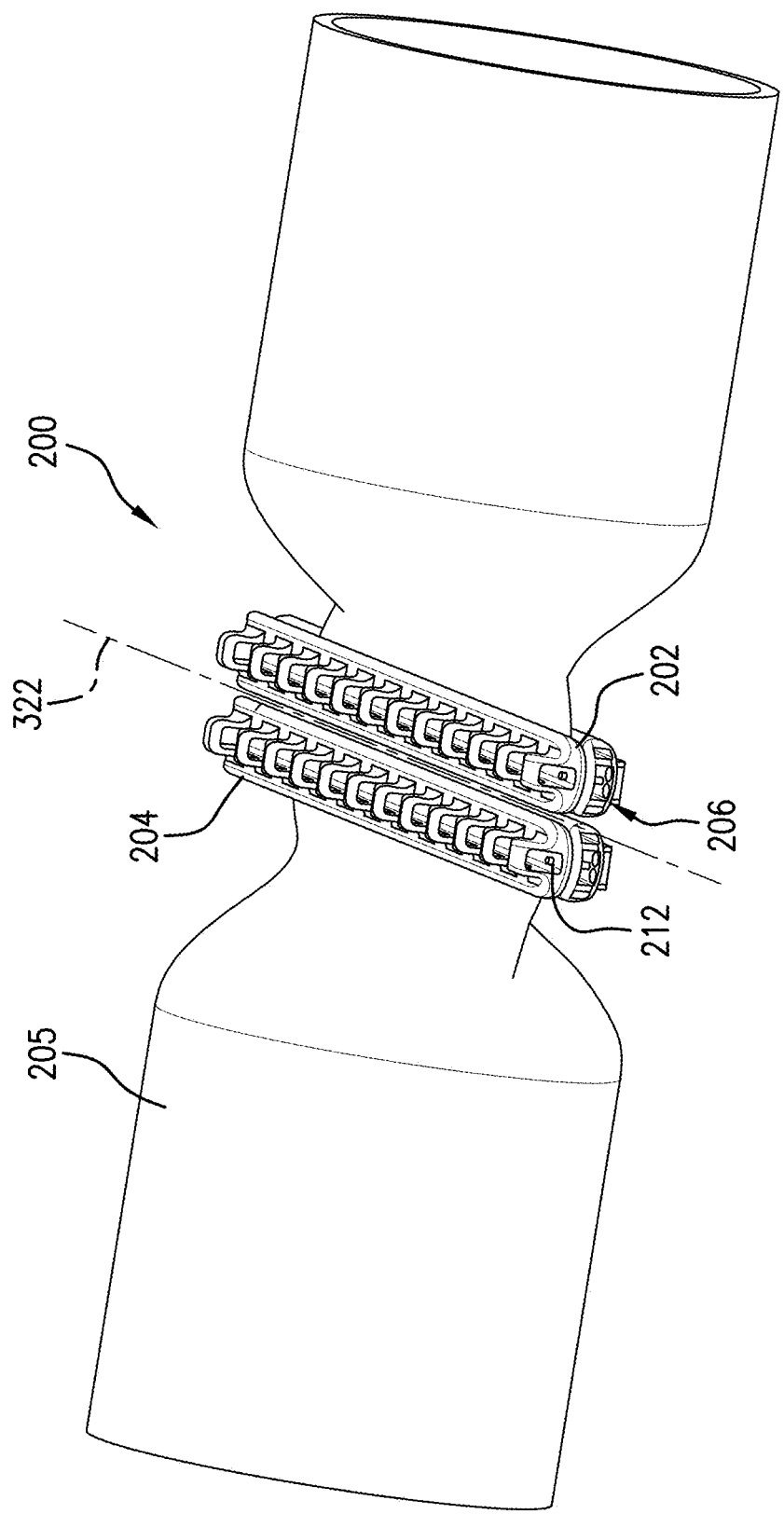
Figure 74:
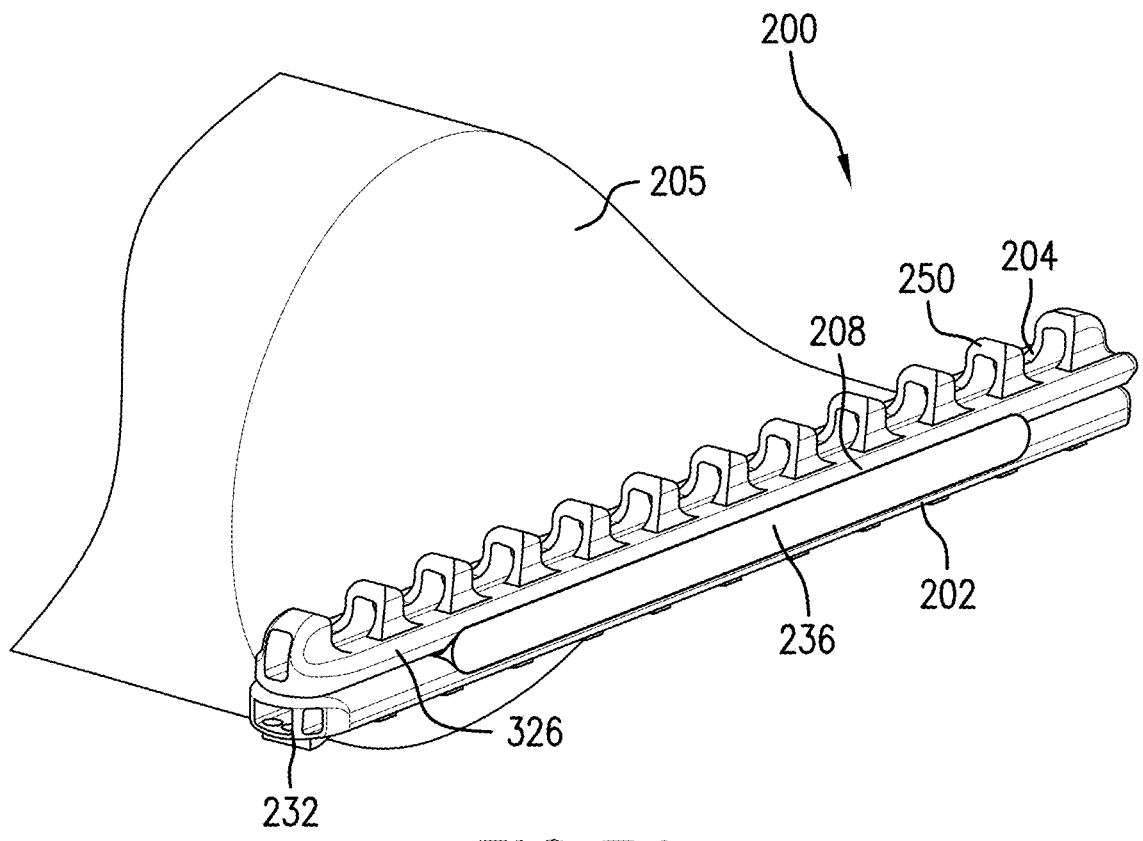
Figure 75:
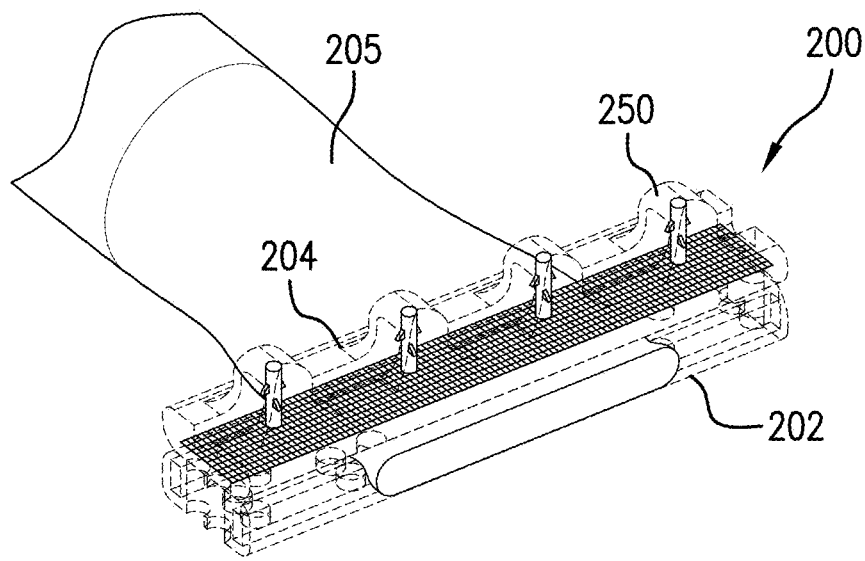
Figure 76:
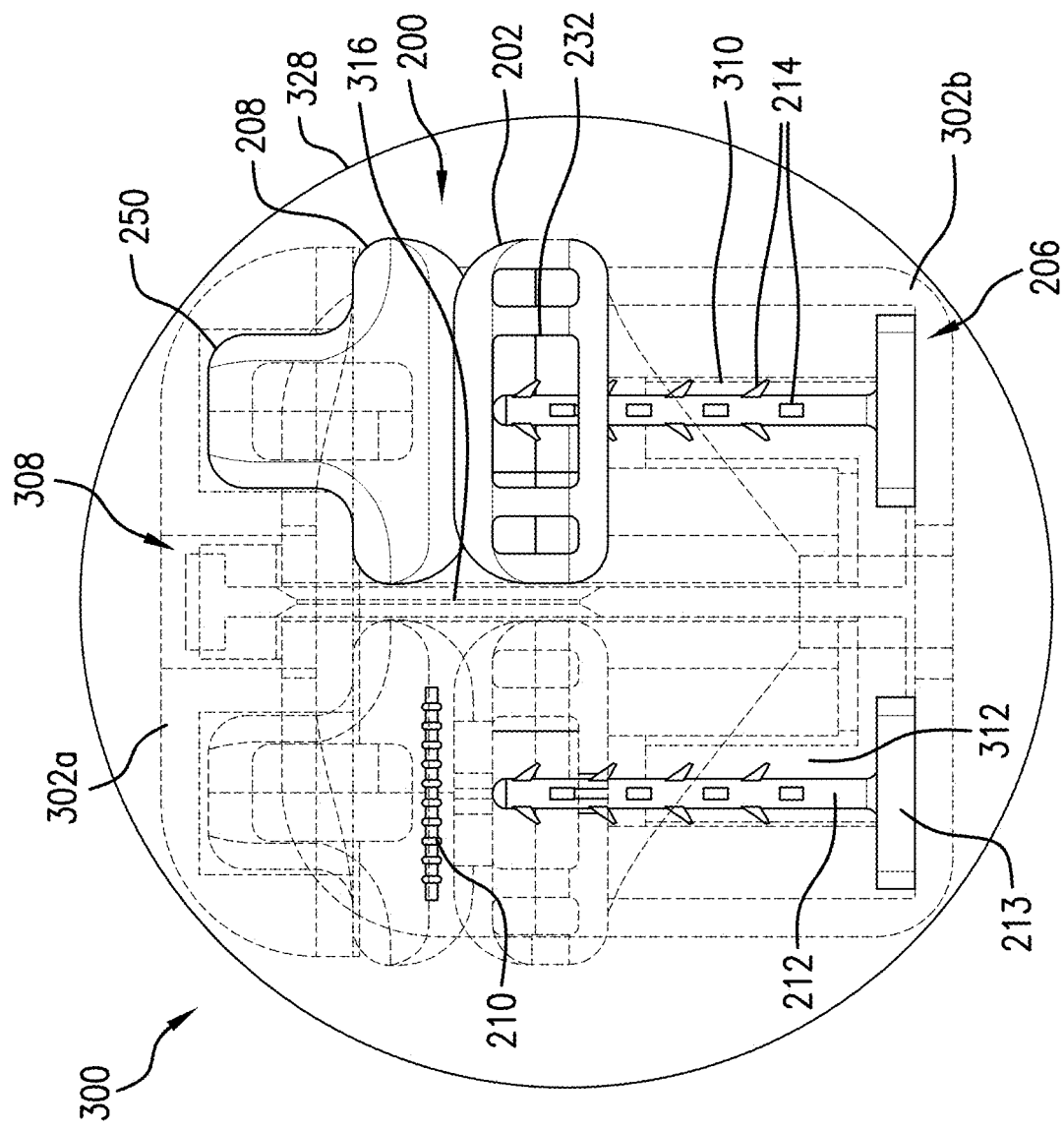
Figure 78A:
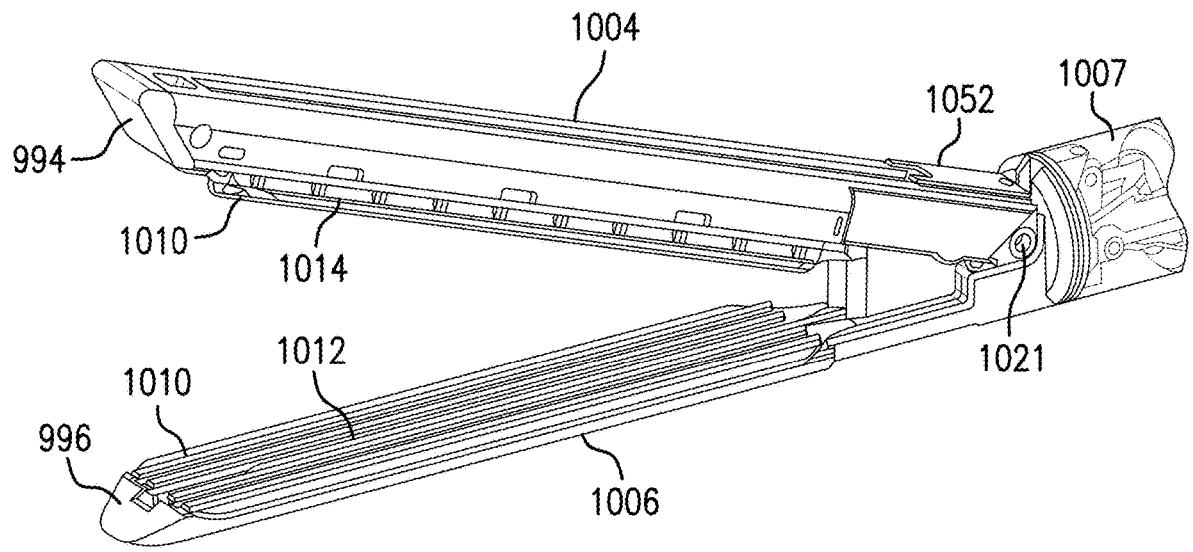
Figure 78B:
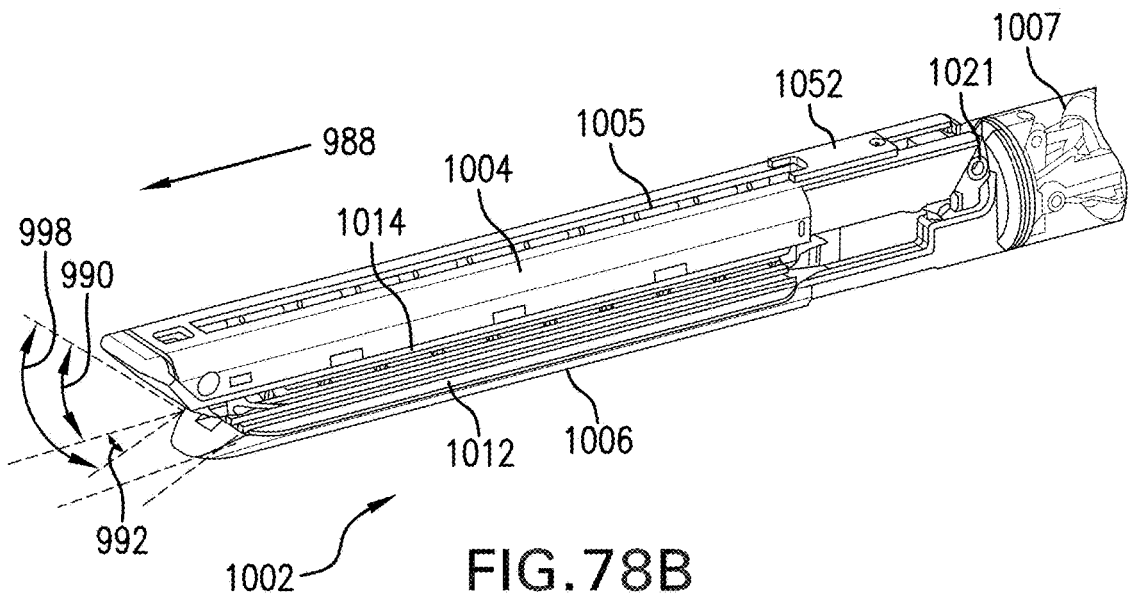
Figure 79:
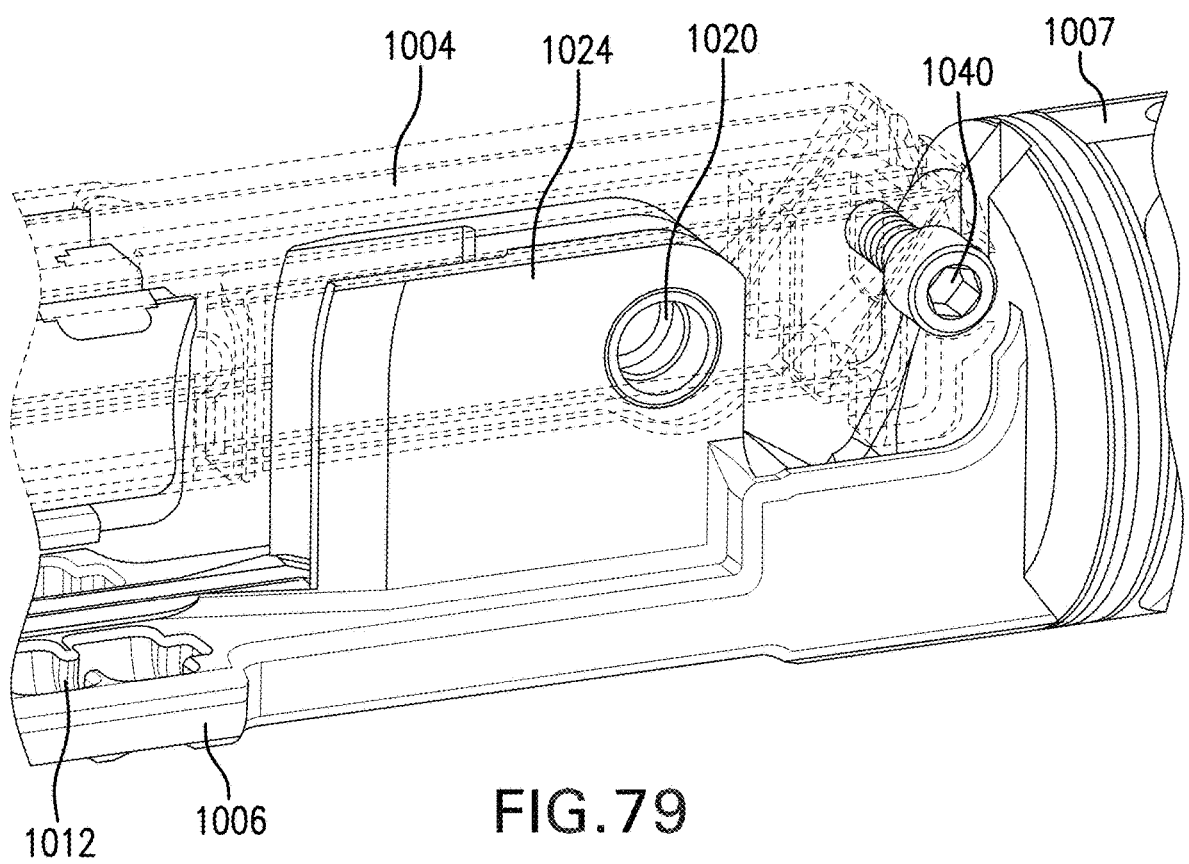
Figure 80A:
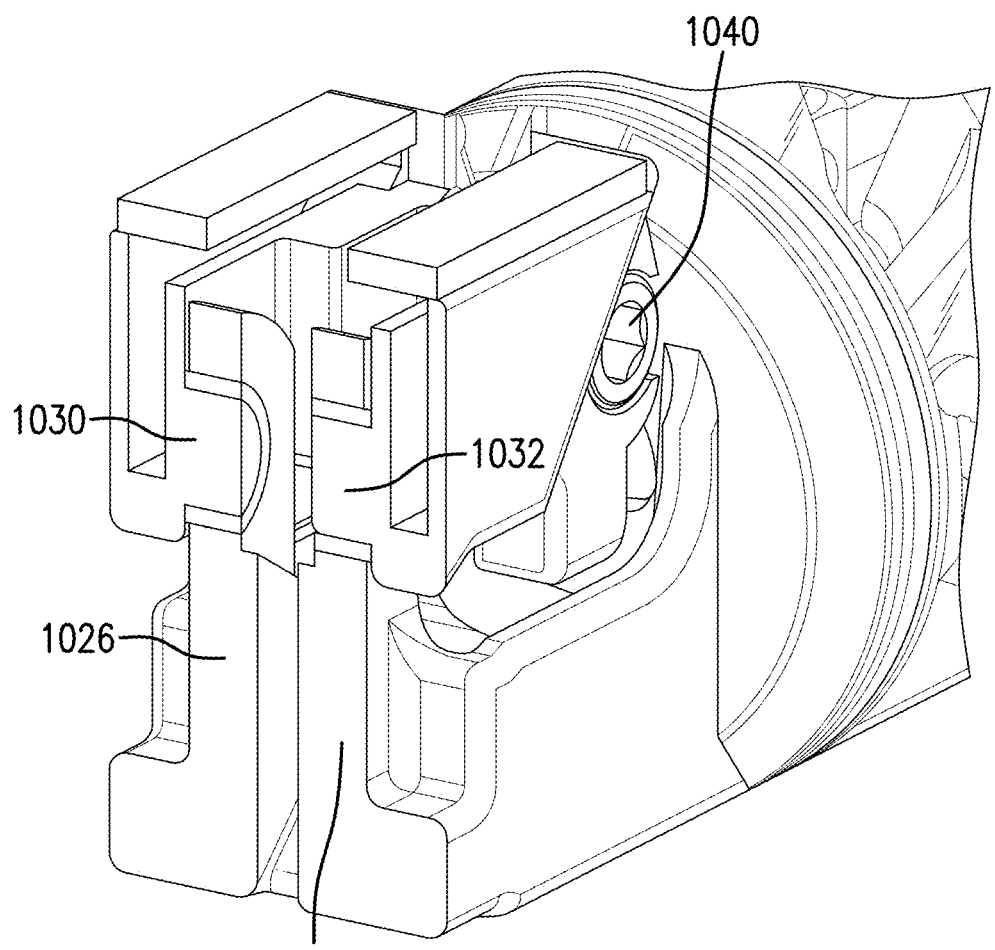
Figure 80B:
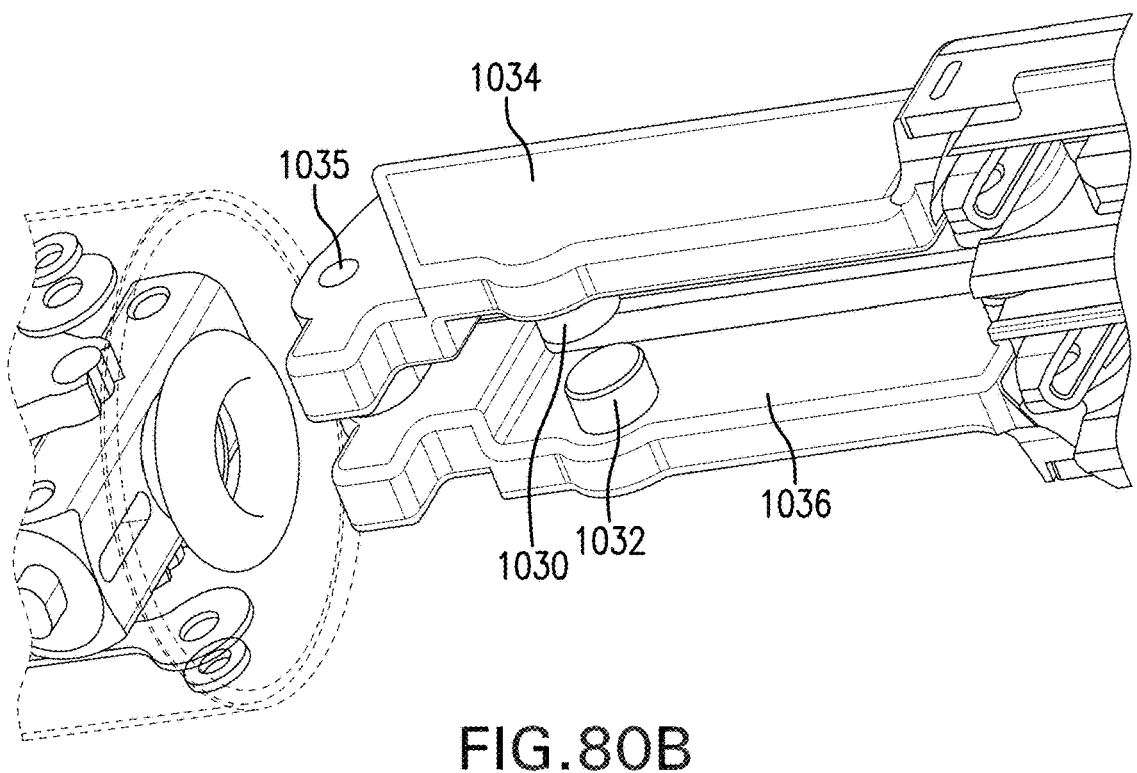
Figure 80C:
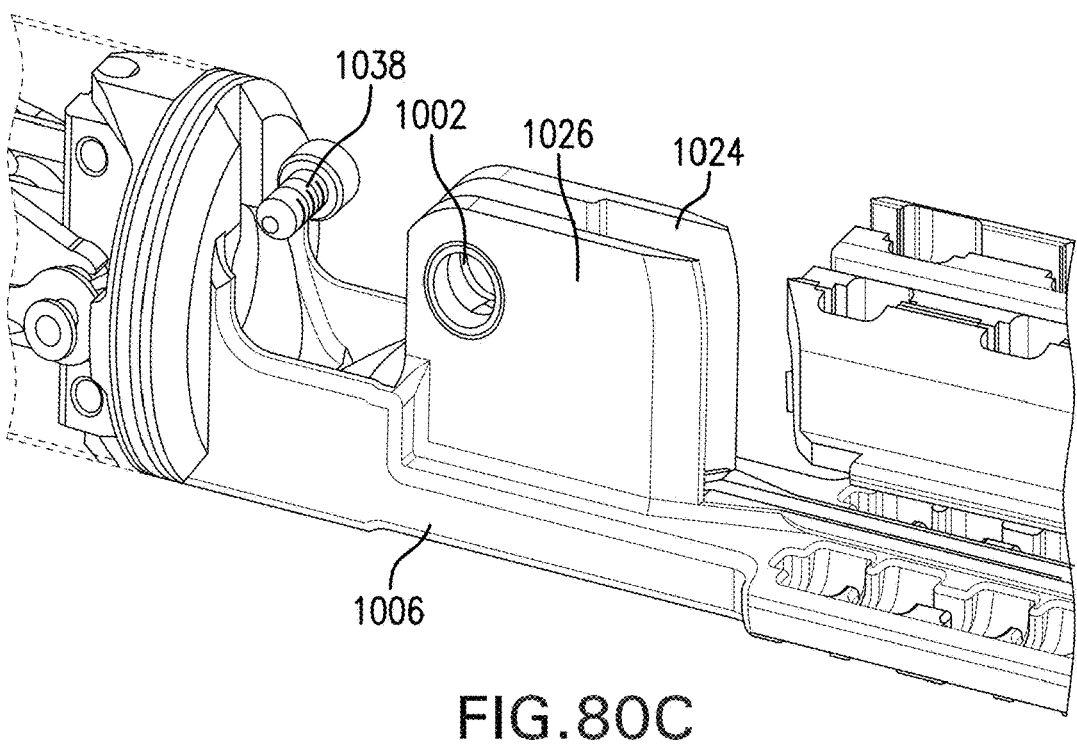
Figure 81A:
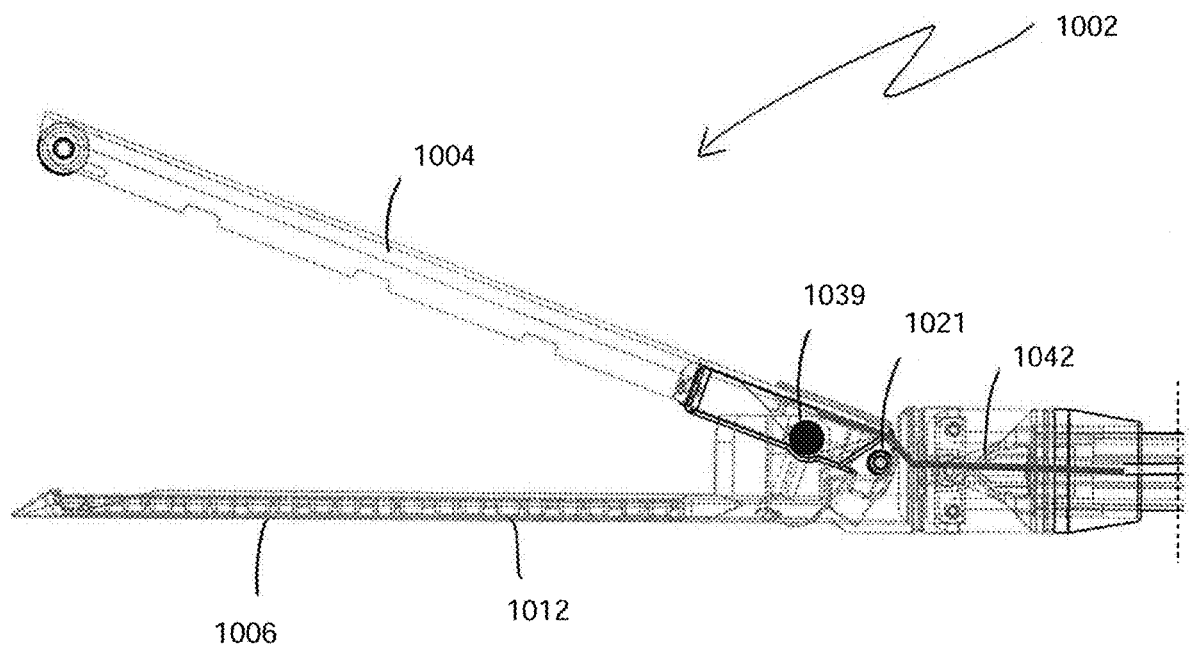
Figure 81B:
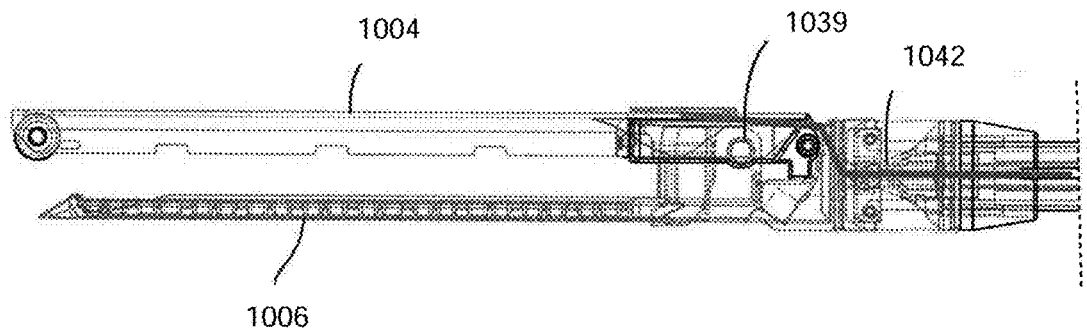
Figure 81C:
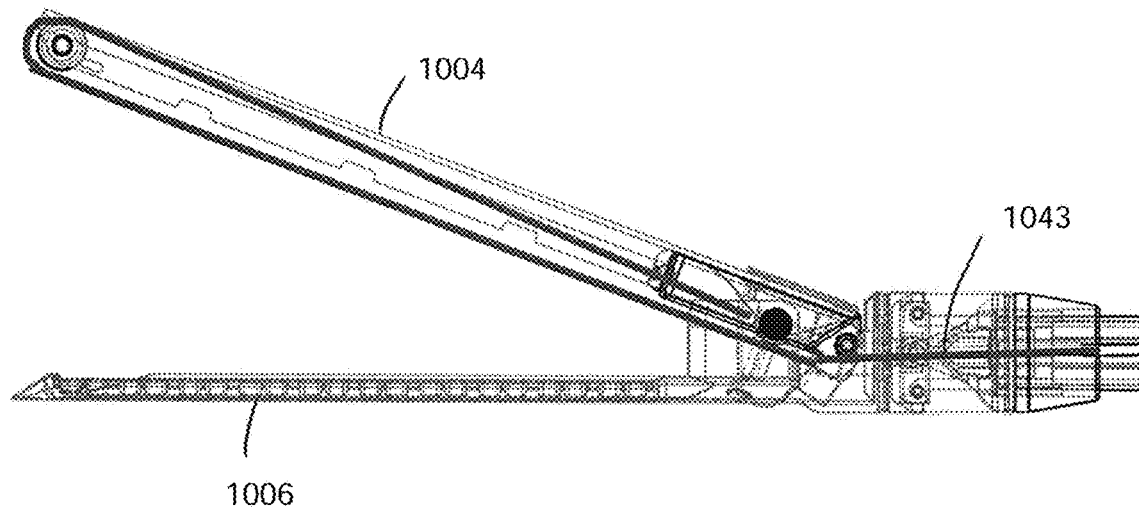
Figure 81D:
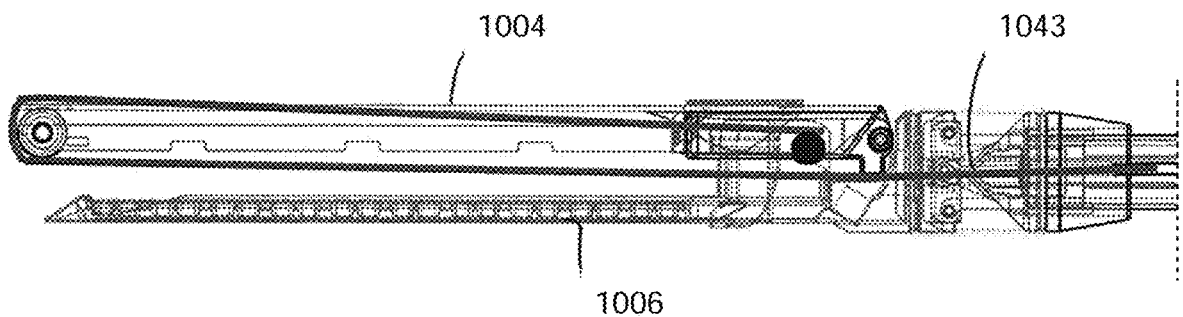
Figure 82A:
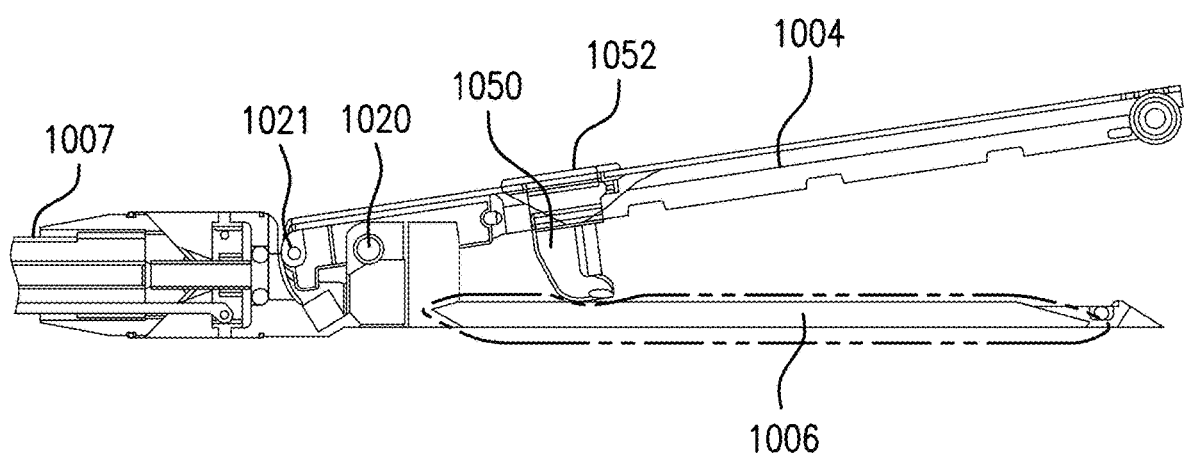
Figure 82B:
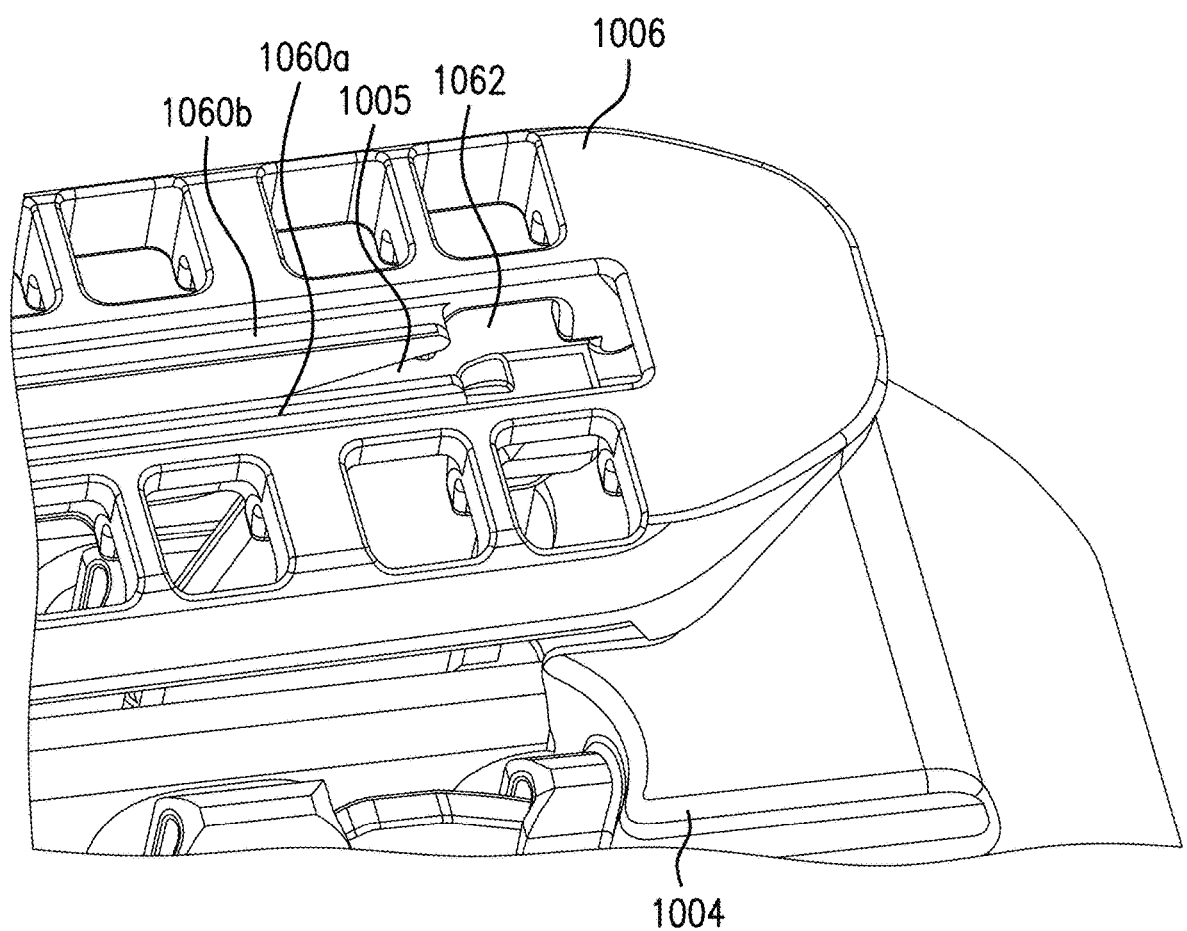
Figure 83A:
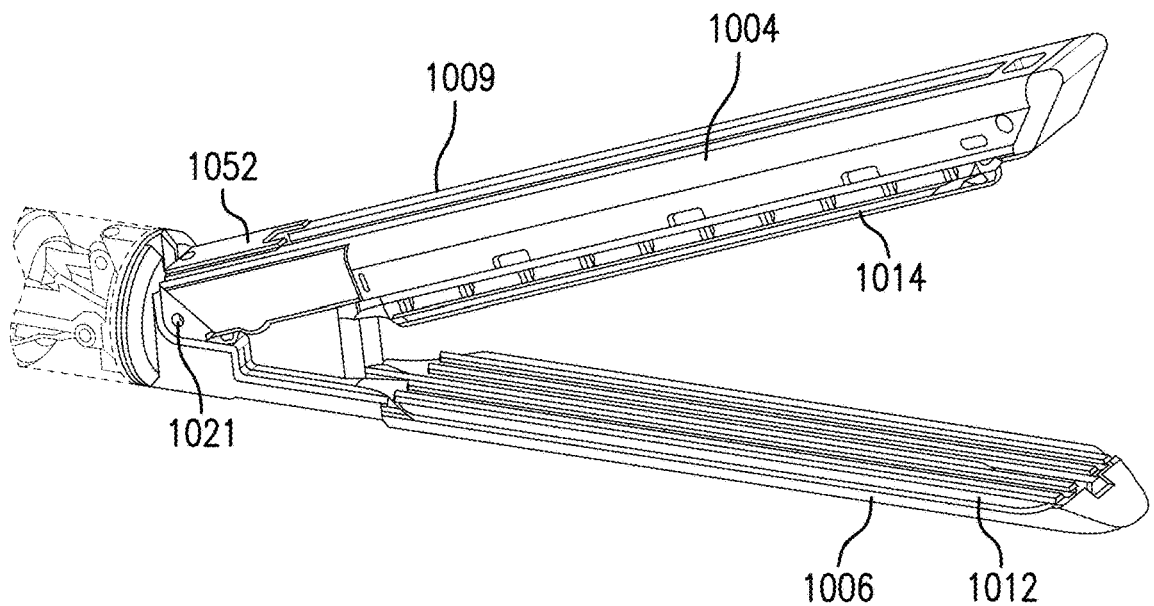
Figure 83B:
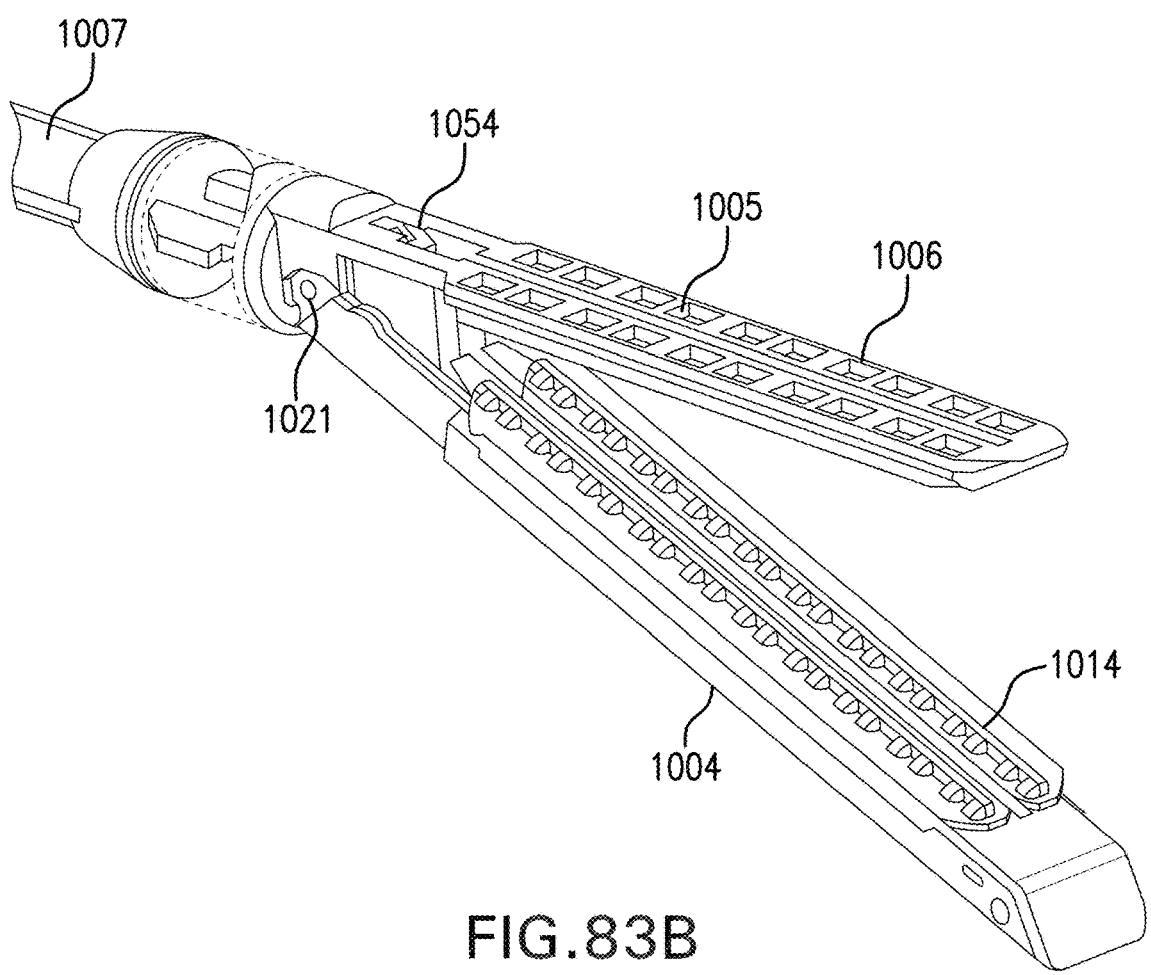
Figure 83C:
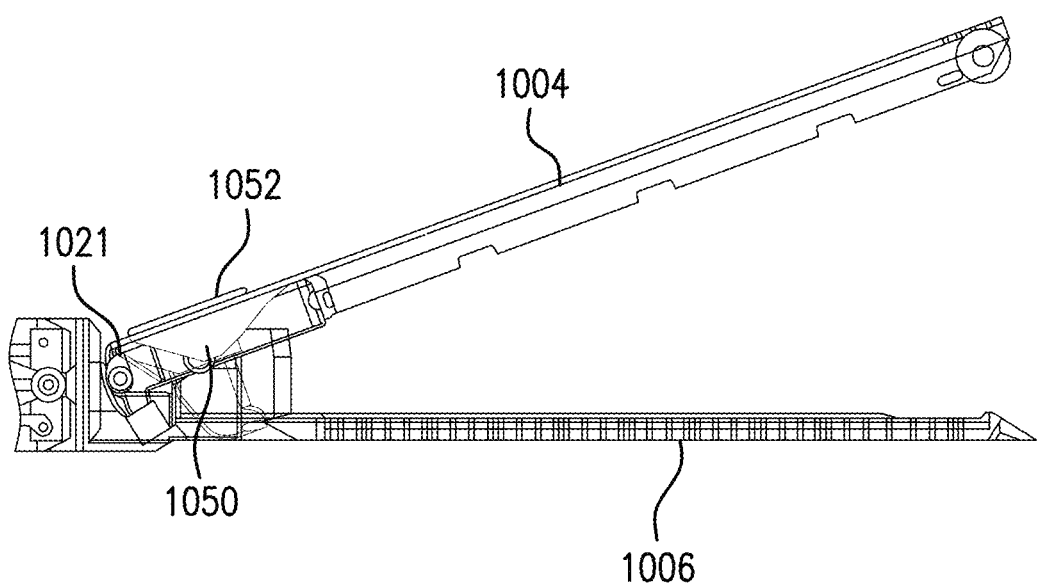
Figure 84A:
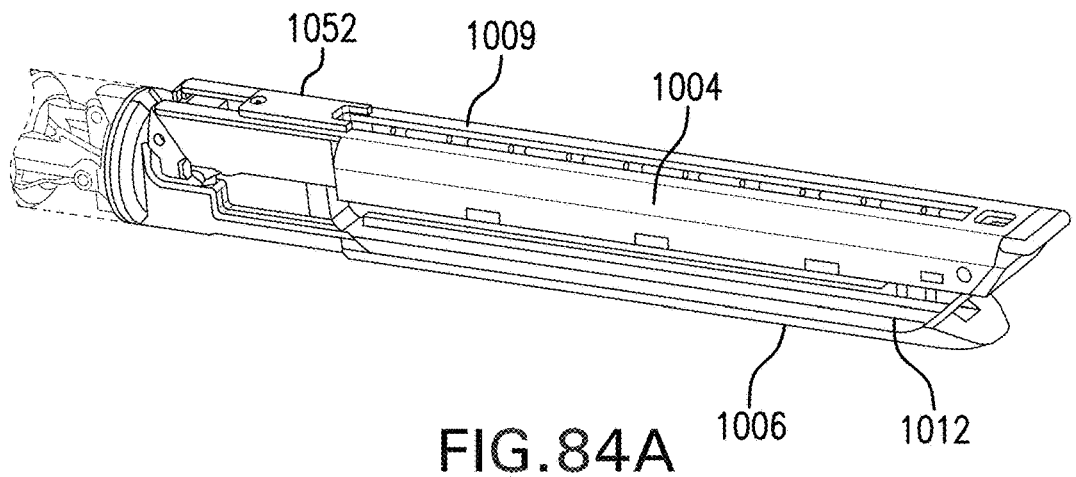
Figure 84B:
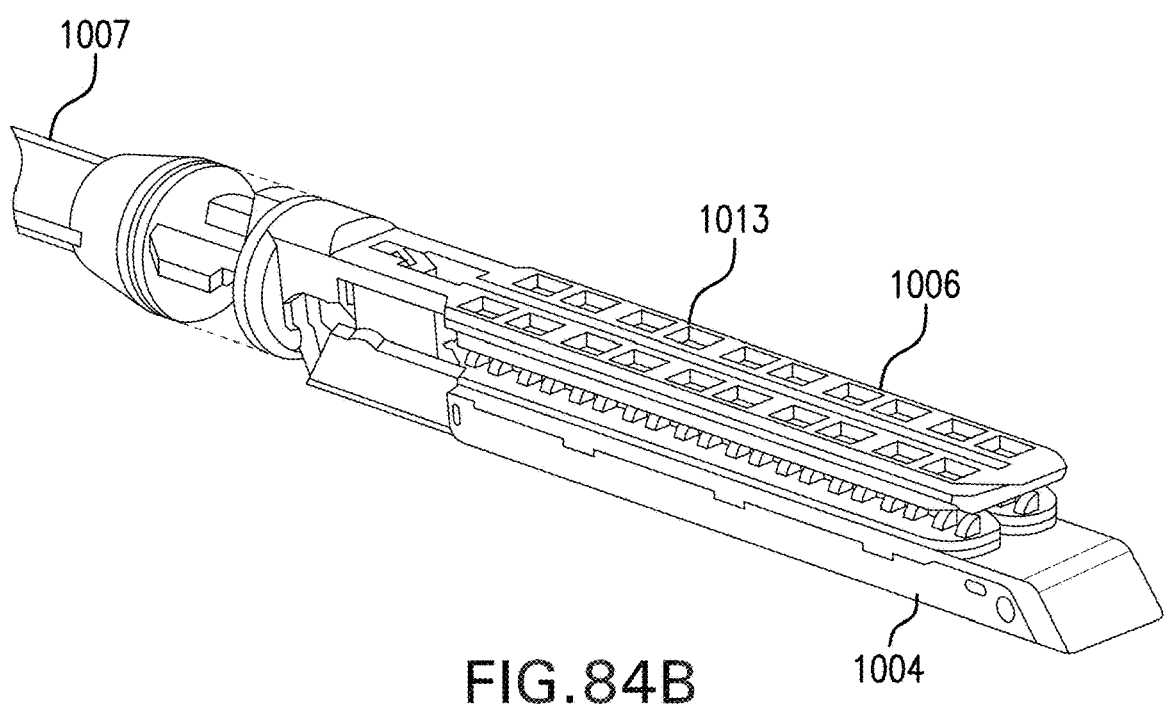
Figure 84C:
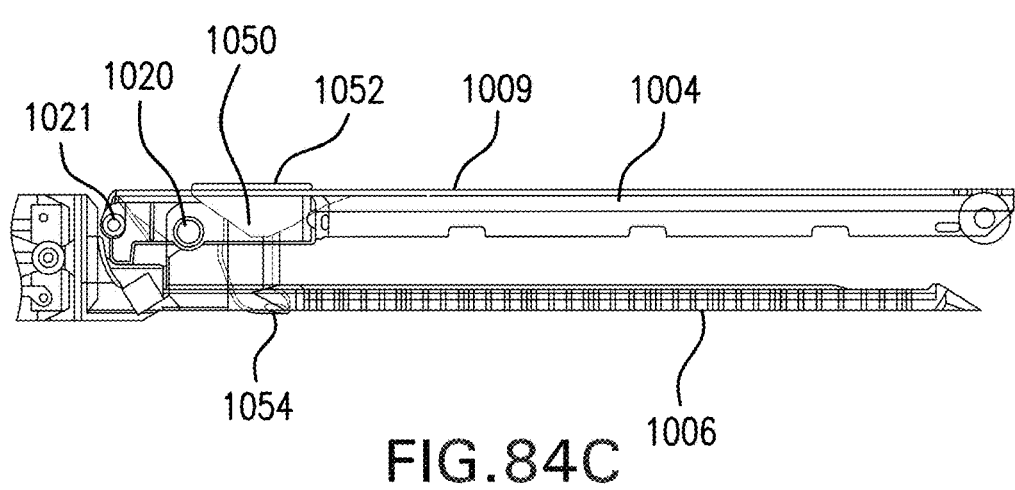
Figure 85A:
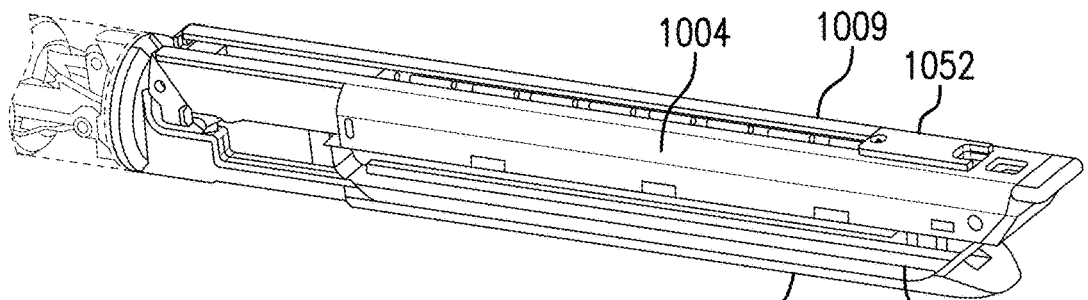
Figure 85B:
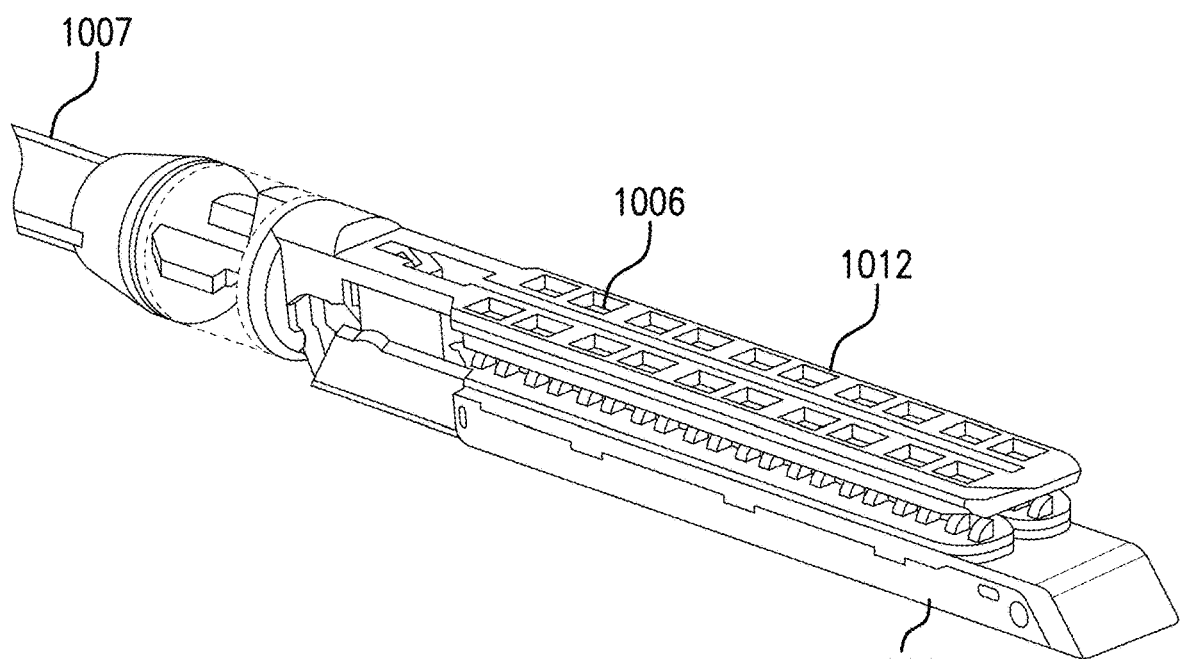
Figure 85C:
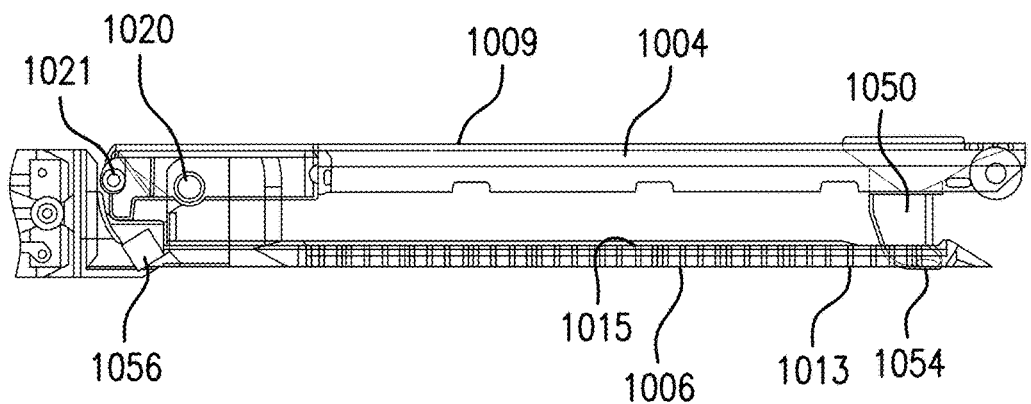
Figure 85D:
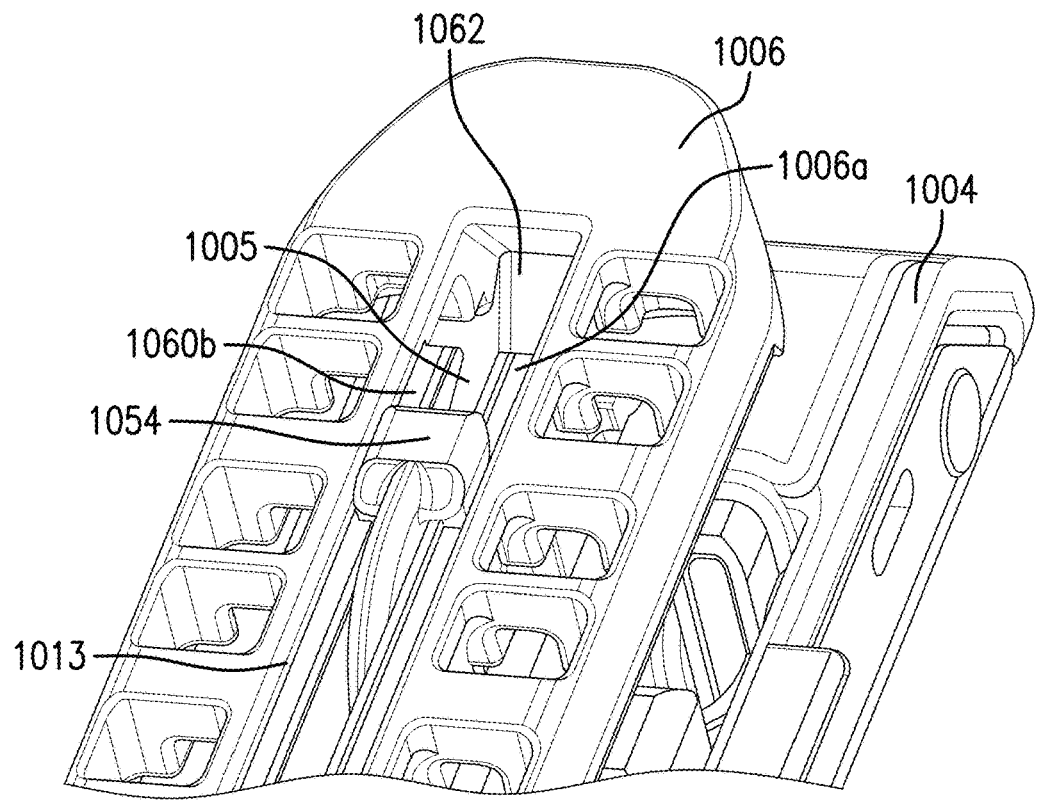
Figure 85E:
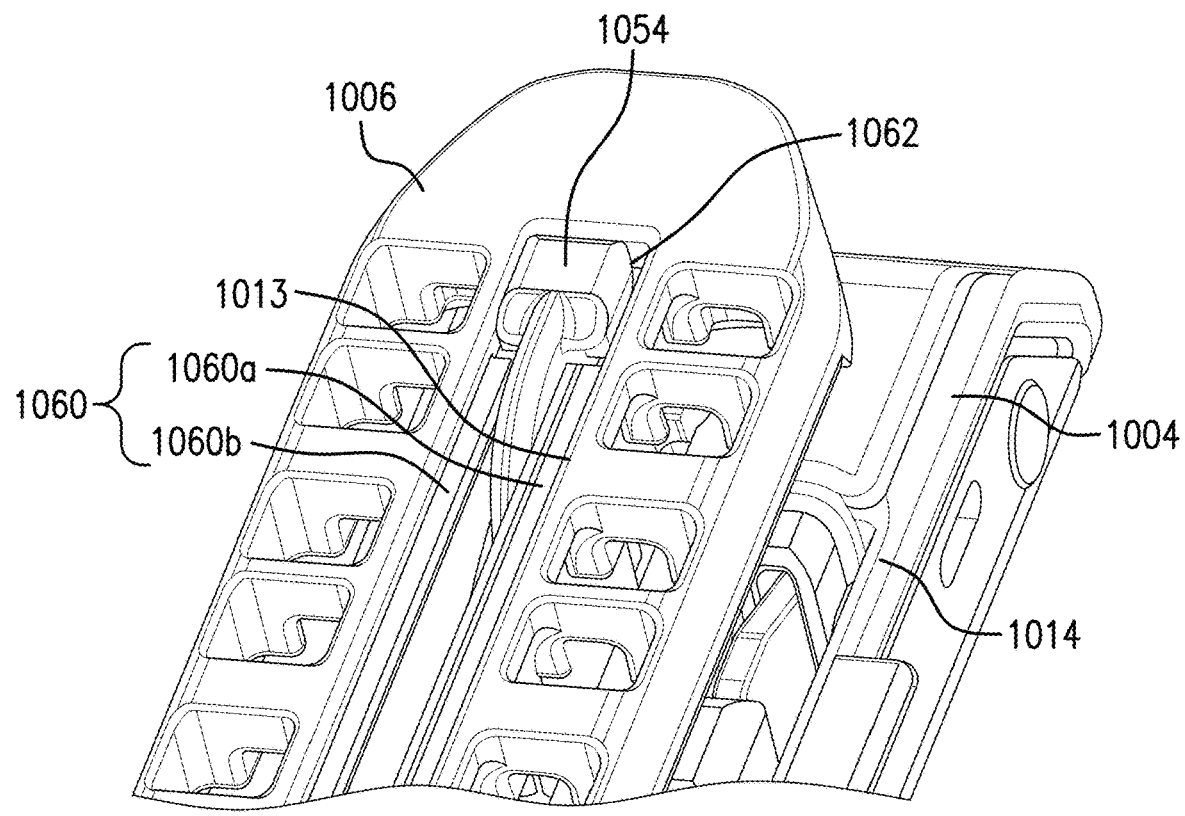
Figure 85F:
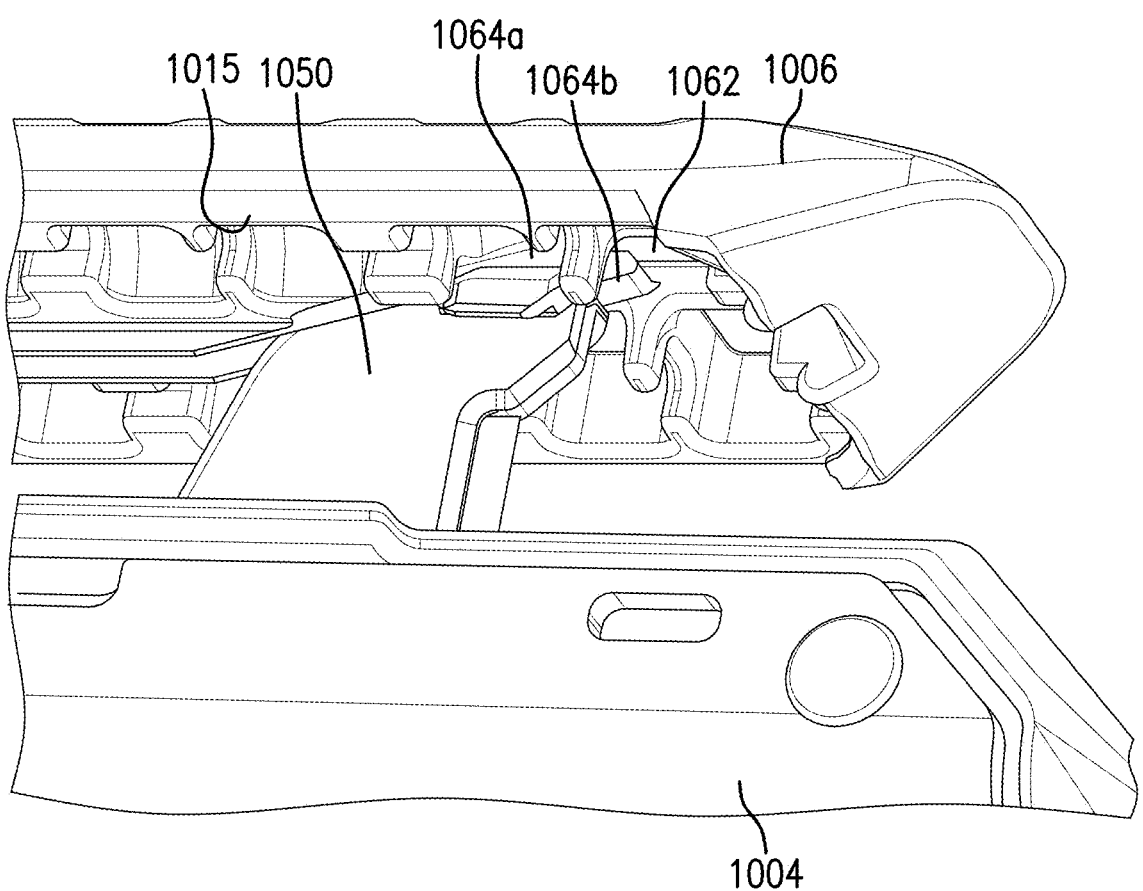
Figure 86A:
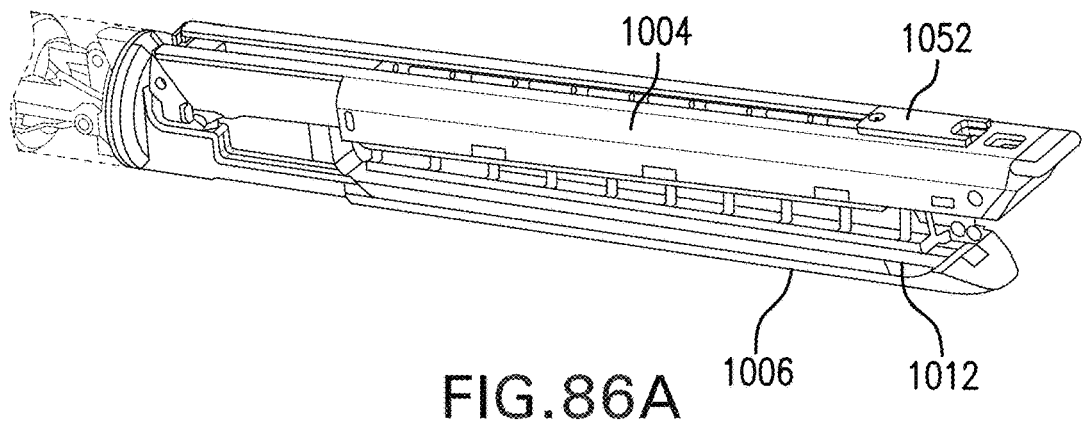
Figure 86B:
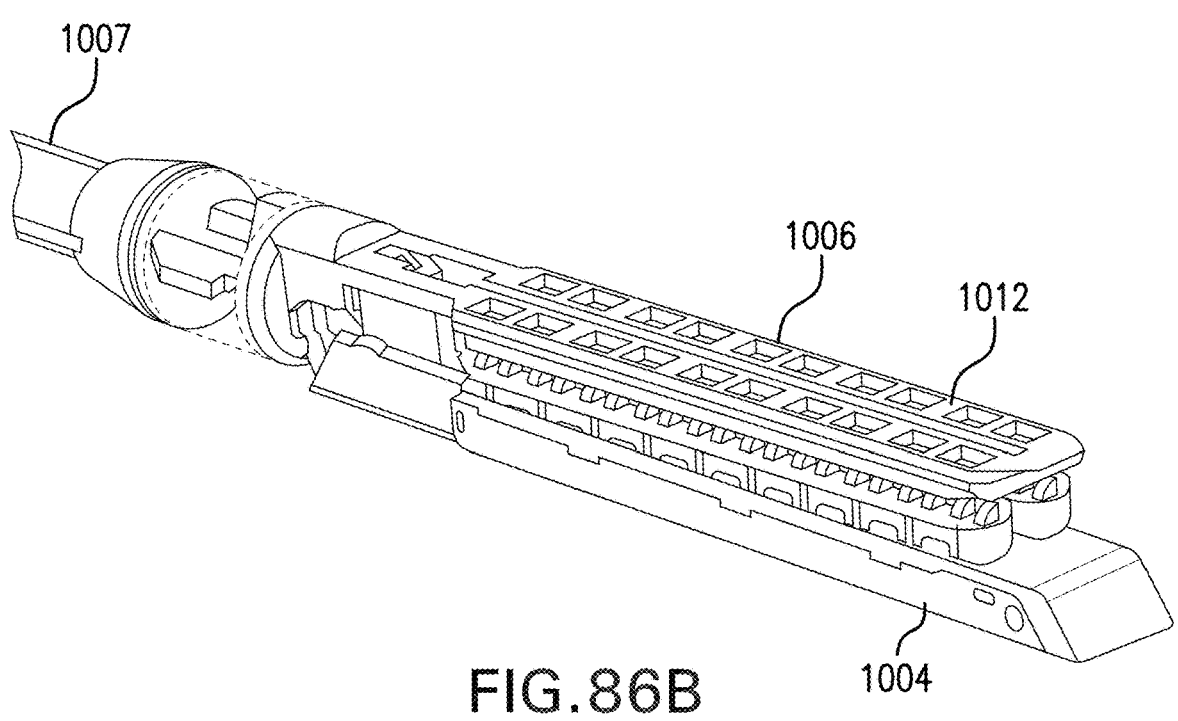
Figure 86C:
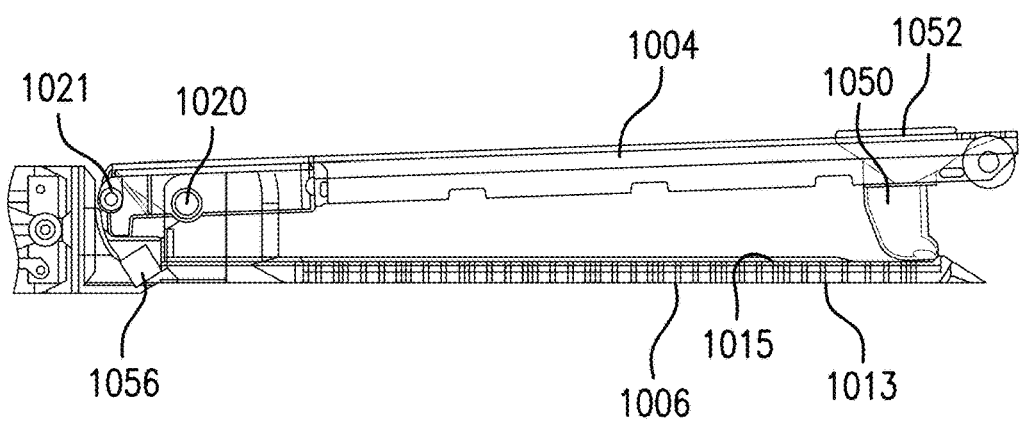
Figure 87A:
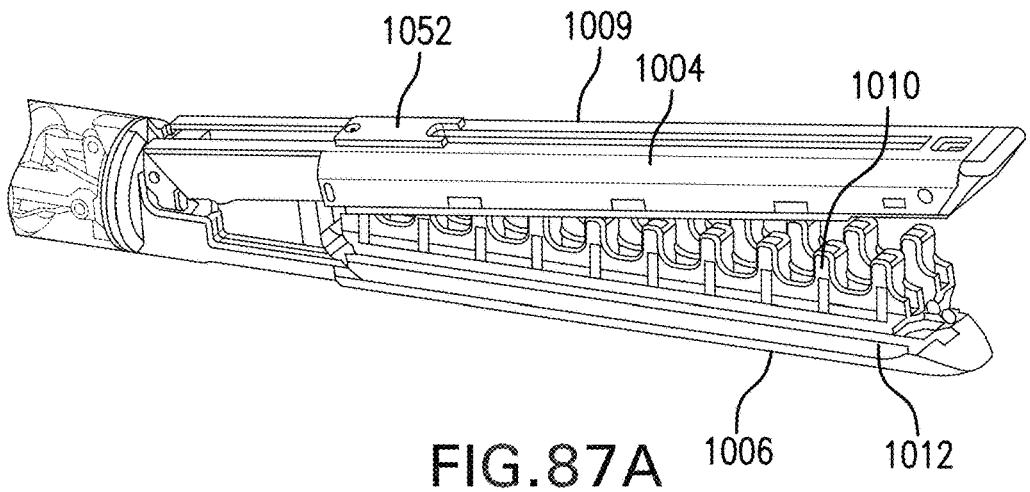
Figure 87B:
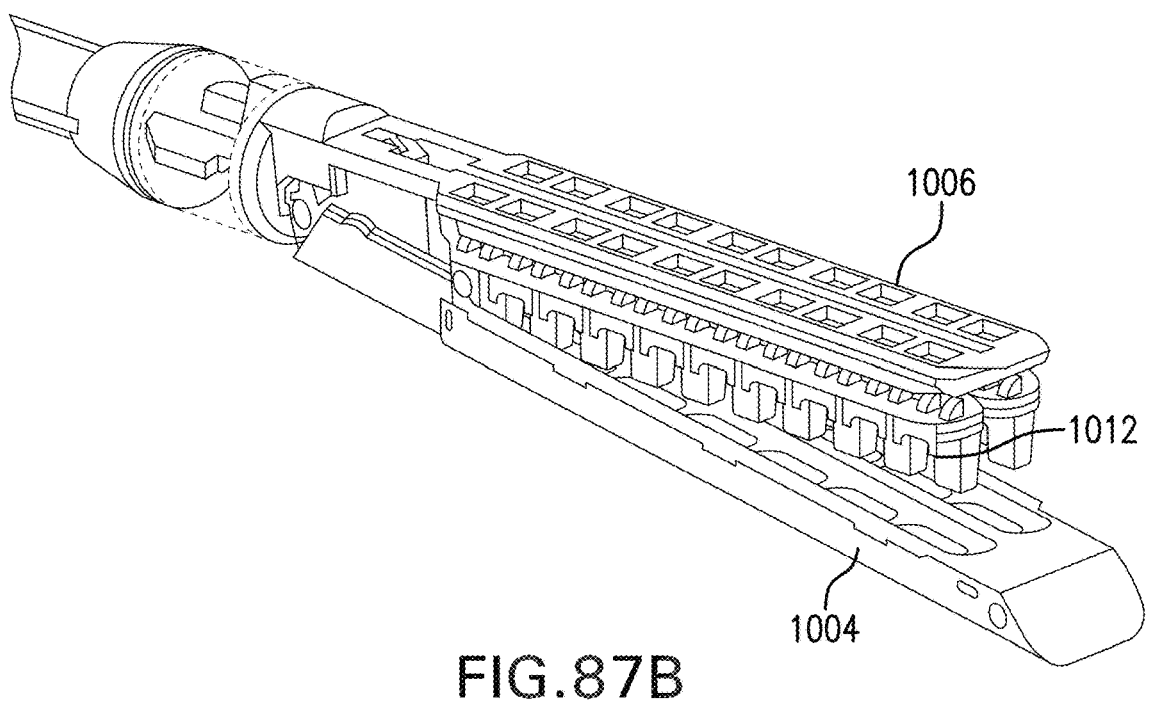
Figure 87C:
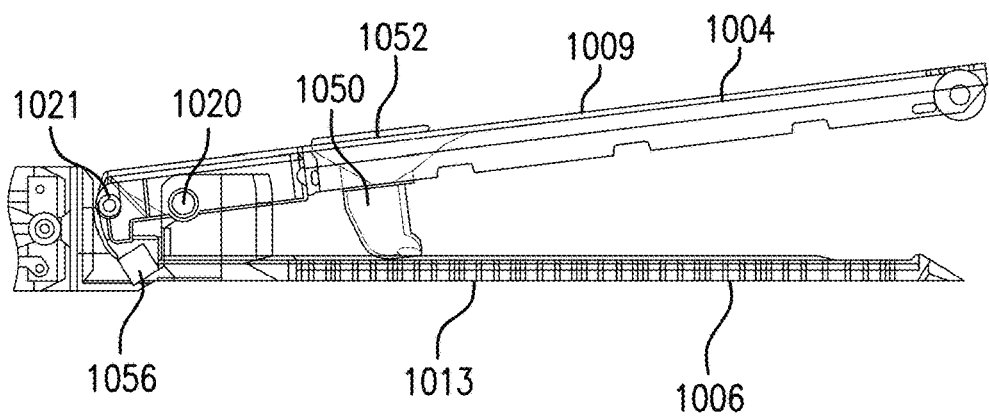
Figure 88A:
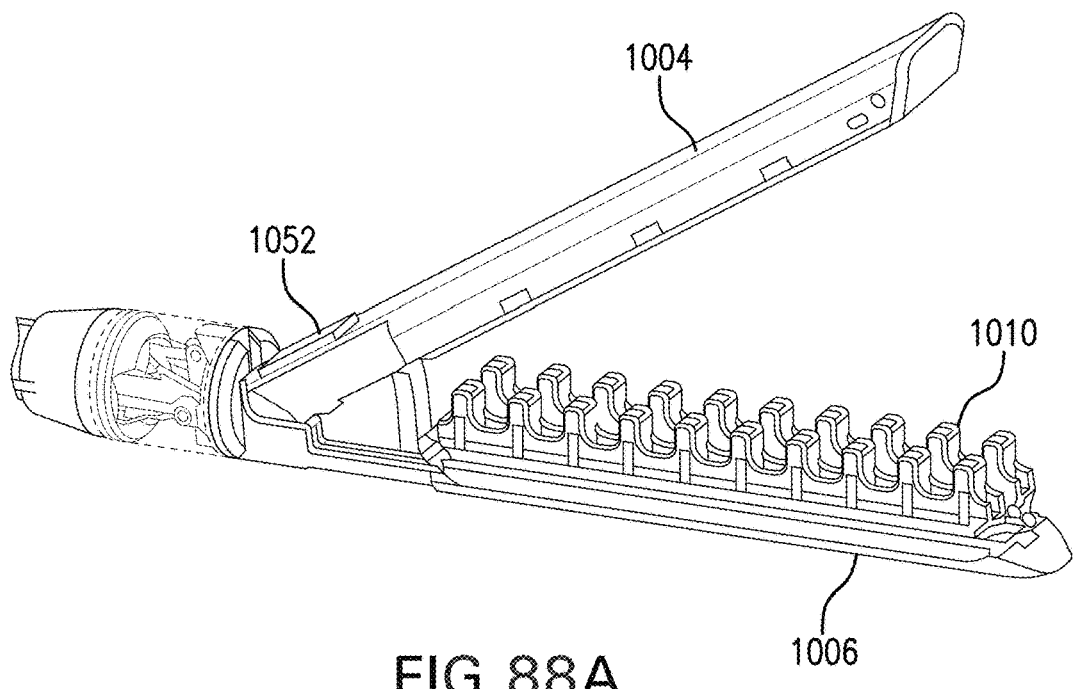
Figure 88B:
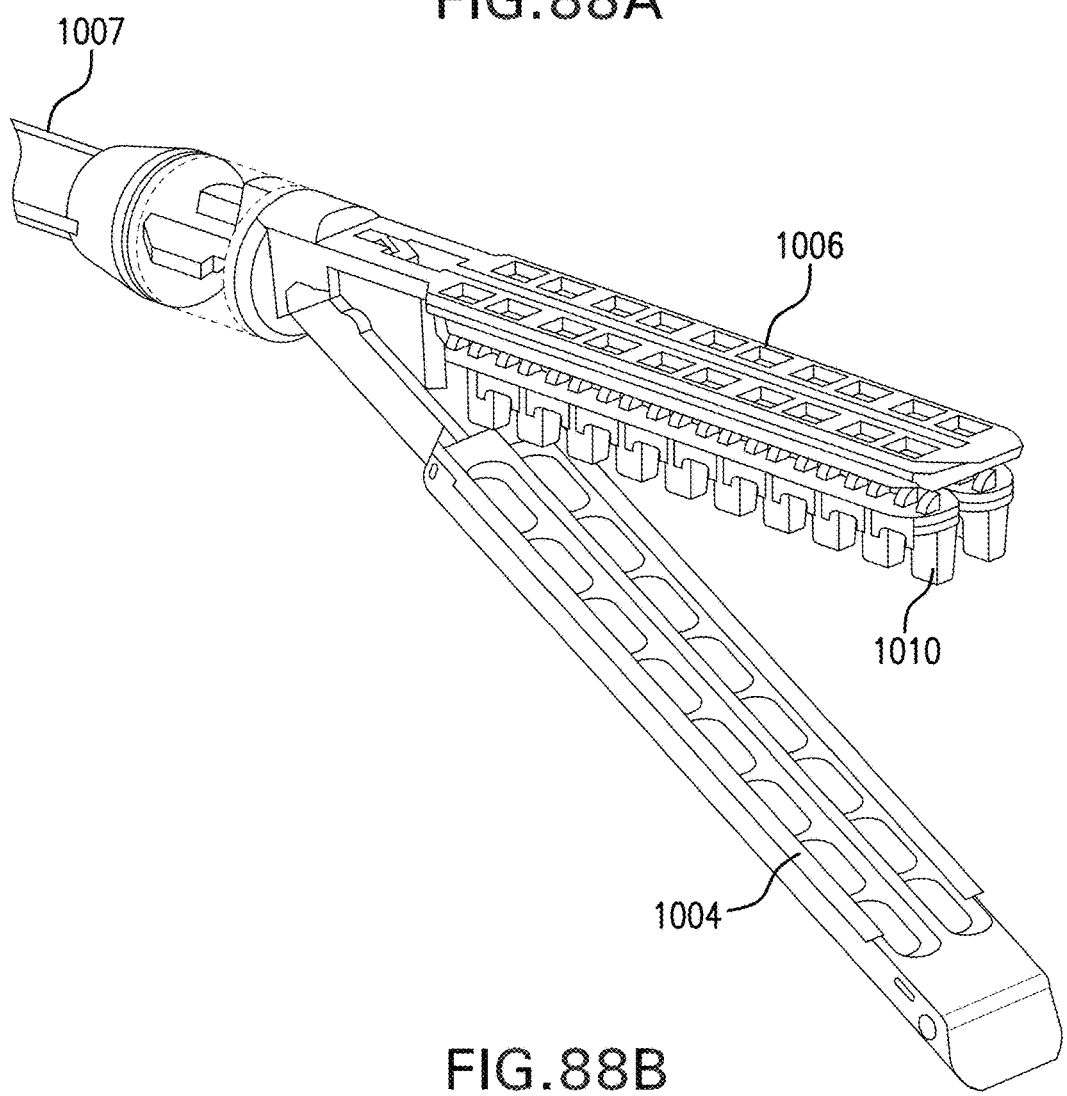
Figure 88C:
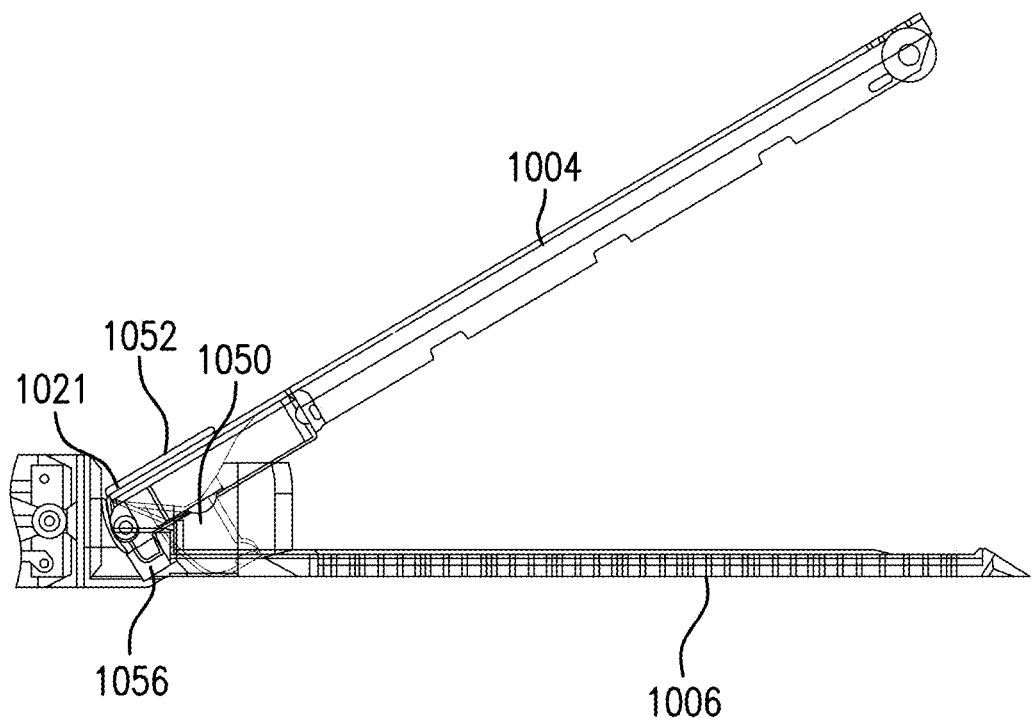
Figure 89A:
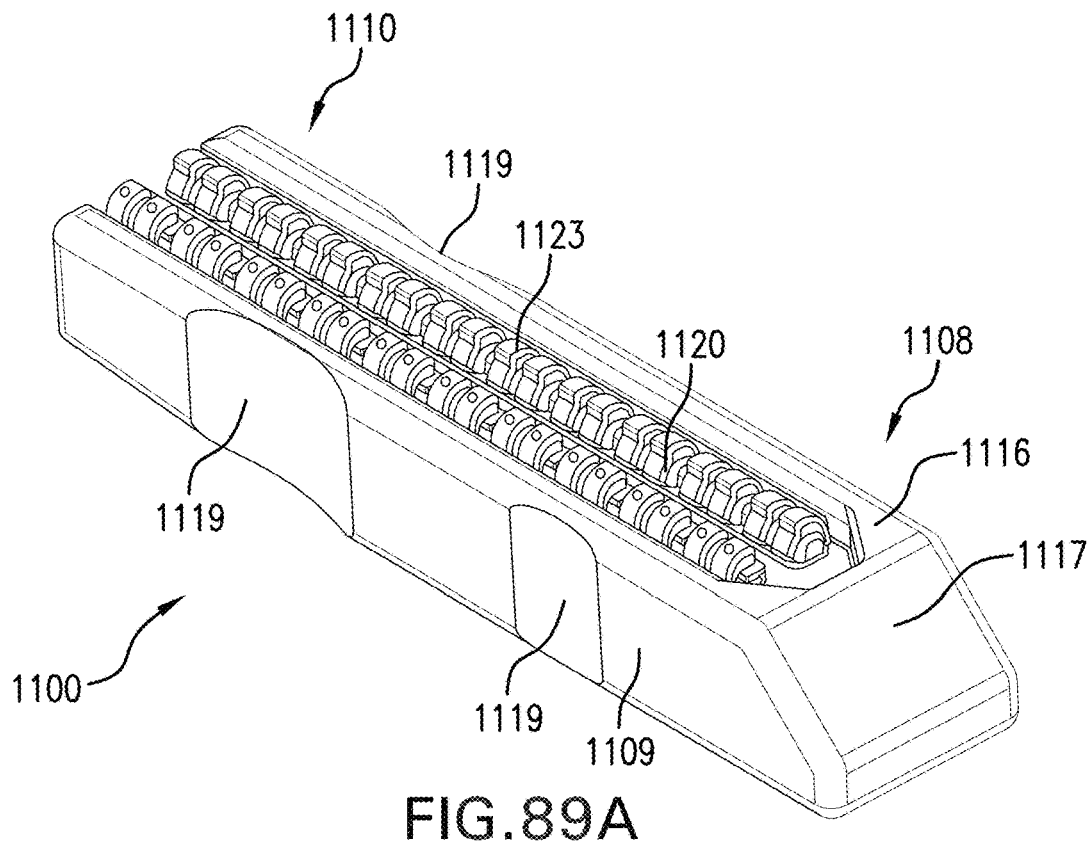
Figure 89B:
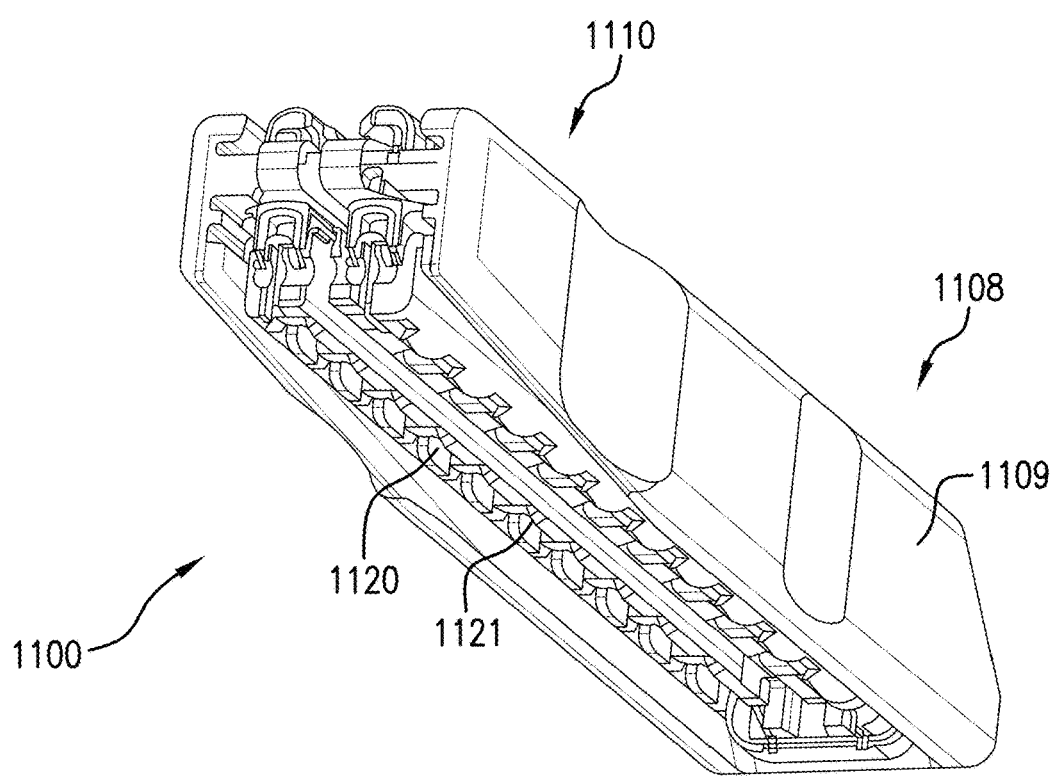
Figure 89C:
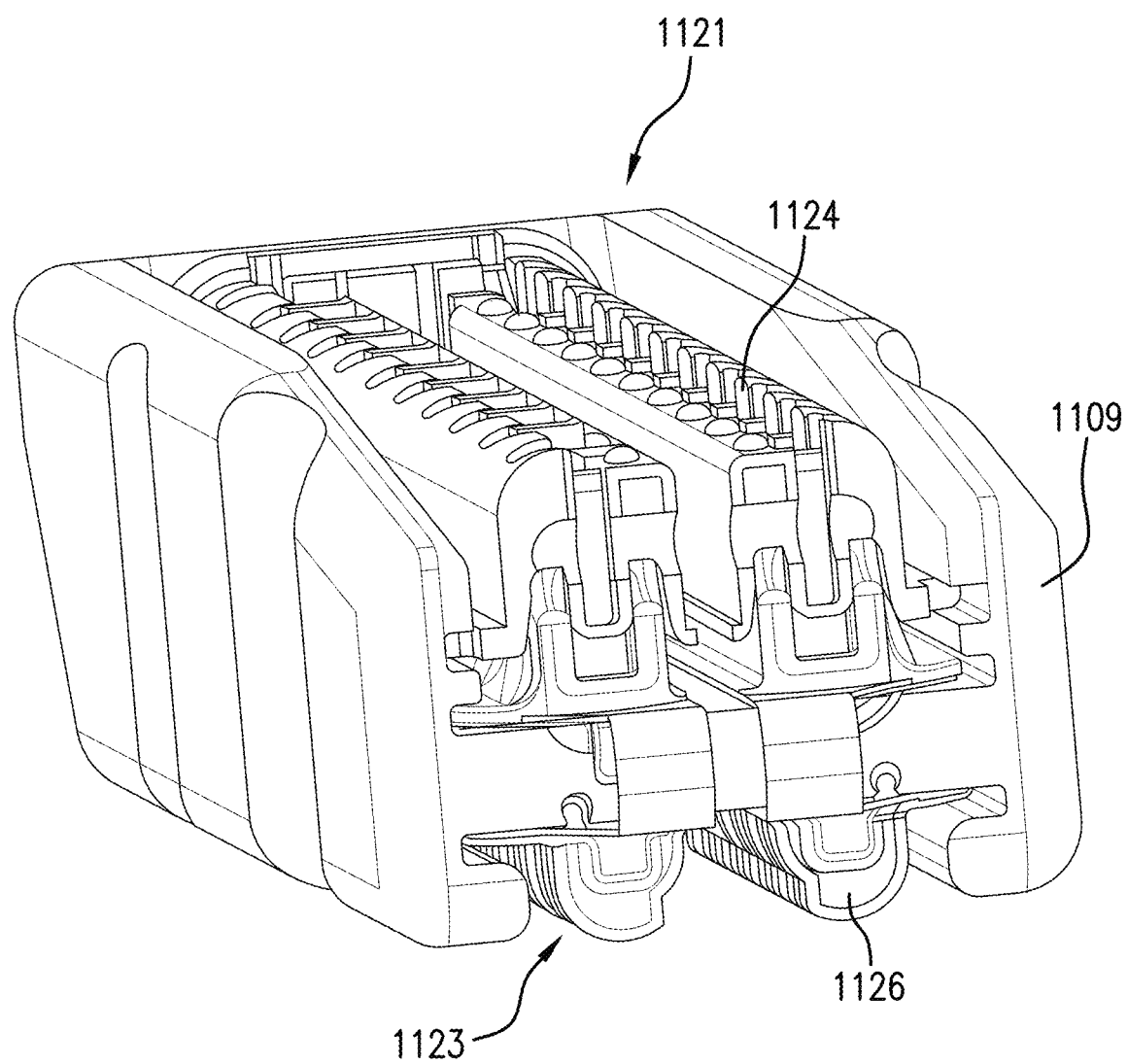
Figure 90:
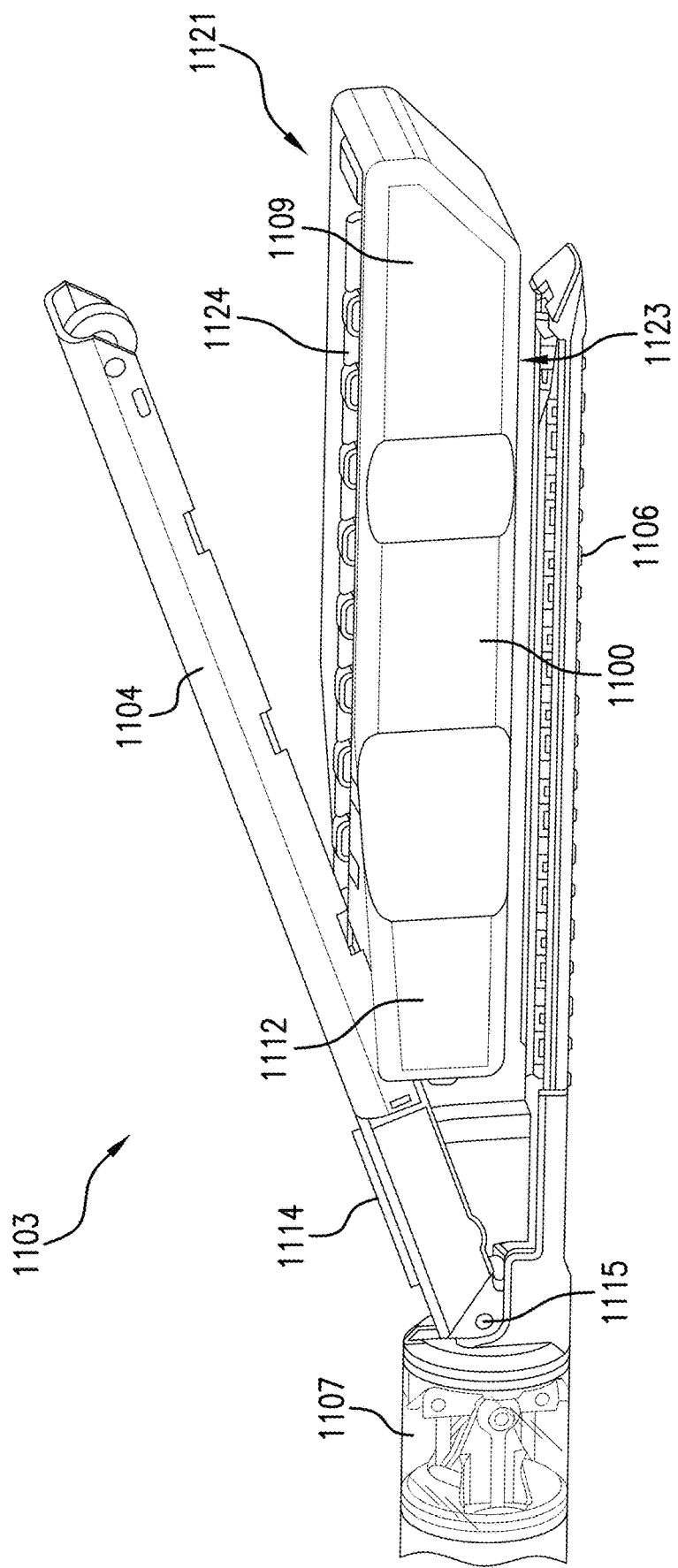
Figure 91A:
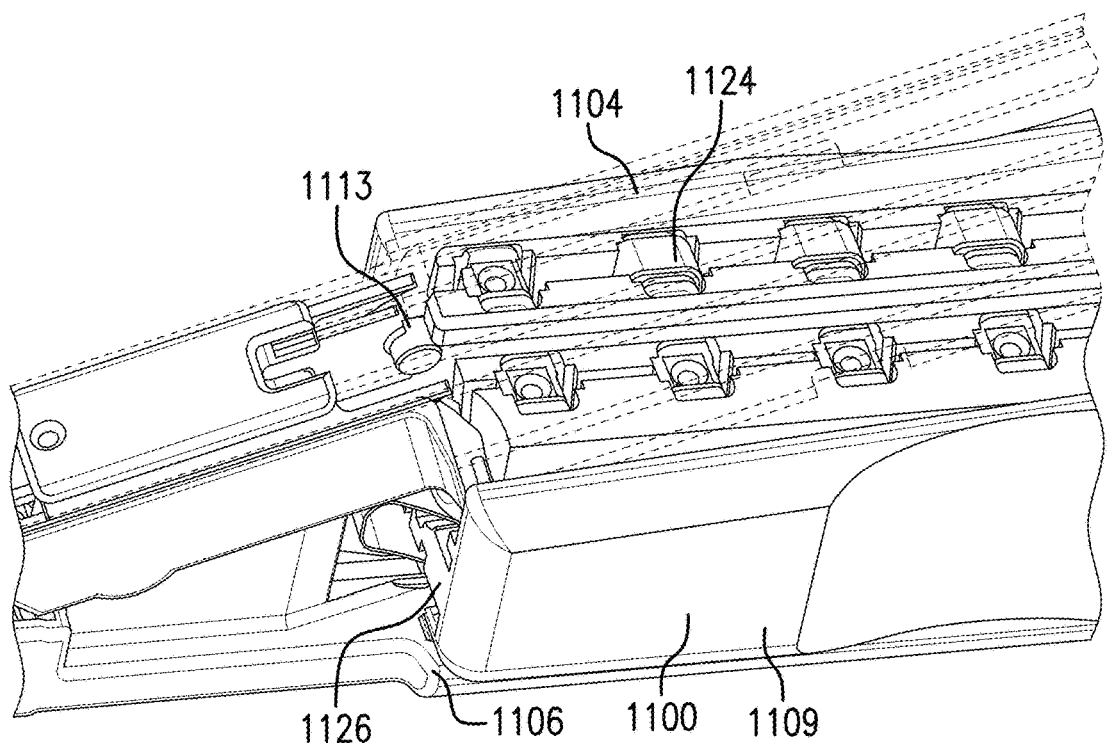
Figure 91B:
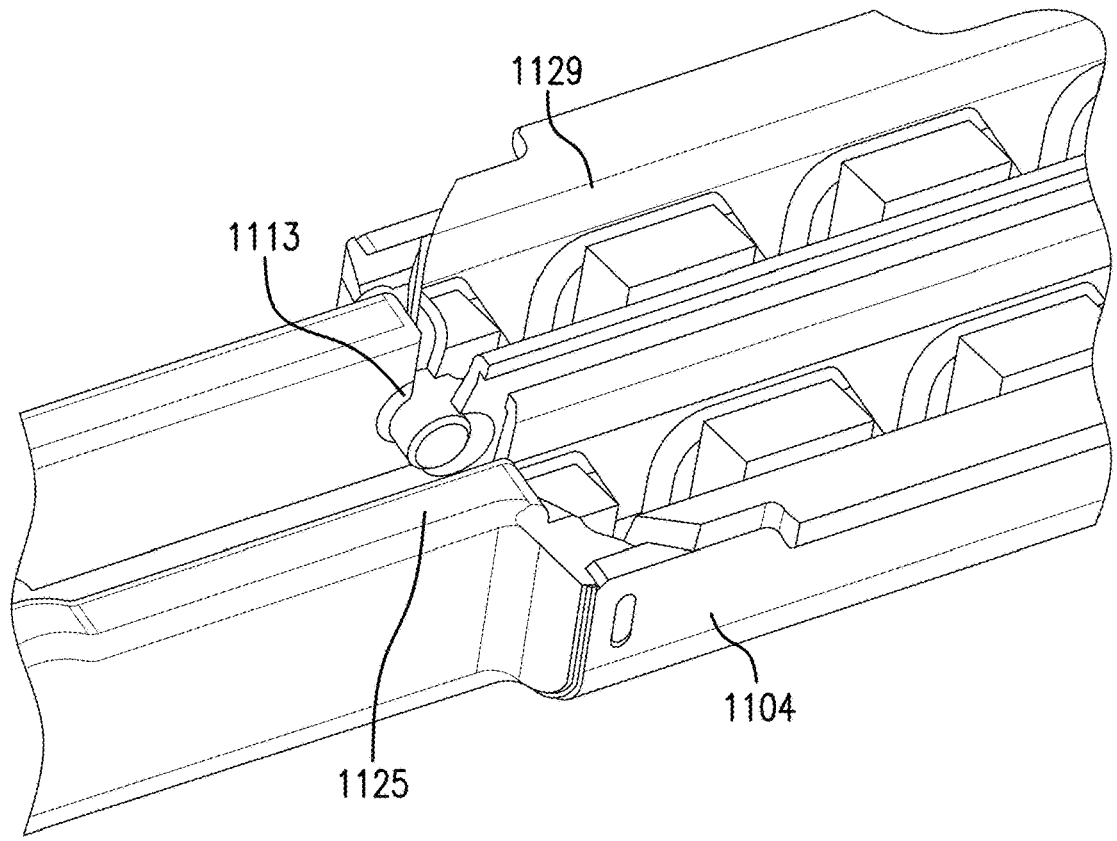
Figure 92:
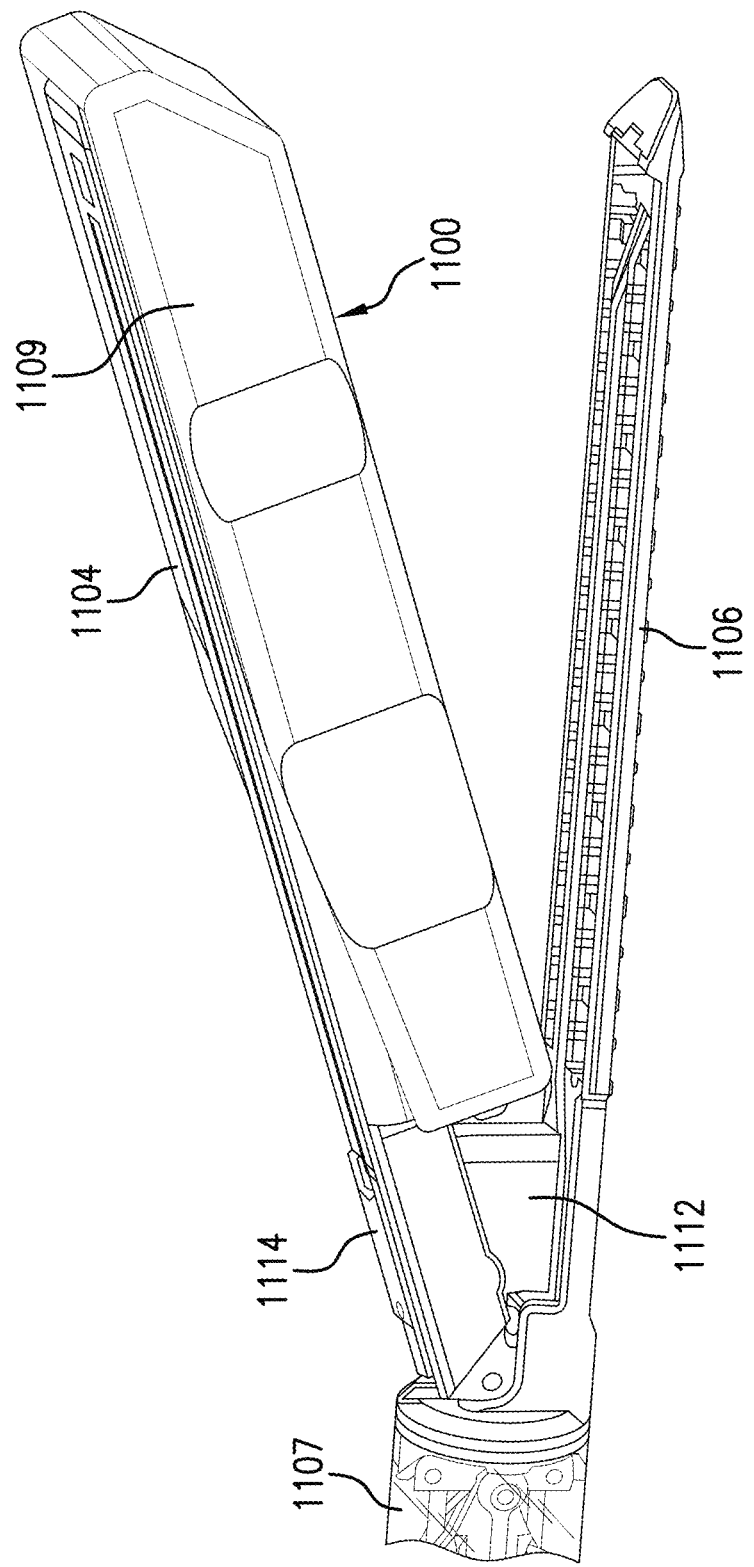
Figure 93A:
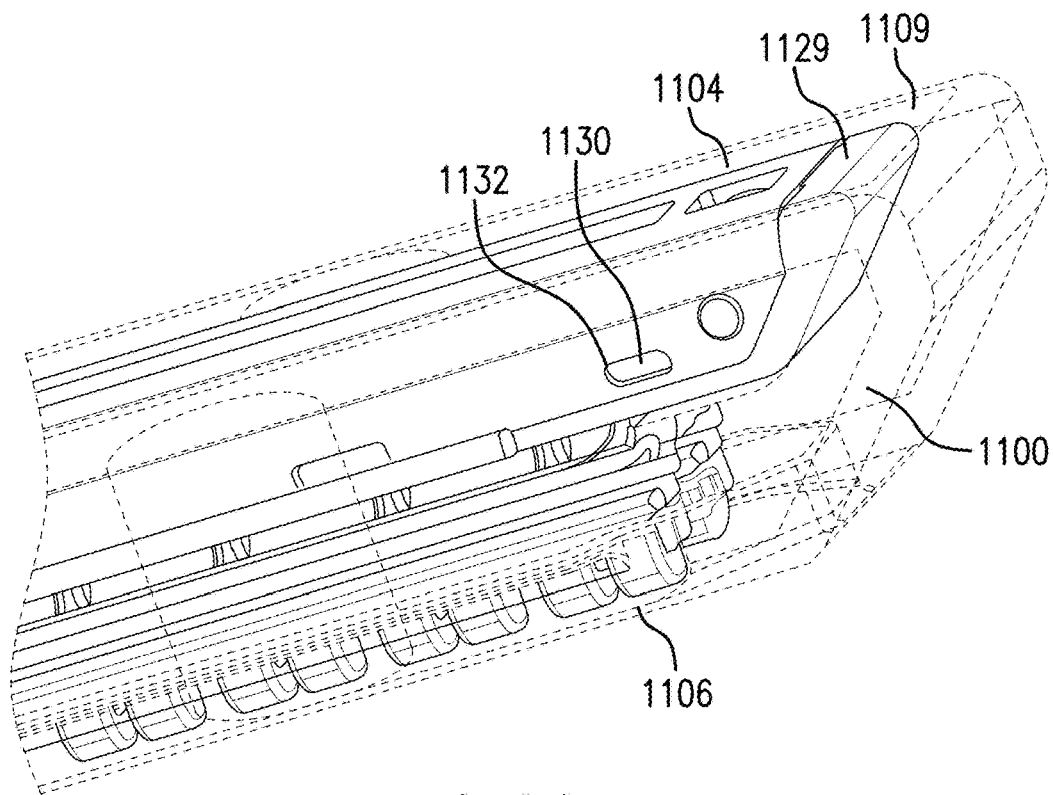
Figure 93B:
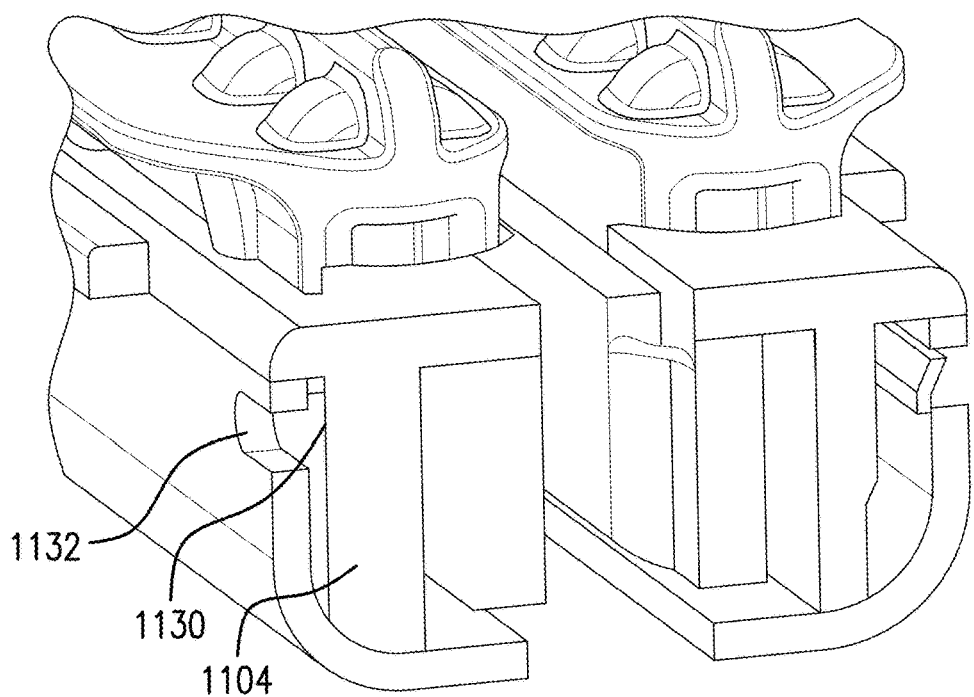
Figure 95B:
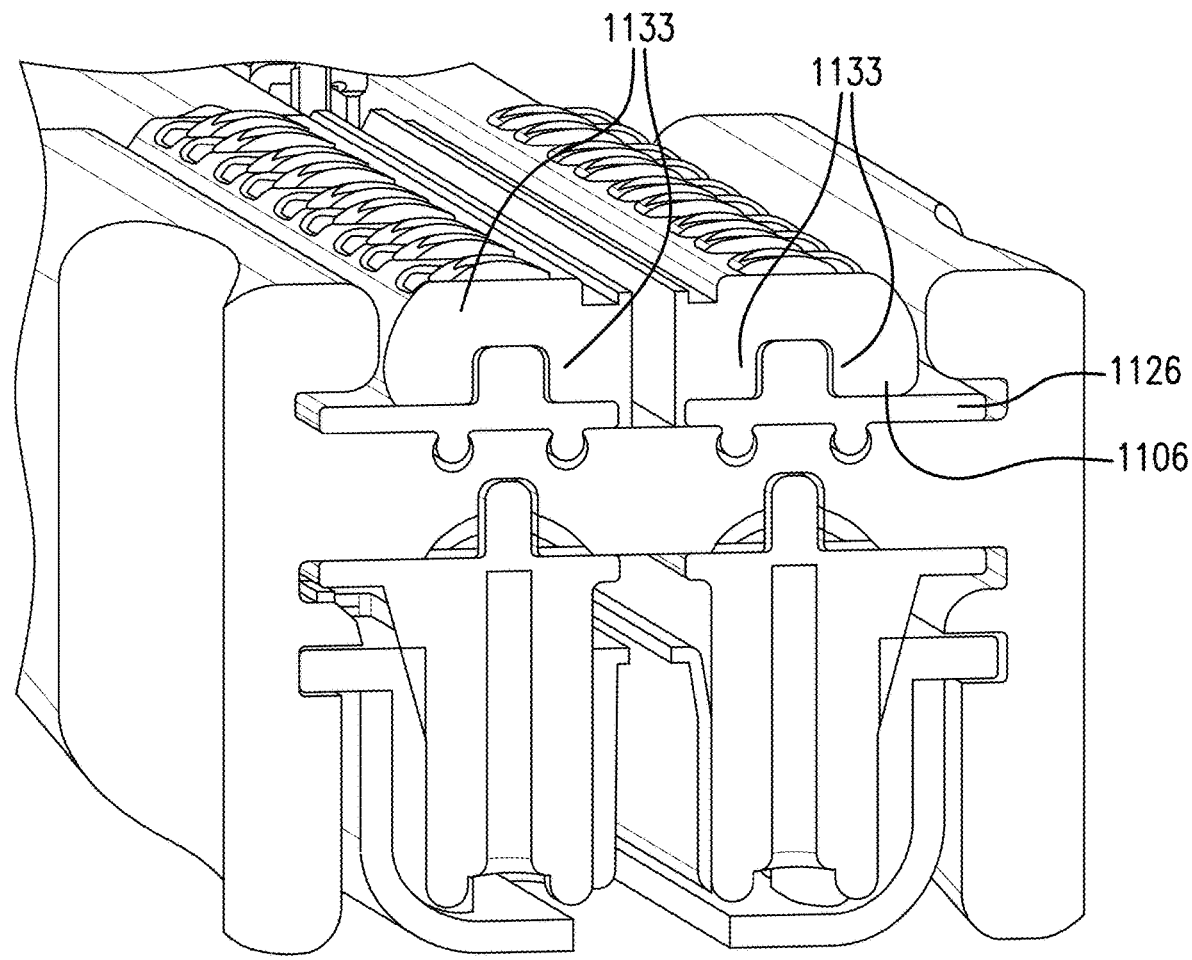
Figure 96:
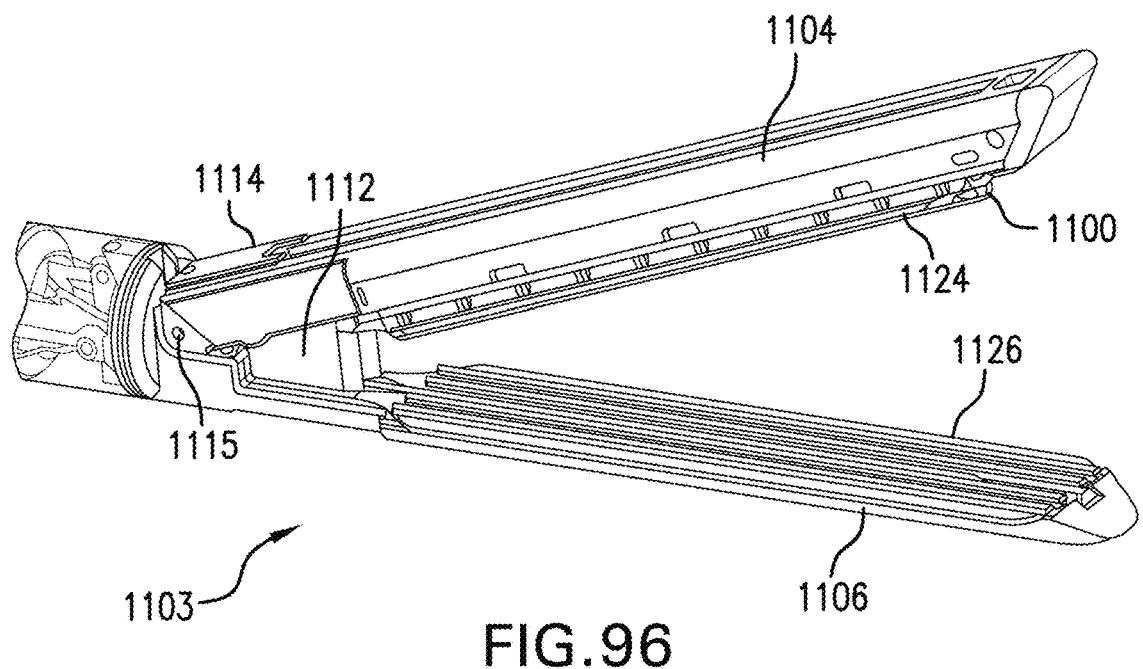
Figures 97A, 97B, 97C:
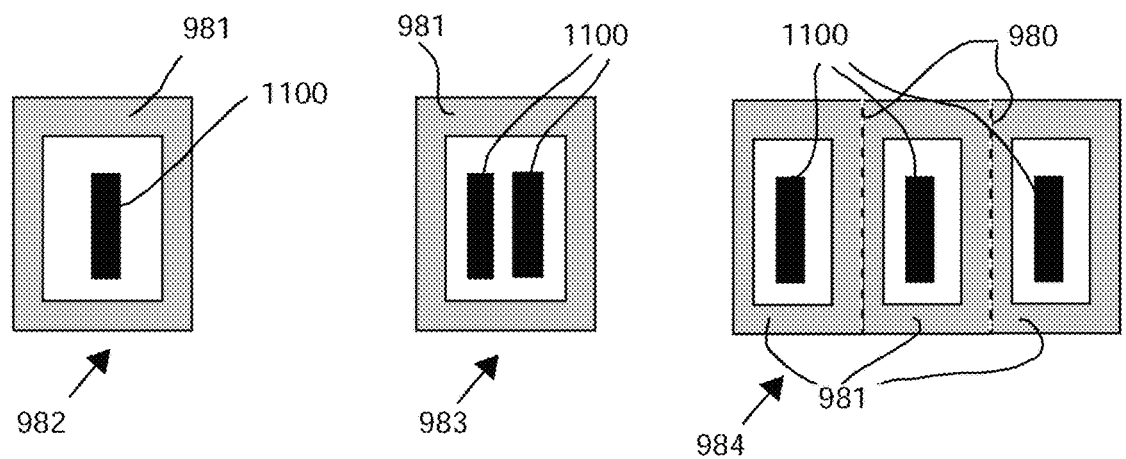
Figure 97D:
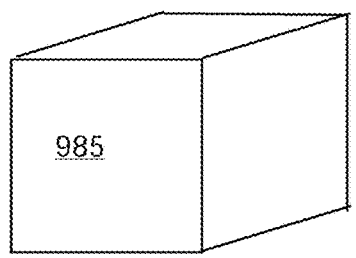

FIGS. 63A-63E schematically illustrate a method of installing two implants in a head-to-tail arrangement;

FIG. 64 is a perspective view of an implant according to an alternate embodiment installed on a representative tissue structure;

FIG. 65 is an enlarged view of a pin/fastener of the implant of FIG. 64 extending through the representative tissue structure;

FIG. 66 is an enlarged perspective view of a portion of the implant of FIG. 64, showing the fastener extending into the receiver;

FIG. 67 is a perspective view of a fastener of an implant according to an alternate embodiment disclosed herein;

FIG. 68 is a perspective view of a fastener of an implant according to another alternate embodiment disclosed herein;

FIG. 69 is a perspective view of a surgical instrument having a set of jaws in an open configuration for positioning the implant of FIG. 64 with respect to the representative tissue structure;

FIG. 70 is a perspective view of the surgical instrument of FIG. 69 with the jaws in a closed position;

FIG. 71 is a perspective view of a proximal end of the jaws of FIG. 69 showing a driver for applying the implant to the tissue structure;

FIG. 72 is a perspective view of a distal end of the jaws of FIG. 70 after the driver of FIG. 71 has applied the implant;

FIG. 73 is a perspective view of a pair of the implants of FIG. 64 installed on the representative tissue sample with a cut made between the implants;

FIG. 74 is a perspective view of the representative tissue structure of FIG. 73 after the cut is made and one half of the tissue structure is removed;

FIG. 75 is a perspective view of the implant of FIG. 64 installed on a smaller tissue structure and with the ends of the implant cropped;

FIG. 76 is an end view illustrating a minimal profile of the instrument of FIG. 69 with the implant of FIG. 64;

FIG. 77 is a perspective view of an implant according to an alternate embodiment having a first half or member connected to a second half or member via a hinge;

FIG. 78A is a perspective view of an alternate embodiment of an end effector, the jaws shown in the open position;

FIG. 78B is a perspective view similar to FIG. 78A showing the jaws in the closed position;

FIG. 79 is enlarged view of a proximal portion of the jaws of FIG. 78B (in the closed position);

FIG. 80A is an enlarged cut away view of the jaws of FIG. 79 taken through the protrusion/opening engagement of the jaws;

FIG. 80B is an enlarged view showing the proximal end of the movable jaw of FIG. 78A;

FIG. 80C is an enlarged view of a proximal portion of the stationary jaw of FIG. 78A;

FIG. 81A is a side view of the jaws of FIG. 78A showing schematically the pull force for effecting initial closure of the jaws;

FIG. 81B is a side view similar to FIG. 81A showing the jaws in the closed position;

FIG. 81C is a side view of the jaws of 81A showing schematically the pull force to effect jaw closure during deployment of the fasteners;

FIG. 81D is a side view similar to FIG. 81C showing the jaws in the closed position;

FIG. 82A is a side view of the end effector assembly of FIG. 78A showing the cam path of the driver tab, FIG. 82B is an enlarged view of the distal end of the end effector assembly of FIG. 82A;

FIG. 83A is a perspective view of the end effector assembly of FIG. 82A showing the jaws in the open position prior to initial advancement of the driver assembly;

FIG. 83B is a perspective view of the end effector assembly of FIG. 83A in the opposite orientation;

FIG. 83C is a side view of the end effector assembly of FIG. 83A;

FIG. 84A is a perspective view of the end effector assembly of FIG. 82A showing the jaws in the closed position upon initial advancement of the driver assembly;

FIG. 84B is a perspective view of the end effector assembly of FIG. 84A in the opposite orientation;

FIG. 84C is a side view of the end effector assembly of FIG. 84A;

FIG. 85A is a perspective view of the end effector assembly of FIG. 82A showing the jaws in the closed position and the driver assembly moved to its distal position;

FIG. 85B is a perspective view of the end effector assembly of FIG. 85A in the opposite orientation;

FIG. 85C is a side view of the end effector assembly of FIG. 85A;

FIG. 85D is an enlarged perspective view of a distal portion of the end effector assembly of FIG. 82A showing the driver tab advanced toward a distal position;

FIG. 85E is an enlarged perspective view similar to FIG. 85D showing the driver tab in its distal position;

FIG. 85F is an enlarged perspective of a distal portion of the end effector assembly of FIG. 82A showing the driver advanced toward its distal position;

FIG. 86A is a perspective view of the end effector assembly of FIG. 82A showing the driver assembly moved to a second position to enable the jaws to slightly open;

FIG. 86B is a perspective view of the end effector assembly of FIG. 86A in the opposite orientation;

FIG. 86C is a side view of the end effector assembly of FIG. 86A;

FIG. 87A is a perspective view of the end effector assembly of FIG. 82A showing the jaws slightly opened as the driver assembly retracts;

FIG. 87B is a perspective view of the end effector assembly of FIG. 87A in the opposite orientation;

FIG. 87C is a side view of the end effector assembly of FIG. 87A;

FIG. 88A is a perspective view of the end effector assembly of FIG. 82A showing the jaws in the open position as the driver assembly is moved to its proximal position;

FIG. 88B is a perspective view of the end effector assembly of FIG. 88A in the opposite orientation;

FIG. 88C is a side view of the end effector assembly of FIG. 88A;

FIG. 89A is a perspective view of one embodiment of a loading assembly;

FIG. 89B is a perspective view of the loading assembly of FIG. 89A showing the other side;

FIG. 89C is cutaway view of the loading assembly of FIG. 89A;

FIG. 90 is a side view of the loading assembly of FIG. 89A being placed in the open jaws of a surgical applicator;

FIG. 91A is an enlarged perspective view showing engagement of the loading assembly of FIG. 89A with the tab of the movable jaw;

FIG. 91B is an enlarged perspective view showing the proximal end of the cartridge portion of the loading assembly of FIG. 89A engaged with the tab of the movable jaw as the loading assembly is rotated into the movable jaw;

FIG. 92 is a side view similar to FIG. 90 showing the loading assembly rotated and snapped into the movable jaw;

FIG. 93A is an enlarged view of a portion of the loading assembly and the jaws showing the reload assembly snapped into the moving jaw;

FIG. 93B is a cutaway view showing the cartridge portion snapped into the movable jaw;

FIG. 94 is a side view similar to FIG. 92 showing the jaws in the closed position;

FIG. 95A is a side view similar to FIG. 94 showing the jaws in the closed position and the loading assembly being slid out from the jaws;

FIG. 95B is a cutaway view showing the receiver member frictionally engaged with the stationary jaw;

FIG. 96 is a side view showing the jaws in the open position with the implant loaded in the movable and stationary jaws; and FIGS. 97A through 97D relate to packaging options for one or more loading assemblies as described throughout the present disclosure.

DETAILED DESCRIPTION

A detailed description of one or more embodiments of the disclosed apparatus, implant and method are presented herein by way of exemplification and not limitation with reference to the Figures.

Various embodiments of surgical implants and tools (apparatus) for installing such implants are described below and illustrated throughout the drawings. For purposes of the description hereinafter, the words "upper," "lower," "right," "left," "vertical," "horizontal," "top," "bottom," "lateral," "longitudinal," "axial," and like terms, if used, shall relate to the apparatus and/or implant, as it is oriented in the drawing figures. When appropriate, the terms "proximal" and "distal" are in reference to a user that uses the tool to deploy the implant, typically towards a portion of a patient's anatomy. The term "distal" shall for instance mean situated further away from the user, while the term "proximal" shall mean situated more towards the user. The phrases "installing/installed on", "installing/installed about", "installing/installed through", and other similar phrases are generally intended to be interchangeable and refer to an implant being used to secure, connect, seal, clamp, compress, and/or fasten various tissue and non-tissue structures, including those internal to a mammalian body cavity as well as those external (e.g., postpartum umbilical cord). The term "surgical structure" as used herein refers to any tissue or non-tissue structure on which an implant is, is to be, or is intended or desired to be secured. The terms "seal", "sealed" "sealing", etc., as used herein refer to slowing, hindering, blocking, and/or otherwise impeding the flow of fluid through, by, past, beyond, or between surgical structures on which an implant is installed. As used herein, the terms "ventrum" and "ventral side" refers to the side of a component (e.g., part of an implant or a tool for installing an implant) that generally faces toward, or abuts, the surgical structure. "Ventrally" likewise refers to the direction generally toward the surgical structure. Oppositely, the terms "dorsum" and "dorsal side" refer to the side opposite from the ventrum, i.e., the side generally facing away from the surgical structure. Likewise, "dorsally" refers to the direction generally away from the surgical structure.

Figure 1:
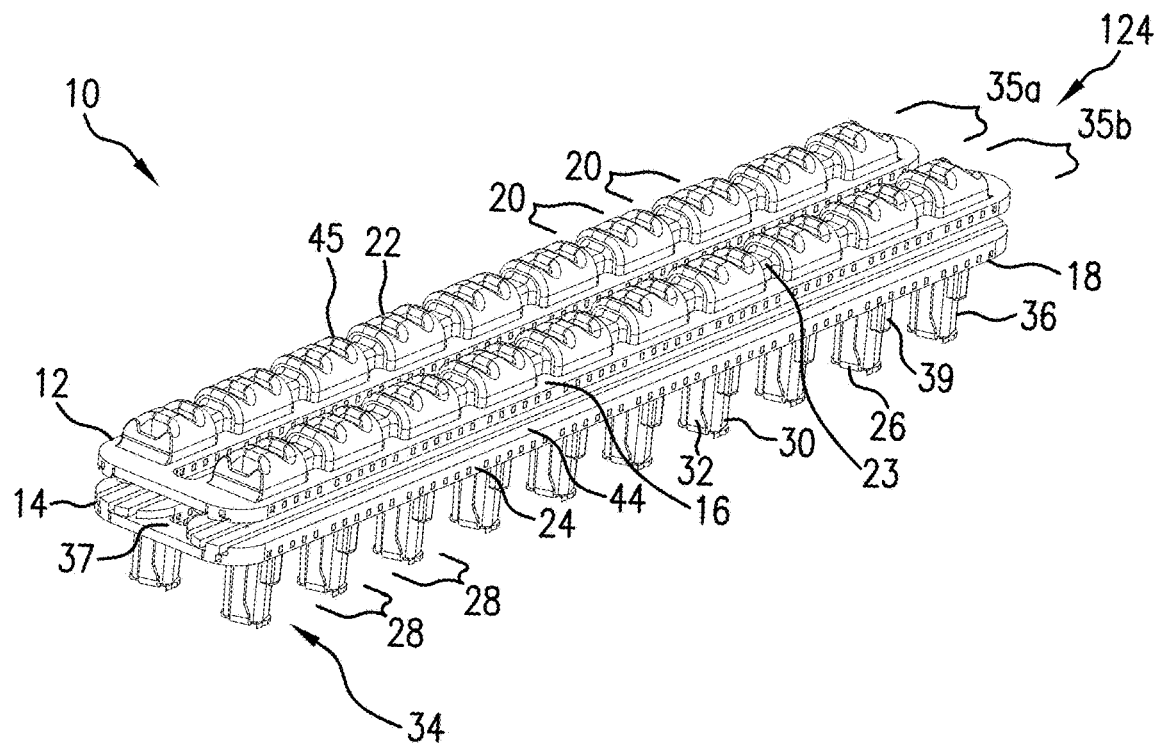
FIG. 1 is a perspective view of an implant according to an example embodiment.
Figure 2:
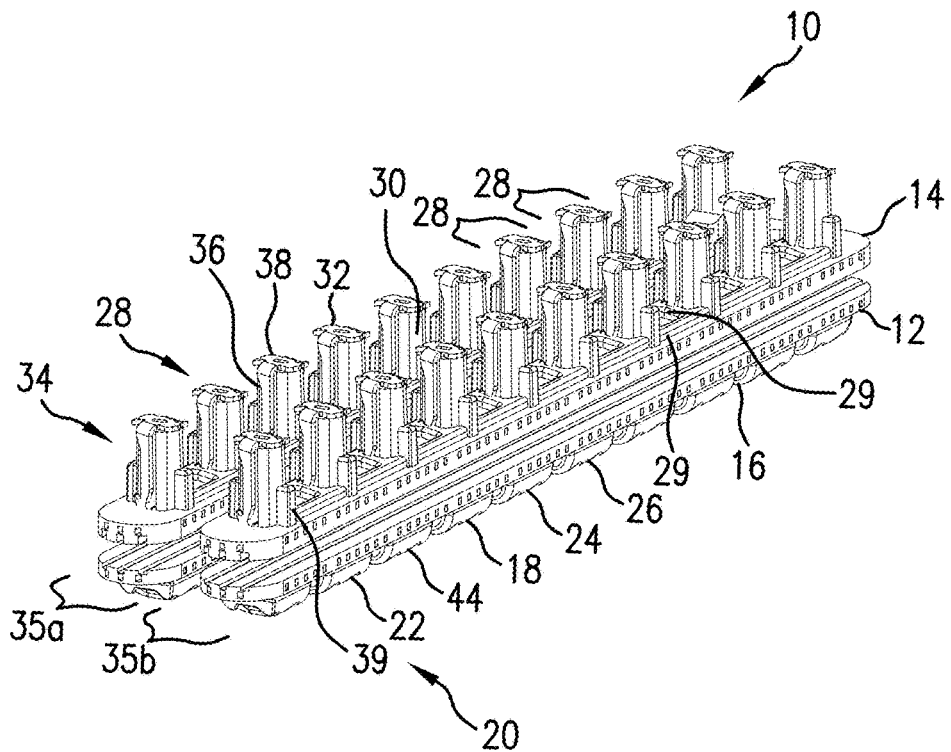
FIG. 2 is a perspective view of the opposite side of the implant illustrated in FIG. 1.
Figure 6:
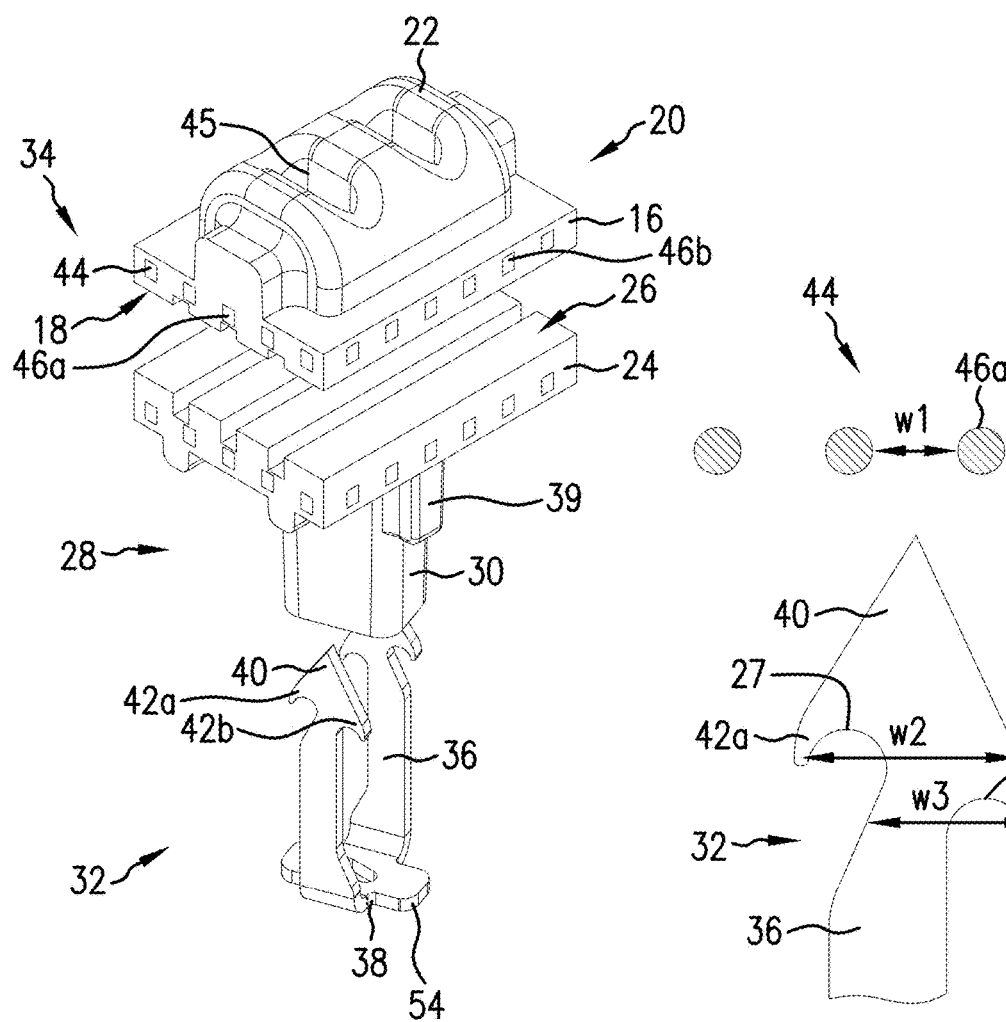
FIG. 6 is a perspective view of the exploded section shown in FIGS. 3 and 4, showing the underside of the perspective shown in FIG. 5.

Referring now to FIGS. 1-2, a surgical implant 10 in accordance with an embodiment is illustrated. The implant 10 is shown to be elongate such that its length exceeds its width, and in the present example is illustrated to include two halves or parts configured to be brought together. In certain embodiments, one of the halves is a receiver member 12 to receive fasteners and the other is a deployment member 14, also referred to herein as a fastener retaining member, fastener supporting member, or fastener carrying member, which supports the fasteners. In other embodiments, features of either of the receiver member 12 and the deployment member 14 can be included instead in the other. For example, each half may include both receiver members 12 and deployment members 14. In certain embodiments the halves are connected in at least one location, either directly or indirectly prior to use and/or activation, while in other embodiments the halves are not connected prior to use and/or activation. As discussed in more detail below, the members 12 and 14 are to be positioned on opposite sides of one or more surgical structures such as tissue, a non-tissue structure, or a tissue structure in combination with a non-tissue structure. The members 12 and 14 are then secured (coupled) together in order to clamp or compress the surgical structure(s) therebetween. As in one example, by clamping or compressing tissue between the members 12 and 14 and holding the tissue in this clamped or compressed state, fluid flow through the tissue or tissue-to-tissue interface can be sealed. In other embodiments, various tissue and/or non-tissue structures (including simulated or artificial tissue structures) may be secured together by the implant 10, with or without the aforementioned sealing.

Examples of tissue structures include, but are not limited to, blood vessels such as the aorta, superior vena cava, inferior vena cava, lobar vessels, the renal artery, organ parenchyma including pulmonary parenchyma, bronchii, lobar bronchi, trachea, atrial appendages, gastrointestinal structures, colon, spleen, liver tissue, etc. The implant 10 can be useful for establishing hemostasis, pneumostasis, or to seal off the flow of other fluids through various other tissue structures within a patient, as well as to connect these tissues and other tissue and non-tissue structures together with or without fluid sealing. Examples of non-tissue structures include PTFE, ePTFE, grafts, stents, textile weaves, braids, and knits, meshes, plugs, gastro-intestinal sleeves, etc. In each of the disclosed embodiments, when the implant 10 is located about two or more structures, the structures may be either the same (e.g., vessel tissue to vessel tissue, bronchii tissue to bronchii tissue, non-tissue to non-tissue, etc.) or different (e.g., bronchii tissue to non-bronchii tissue (including for instance PTFE), gastrointestinal tissue to non-gastrointestinal tissue or structures such as textile or PTFE sleeves, etc.).

In an exemplary embodiment, the receiver member 12 includes a receiver base 16 having a surgical structure contacting surface 18 located at one side thereof, which may be referred to herein as its ventrum or ventral side. As can be seen, for example in FIG. 1, the receiver member 12 is formed of an essentially repeating pattern of segments 20, with each of the segments 20 including a shield or roof 22 extending dorsally from a portion of the receiver base 16 in proximity to each of the shields 22. As shown, the shields 22 are arranged along rows substantially parallel to a longitudinal axis of the receiver member 12 positioned opposite the fasteners 32 to shield the penetrating tips of the fasteners 32 as described below. Similarly, the deployment member 14 includes a base 24 having a surgical structure contacting surface 26 along its ventrum. Contained within the base 16 is a retainer discussed in more detail below. The surgical structure contacting surfaces 18 and 26 are generally arranged to face each other and to be contacted against opposite sides of a surgical structure or multiple adjacent surgical structures in order to clamp, secure or compress the structure between the oppositely positioned surgical structure contacting surfaces and provide the aforementioned sealing, securing, and/or fastening functions of the implant 10. The deployment member 14 is formed from a plurality of segments 28, which correspondingly repeat with respect to the segments 20 along the length of the implant 10.

Each of the segments 28 is shown to include a resilient and/or compressible member, suspension, spring, or biasing element, represented generally as a tower 30 (or tower-like structure) extending dorsally from the base 24 in a direction substantially perpendicular to the base 24 of the fastener supporting member 14 and a clip, anchor, or fastener 32 disposed with each of the towers 30. As shown, the fastener 32 straddles a respective tower 30 so the base of the fastener 32 exerts a force against the base of the tower 30 when deployed to compress and deform the tower 30. As described in more detail below, each tower 30 is compressible in accordance with the distance of advancement of the fastener engageable with the tower, and the distance of advancement is dependent on a thickness of tissue or other surgical structure clamped between tissue contacting surfaces of the receiver member 12 and deployment member 14, through which the fasteners 32 advance. The segments 20 and 28 are preferably arranged in pairs, with each pair of segments 20 and 28 forming a fastener subassembly 34. It is to be appreciated that any number of the subassemblies 34 can be repeated in either patterns or randomized series in order to form the implant 10 in a variety of differently sizes and/or shapes to accommodate a variety of different tissue types, geometries, sizes, and shapes. For example, the number of the subassemblies 34 can be increased or decreased in order to change the length of the implant 10. For example, in one embodiment, an implant may be formed as a single one of the subassemblies 34 and used for tacking or securing surgical structures together. In another embodiment, an implant includes a single one of the subesassemblies 34 and is used for tacking a hernia mesh to an underlying muscle tissue structure. Additionally, it is noted that if the implant 10 is longer than necessary or desired than the length required to complete a task (e.g., the implant 10 exceeds the width of the surgical structure), any excess ones of the subassemblies 34 (i.e., those that do not have any tissue positioned between the members 12 and 14) can be cut or trimmed off as desired. Unlike staples, which may be left behind in great number inside of a patient, the aforementioned approach can be used, for example, to limit the amount of excess material left within a patient after a surgical procedure. It is also noted that multiples of the implant 10 can be installed sequentially, e.g., in a head-to-tail or tail-to-head sequence. For example, it some situations it may be unfeasible or undesirable to manufacture, install, or handle extraordinarily long implants (e.g., having dozens of the subassemblies 34), so multiple shorter implants may be used instead and may be installed in series. As another example, it may be desirable to install implants along a non-linear path, and thus multiples of the implant 10 may be installed in series, but at angles with respect to each other. As one example, the implants 10 may be installed in this sequential or head-to-tail arrangement during a lung resection procedure, which may require both a relatively long and non-linear section of tissue to be sealed.

The subassemblies 34 in the illustrated embodiment as shown for example in FIGS. 1-2 are arranged in two substantially identical and parallel rows 35a and 35b (collectively, "the rows 35"), connected by a bridge 37. The rows 35 form a channel, guide, or pathway in order to facilitate the cutting of the surgical structure located between the rows 35 after installation of the implant 10, as discussed in more detail below. One row (e.g., FIG. 33), as well as more than two rows (not shown), are both additionally contemplated in various embodiments.

One of the fastener subassemblies 34 is shown according to one embodiment in more detail in the exploded views of FIGS. 3-6. In the illustrated embodiment, the fasteners 32 each include a pair of shanks, pins, or legs 36 extending from base or body 38 that straddle their corresponding towers 30 and extend ventrally from a body 38 of the fasteners 32. Each of the legs 36 may terminate in a penetrating tip 40 that is configured to pierce through whatever surgical structure is located between the receiver and deployment portions 12 and 14, including but not limited to human tissue. Initially, the tips 40 may be embedded completely within the base 24, or protrude partially out through the surgical structure contacting surface 26 of the base 24. The legs 36 may have a barbed or hooked region located at or proximally with respect to the tip 40. In the illustrated embodiment, each of the tips 40 includes two hooks or barbs 42a and 42b (collectively, "the barbs 42"), positioned on opposite sides of the leg 36. In one embodiment, the barbs 42 are offset from each other along the length of the legs 36, e.g., with the barb 42a being located further along the length (further from the base or body 38) of each leg 36 than the barb 42b. One advantage of such an offset is to facilitate the accommodation of different tissue thicknesses, even across the same tissue structure. In other embodiments the barbs can be aligned rather than offset. It is to be appreciated that in other embodiments contemplated herein, one of the fasteners 32 may be formed with only a single leg, or more than two legs, which extend from the body 38. Additionally, in other contemplated embodiments, one of the legs 36 may include a single barb or hook 42, or more than two such barbs or hooks positioned at various locations along the length of their corresponding legs 36. The legs 36 are shown extending substantially perpendicular from the base but alternatively can extend at acute or obtuse angles from the base 38.

Figure 7A:
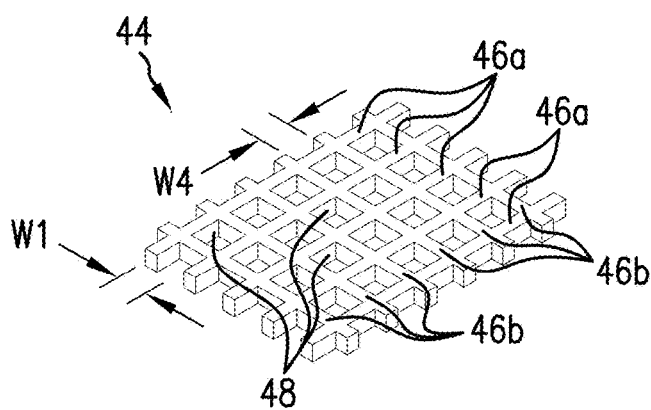
FIG. 7A is a perspective view of a retainer of the implant of FIG. 1.
Figure 7B:
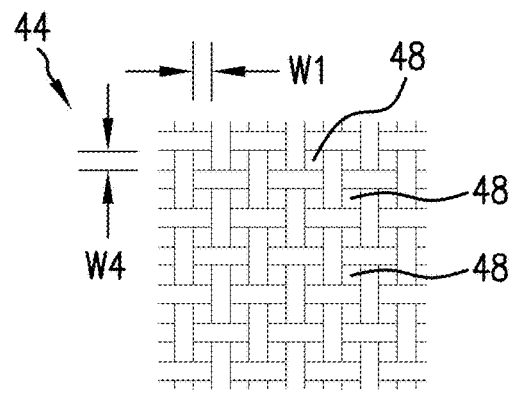
FIG. 7B is an overhead view of a retainer according to an example embodiment of the present disclosure.

During installation of the implant 10 on or about a structure, the fasteners 32 are driven or actuated toward the towers 30 against a reactionary resilient force exerted by the towers 30. Forces applied to the fastener 32 therefore compress (and deform) the towers 30 toward the base 24 or deployment member 14 as the base of the fasteners 32 engages the base of towers 30 to apply a force thereto to compress and deform the respective towers 30 so the towers 30 move from a first configuration to a second configuration. Actuation of the fasteners results in the tips 40 of the fasteners 32 being driven out from the base 24 of the deployment member 14, through any surgical structure on which the implant 10 is installed, and into the receiver base 16 of the receiver member 12. In various embodiments, the receiver base 16 may include a retainer 44 disposed therewith, e.g., disposed on and/or embedded therein as shown throughout the Figures. A representative portion of the retainer 44 (with the bases 16 and 24 removed for clarity) is shown schematically in FIGS. 7A and 7B, of which FIG. 7B shows a retainer embodiment fabricated in an interlaced manner. The fasteners 32 may be driven with sufficient force to compress the towers 30 and any structures between the structure contacting surfaces 18 and 26 of the members 12 and 14, to the point at which the tips 40 pass through or by the retainer 44. The retainer 44 is arranged with respect to the tips 40 to enable the barbs 42 to move relative to the retainer 44 in one direction, i.e., the actuation direction for the tips 40 (which is initially towards the ventrum, i.e., the ventral direction with respect to the deployment member), but becomes the dorsal direction (with respect to the receiving member) after the tips 40 have passed through the surgical structure), but for one or more of the barbs 42 to engage with, catch, and/or otherwise grab the retainer 44 to prevent or limit movement thereof in the opposite direction. The base 24 can also include a retainer embedded therein, e.g., in order to help strengthen, or add stiffness and/or rigidity to the member 14 as well as to retain the fasteners 32 in their initial, unfired configuration via similar engagement with the barbs 42. Such retainer supported/positioned in base 14 can be the same as the retainer 44, or its variants, described herein.

In various embodiments, the tips 40 may protrude through the opposite (i.e., dorsal) side of the base 16 from the surgical structure contacting (i.e., ventrally located) surface 18 when engaged with the retainer 44. As shown in the Figures, one or more shields 22, each having one or more cavities or pockets 45 that receive the tip(s) 40 when the tips 40 are so protruding, are positioned opposite the fasteners 32 and are generally aligned with the legs 36 of the fasteners 32. In this way, the shields 22 can provide protection from the tips 40, e.g., protection to shield from inadvertent contact of the tips 40 by a medical professional or other tissue structures within the patient if the implant 10 is to be left inside of the patient. In one embodiment, the shields 22 do not include the pockets 45, such that the tips 30 are completely surrounded by and embedded within the shields 22.

In the illustrated embodiment, the retainer 44 includes longitudinal or lengthwise strands 46a and transverse or widthwise strands 46b (collectively "the strands 46") with a plurality of interstices or openings 48 formed by spacing between the plurality of strands. It is to be understood that the strands 46 generally represent any wire, bar, cord, slat, strut, spoke, fiber, thread, tine, filament, cable, or other elongated element. In one embodiment, the retainer 44 is a woven, knitted, or braided mesh, or other grid-like structure. In one embodiment, the strands 46 are arranged in a random or irregular pattern, such as a felt, or a non-woven pattern, such as TYVEK brand material made commercial available by DuPont. The strands 46a may be separate from each other and/or separate from the strands 46b. Alternatively, the strands 46 may be integrally formed, fused, or affixed together. In FIG. 7B, the stands are interlaced with alternating overlapping portions and with interstices 48 between the strands. It is further understood that in some embodiments, strands can exist in a first direction only. The first direction in some embodiments may be generally along the lengthwise (i.e., longitudinal) direction of the implant 10, and in other embodiments it may be the transverse direction along the width. In embodiments in which the length of the implant 10 is significantly larger than its width, similar to the illustrated embodiments of FIG. 1, it may be desired for the barbs 42 to be aligned to catch and engage with the longitudinal strands 46a, as these strands share a greater contact area with the material of the bases 16 and/or 24 than the transverse strands 46b, and thus are more likely have a sufficient degree of interference or friction with the bases to withstand the relatively high loading that may be required for some surgical structures, e.g., particularly thick structures, without damage to the implant 10 or loss of function. Other embodiments are contemplated wherein additional features are included with the strands such as anchors to enhance the interference or friction with the bases.

Figure 49:
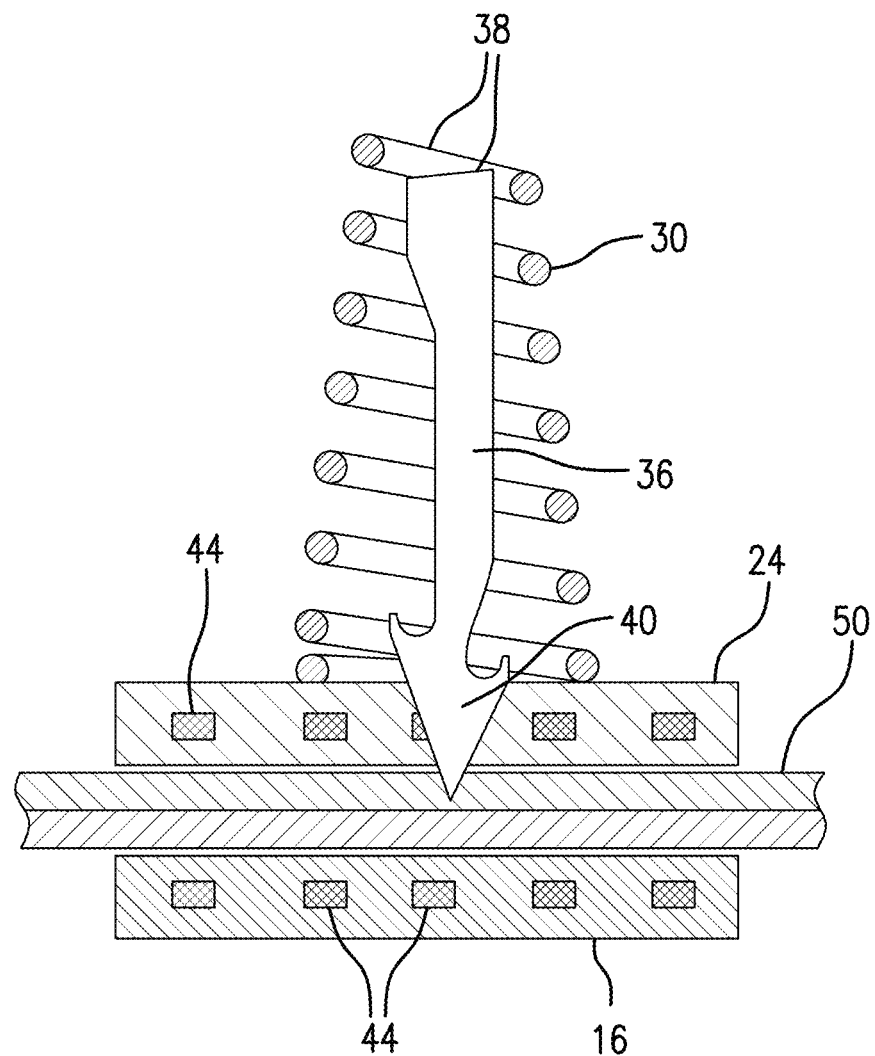
FIG. 49 shows an elevation view of a fastener of another example embodiment.

In various embodiments, the towers 30 are integral to or unitary with the base 24, while it is contemplated in other embodiments that towers may be formed separately from the base. The towers 30 are configured with a structural shape and of a material that allows for a suitable degree of compressibility, such that when force is exerted on the towers 30 towards the base 24 (i.e., ventrally) by the base 38 of the fasteners 32, either directly or indirectly, the strain of the towers 30 is more than any strain encountered by the base 24. The towers 30 may be formed of a resilient material, such that upon removing the actuation force from the fasteners 32, the towers 30 attempt to revert back to their original shapes and exert a corresponding tensile force on the fasteners 32 in a direction opposite to actuation. That is, the towers 30 form biasing or counterforce members to exert a counterforce in a direction opposite to the direction in which the fasteners 32 are deployed (advanced). In this way, the towers 30 function similarly to compression springs, and in fact, may be replaced or supplemented by such springs (e.g., see FIG. 49 illustrating spring 30A) or other resilient elements in various embodiments. For example, in one embodiment the towers 30 may each be configured as a resilient, flexible plug made from an elastomeric material, such as silicone rubber, that protrudes upward from base 24. The plug can be formed as a protrusion having any desired geometric configuration, including but not limited to a cylindrical, rectangular or dome structure. The towers 30 can each be operatively associated with one of the fasteners 32 so as to upwardly, or dorsally, bias the fastener 32 relative to the base 24. The resilient force exerted by the towers 30 on the bodies/bases 38 of the fasteners 32 causes one or more of the barbs 42, having been driven through the retainer 44 during actuation, to engage and grab one or more of the strands 46 of the retainer 44. The upward or dorsally directed bias against the fastener 32 resulting from the spring and/or suspension properties of the tower 30, such as when the fastener 32 extends over an exterior surface of the tower 30, exerts a pull force on fastener 32 as the barbs 42 latch on a portion of the retainer 44. In this way, the compressed towers 30 continue to exert a force to pull the receiver member 12 toward the deployment member 14, after the receiver member 12 and deployment member 14 are coupled together by the fasteners 32, thereby sandwiching, compressing, or clamping the surgical structure therebetween. It should be appreciated that towers are in one embodiment substantially cylindrical and have a height exceeding its width. Circular, oval, rectangular and other cross-section configurations are also contemplated. Additionally, the composition or configuration of the towers can be varied to vary the force applied to the fasteners. Additionally, within each implant, towers of varying force can be provided (e.g., different towers having different force magnitudes and/or profiles per given strain or compression).

The fastener 32 and its related components can be arranged with a variety of dimensions to allow for the system to function appropriately. For example, the maximum amount of strain allowed for a tower in addition to the strain of each of the bases when compressed may be larger than or equal to the sum of (i) the amount of distance the barbs must travel to reach the tissue contact surface of the deployment member, (ii) the thickness of the compressed surgical structure, and (iii) the amount of distance the barbs must pass through the receiver member 12 in order to extend through the structure positioned between the halves of the implant 10 and latch onto the retainer member 44.

Advantageously, the resiliency and/or spring-like nature of the towers 30 provides for suitable tension to be maintained between the halves of the implant (e.g., the members 12 and 14) to suitably handle variable pressure fluctuations that may lead to a burst condition within the structure being secured or sealed by the implant 10. For example, if the implant 10 is installed on a structure to provide fluid sealing, and the seal produced therefrom experiences a pressure spike, e.g., due to the patient coughing following a lung resection procedure with the implant 10, or some other event, the towers 30 are sufficiently elastic to allow for strain, and will thus flex and/or compress to assist in absorbing excess forces. This helps to accommodate the spike in the pressure without damaging the implant 10. Furthermore, even if the seal is breached due to the pressure burst, such that fluid leaks through the seal made by the implant 10, the resiliency of the towers 30 will cause the towers 30 to continue to exert a clamping pressure between the members 12 and 14. This will result in the implant 10 resealing the tissue or surgical structure once the pressure spike has subsided. Oppositely, known staples from known stapling techniques are not sufficiently elastic, and are highly likely to rip or tear out during high pressure events, and thus be completely unable to reseal after experiencing a pressure spike, which may require an additional surgery to be performed in order to re-staple the damaged area.

It is additionally noted that the forces exerted by the towers 30 on the fasteners 32, which is communicated to the surgical structure via the fasteners 32 engaging the retainer 44 in the member 12 and pulling the members 12 and 14 toward each other, can be set in a range sufficiently high to promote sealing and/or closure, while not being so high as to cause necrosis of tissue on which the implant 10 is installed. For example, in one embodiment, the forces exerted by the towers 30 on the fasteners 32 causes the pressure exerted on surgical structures by the members 12 and 14 at the tissue contacting surfaces 18 and 26 to be in the range of about 3 g/mm$^2$ to 25 g/mm$^2$, or more preferably in the range of about 5 g/mm$^2$ to about 15 g/mm$^2$, although other ranges can also be utilized if desired. For example, some tissue types, e.g., bronchii, may benefit from larger pressures, e.g., 10 g/mm$^2$ and greater, while other tissue types, e.g., blood vessels, may benefit from smaller pressures, e.g., between about 5 g/mm$^2$ and 7 g/mm$^2$. It is also noted that since the towers 30 function akin to springs, the spring constant, resiliency, stiffness, and/or rigidity of the towers 30 can be set to variably alter the force exerted by the towers 30 depending on the amount the towers 30 are compressed. Since increased compression of the towers 30 occurs when installing the implant 10 on thicker structures, setting the variable force exerted by the towers 30 can be useful, e.g., for setting a first, relatively lower pressure at relatively small thicknesses for smaller and/or more delicate structures, such as blood vessels (e.g., 5 g/mm$^2$ and 7 g/mm$^2$), and a second, relatively greater pressure at relatively large thicknesses for larger and/or more robust structures, such as bronchii (e.g., 10 g/mm$^2$ or greater).

Figure 13B:
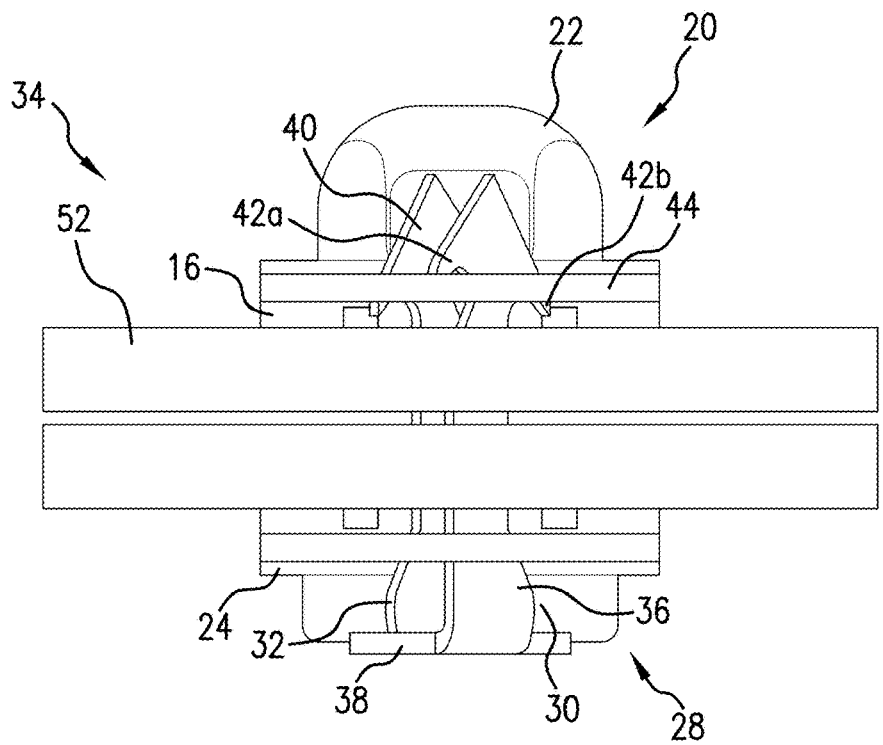
FIG. 13B is another side view of the implant of FIG. 9 engaging the relatively thin structure.

It is noted that by way of the resiliency and/or compressibility of the towers 30, the implant 10 is able to accommodate a range of surgical structure thicknesses approximately equal to the compressible height of the towers 30 (e.g., the distance between the initial height h1 as shown for example in FIG. 3 and the fully compressed height h3 as shown in FIG. 13A). For example, in one embodiment, the towers 30 have an compressible height (e.g., the distance between the initial height h1 and the fully compressed height h3), of approximately 0.1" (2.54 mm), and with this single geometry are capable of accommodating a corresponding approximately 2.5 mm surgical structure thickness range (the surgical structure thickness determined after compression by any jaws or other components of a device for installing the implant 10, e.g., those applicators described herein). For example, the 0.1" compressible height towers may be capable of sealing/closing the implant 10 (that is, latching onto the retainer 44 in the receiving member 12) when there is no structure between the members 12 and 14, i.e., a thickness of zero; or a surgical structure having a thickness of approximately 2.5 mm; or any structure having a thickness in the range between zero and about 2.5 mm. Contrarily, staplers require multiple different staple sizes to handle different tissue thicknesses. Some manufacturers color code their staples depending on size in order to assist in a medical professional determining the correct staple to use, depending on the thickness of the tissue to be sealed or closed, for each specific procedure. That is, each of these staple sizes, e.g. color coded staple sizes, is configured to accommodate a very specific tissue size or very small range of tissue sizes, e.g., a range of only about 0.25 mm or less. In this way, it can be stated that known staples are essentially fixed thickness devices, while the implant 10 and other implants disclosed herein are variable thickness devices.

It is also noted that while the height of the towers 30 assists in defining the thickness range that can be accommodated, e.g., a 2.5 mm range, the length of the legs 36 of the fasteners 32 helps to set the start and end points for the range. For example, the length of the legs 36 between the body or base 38 and the end of the tips 42 can be set to be approximately equal to, and/or slightly shorter than the initial height of the tower 30, such as in the illustrated embodiment. In this way, the fasteners 32 will be able to slightly compress the towers 30 and thus the tips 42 catch, latch, or grab the retainer 44 in the member 12 even if there is no tissue or other surgical structures located between the members 12 and 14. In this embodiment, setting the compressible height, e.g., h1, of the towers 30 to the aforementioned 2.5 mm will set the 2.5 mm range to span between 0 (no surgical structure) and about 2.5 mm. Consider, as one example, increasing the length of the legs 36 by "x" units of distance. In this embodiment, if there is no tissue positioned between the members 12 and 14, the tips 42 would protrude through and extend past the retainer 44 by a distance approximately equal to "x" without compressing the towers 30 (and without compression, the tips 42 would not be pulled against the retainer 44 for maintaining the members 12 and 14 of the implant closed or secured together). Suitable compression of the towers 30 to engage the tips 42 with the retainer 44 would not occur in this embodiment until the thickness between the members 12 and 14 is increased in an amount equal to "x". That is, increasing the length of the legs 36 by "x" distance will shift the start and end points of the range by this distance "x", but while maintaining the same magnitude for the range. For example, if the compressible height of the towers 30 is again about 0.1" (thereby enabling the implant to accommodate a 2.5 mm range), and the amount "x" is about 1 mm, then the implant in this embodiment would seal from about 1 mm to about 3.5 mm (i.e., the range still having a magnitude of about 2.5 mm, but shifted up by 1 mm due to the increase in length of the legs 36). In this way, those of ordinary skill in the art will appreciate that by changing the compressible height of the towers 30, as well as the length of the legs 36 relative to the initial height h1 of the towers 30, both the magnitude of the range and the starting/ending points of the range can be selected as desired and/or required for various procedures.

Advantageously, it would require many differently sized prior art staples in order to accommodate this same tissue thickness range (e.g., a 2.5 mm range) that may be handled by the presently disclosed implants. It is noted that the compressible tower height of approximately 0.1" is one example only and that other heights may be selected. Further, the tower height may be selected such that the implant 10, with an accompanying applicator device (e.g., such as those discussed below), are together capable of fitting within a desired cannula size, e.g., a 12 mm port suitable for minimally invasive procedures. In other embodiments, the height of the towers 30 may be increased or decreased to change the magnitude of the range, thereby creating variable ranges of thicknesses that can be accommodated. For example, an approximately 0.2" compressible tower height may fit in a 15 mm sized cannula and accommodate an approximately 5 mm thickness range, or an approximately 0.05" compressible tower height may accommodate an approximately 1.25 mm range. Additionally, the length of the legs 36 relative to the initial height of the towers 30 may be set as described above to set the start and/or ending points for the range of any given magnitude. For example, the length of the legs 36 may be increased by a distance "x" to increase the minimum thickness that can be sealed or closed by the implant by "x", or decrease by a distance "y" in order to decrease the minimum thickness that can be sealed or closed by the implant by "y" (down to the minimum of 0 thickness, or no surgical structure).

In one embodiment, the bases 16 and 24 of the deployment (fastener supporting) member 14 and receiver member 12, respectively, are made of a relatively soft, flexible, penetratable and/or puncturable, but also resilient material, such as silicone rubber. This enables the tips 40 of the fasteners 32 to be actuated into and/or through the bases 16 and 24 without significantly degrading the integrity of the implant 10. It is noted that the bases 16 and 24 may, alternatively or additionally, be made of one or more other biocompatible materials suitable for implantation, such as, but not limited to, polyurethane, thermoplastic elastomer (TPE), natural rubber, latex, bio-absorbable polymers, or other polymers or elastomers. The towers 30 may also be made of any combination of these or other materials. In one embodiment, the retainer 44 is made from a relatively stronger material, such as polyethylene terephthalate (PET), polyetheretherketone (PEEK), nylon, or other polymers, as well as fibrous materials such as cotton, KEVLAR brand synthetic fibers made commercially available from DuPont, etc., in order to lend additional strength, e.g., tensile strength, stiffness, rigidity, and/or resistance to bending, to the implant 10, as well as to suitably engage with and retain the fasteners 32 via the barbs 42. Other materials for the retainer 44 include various relatively high tensile strength polymers, as well as biocompatible metals such as stainless steel, titanium, nitinol, etc., although those of ordinary skill in the art will recognize biocompatible materials other than those listed herein that would perform suitably for the bases 16 and 24, the towers 30, and/or the retainers 44.

The difference in the material properties including the use of different materials of the retainer 44 and the bases 16 and 24 provides many benefits appreciable by those of ordinary skill in the art. For example, relatively stiff materials, such as buttresses used in the stapler arts, have been known to cause abrasions between the relatively stiff materials and the tissue surrounding their implantation. Advantageously, providing the retainer 44 as a relatively stiffer material and embedding the retainer 44 within base 16 and/or base 24 in certain embodiments disclosed herein enables the implant 10 to obtain both the stiffening properties of the retainer 44 and the low-abrasion and compliable properties of the bases 16 and/or 24.

Figure 8:
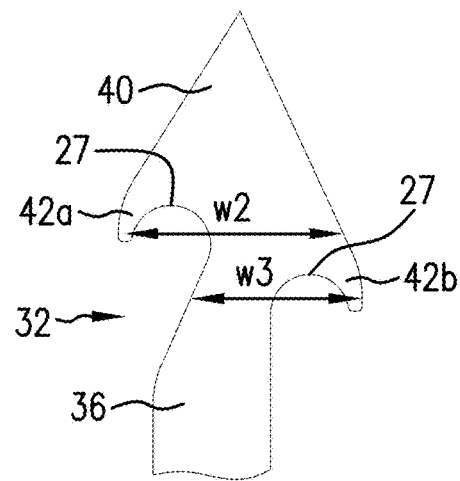
FIG. 8 is a partial view of a tip portion of a fastener of the implant of FIG. 1.
Figure 11:
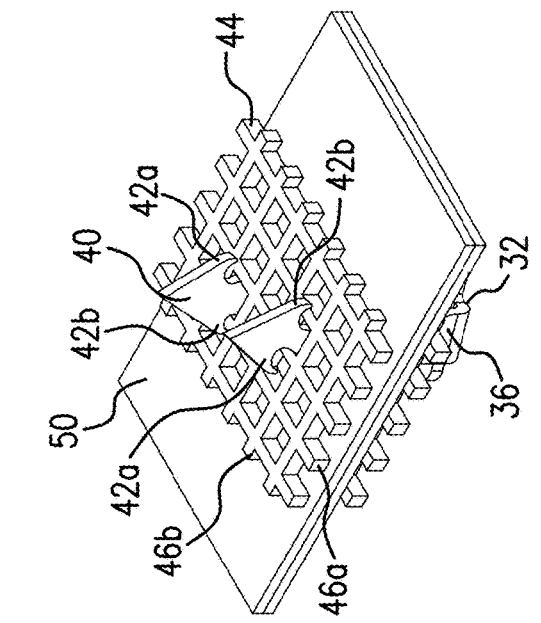
FIG. 11 is a perspective view showing the tips of the legs of the implant illustrated in FIG. 9 catching on or otherwise engaging the retainer, with portions of the implant removed for clarity, the view rotated with respect to the orientation of FIG. 9.

In one embodiment, strands of retainer 44 are arranged in a direction generally perpendicular to a first orientation of tip(s) 40 (FIG. 11). A width of interstices 48 (see FIG. 7A) existing between the strands 46, shown by cross-section in FIG. 8 to be perpendicular with the drawing sheet (i.e., in and out of the page) with the reference numeral w1, is smaller than the horizontal widths of the tip 40 with respect to each of the barbs 42a and 42b, which widths are designated in FIG. 8 with reference numerals w2 and w3, respectively. In this way, the strands 46 that contact each of the tips 40 are moved with respect to and/or pushed apart by the tips 40 (facilitated by the angled or tapered shape of the tips 40) to the widths w2 and/or w3 as the tips 40 are actuated/advanced into the base 16. By making the bases 16 and/or 24 from a flexible, yet resilient and/or elastically deformable material, such as silicone rubber, after one or more of the barbs 42 of the tips 40 are forcibly moved through the retainer 44, the resiliency of the material of the receiver base 16 causes at least one of the strands 46 of the retainer 44 to revert back to, or towards, the initial width w. The material of the retainer 44 can additionally or alternatively provide resiliency to assist in reverting the strands 46 back toward their original configuration. When reverted back towards the original width w1, the strands 46 are positioned in alignment with one or more of the undercuts 27 formed by barbs 42, resulting in the aforementioned engagement between the retainer 44 and the fasteners 32, as shown in FIG. 11. In one embodiment, the strands 46 have a cross-sectional sectional round shape and associated radius that is less than 1.75 times any radius formed by the undercuts 27, more preferably less than 1.3 times, and even less than 1.0 times the radius of the strands. It should also be noted that in embodiments wherein the retainer has strands in different, generally orthogonal directions, the width(s) w4 (see FIGS. 7A and 7B) (which would be orthogonal to the widths w1) would be arranged such that tips 40 would be able to travel beyond any interstice formed between the adjacent strands. While many dimensions of w4 would be possible, non-limiting examples include between 1 times the magnitude of the thickness of barb 42, and six times the magnitude of barb 42. Depending on the dimension of w1, w4 could of course be smaller than the thickness of barb 42. The retainer 44 restricts movement of the fasteners 32 in a direction opposite to a direction of deployment of the fasteners 32 after the fasteners 32 have advanced through the interstices 48 and are engaged with the retainer 44.

Advantageously, the use of the retainer 44 and the fasteners 32 may help to avoid the need for accurate alignment between the members 12 and 14, the retainer 44 and the fasteners 32, etc., or for strict manufacturing tolerances for any of the components of the implant 10 in some embodiments. For example, by setting the width w1 between each set of adjacent strands 46 of the retainer 44 to be smaller than the widths of the tips 40 at the barbs 42, the fasteners 32 do not need to be accurately aligned with the retainer 44 before actuating the fasteners 32. That is, the barbs 42 will engage any part of the retainer 44, so it is unimportant where the tips 40 of the fasteners 32 are received by the receiver member 12 and penetrate into the base 16. For example, even if the members 12 and 14, are slightly misaligned during manufacture, and may become slightly misaligned during firing, the legs 36 of the fastener 32 become slightly tilted or bent (e.g., due to actuation through tissue or through the bases 16 and/or 24), or if there are manufacturing variances or loose tolerances in the size of the components of the implant 10 or positioning of the retainer within the base 16 (e.g., the interstices 48 are not exactly centered on the tips 40), etc., the barbs 42 will regardless catch on some portion of the retainer 44 and maintain the position shown for example in FIG. 11, and the implant 10 will function properly.

The implant 10 is designed to be installable on a range of different surgical structures including those varying in size and/or type. As noted above, the towers 30 are compressed by the fasteners 32 when the fasteners 32 are actuated toward the receiver member 12. Advantageously, the range that the towers 30 can be compressed (i.e., the strain applied)

enables the implant 10 to accommodate a corresponding variable range of surgical structure thicknesses between the structure contacting surfaces 18 and 26. For example, as illustrated in FIG. 3, the tower 30, in its uncompressed state, initially has a height h1. It is noted that the height of the towers 30 may be reduced from a maximum unstressed height after the fasteners 32 are added, e.g., due to the fasteners 32 engaging with a retainer disposed within the base 24, but that reference to the height h1 as the initial height is suitable in any event for purposes of comparison herein.

Figure 9:
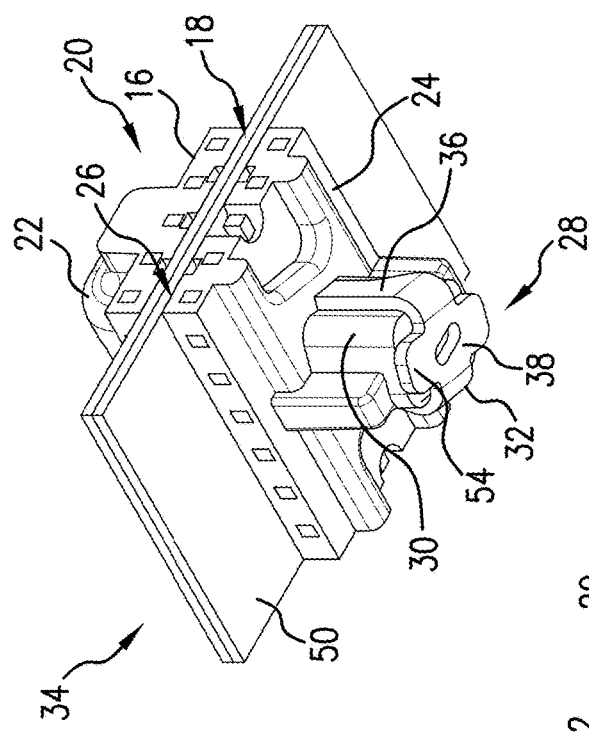
FIG. 9 is a perspective view of a section of the implant of FIG. 1 engaging a relatively thin structure.
Figure 10A:
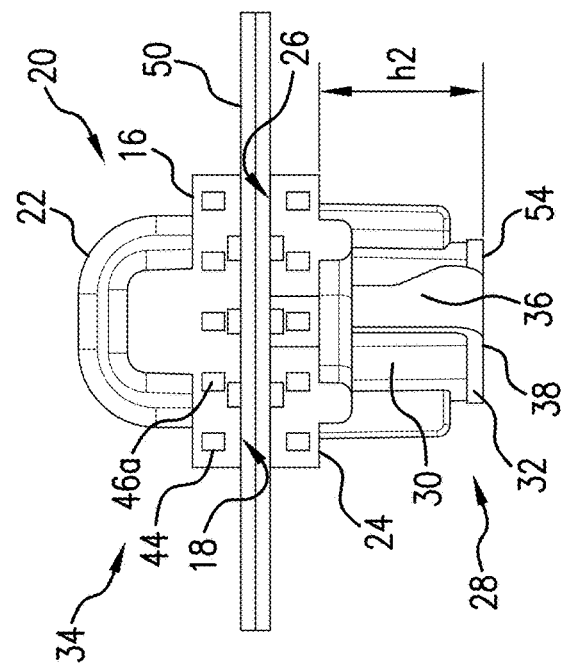
FIG. 10A is a side view of the implant of FIG. 9 engaging the relatively thin structure.
Figure 10B:
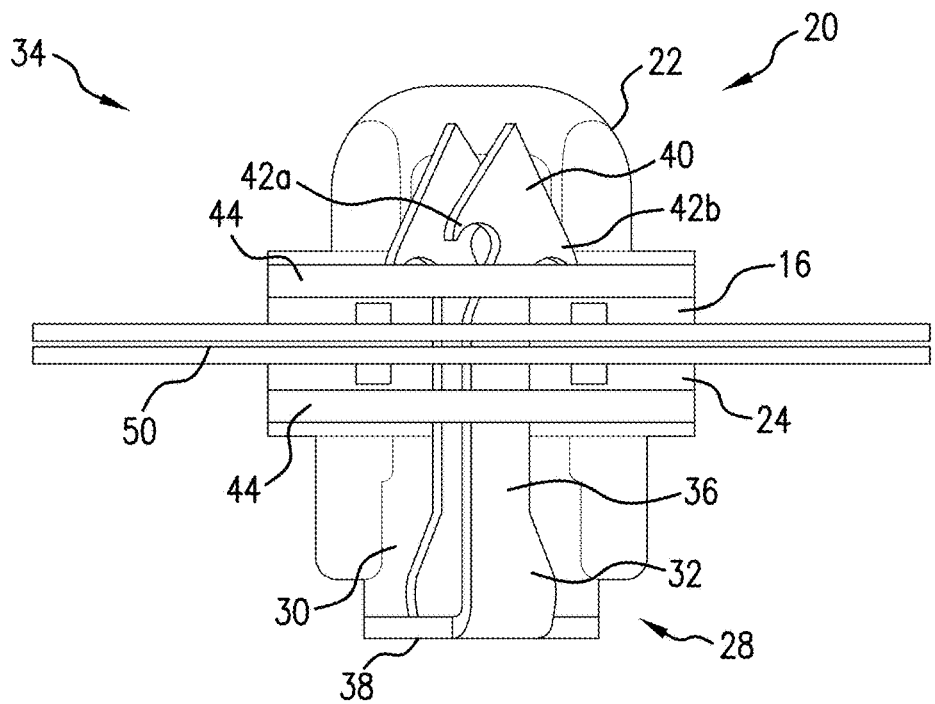
FIG. 10B is another side view of the implant of FIG. 9 engaging the relatively thin structure.
Figure 10C:
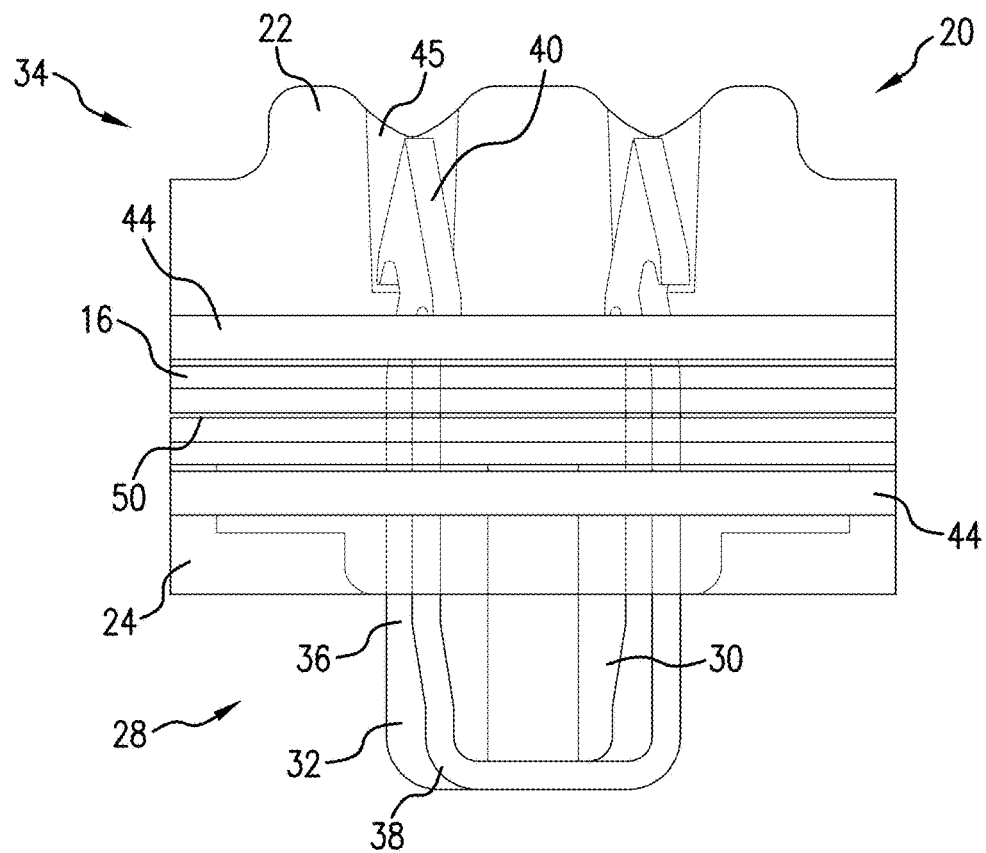
FIG. 10C is another side view of the implant of FIG. 9 showing the implant engaging the relatively thin structure, with barbs catching or otherwise engaging a retainer.
Figure 13C:
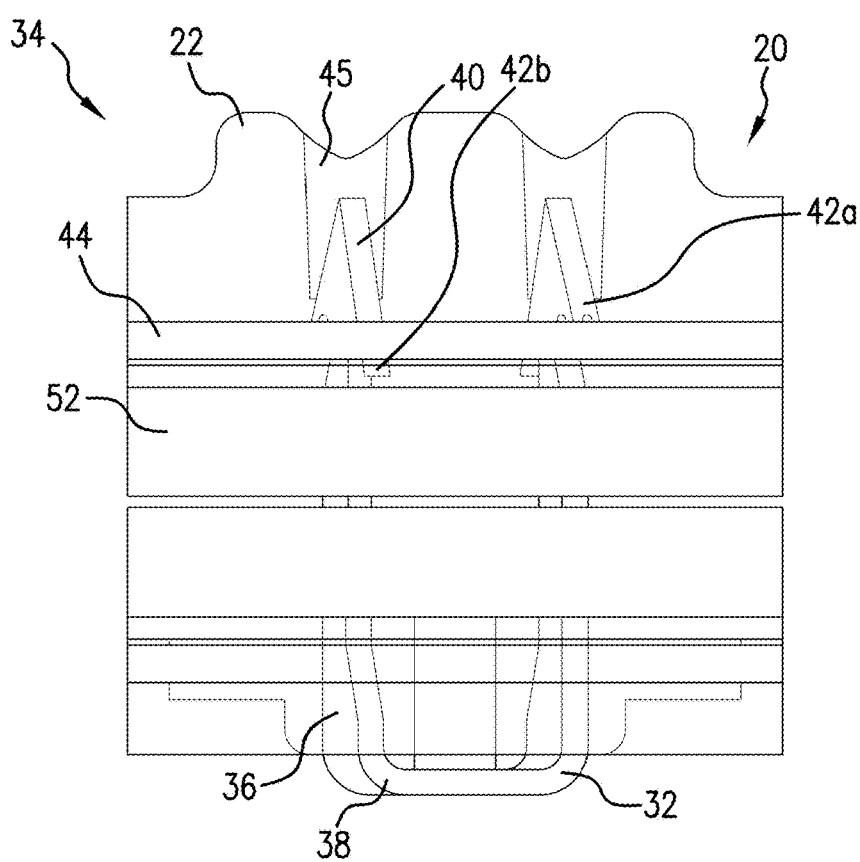
FIG. 13C is another side view of the implant of FIG. 9 showing the implant engaging the relatively thick structure, with barbs catching or otherwise engaging a retainer.

FIGS. 9-11 show an example of one of the subassemblies 34 sealing a thin surgical structure 50, at which the towers 30 have a partially compressed height h2, and FIGS. 12-14 show an example of one of the subassemblies 34 sealing a thick surgical structure 52, at which the towers 30 have a minimum or fully compressed height h3. As the thickness of the surgical structure increases, the towers 30 are further compressed from their initial height h1 toward the minimum height h3 in order to enable the legs 36 of the fasteners 32 to span the increased difference and engage with the retainer 44. It should also be recognized that surgical structures of varying thickness can be fastened and/or sealed with the same implant, such that some towers of the implant compress to the height h2 while others compress to height h3, or to other heights between the heights h1 and h3, while in their retained state. Advantageously, even if different towers 30 of the same implant 10 are compressed to different heights, e.g., due to the surgical structure having different thicknesses, the surgical structure contacting surfaces 18 and 26 will not become distorted, wrinkled, buckled, bent, etc., and therefore be able to contact flush against the surgical structure along the entire length of the implant 10. Stated differently, the independent compressibility of each of the towers 30 allows for adjacent towers 30 to compress to different degrees independently of and without imparting potentially undesirable stresses to adjacent towers 30 when the implant 10 is installed on surgical structures of varying thicknesses.

Figure 15:
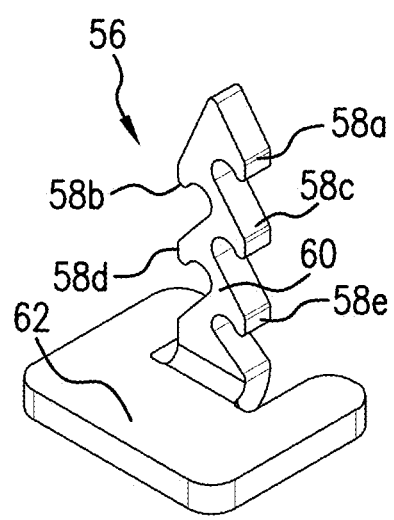
FIG. 15 is a perspective view of a fastener according to an example alternative embodiment.

The offset between the barbs 42a and 42b along the length of the legs 36 can also facilitate the accommodation of each size of the fasteners 32 to be usable for a range of surgical structure thicknesses. This functionality can be appreciated by comparing FIGS. 11 and 14. Specifically, in FIG. 11, the structure 50 is relatively thin, so the tips 40 are able to easily extend deeply through the receiver member 12, such that both of the barbs 42a and 42b pass fully through the retainer 44, and the barbs 42b engage therewith when the driving force is released. In the embodiment of FIG. 14, the increased thickness of the structure 52 may be such that only the barbs 42a, further along the length of the legs 36, are able to penetrate fully through and be retained by the retainer 44. It is to be appreciated that any number of barbs may be included along the length of the leg(s) of the fasteners and that each fastener may have any number of legs. For example, a fastener 56 is shown in FIG. 15 having five barbs 58a-e along its length, and only a single leg 60 extending from a body 62.

Figure 16A:
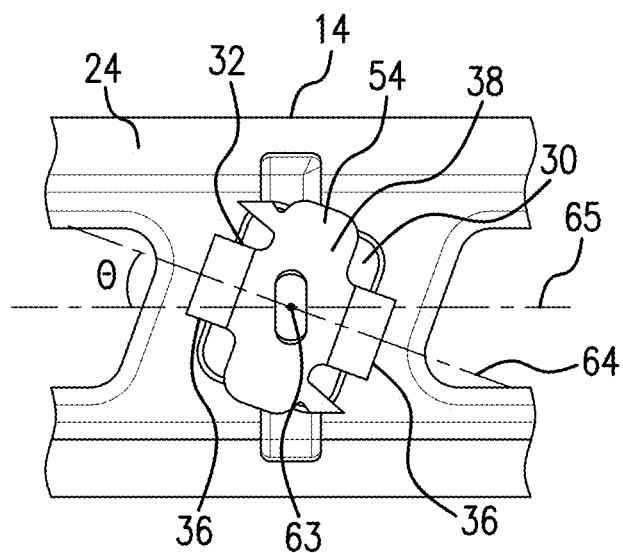
FIG. 16A is a top view of the section of an implant according to an example embodiment.
Figure 16B:
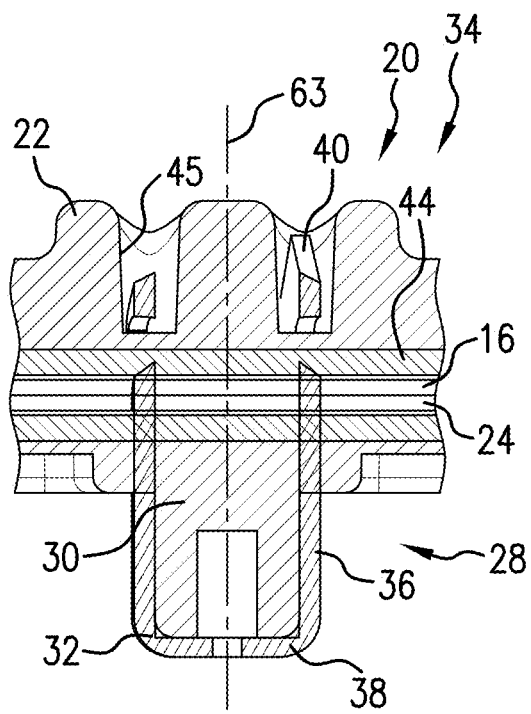
FIG. 16B shows a sectional view taken through section line 64 of FIG. 16A.

It is additionally noted with respect to FIG. 11 that the barbs 42 can be arranged to face opposite from each other, as with the barbs 42a in this Figure, such that the retainer 44 is grabbed by the fasteners 32 at different locations, e.g., at different ones of the strands 46a, as illustrated. This may be helpful in some embodiments to spread out the loading on the retainer 44, e.g., and prevent localized overloading of a single strand or of the implant 10. That is, the barbs are positioned in interstices along different lines of the interstices. If desired, e.g., in order to further spread out the loading, the fasteners 32 may additionally or alternatively be rotated, offset, or misaligned with respect to the members 12 and 14, the retainer 44, the strands 46, etc. That is, as shown by example in FIG. 16A, the legs 36 of the fastener 32 may be rotationally orientated about an axis 63 of the towers 30 by an angle θ, such that a line 64 bisecting the legs 36 is rotationally offset by the angle θ with respect to a datum line 65 (which may be oriented to be parallel with the member 14 and/or bisect the member 14). In one embodiment, the angle θ is between about 5° and about 45°, and in a further embodiment, the angle θ is about 20°, although those of ordinary skill in the art can select other angles outside of these values, including arranging the axes 64 and 65 to be parallel or perpendicular to each other. It is also contemplated that different legs 36 of different fasteners 32 may be oriented to different degrees.

Figure 17:
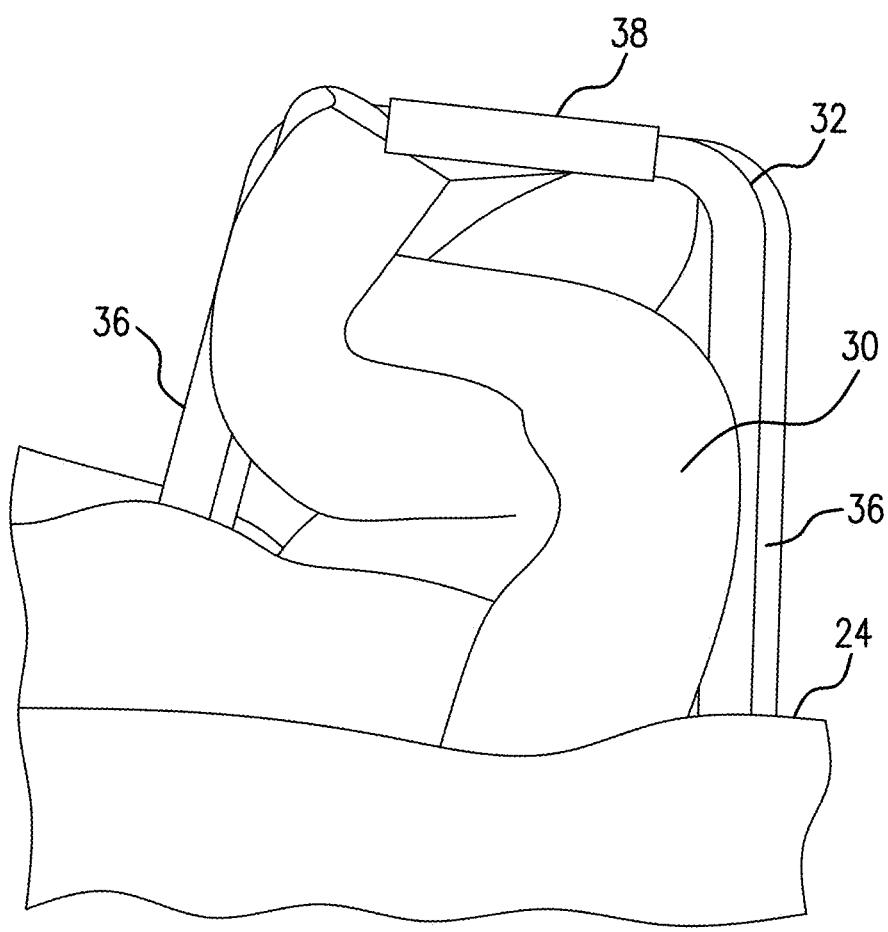
FIG. 17 shows a tower of the implant under compression, according to an example embodiment.

It is noted that the towers 30 are shown schematically in their compressed states throughout many of the Figures for clarity of illustration, but that in actual use some degree of buckling, twisting, bending, or bulging of the towers 30 may occur during compression by the fasteners 32. One such example of the compression of one of the towers 30 is illustrated in FIG. 17, in which the illustrated tower 30 is buckling, bending, and bulging due to compression caused by the fastener 32. It can be appreciated that in addition to connecting the two legs 36 together, the body 38 may also be shaped to assist in maintaining engagement between the fasteners 32 and the towers 30. For example, the fasteners 32 in the illustrated embodiment include a pair of wings 54 (e.g., FIGS. 6 and 9) to increase the contact area between the fasteners 32 and the towers 30 and thereby maintain contact with the towers 30 even as they change shape during bucking, bulging, bending, or other distortion. It is also noted that one or more supports 39 may optionally be included with the towers 30 in order to assist in setting the rigidity, bending stiffness, or other properties of the tower 30 (e.g., thereby influencing the force exerted by the towers 30 during compression), and/or to assist in directing the aforementioned buckling, bending, etc., to occur in a more consistent and/or predictable manner. For example, in the illustrated embodiment, the supports 39 are located approximately equally spaced between the legs 36 of the fastener 32 in order to promote the buckling to occur under the body 38 and to assist in preventing the tower 30 from becoming disengaged from the fastener 32 during compression.

Figure 18:
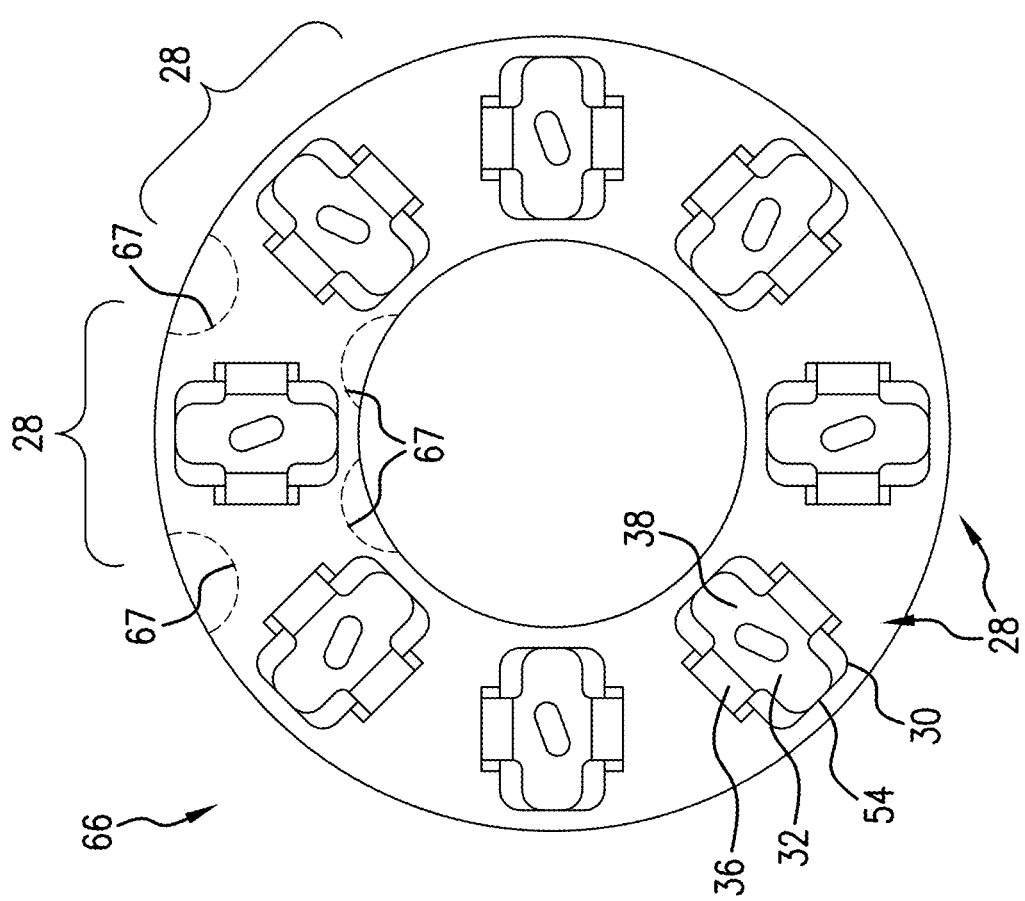
FIG. 18 is a top view of an implant according to an example embodiment, showing the implant configured in a curved array such as a circular array.
Figure 22:
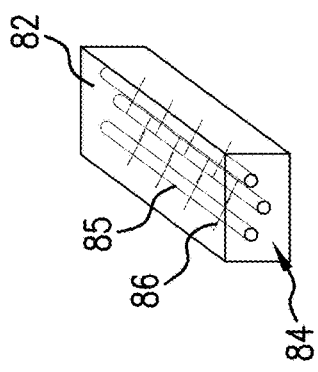
FIGS. 20 through 26 show perspective views of various retainer constructions, according to various example embodiments.
Figure 26:
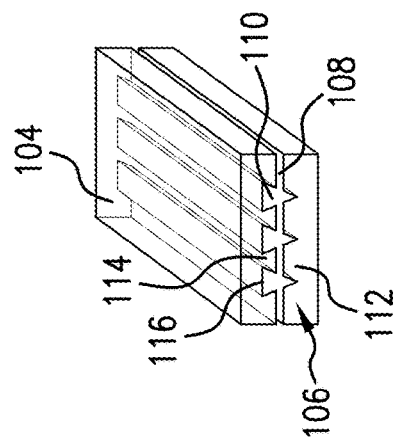
Figure 21:
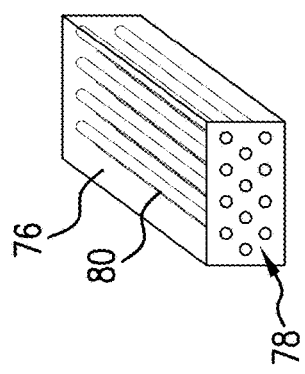
Figure 24:
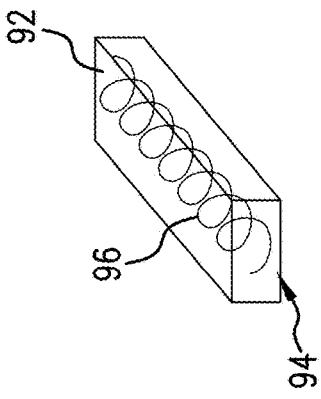
Figure 25:
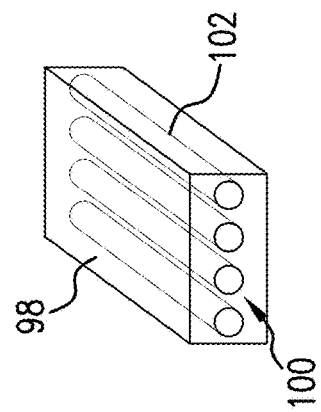

The implant 10 is illustrated in a variety of disclosed embodiments to be essentially longitudinally straight and elongate, having a first end and a second end (e.g., see FIGS. 1-2, 27, 28, 31-33). In these embodiments, the individual fasteners are arranged along a longitudinally extending row substantially parallel to a longitudinal axis of the fastener supporting member, and the fastener supporting member has a length exceeding its width (and the width of the fastener receiving member which also has a length exceeding its width). If multiple rows are provided, the rows are preferably substantially parallel. It is to be understood that other implant shapes can be used. For example, FIG. 18 shows a top view of an implant 66 according to an alternate embodiment. As can be seen in this Figure, the implant 66 is circular, disc, or ring shaped, with a plurality of the segments 28 disposed thereabout (a plurality of the segments 20 in a receiving member would be arranged opposite thereto, but are hidden from view in FIG. 18). Such an implant may be useful, for example, in so-called end-to-end, side-to-side, and/or end-to-side operations, such as gastric bypass in which an end section of a patient's intestine is secured to the patient's stomach about an opening formed in the wall of the stomach. A circular cutting knife (including for instance a knife that can follow a circular path consistent with the circular implant 66) can be utilized with the device applying circular implant 66.

Figure 19:
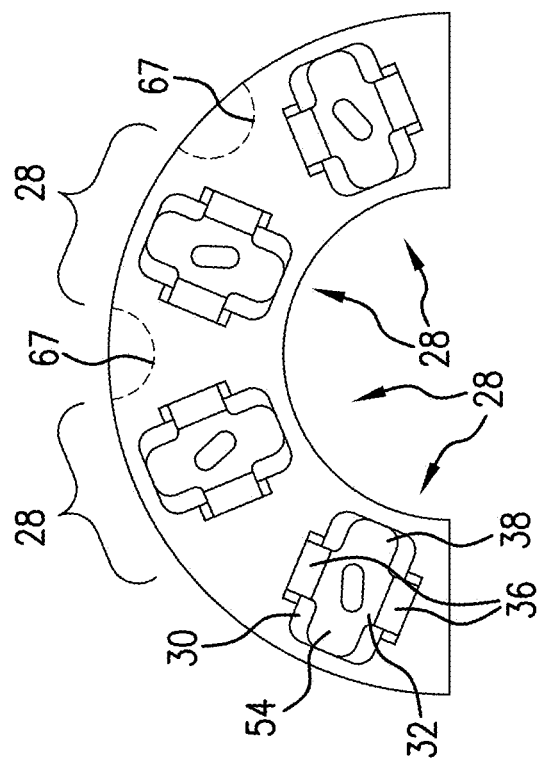
FIG. 19 is a top view of an implant according to an example embodiment, showing the implant configured in an arcuate or curved array, such as a partial circular array.

An implant 68 is illustrated in FIG. 19 according to another embodiment. The implant 68 is shaped along an arc or curve, and also includes a plurality of the segments 28 (corresponding to a plurality of the segments 20 of a receiver member, hidden from view in FIG. 19). Such an implant may be useful for complex tissue structures, or bulk tissue structures having curvature thereto, such as lungs or other organs. The implant is shown in an approximately 180° arc, however, implants of larger and smaller arcs may be desirable depending on the particular surgical procedure. An arcuate cutting knife or blade (or at least a blade intended to follow the general path of the arc-shaped implant) can be utilized. Additionally, in any of the disclosed embodiments, the outermost lateral regions of the bases of the implants may be cut or "scalloped" (see for example dotted border 67 shown in FIGS. 18 and 19) in a manner that provides for enhanced bending in a direction that facilitates allowing additional curvature to arrange the implant 66 or 68 to a final shape different than its original shape.

It is also to be understood that the retainer 44 can take a plurality of other forms embedded or supported within the base of a receiver member. For example, FIGS. 20-26 depict various receiver bases having different retainers therein, which can be used additionally with, or alternatively to, the retainer 44. As with the base 16 and the retainer 44, each of the bases and retainers in FIGS. 20-26 can be arranged with the base made of a relatively soft, flexible, or penetrable material, while the retainer is made from a relatively stronger or stiffer material, or a material otherwise having different material properties, including but not limited to different moduli of elasticity, Shore hardness values, yield strengths, etc.

Figure 20:
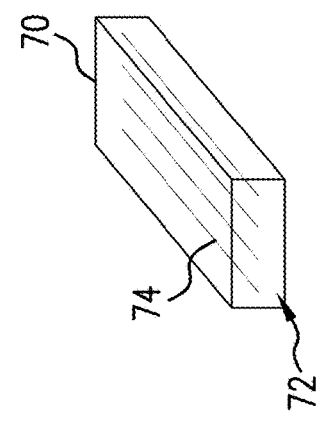
Figure 23:
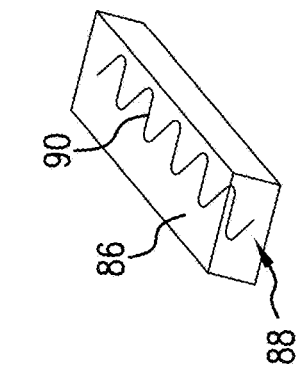

An exemplary receiver base 70 in FIG. 20 includes a retainer 72, which takes the form of a plurality of strands 74. The strands 74 resemble the longitudinal strands 46a of FIG. 7A, but without the transverse strands 46b, and are also preferably arranged to be coplanar with each other, and/or parallel to the dorsum of the base 70. An exemplary receiver base 76 in FIG. 21 has a retainer 78 that substantially resembles the retainer 72, being formed from a plurality of longitudinal strands 80. Unlike the retainer 72, the strands 80 of the retainer 78 are located at a plurality of different heights within the base 76, and therefore not all are coplanar with each other. A receiver base 82 in FIG. 22 includes retainer 84 formed from a plurality of longitudinal strands 85 having transverse pins, arms, or fingers 86 extending therefrom. Such transverse members may be formed unitarily with the strands 85, or alternatively may be non-unitary and attached or connected. A receiver base 86 in FIG. 23 includes a retainer 88 formed by one (shown) or more (not shown) undulating or sinusoidal strands 90. A receiver base 92 in FIG. 24 includes a retainer 94 formed by one or more coiled, helical, or spiraling strands 96. A receiver base 98 in FIG. 25 includes a retainer 100 formed by a plurality of fuzzy, tangled, intertwined, yarn-like, or braided strands 102. A receiver base 104 in FIG. 26 includes a retainer 106 formed by a plate or membrane 108 having a plurality of tapered elements 110. The tapered elements 110 form an entry opening 112 that is significantly larger than an exit passage 114 due to shoulders 116. In this way, the tips 40 of the fasteners can pass by the entry passage 112, pierce through the membrane 108, and push the elements 110 aside to pass through the exit passage 114 while moved in the actuation direction, and then be caught on the shoulders 116. The retainers of FIGS. 20-26 can extend the full length or partial length of the receiver base, and can extend the full width or partial width of the receiver base. The retainers of the embodiments disclosed herein can in certain embodiments be fully embedded in the receiver member such that it is out of contact with tissue or other surgical structure engaged by the implant.

Figure 27A:
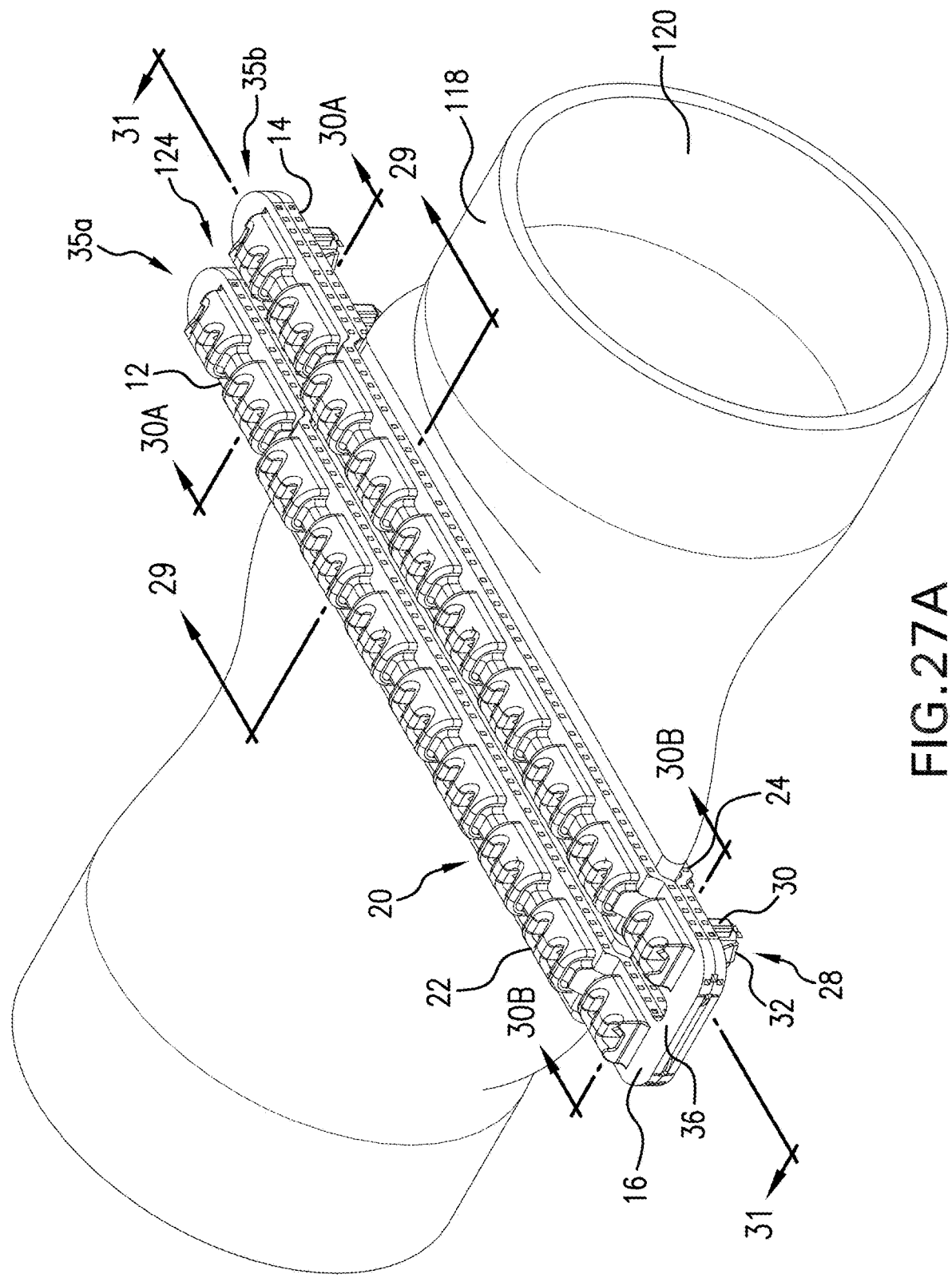
FIG. 27A is a perspective view of an implant placed about a tissue or vessel structure according to an example embodiment.
Figure 27B:
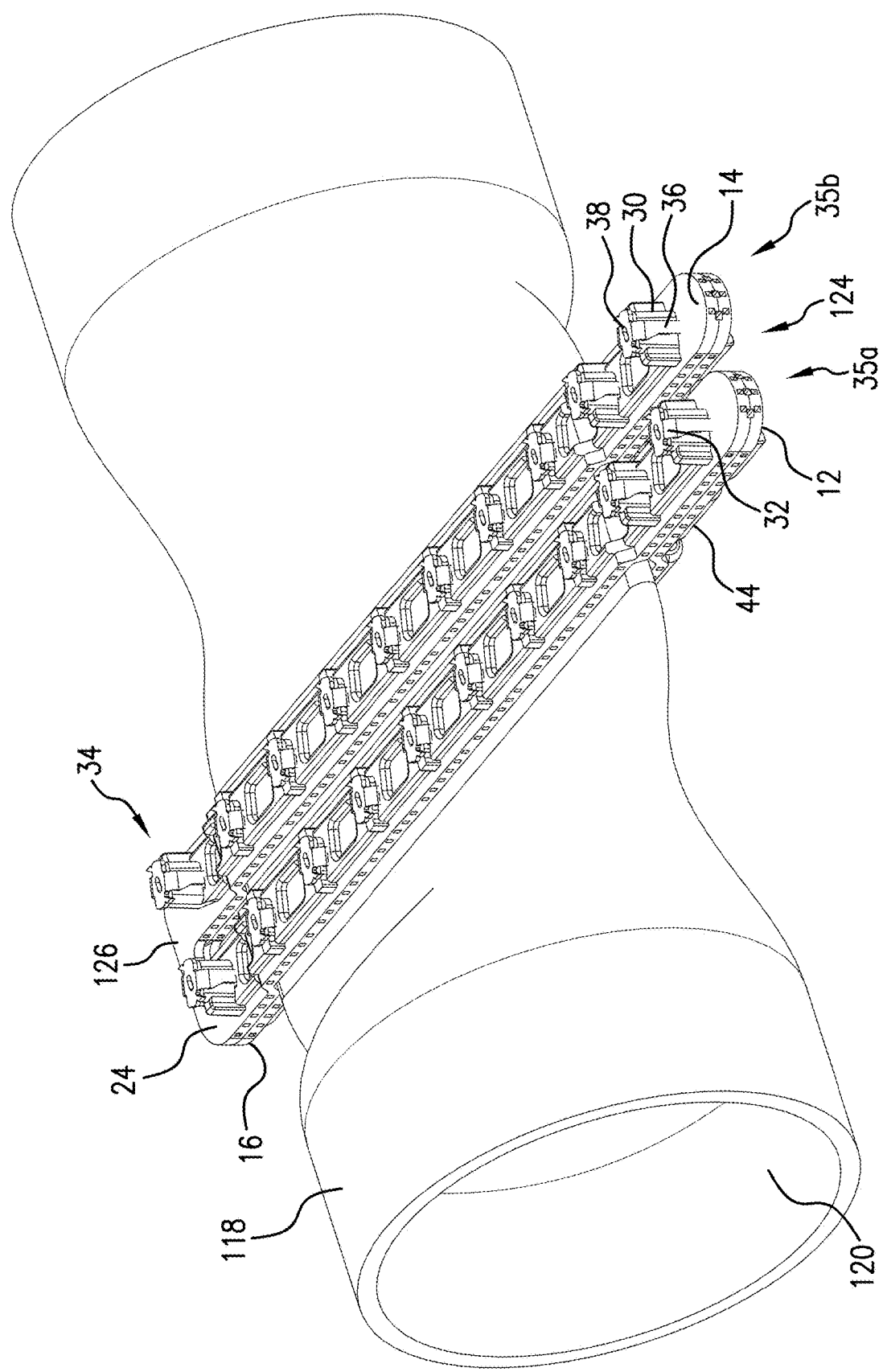
FIG. 27B is a perspective view of the implant shown in FIG. 27A from the opposing side.
Figure 27C:
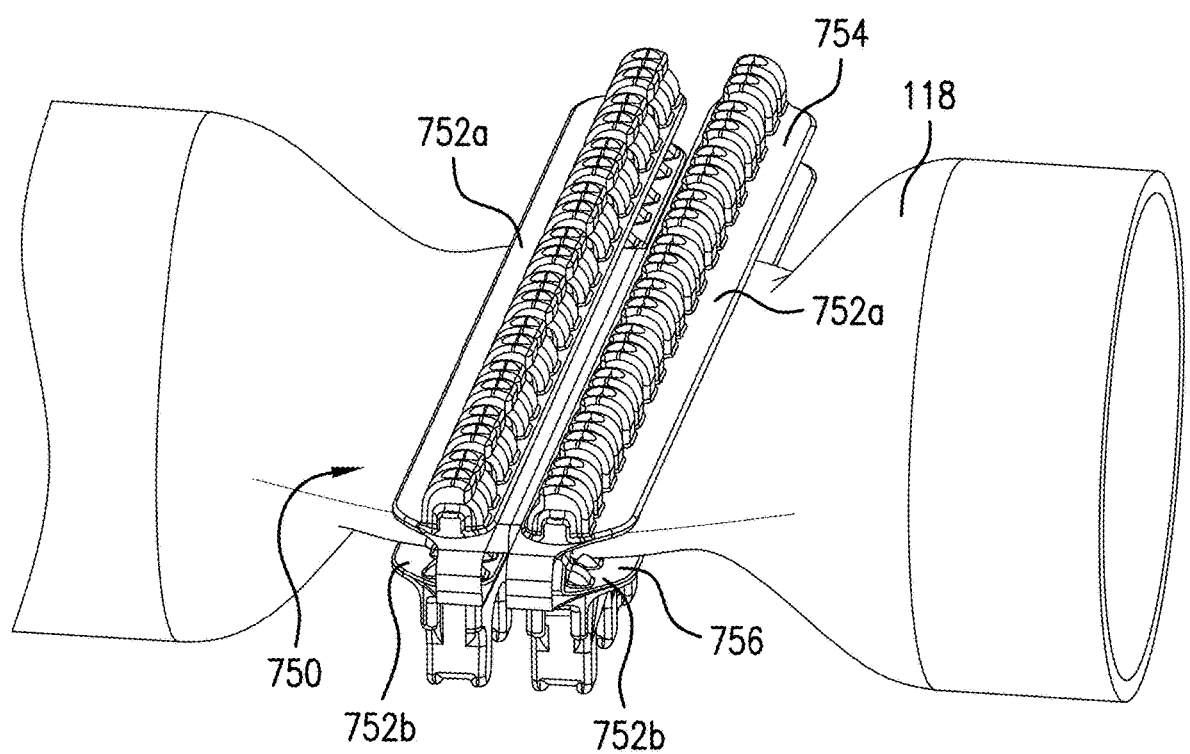
FIG. 27C is a perspective view of the implant placed about a tissue or vessel structure according to another example embodiment.

FIGS. 27A and 27B illustrate the implant 10 of FIGS. 1 and 2 installed on a vessel 118 type of surgical structure, e.g., a conduit such as a vein or artery. The vessel 118 includes a lumen 120 extending therethough, i.e., preferably for carrying blood. Installing the implant 10 on the vessel 118 (that is, compressing the vessel 118 between the members 12 and 14, and securing (coupling) the members 12 and 14 together with the fasteners 32, closes or pinches off the lumen 120, which may be useful, for example, in preventing or impeding blood flow through the lumen 120 of the vessel 118. It may be desired, for example, to seal off a blood vessel during a vessel harvesting operation, e.g., in preparation of using the harvested vessel in a graft surgery such as CABG. For example, in order to harvest a vessel, a first one of the implants 10 can be installed in a first location of a target vessel, a second one of the implants 10 installed at a second location of the vessel, with the vessel portion between the two implants 10 removed from the patient.

FIGS. 27C-27F illustrate an alternate embodiment of an implant installed on a vessel type of surgical structure. The implant 750 is identical to the implant 10 except for the provision of flaps or flanges 752. Therefore, only the flaps 752 will be discussed in detail, it being understood that the implant 750 includes a receiver member, deployment member, compressible members, e.g., towers, fasteners, retainers, etc., in the same way as described in detail with regard to implant 10. Consequently, the discussion of implant 10 (and its variations of structure and components) is fully applicable to the implant 750 of FIGS. 27C-27F. Implant 750 has a pair of flexible flaps 752a on the receiver member 754 and a pair of flexible flaps 752b on the deployment member 756. The flaps 752a, 752b are referred to collectively as the flaps 752. The flaps 752 create a softer sealing pressure gradient of tissue. The flaps 752 extend from the edge of both the receiver member 754 and the deployment member 756, extending radially (laterally) on opposing sides of these members 754, 756. In the preferred embodiments, the flaps 752 have a sufficient width to perform their pressure distribution function but are of small enough width so they do not require an increase in the overall width of the jaws of the applicator which support the receiver member 754 and the deployment member 756.

Figure 27D:
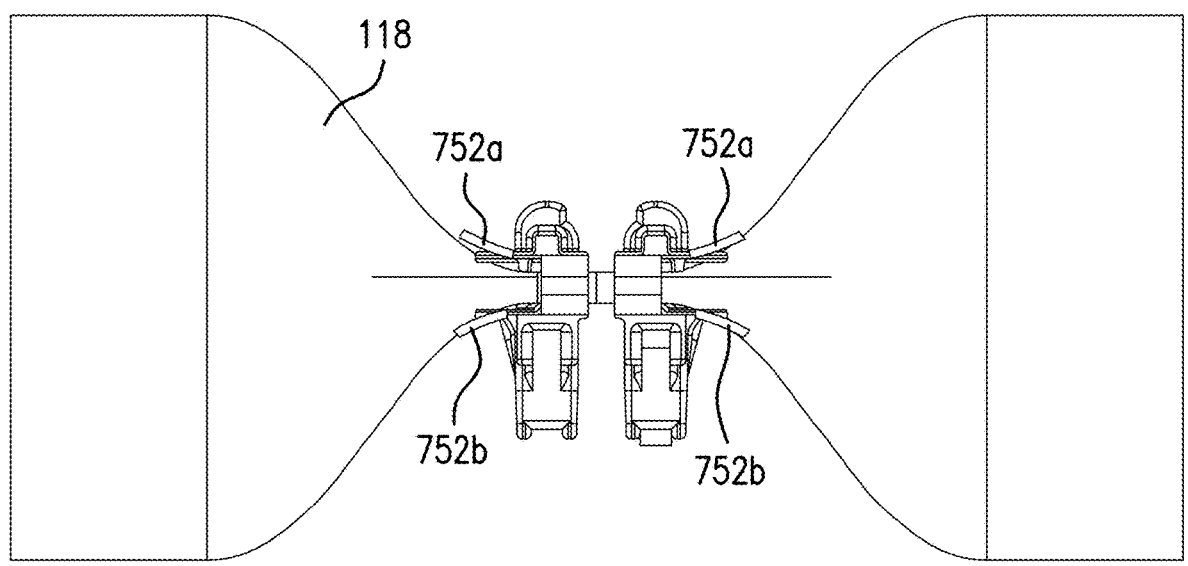
FIG. 27D is an end view of the implant of FIG. 27C.
Figure 27E:
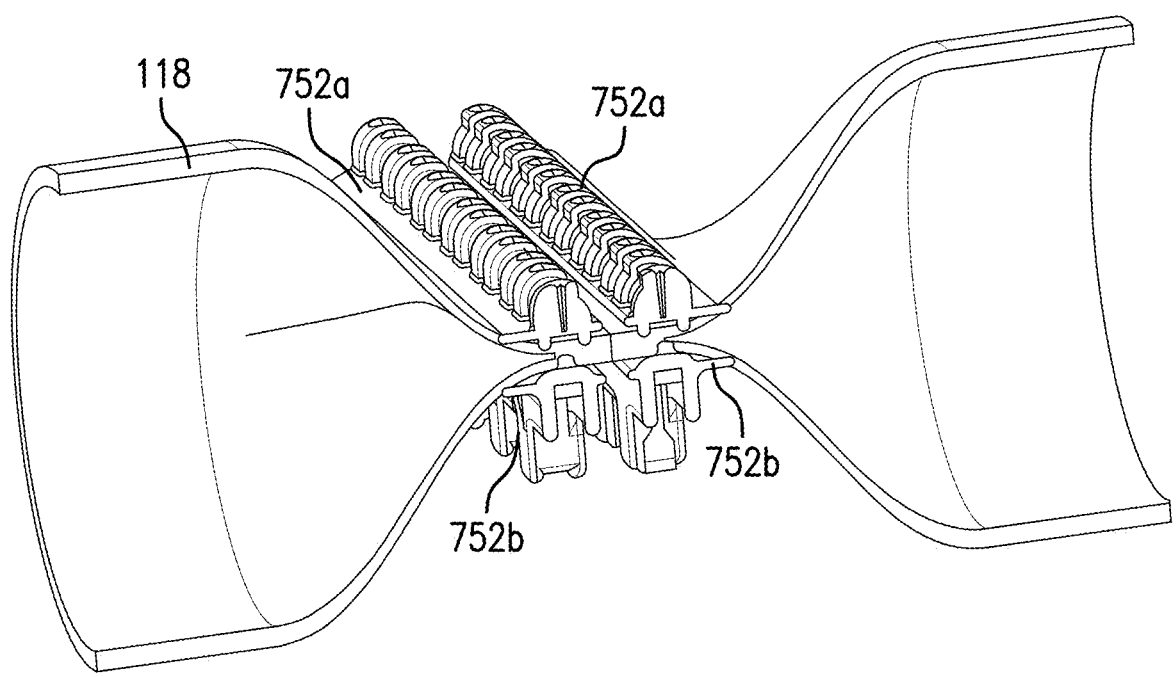
FIG. 27F is a close up view of the implant of FIG. 27E (with the vessel not shown)
FIG. 27G is a close up view of an alternate embodiment of the towers of the implant.

In the illustrated embodiment, the flaps 752 are a continuation of the implant material itself, such as a continuation of the silicon and retainer, e.g., mesh, and are formed with sufficient stiffness to distribute the sealing pressure over a greater distance than would be distributed in the absence of the flaps. In some embodiments, the flaps 752 can distribute the sealing pressure on vessel 118 over a distance of approximately 3 mm, although other sizes, configurations and structure of the flaps are also contemplated to distribute pressure over different distances. The end view of FIG. 27D shows the flexure of the flaps 752 when applied to tissue or to surgical structure; the end views of FIGS. 27E and 27F do not show such flexure. The vessel 118 is shown by way of example as the implant 750 can be applied to other structures as well. Additionally, other implants described herein could be provided with the flaps to distribute the pressure.

As can be appreciated, with the provision of the flaps 752, which extend radially from the implant 750, and illustratively extend along the length of the implant 750, instead of going from sealing pressure to no pressure in a short distance which can increase the risk of tearing tissue, the flaps 752 spread the pressure gradient from sealing to no pressure over a greater distance to thereby reduce stress on tissue. In order to seal tissue, the tissue (or other surgical structure being clamped between the deployment and receiver members) needs to be brought into approximation, and this transition from bulk tissue to sealed tissue creates significant stresses on the tissue. The amount of stress is dependent on how quickly the sealing pressure is developed. The sharper the change in pressure, the greater the stress of the tissue, and the greater the stress on the tissue, the greater the chance that the tissue can tear and create a leak. An example of such occurrence is in lung parenchyma which in certain applications can transition from bulk tissue of about 30 mm thickness to sealed tissue at less than 4 mm thickness. Lung parenchyma is also fragile, and if such change occurs over too short a distance, the tissue may be overstressed and can tear, which can adversely affect the sealing function. Such abrupt transition is not fully accounted for in current staples.

The stiffness of the flaps 752 can be varied to provide increased stiffness for use, for example, in stiffer tissue. The length of the flaps can also be varied, e.g., extending the entire length of the implant or over less than the entire length. Moreover, the flaps 752 as described above are a continuation of the implant composed for example of silicon, e.g., the same material as the deployment member 756 (which can be the same materials used for deployment member 14) and the receiver member 754 (which can be the same materials as used for the receiver member 12), with a portion of the retainer, e.g., mesh, contained (e.g., embedded) therein. Alternatively, the flaps could not include the retainer therein and/or the flaps could be made of a different material than the deployment member 756 and/or the receiver member 754. The flaps 752 also could be separate components and not integral with the implant material, i.e., not integral with the deployment member 756 and/or receiver member 754. Alternatively, the flap could be provided on only one of the receiver member 754 or deployment (fastener supporting) member 756 and not on both the receiver member and deployment member as described above.

Figure 27F:
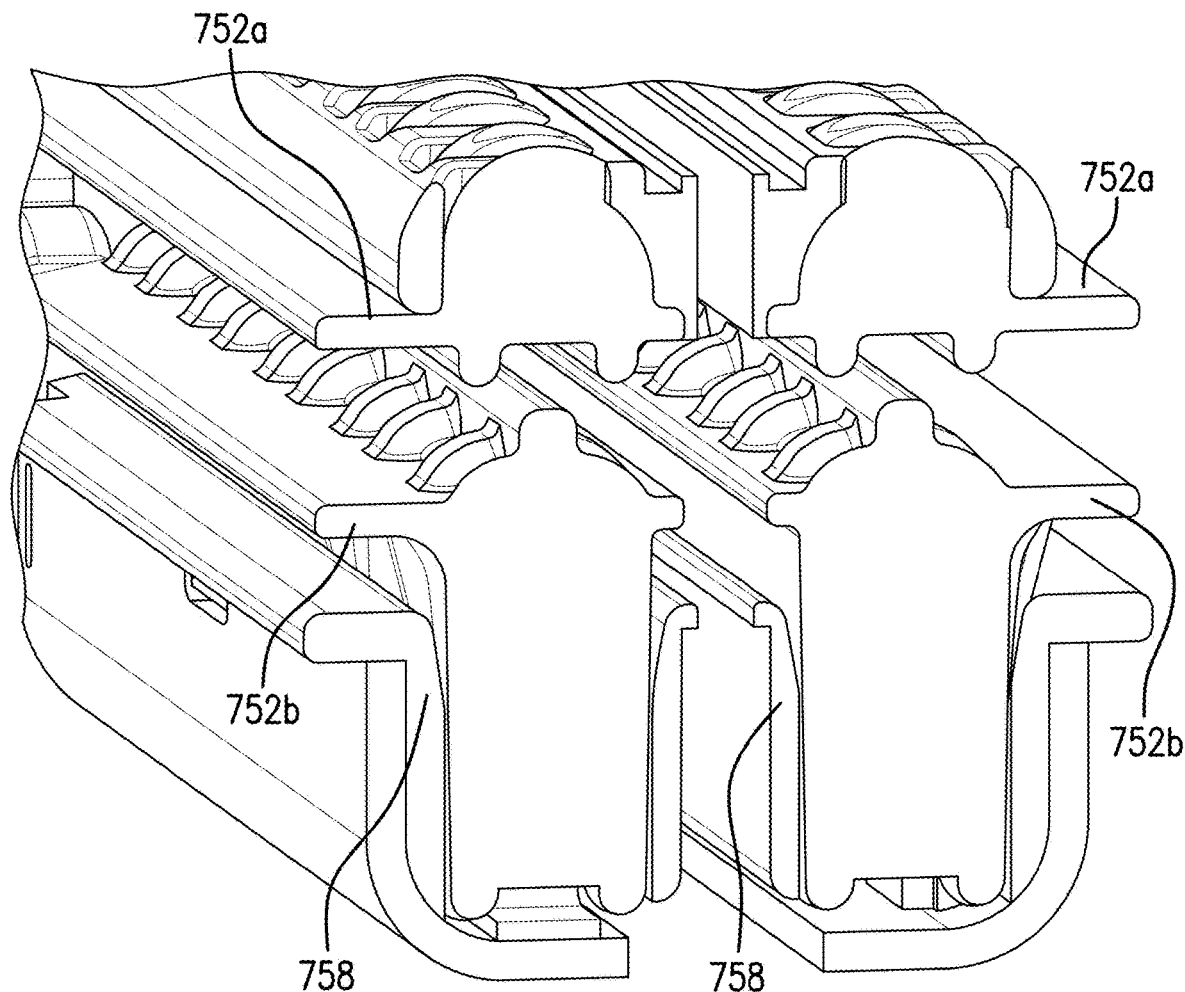

As also shown in the embodiment of FIG. 27F, a gap or space 758 can be provided in the implant 750 adjacent the compressible members. This provides space for the compressible members, e.g., towers 30, of the implant to laterally expand when compressed by the fasteners 32, or other fasteners disclosed herein. Such gap 758 facilitates release of the fasteners 32 from the jaw of the applicator which applies the implant. (The applicator for applying the implant is described below). That is, when the towers 30 are compressed by the fasteners 32 in the manner described above, since they have room to expand laterally, the possibility of the towers 30 binding to the jaw and not releasing easily from the jaw is reduced.

Figure 27G:
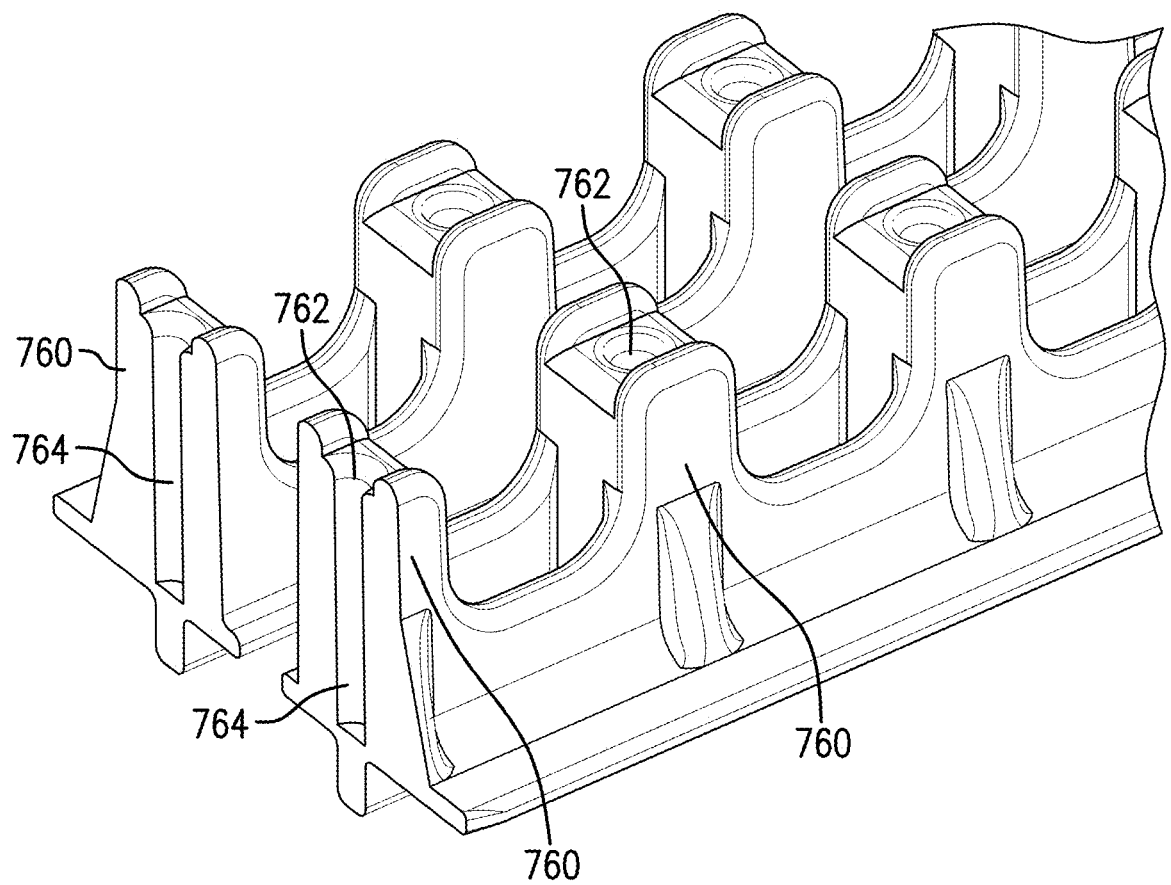
Figure 28:
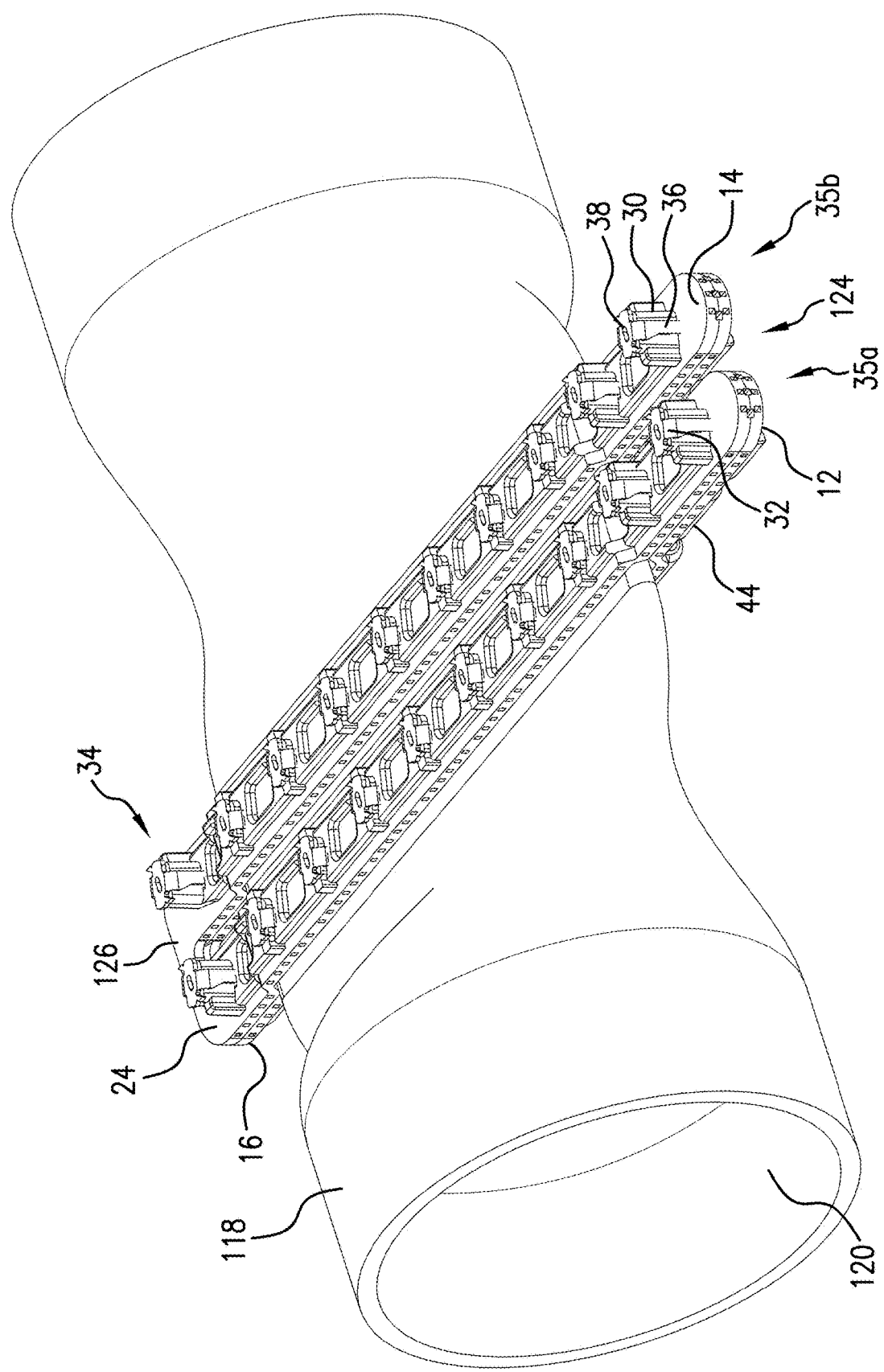
FIG. 28 is a perspective view of an implant placed about a tissue or vessel structure according to an example embodiment.

FIG. 27G illustrates an alternate embodiment of the compressible members of the present disclosure which reduce the extent of lateral expansion which can be beneficial in certain applications. As shown, the compressible members of the implant which are engaged and compressed (deformed) by the fasteners 32 in the manner described above as the fasteners 32 are advanced from the deployment member 14 toward and into the receiver member 12, are in the form of tower like structures as in towers 30 of FIG. 5. However, in this alternate embodiment, the towers, designated by reference numeral 760, have an opening 762 at its dorsal end and an elongated channel 764 extending therethrough, or at least partially therethrough. The channel 764 provides a hollowed out area to give the tower 760 volume to expand into when compressed by its respective fastener 32, or other fasteners described herein. The channel 764 is shown centered within the tower 760, aligned with the longitudinal axis of the tower 760. By enabling expansion in an interior toward the longitudinal axis of the tower 760, the extent of radial (lateral) expansion in directions away from the longitudinal axis is reduced which can reduce the likelihood of the towers 760 binding to the applicator jaw and make release of the implant from the applicator jaw easier. Release with minimal force reduces the risk of injuring sealed tissue or dislodging the fasteners or implant. For clarity, not all of the towers are labeled in FIG. 27G. Note also that FIG. 27G shows two of the towers sectioned (one in each of the longitudinally extending rows) to better illustrate the channel 764. Note the towers 760 with channels 764 can be utilized with the feature of gap 758 of FIG. 27F or used without such feature. The compressible members 760 with channels 764 can be used with other implants described herein and can be arranged aligned with the longitudinal axis of the fastener supporting member or at an angle to the longitudinal axis in accordance with the various embodiments described herein.

Referring back to implant 10, in order to facilitate removal of a portion of the tissue structure in which the implants disclosed herein are installed, e.g., for harvesting a portion of the vessel 118, removing cancerous tissue or tumors, performing a gastric bypass, etc., the implant 10 in the illustrated embodiment includes the two rows 35a and 35b. A channel 124 is formed between the two rows 35. By first actuating the fasteners 32 in both of the rows 35 and then cutting the tissue along the channel 124 between the rows 35, the tissue structure on both sides of the cut will be sealed by the implant 10. The bridge(s) 37 (see FIG. 1) connecting between the rows 35 may be severed during cutting. While the bridges 37 are shown in various embodiments to be on one end of elongate implants, in embodiments contemplated herein, they may be on both ends.

Figure 30A:
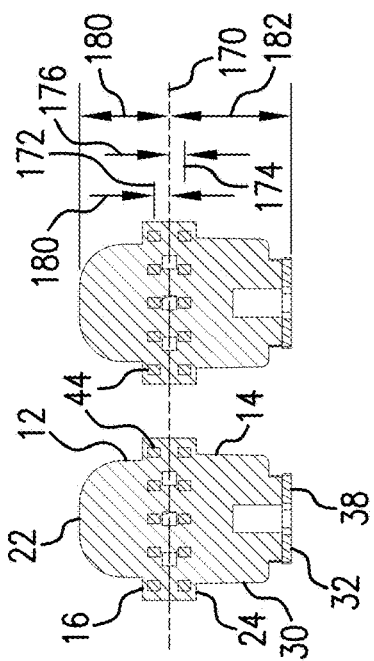
FIG. 30A shows a cross-sectional view of the implant taken about section line 30A-30A in FIG. 27A.
Figure 30B:
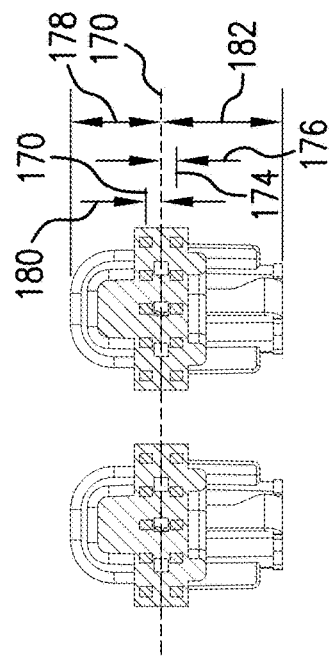
FIG. 30B shows a cross-sectional view of the implant taken about section line 30B-30B in FIG. 27A.
Figure 29:
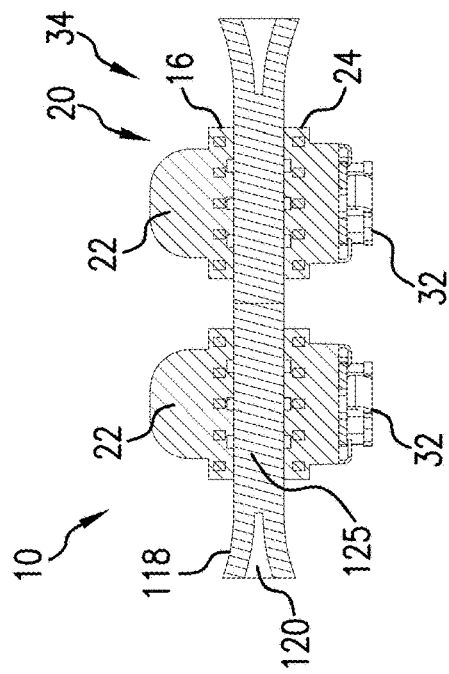
FIG. 29 shows a cross-sectional view of the implant taken about section line 29-29 in FIG. 27A.
Figure 31:
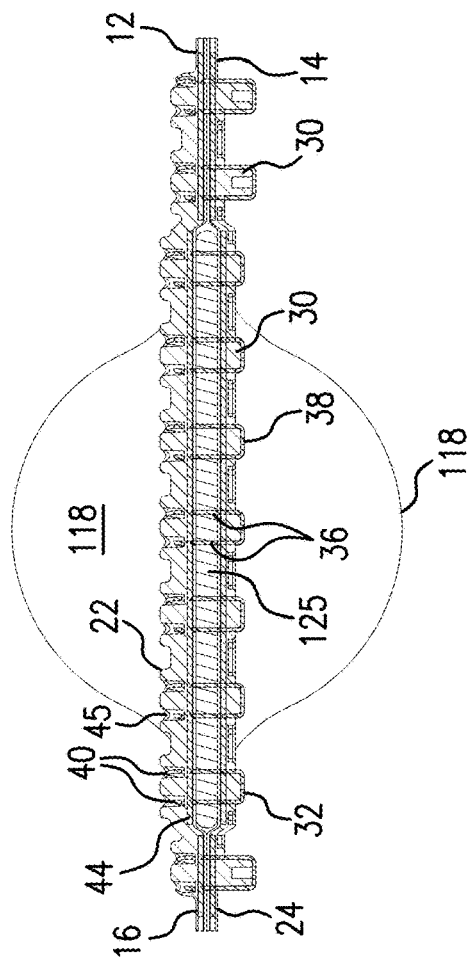
FIG. 31 shows a cross-sectional view of the implant taken about section line 31-31 in FIG. 27A.

A seal 125 in the tissue or vessel 118 formed by the implant 10 can be seen in FIGS. 30A and 31. The seal 125 represents the portion of the vessel 118 that is compressed or clamped by the implant 10 and can be helpful, for example, in preventing, blocking, hindering, or otherwise impeding the flow of blood through the vessel 118. The above-discussed independent compressibility of the towers 30 and the operation of the towers 30 compressing to various degrees in response to different surgical structure thicknesses are also easily appreciable in view of the cross-sections of FIGS. 29-31. For example, it can be clearly seen that the height of the towers 30 in FIG. 30A, which Figure is taken in cross-section at a location with no tissue, is substantially less than the height of the towers 30 in FIG. 29, which Figure is taken in cross-section through the implant 10 installed on the vessel 118. FIG. 30B is a cross-section taken through the region between the towers 30 and not in contact with the tissue or vessel, as shown by section line 30B-30B of FIG. 27A FIG. 31 is a longitudinal cross-section extending down the longitudinal length of a row of the implant 10, which also shows the difference in the compressed tower height in response to tissue thickness.

Figure 32:
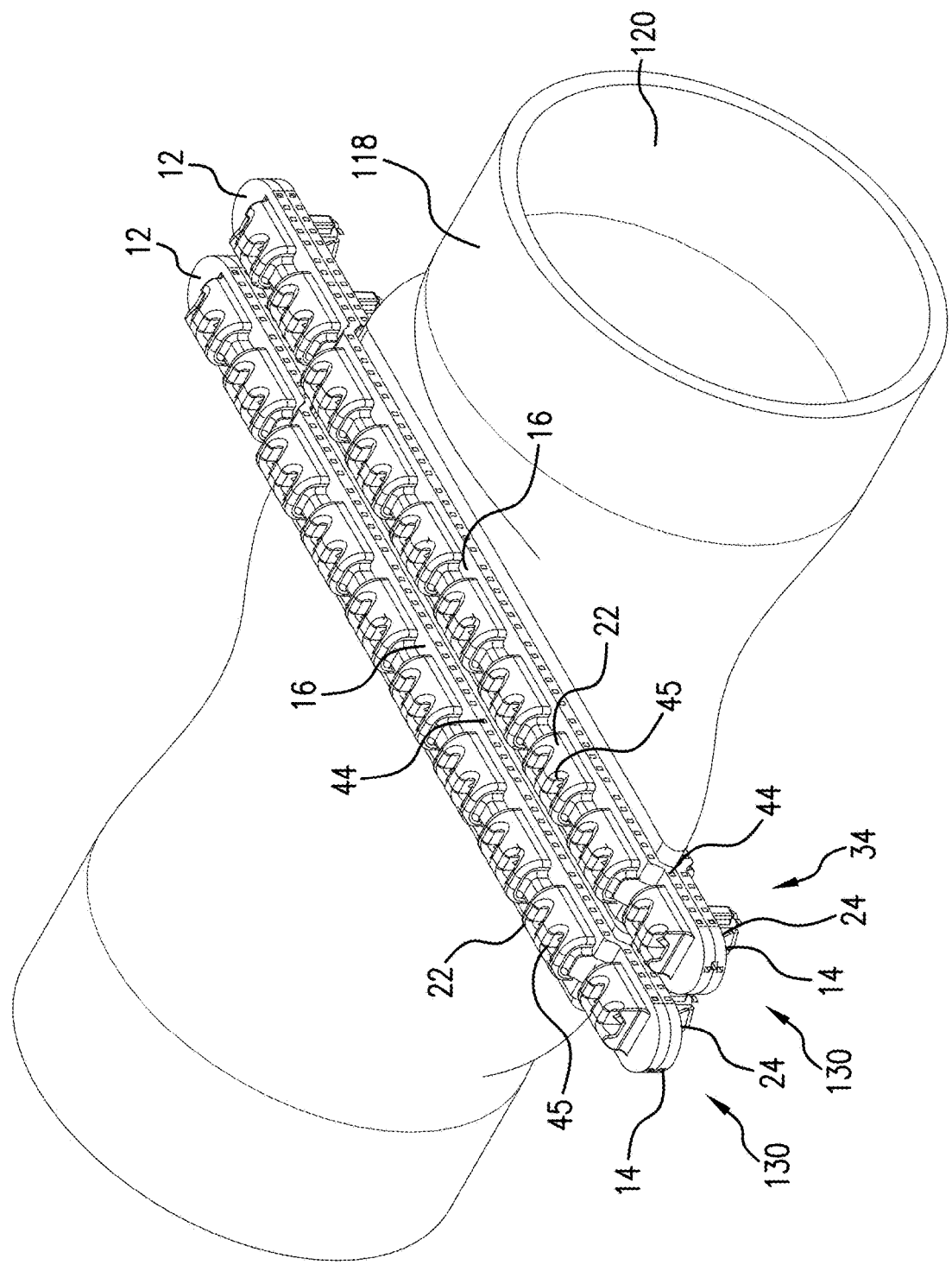
FIG. 32 is a perspective view of two single row implants placed about a tissue or vessel structure according to an example embodiment.
Figure 33:
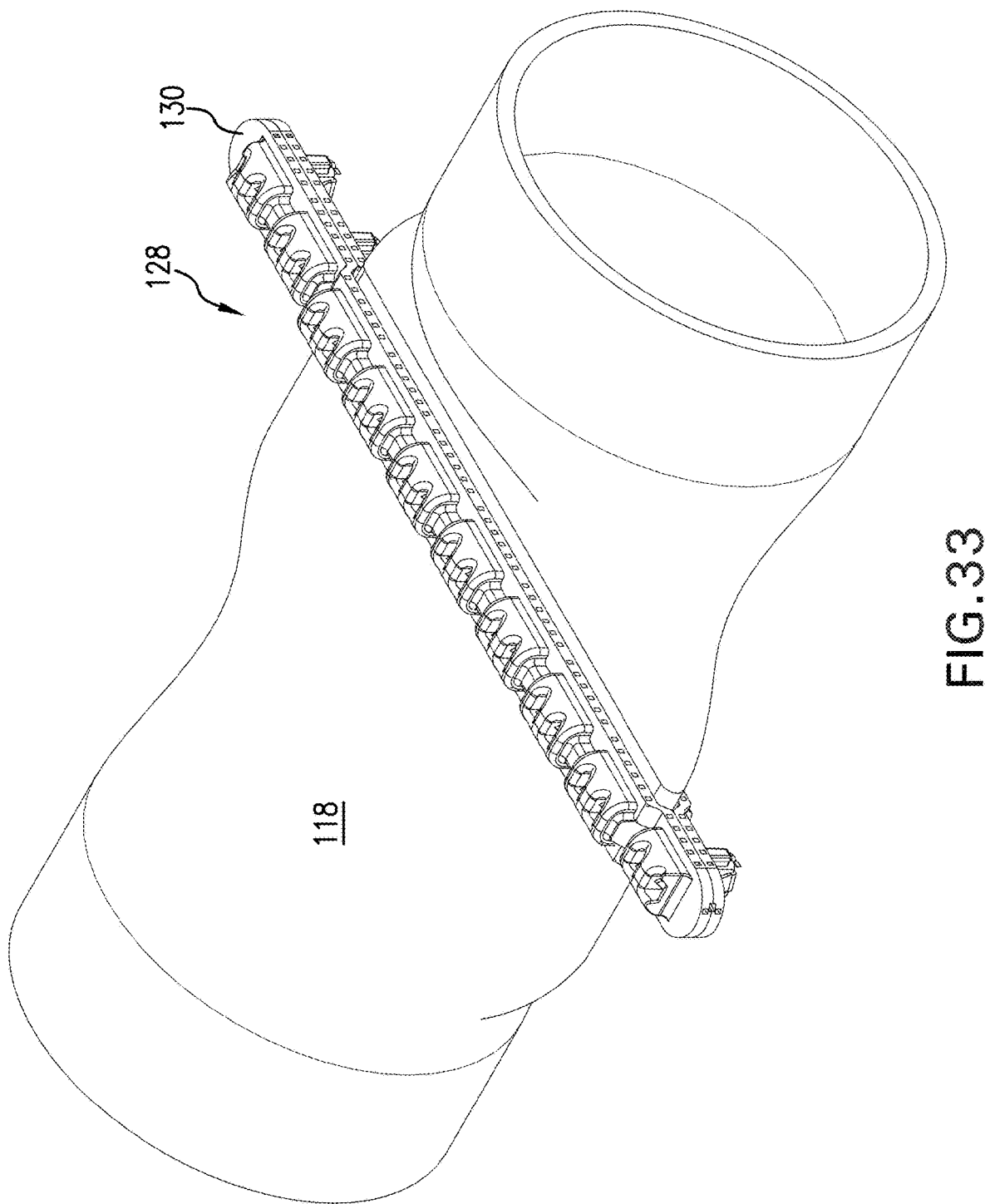
FIG. 33 is a perspective view of a single row implant placed about a tissue or vessel structure according to another example embodiment.

An implant 128 according to another exemplary embodiment is shown in FIG. 33. The implant 128 resembles the implant 10, but includes only a single row 130 of the fastener subassemblies 34. The implant 128 may be useful in situations in which a cut is not required, or in which sealing on only one side of the cut is desired. If sealing is desired on both sides of a cut, then two of the implants 128 can be installed adjacent to each other on the vessel 118 or other surgical structure in order to create a suitable cutting channel, as illustrated in FIG. 32.

Figure 35:
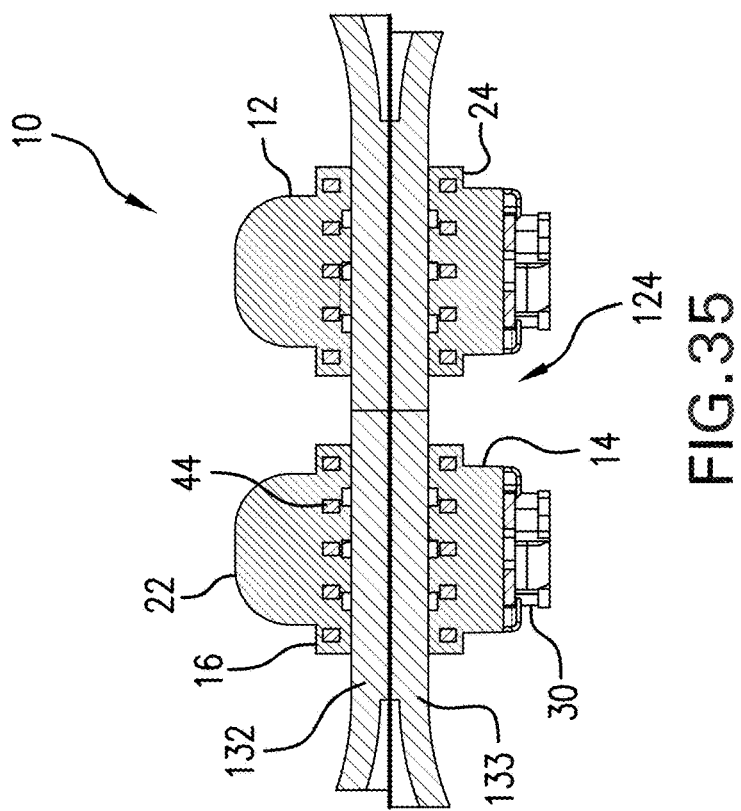
FIG. 35 is an enlarged view of the area indicated in FIG. 34.
Figure 34:
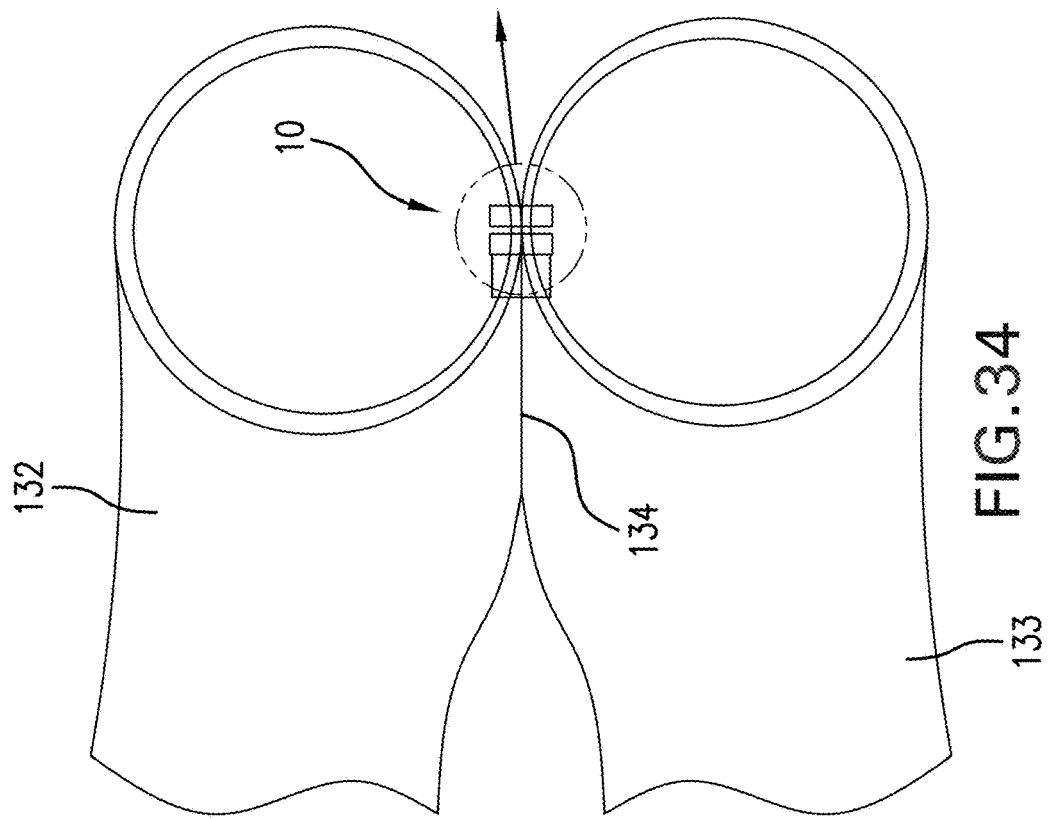
FIG. 34 schematically illustrates a side-to-side connection for an anastomosis formed by an implant according to one embodiment disclosed herein.

It is again to be appreciated that blood vessels are only one type of tissue structure that can be fastened and/or sealed and blood flow is only one example of a fluid flow that can be impeded by use of the implant 10. In one embodiment, the implant 10 is installed in organ parenchyma in order to facilitate the removal of a portion of the organ, e.g., a tumor or cancerous growth. In another embodiment, the implant 10 is used to complete a gastrointestinal bypass. In one embodiment, one or more of the implants 10 are installed in a patient's lung parenchyma in order to prevent the leaking of air while removing a portion of the patient's lung. It is appreciated by those of ordinary skill in the art that the implants 10 can be used for not only hemostasis and pneumostasis, but to seal off the flow of other desired fluids from various tissue structures. One example embodiment for connecting a first surgical structure 132 to a second surgical structure 133 is shown in FIGS. 34 and 35. In one embodiment, the first and second surgical structures represent intestinal structures, and the implant 10 is useful for performing an intestinal anastomoses. In such a procedure, one or more of the implants 10 are installed with the corresponding receiver members 12 in the first structure 132 and the deployment members 14 in the second structure 133, which are connected together with the fasteners 32 and retainer 44 as disclosed above. This connects the first and second structures 132 and 133 along a length thereof to create a so-called side-to-side connection 134. It is again noted that this is provided as just one example of a procedure that can be performed with assistance of embodiments of the present invention described herein and is accordingly not intended to be limiting.

Implant Method of Manufacture and Fabrication

Implants consistent with the present disclosure may be constructed in a variety of ways. In certain embodiments for example, fabrication of the implant may involve (i) molding at least two implant halves (e.g., the receiver member 12 and/or the deployment member 14) or bases (e.g., the base 16 and/or the base 24 of the deployment member 14) with one or more molding steps, (ii) assembling one or more fasteners (e.g., the fasteners 32) to (or alternatively molding with) the one or more bases and/or implant halves. (iii) placing the one or more bases and/or implant halves in alignment with an end effector (e.g., jaws of an applicator, device, instrument, or mechanism for installing implants, such as those discussed below in more detail) and/or the other of the one or more bases and/or implant halves, and (iv) sterilizing the one or more bases and/or implant halves. The molding step may involve co-molding or over-molding with the base one or more strands, web structure, knit structure, woven structure, mesh, and/or any other structure suitable for a retainer (e.g., the retainer 44) or to impart stiffening properties to the base. The mold cavity(ies) are configured based on both the desired shapes of the bases (e.g., the bases 16 and/or 24) and/or implant halves (e.g., the receiver member 12 and/or the deployment member 14) as well as the shrinkage characteristics of the molded material to produce one or more bases and/or implant halves. The bases and/or implant halves may for instance have the same, similar, or even different structures, as exemplified by the drawings of the present disclosure. The mold cavities forming the ventrum surface(s) of the bases and/or implant halves may have one or more protrusions that assist in placing a retainer (e.g., the retainer 44) and/or retaining elements such as strands/knit/mesh/weave, etc. (e.g., the strands 46) a predetermined distance away from the ventrum surface (e.g., the surfaces 18 and/or 26) of the implant (e.g., the implant 10). This may be formed by example via the use of one or more lengthwise protrusions, and may result in one or more corresponding grooves 17, (best shown in FIGS. 5 and 6) at the ventrum surface. Instead of the ventrum surface, portions of the dorsal surface may be used as an alternative means to accomplish the same.

The bases and/or implant halves are preferably formed of a relatively soft, flexible, penetrable and/or puncturable, but also resilient material, such as silicone rubber, as discussed above. The silicone rubber or other material may be injection molded or cast. The towers 30 formed within the implant may be molded of the same material as the bases, or alternatively may be co-molded or over-molded of a different material, or optionally of the same material family but having different specific properties such as elasticity and/or Shore A hardness.

Additionally, the mold cavities/core pins, etc. used for forming the bases and/or implant halves are sized and shaped such that when the implant 10 is represented as a beam, each half thereof (e.g., the receiver member 12 and/or the deployment member 14) will have a neutral axis 172, 174 (i.e., theoretical location where bending stress is zero) along the length of each half and that is closer to the ventrum (or plane of contact 170 when no tissue or structure is disposed between the halves) than the dorsum portion of each half (see FIGS. 30A and 30B). The location of the neutral axis will move depending on the relative second area moment of inertia and stiffness properties along the implant 10. This is illustrated for example in FIGS. 30A and 30B, wherein the neutral axis 172, 174 is schematically represented for each of the respective cross-sections. In one exemplary embodiment, the neutral axis 172 of the receiver member 12 is closer to the ventrum than for the corresponding neutral axis 174 of the deployment member 14. When a retainer 44 having a material property of a higher modulus of elasticity than the material chosen for the base (or overall receiver member/deployment member) is integrated to the bases of each halves, the neutral axis is moved even more towards the ventrum. This results in a neutral axis for at least one, and preferably both halves, in which the height 180, 176 of the neutral axis 172, 174 from the ventrum or plane of contact 170 is about 40% or less than the section's overall height 178, 182, possibly about 35% or less, more preferably about 30% or less, even more preferably about 25% or less, and in certain embodiments about 20% or less. In certain embodiments, the modulus of elasticity for the retainer 44 is 100 times greater than that of the molded portions of the receiver member and deployment member, more preferably 200 times greater, even more preferably 400 times greater, even more preferably 600 times greater, even more preferably 800 or even 1000 times greater. Additionally, in some embodiments the shape and material properties may be chosen such that the resulting half (including retainer 44) would have a bending stiffness (i.e., modulus of elasticity multiplied by the second moment of area) of about $1.3 \times 10^{-11}$ MPa m$^4$ or greater, more preferably $1.8 \times 10^{-11}$ MPa m$^4$ or greater, even more preferably $2.2 \times 10^{-11}$ MPa m$^4$ or greater, more preferably $2.7 \times 10^{-11}$ MPa m$^4$ or greater, and even more preferably $3.0 \times 10^{-11}$ MPa m$^4$ or greater.

The strands (e.g., the strands 46) of the retainer may be formed as either unique strands, or optionally as a portion of a knit, mesh, weave or similar structure, of which the material chosen may be polypropylene, polyester (PET), PEEK, Nylon, or the other materials discussed above, and/or combinations thereof. When multiple connected or formed strands are used (such as in a mesh), a variety of spacings or openings may be chosen depending on the size of the fastener selected. Openings (e.g., the interstices 48) may be for example anywhere from 0.500 inches to 0.001 inches, more preferably 0.250 inches to 0.005 inches, even more preferably 0.100 inches to 0.010 inches, and even more preferably 0.050 to 0.020 inches, and yet further between 0.025 inches to 0.030 inches. The open areas (e.g., the interstices 48) between crisscrossing strands (e.g., the strands 46) when utilized are preferably sized in accordance with the size and shape of the fastener (e.g., the fastener 32) chosen. Examples may include, for instance, ranges between 0.001 sq.in. to 0.100 sq.in., more preferably 0.0001 sq.in. to 0.0080 sq.in., even more preferably 0.0002 sq.in. to 0.0020 sq. in., 0.0003 sq.in. to 0.0012 sq.in., and most preferably about 0.0005 sq.in. to 0.0010 sq.in. Such open spaces (e.g., the interstices 48) may be square, rectangular, diamond-shaped, and/or other types of polygonal shapes may be utilized. Triangular and circular or elliptical shapes are also contemplated, as well as any of the shapes and structures shown by example in FIGS. 7a and 7b (shown without the base) and FIGS. 20-26 (shown with the base).

In a sample embodiment, a mesh having a crisscrossing construction forming generally square openings of a precision polyester is chosen (see for example FIG. 7B). Such meshes may be sourced for instance through McMaster-Carr (Robbinsville, N.J., USA). The mesh is cut in a manner that facilitates its later placement into a mold cavity. Preferably, the mesh is cut such that the mesh self-aligns to be generally centered in the mold cavity chosen for the base(s) (e.g., the bases 16 and/or 24). The mesh is then placed in the mold, and then formed within liquefied silicone under conditions that permit the silicone to form around the mesh. While many silicones, such as medical grade and/or food grade silicones may work, implant grade silicones are preferred. Preferably, the hardness of the silicone (once cured) is of a Shore A durometer between 5 and 55, more preferably 10 and 45, more preferably 20 and 40, and most preferably about between 25 and 35, such as 30. Of course, materials with a Shore A durometer above 55 or below 5 may also be used depending on the situation. Materials may be sourced from a variety of vendors, including for instance Applied Silicone Corporation (Santa Paula, Calif., USA), and Dow Corning Corporation (Corning, N.Y., USA) under the trade name SILASTIC.

Figure 43A:
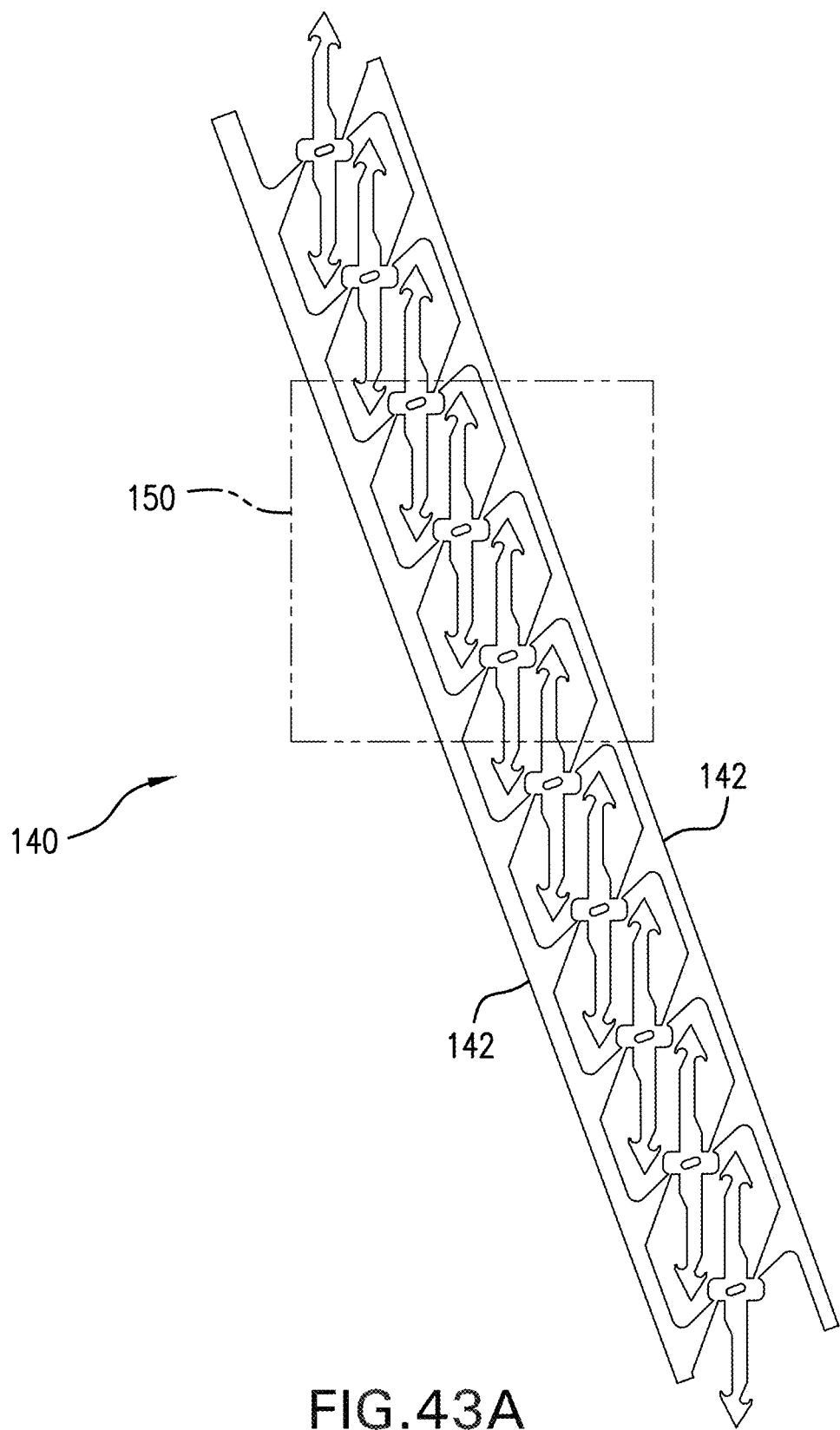
FIG. 43A is a top view of a strip of formed fasteners according to an example embodiment.
Figure 43B:
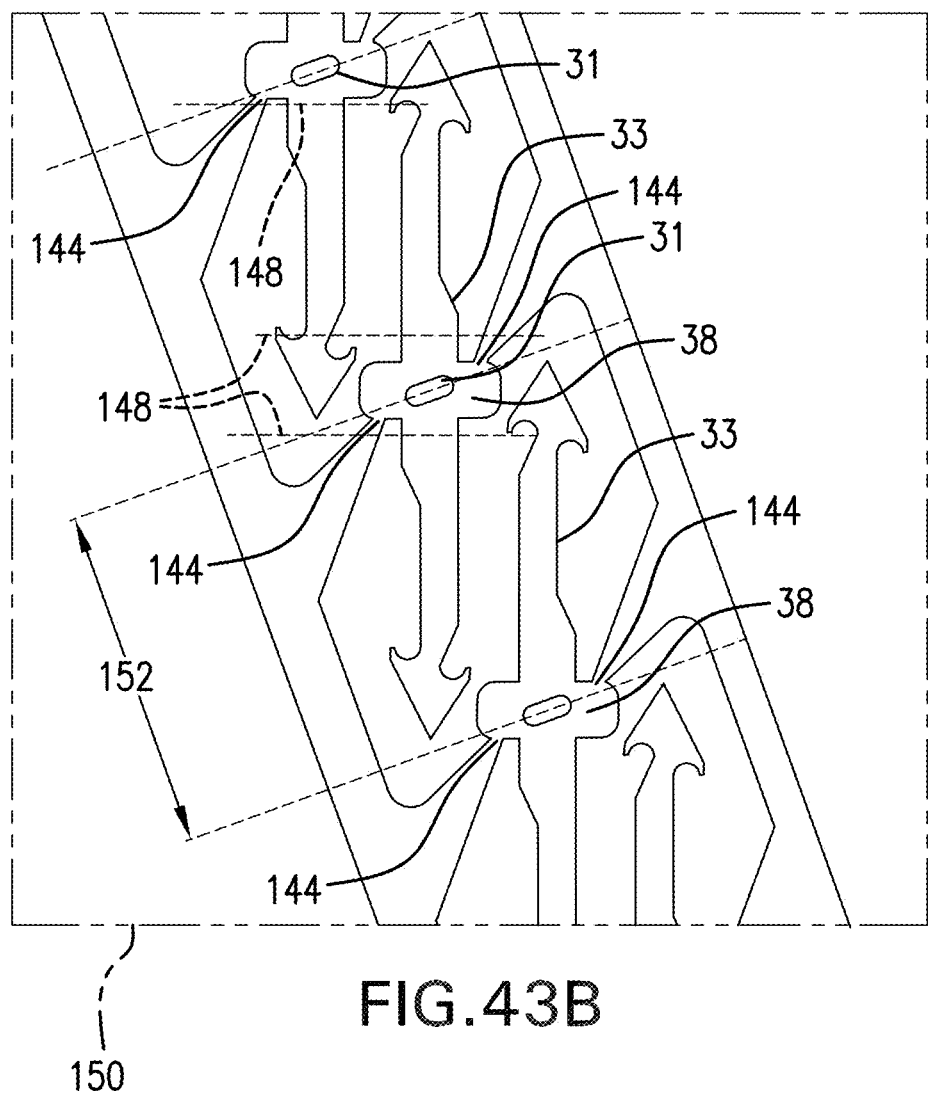
FIG. 43B is a detail view taken about border 150 of FIG. 43A.

After the mold cavity has been set and filled, the liquefied silicone is cured and removed for subsequent assembly with a fastener. Before, during, or after the process of forming the halves, one or more fasteners (e.g., the fasteners 32) are fabricated for being joined or integrated with at least one of the halves. In an example embodiment, the fasteners 32 are first formed in a strip 140 of metal (e.g., 304 or 301 stainless steel) through a chemical etching process, although other machining processes such as wire EDM and stamping/punching and/or die cutting may be used. The resulting strip 140 is illustrated in FIGS. 43A and 43B, and has one or more outside edges 142 connected to the fastener bodies 38 of each flat-formed fastener body 33 at one or more locations 144 per fastener body 38. The flat-formed fastener bodies 38 are shown in FIGS. 43 and 44 to be radially oriented in an overlapping pattern, offset a width or distance 152 as shown in FIG. 43B. The offset distance(s) 152 preferably is chosen so that each fastener 32 aligns with its respective tower 30 of the half it will be integrated with.

Figure 36:
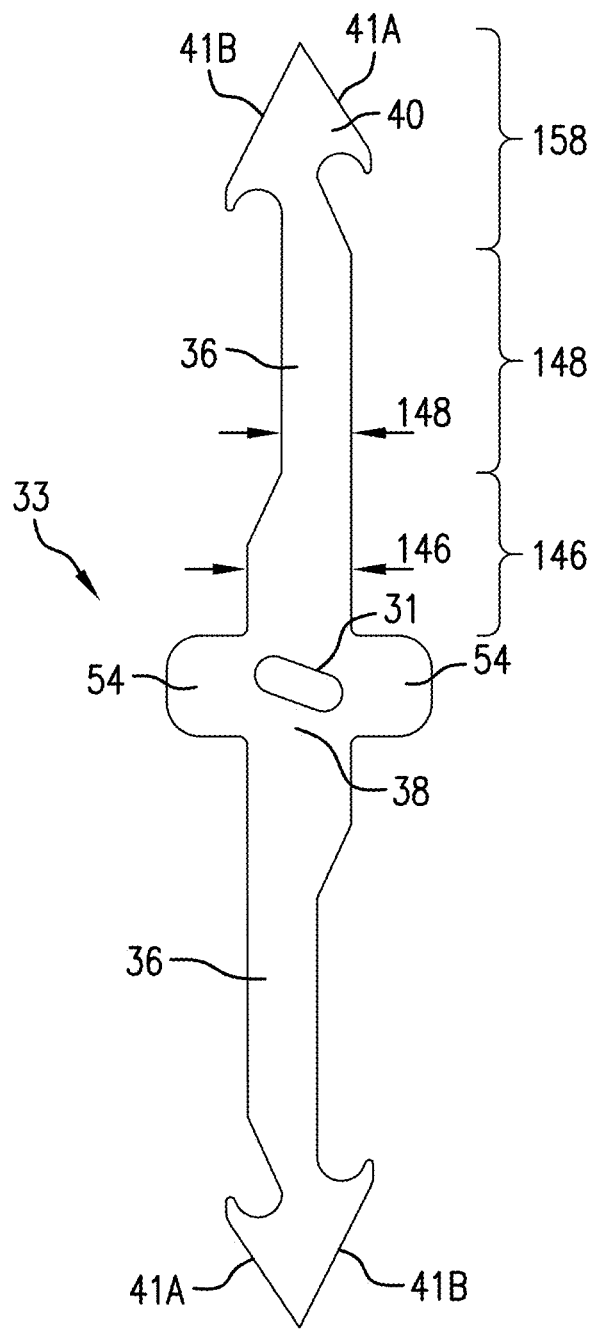
FIG. 36 is an elevation view of a flat-formed fastener of the implant according to an example embodiment.
Figure 40:
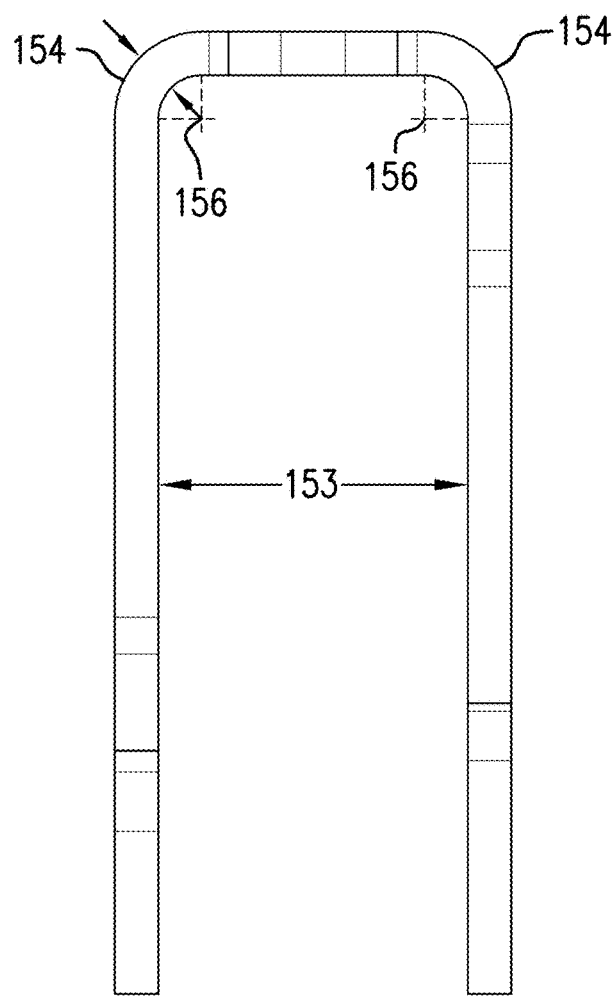
FIG. 40 is a side view of the fastener of FIG. 38.

The strip 140 is then placed in a forming tool (not shown) which aligns the strip 140 with one or more anvils (not shown) to facilitate bending of the one or more of the legs 36 to an orientation generally normal/perpendicular to the plane of the strip 140. Alignment with the forming tool may be achieved with the assistance of alignment apertures 31. Sufficient pressure is then applied against the legs 36 to transform the flat-formed fastener body 33 shown in FIGS. 36 and 37 into the shaped fastener 32 of FIGS. 38-42. While the primary leg 36 of the fastener may have a single width throughout, in other embodiments it may have a wide section defined by the width 146 as well as a narrower section defined by a width 148, as shown in FIG. 36. A bend 154 caused by the deforming step may occur within any portion of the leg 36 but preferably occurs within the wide section 146 for those legs 36 having varying widths, and forms a curve about an axis 156 that provides a smooth transition between the leg 36 and the body 38. Additionally, a spacing 153 of the legs (FIG. 40) is chosen such that there is little, minor, or no interference between the fastener 32 legs 16 and the towers 30 once assembled together. That is, preferably the spacing 153 exceeds the width of the tower 30 over which the fastener is mounted.

Figure 37:
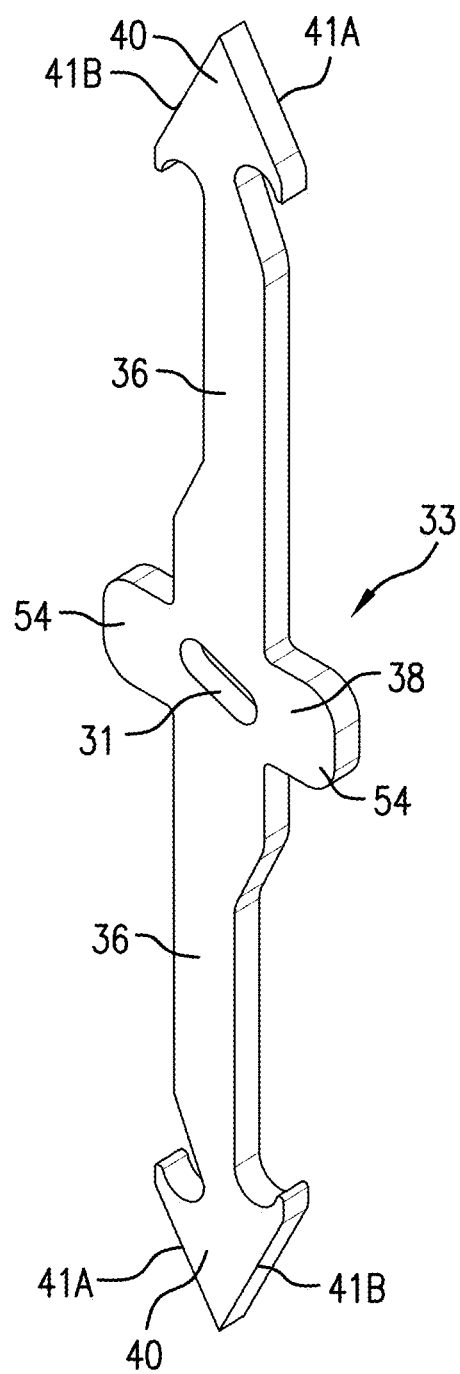
FIG. 37 is a perspective view of the fastener of FIG. 36.
Figure 38:
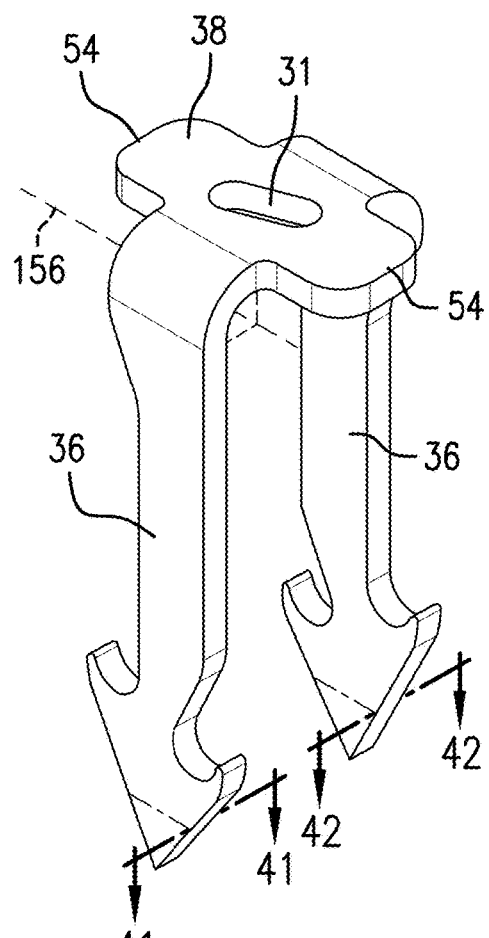
FIG. 38 is a perspective view of the fastener of FIG. 36 in a bent configuration.
Figure 39:
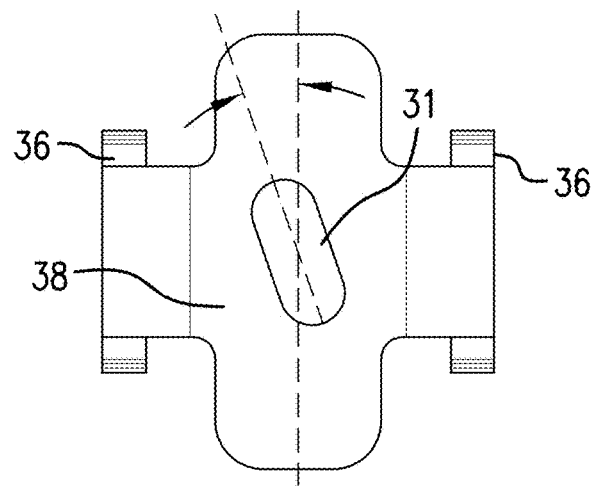
FIG. 39 is a top view of the fastener of FIG. 38.
Figure 41:
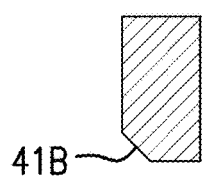
FIG. 41 is a sectional view taken about section line 41-41 of FIG. 38.
Figure 42:
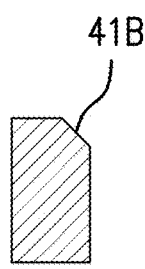
FIG. 42 is a sectional view taken about section line 42-42 of FIG. 38.

The tips 40 of the shaped fastener(s) 32 may optionally then be sharpened on one or more of their edges to achieve a sufficient reduction in penetrating forces depending on the material(s) of the bases 16 and/or 24, as well as the tissue or structure intended to be pierced. As shown in the embodiment of FIGS. 41 and 42, edges 41B are beveled or sharpened, and may in some embodiments only be beveled on the outermost surface of the legs 36. The beveling may occur when the fastener is flat-formed as shown in FIGS. 36 and 37, or alternately when it is formed in a bent configuration as shown for example in FIGS. 38-42. Other tip designs could alternately be provided.

One or both of the towers 30 and fasteners 32 may be lubricated to facilitate reciprocal movement of each structure with respect to the other. In some instances, the fastener 32 may be dip coated into PTFE to reduce the friction should contact occur between the fastener 32 and tower 30. Other lubricants may also be suitable.

Each fastener 32 may subsequently be aligned with a corresponding one of the towers 30. This may be achieved individually or simultaneously with a plurality of the fasteners 32. For instance, when the bent fasteners 32 are still interconnected in the strip format 140, the strip 140 can be used as an alignment tool for facilitating assembly of the fasteners 32 simultaneously onto multiple ones of the towers 30 of a deployment member 14. The alignment apertures 25 (see FIG. 5) located within the bases 24 on opposite sides of the towers 30 may be provided to further facilitate assembly, by providing a guiding hole for the tips 40 to be placed in during the alignment step of the fabrication process. Once properly aligned, the fasteners 32 may be secured to the base in a variety of manners. In one such exemplary embodiment, frictional forces maintain the connection between the fastener and the half. In another embodiment, the tips 40 are retained within the base (e.g., the base 24) of the half (e.g., the deployment member 14) associated with the tower via engagement of one or more retaining elements or strands (e.g., the strands 46) of the retainers (e.g., the retainer 44) positioned in the deployment member 14.

When assembled via the strip 140, a post-assembly process involving the cutting of the fasteners 32 from the strip outside edges is performed. Instead of a post-assembly process, separation of the fasteners can occur before attachment to the corresponding base (e.g., the bases 16 and/or 24) and/or implant halve(s) (e.g., the deployment member 14). This may allow for in-mold assembly of the fastener with the base and/or half as well as in other embodiments co-molding or over-molding of the fastener (e.g., the fastener 32) to the bases and/or halve(s).

Figure 44A:
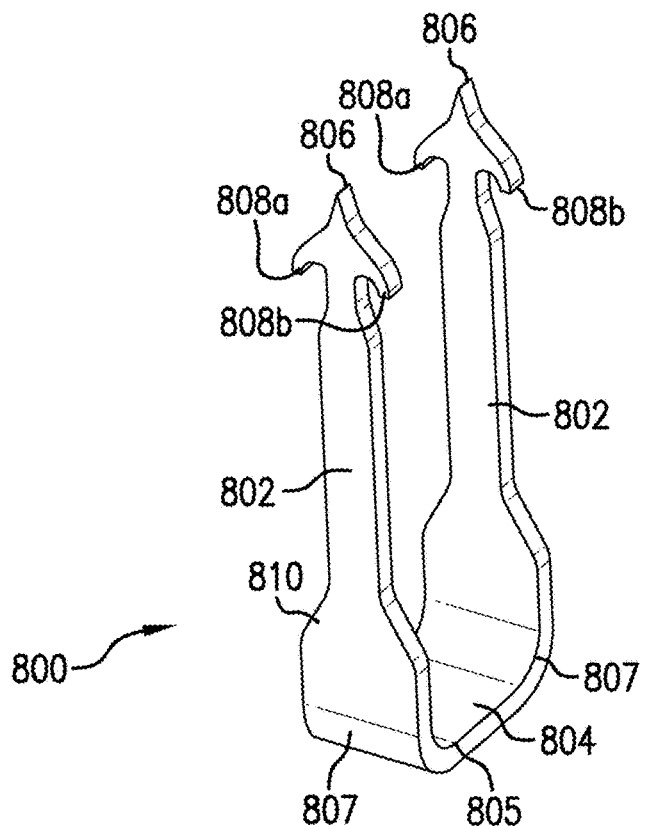
FIG. 44A is a perspective view of a fastener of an implant according to an alternate embodiment disclosed herein.
Figure 44B:
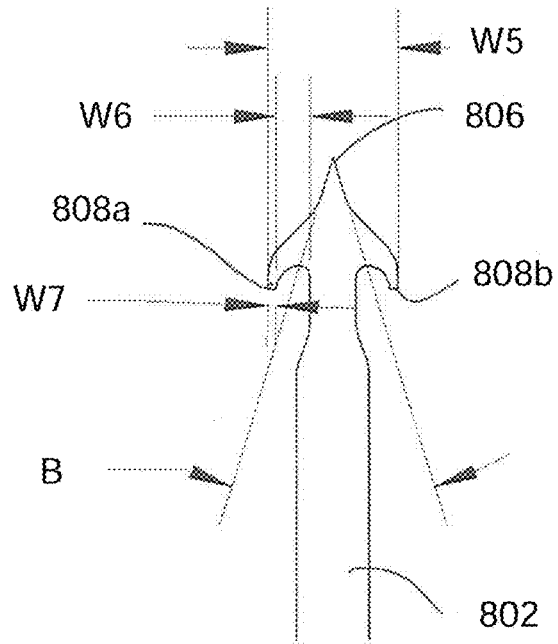
FIG. 44B is a side view of the leg of the fastener of FIG. 44A.

FIGS. 44A and 44B illustrate an alternate embodiment of a fastener of the implant of the present disclosure The fastener 800 has a base 805 and pair of legs 802 extending substantially perpendicular therefrom. It should be appreciated that alternatively, the legs 802 can extend at a different angle from the base 805. The base 805 has a planar (flat) or substantially planar (flat) surface that transitions on opposing sides into curved surfaces or bends 807, transitioning into legs 802. The legs taper at region 810 and terminate in penetrating tips 806. Each leg 802 has a pair of barbs 808a, 808b (collectively barbs 808) at a distal portion. Barbs 808a, 808b are preferably identical in configuration and are axially (longitudinally) aligned with respect to the fastener leg 802. Thus, the barbs 808a, 808b are on the same level and symmetrical around the centerline of the fastener 800 so the fastener 800 can pierce the tissue in a straight manner. As discussed herein, in some embodiments, the barbs of the fasteners can be axially (longitudinally) offset with respect to the legs which has certain advantages. In this embodiment, the barbs are aligned which provides other advantages in certain applications of the fastener.

The aligned barbs of FIGS. 44A and 44B provide a lesser force to penetrate tissue, reduce the chances of twisting as the fastener 800 passes through the tissue or other surgical structure and provide for more consistent entanglement with the receiver 44, e.g., mesh, to thereby improve barb to retainer hold strength and reliability. The aligned barbs also provide for more tissue capacity because the offset barbs require a longer fastener or thinner tissue to fit into a given cannula diameter. Thus, by making the barbs 808a, 808b the same distance from the base 804 of fastener 800, the distance the barbs 808a, 808b need to be driven (as compared to offset barbs) is minimized and the tissue thickness is maximized. For example, in some embodiments, the tissue thickness capacity is increased about 0.5 mm with the aligned barbs 808a, 808b.

The fastener 800 can also be designed with other features to reduce the force to drive the fastener 800 through tissue. For example, the fastener can be coated with material such as PTFE and can be electropolished to remove any burrs or surface roughness. In some embodiments, the penetrating tip can be sharpened to an angle of about 35 degrees (see angle B of FIG. 44B). The fastener 800 can be formed from a metal sheet using a chemical etching process and in some embodiments formed with this 35 degree angle to achieve both sufficient sharpness to penetrate surgical structure and desired penetration force. It should be appreciated that 35 degrees is provided by way of example as other angles can be utilized to obtain desired penetrating force and sufficient sharpness. The tip can be formed by various processes, including by way of example a grinding process after the fastener is formed from a sheet using a chemical etching process.

FIG. 44B illustrates certain dimensions of the fastener 800 to optimize penetration of surgical structure and engagement with the receiver 44 of the receiver member 12 discussed above. It should be appreciated that these dimensions are provided by way of example as other dimensions are also contemplated for the fastener 800. In FIG. 44B, the fastener 800 has an increased barb distance w6 (as compared e.g., to the barbs of FIG. 38) of about 0.013 inches. This improves retention with the retainer, e.g., mesh, to reduce the chances of the fastener 800 slipping out of the retainer 44. The width w7 of the barb securement portion is shown increased (as compared to the barbs of FIG. 38) by about 0.003 inches so that it is not degraded when the fastener 800 is electropolished, i.e., metal is removed from all the surfaces. Additionally, the distance w5 of the barb portion, i.e., the width of the fasteners at the outermost regions of the barbs 808a, 808b, is about 0.050 inches. This is wider than the region of the fastener below (proximal/dorsal of) the barbs 808a, 808b so the retainer, e.g., mesh, springs back after the barbs 808a, 808b pass through the openings in the retainer 44, and the retainer 44 is thus held securely under the barbs 808a, 808b.

Figure 44D:
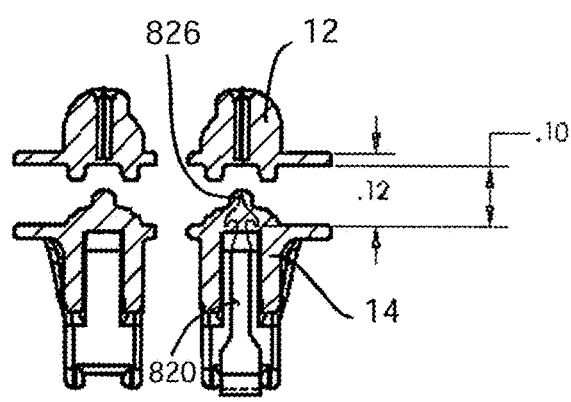
FIG. 44D is a transverse view of the fastener of FIG. 44C fully contained within the implant prior to firing.
Figure 44E:
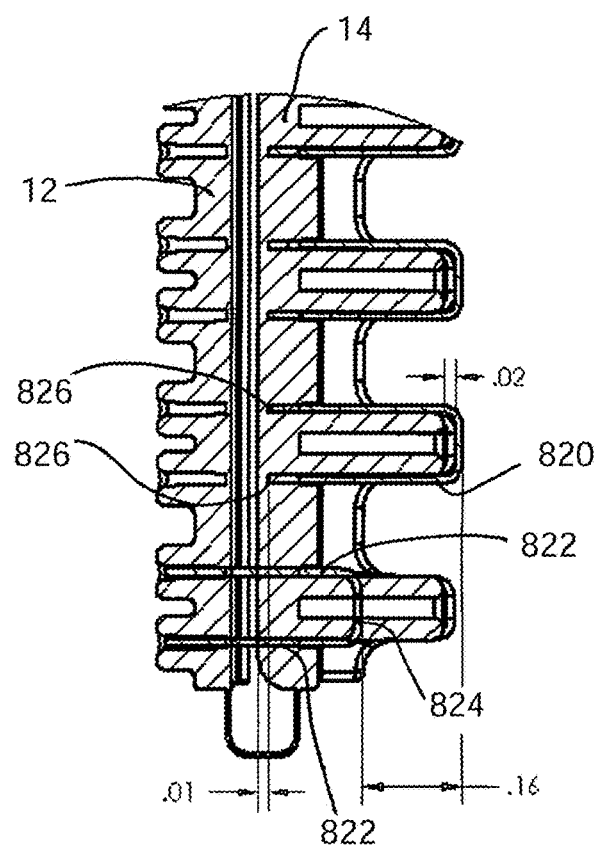
FIG. 44E is a longitudinal sectional view of a portion of the implant showing one of the fasteners of FIG. 44D advanced through the deployment member and other fasteners not yet advanced.
Figure 44C:
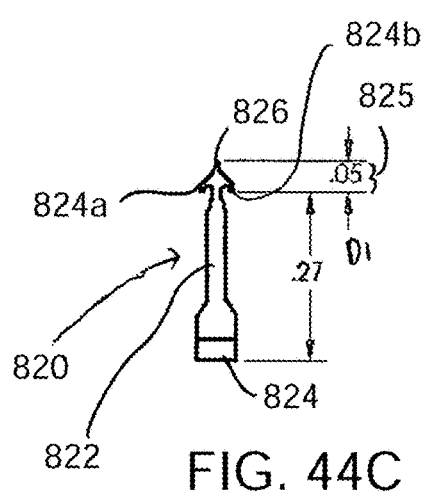
FIG. 44C is a side view of the leg of a fastener of an implant according to an alternate embodiment disclosed herein.

In the alternate embodiment of FIG. 44C-44E, the fastener 820 is identical to the fastener 800 except for the elongated hook portion 825. Thus, like fastener 800, fastener 820 has a pair of legs 822 extending from a base 824 and terminating in penetrating tips 826. Also, like fastener 800, fastener 820 has a pair of symmetrical longitudinally (axially) aligned barbs 824a, 824b. The fastener 820 differs from fastener 800 in that the hook portion 825 has a longer length and thus the barbs 824a, 824b can also be elongated as compared to barbs 808a, 808b of FIG. 44A. In a preferred embodiment, the distance D1 of the hook portion, measured from the outermost point of the penetrating tip 826 of the fastener 800 to the lowermost (proximalmost/dorsalmost) point of the barb 824a is about 0.050 inches. The extended length achieves the balance of accommodate thicker tissue without extending past the material of the deployment member 14 in the pre-fired position as shown in FIGS. 44D and 44E.

The advantage of the extended hook portion can be understood in terms of an example. As shown in FIG. 44D, the fired fastener 820 is driven about 0.16 inches. With a tissue thickness of 0.10 inches (2.5 mm), the barb 824a, 824b needs to be driven at least 0.12 inches. Thus, it has a margin of error of 0.04 inches (1 mm), to assure successful engagement with the receiver member 12. This also means that after the jaws are opened, the tissue can expand and additional 1 mm, i.e., to 3.5 mm as the barb catches onto the retainer 44, e.g., mesh, within the receiver member 12. Thus, the fasteners 820 can cover a large range of tissue.

To fit thicker tissue, the cartridge containing the fasteners 820 can be set back from the issue contacting surface of the deployment member 14. In one example, it is set back about 0.050 inches. When the jaws are closed to approximate the receiver member 12 and deployment member 14 and clamp thick tissue structure between the tissue contacting surfaces of the deployment 14 and receiver member 12, the deployment member 14 is pushed back against the cartridge containing the fasteners 820 up to this 0.50 mm. This also provides the benefit that as the thick tissue is compressed, the tips 826 of fasteners 820 can be slightly exposed from the cartridge to keep the tissue from being squeezed out of the jaws.

Figure 44F:
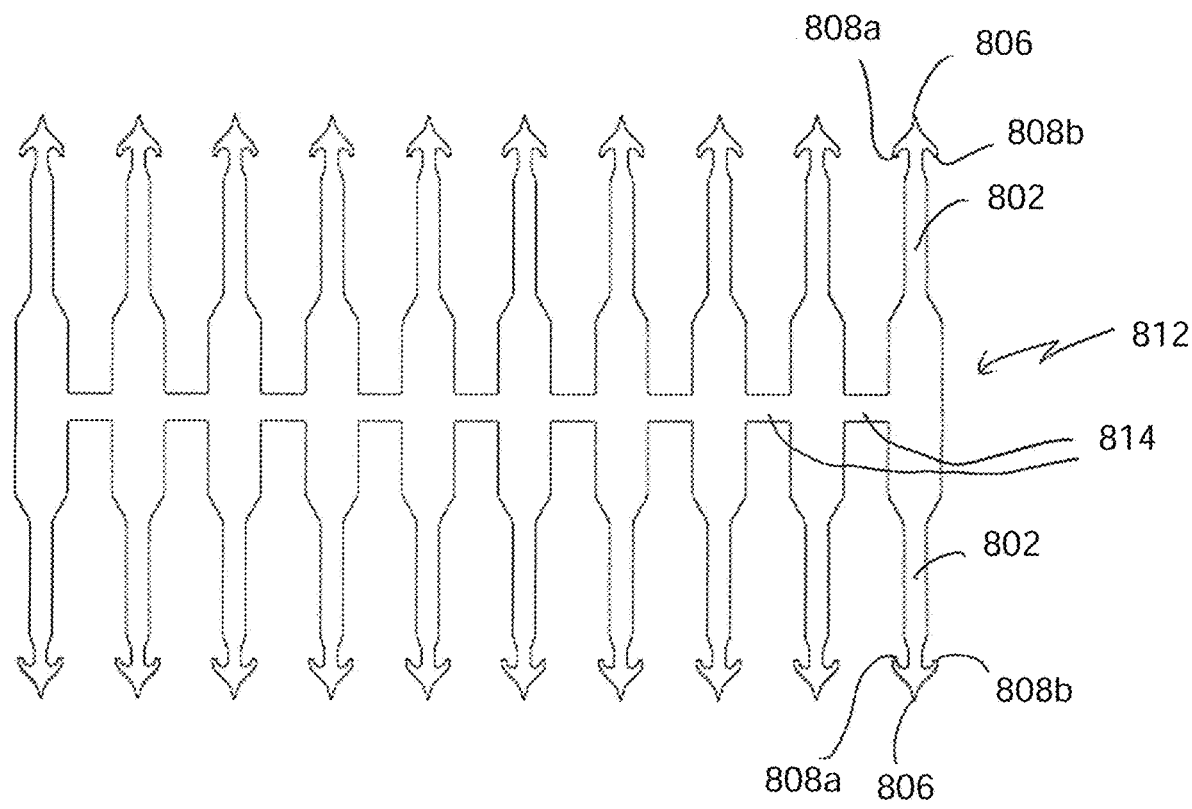
FIG. 44F is a top view of a strip of the formed fasteners of FIG. 44A.
Figure 44G:
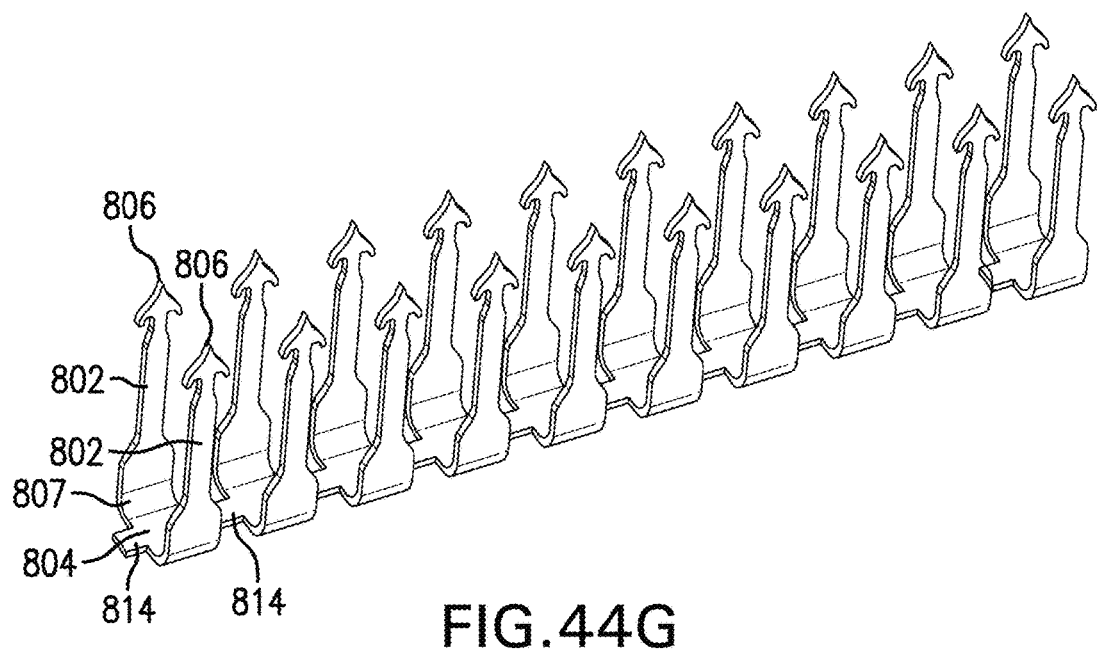
FIG. 44G is a perspective view of the strip of fasteners of FIG. 44E bent to form U-shaped fasteners.

FIGS. 44F and 44G illustrate one process of forming the fasteners 800 of FIG. 44A. In this embodiment, the fasteners are formed on a strip 812. The strip 812 enables the fasteners 800 to be made in sets in a continuous process so that a large number of sample parts need not be handled in manufacturing. Also, keeping the fasteners 800 together allows them to undergo additional processes after initial cutting (or chemical etching or stamping) in a controllable manner, thereby reducing the cost of manufacture. As shown in FIG. 44F, the fasteners 800 are aligned and connected along bridge or connector 814. Note, for clarity, only one of the fasteners is labeled in FIGS. 44F and 44G, The leg 802 and half of the base 804 extends in one direction from the connector 814 and the other leg 802 and other half of the base 804 extends from connector 814 in the opposite direction. As shown, ten fasteners are connected along connector 814, however, it is also contemplated that a fewer or greater number of fasteners can be connected along connector 814 and provided on a single strip. Also, as shown, the fasteners are positioned perpendicular to the connector 814 to provide several advantages discussed below, however, in alternate embodiments, they are aligned at a different angle to the connector 814. If desired, all of the fasteners for the implant can be formed from the single strip 812, although, alternatively, sets of strips 812 each containing a subset of the total fasteners for the implant can be formed.

In the next manufacturing step after formation of strip 812, the fasteners 800 are bent to the position of FIG. 44G. The fastener strip 812 can be sharpened using a grinding process (after before or after the fasteners 800 are bent to their U-shaped configuration of FIG. 44E). The fasteners 800 can then be cleaned and coated, such as with a PTFE coating or other coatings, then cut apart and inserted into the deployment member, e.g. the silicone/mesh of the deployment member 14 discussed above. Although the fasteners 800 on the strip 812 are shown as being identical, in alternate embodiments, different fasteners can be provided on the strip. Additionally, the fasteners of the other embodiments disclosed herein can also be formed in strips as in FIG. 44D.

Note the positioning of the fasteners 800 perpendicular in the strips 812 allows the entire set of fasteners to be bent to the position of FIG. 44G at one time, sharpened at one pass and cut apart for insertion into the deployment member 14. It also eliminates the need for pushers as described in more detail below. Further, the bend 807 in the fasteners which places it perpendicular to the driver cam surfaces (discussed below) reduces twisting/rotating of the fasteners 800 during firing.

Various materials are described herein for the retainer. In one embodiment, for use with the fastener 800 or other fasteners described herein, the retainer in the form of a mesh can be composed of polyester (as noted above) to increase the strength of the mesh. Further, if desired to further increase the strength of the mesh, the weave of the mesh can be reduced. A tighter weave can increase the resilience of the mesh to reform after the barbs 808a, 808b pass therethrough, thus being caught under the barbs 808a, 808b.

Figure 45:
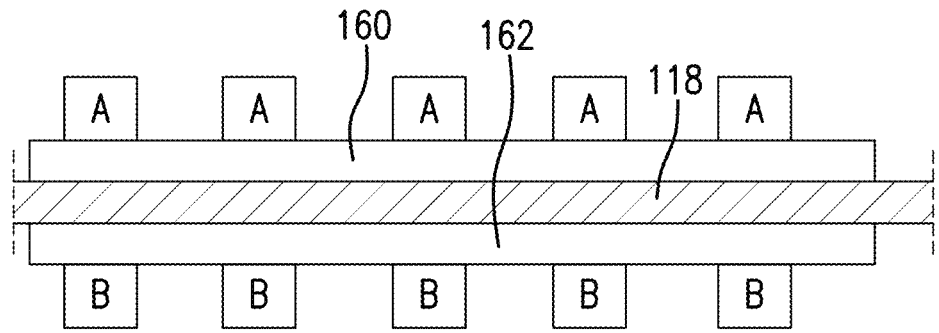
FIG. 45 is a schematic sectional elevation view of a fastener system according to an example embodiment.
Figure 46:
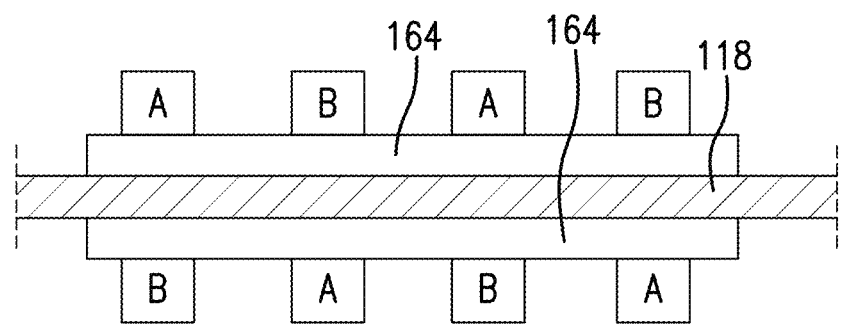
FIG. 46 shows a schematic sectional elevation view of a fastener system according to an alternate example embodiment.
Figure 47:
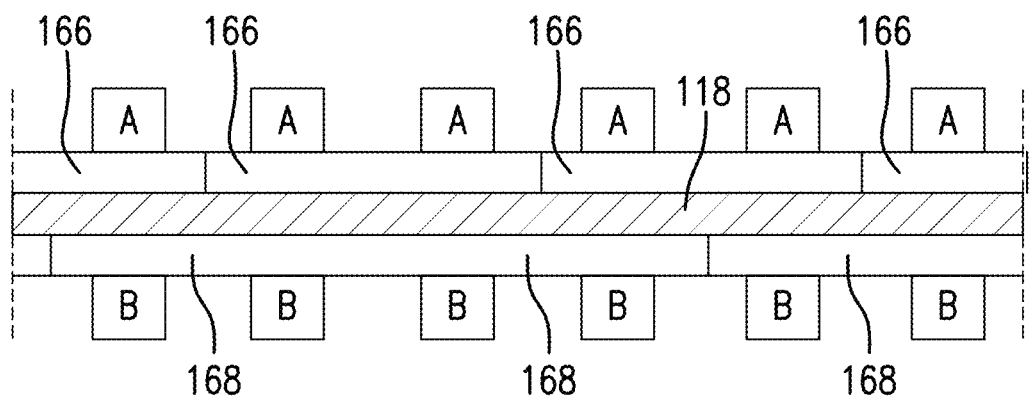
FIG. 47 shows a schematic sectional elevation view of a fastener system according to another alternate example embodiment.

In addition to the aforementioned embodiments, additional embodiments are contemplated. FIG. 45 represents a schematic representation of pairs of fastener/tower structures or deployment segments (e.g., one of the deployment segments 28 of FIG. 1) (referenced as segments A) aligned with receiving segments B (e.g., one of the segments 20 of FIG. 1). While FIG. 45 illustrates an arrangement of segments A and B on different halves 160, 162, alternatively the can be arranged on the same half 164, as illustrated in FIG. 46. For example, instead of designated deployment and receiving halves, an implant may be formed from essentially identical halves 164 having alternating deployment and receiving segments. That is, in one embodiment, the implant halves include alternating ones of the segments 20 and 28, as represented schematically by the segments A and B in FIG. 46. Furthermore, the halves do not have to have an equal quantity of segments B to align with the quantity of segments A, nor are the halves required to directly overlap to the corresponding half, as represented in FIG. 47 wherein a first and second of the segments A of a first half 166 may align with segments B of different half 168. This may allow for linking multiple halves together when the length of one half is insufficient for a certain procedure. Many other permutations are of course possible due to the flexible nature offered by the disclosed embodiments. Additionally, the deployment member can be positioned on the moving jaw and the receiver member positioned on the stationary jaw as an alternate to the aforedescribed positioning. An example of this configuration is described below with reference to FIG. 79.

Figure 48:
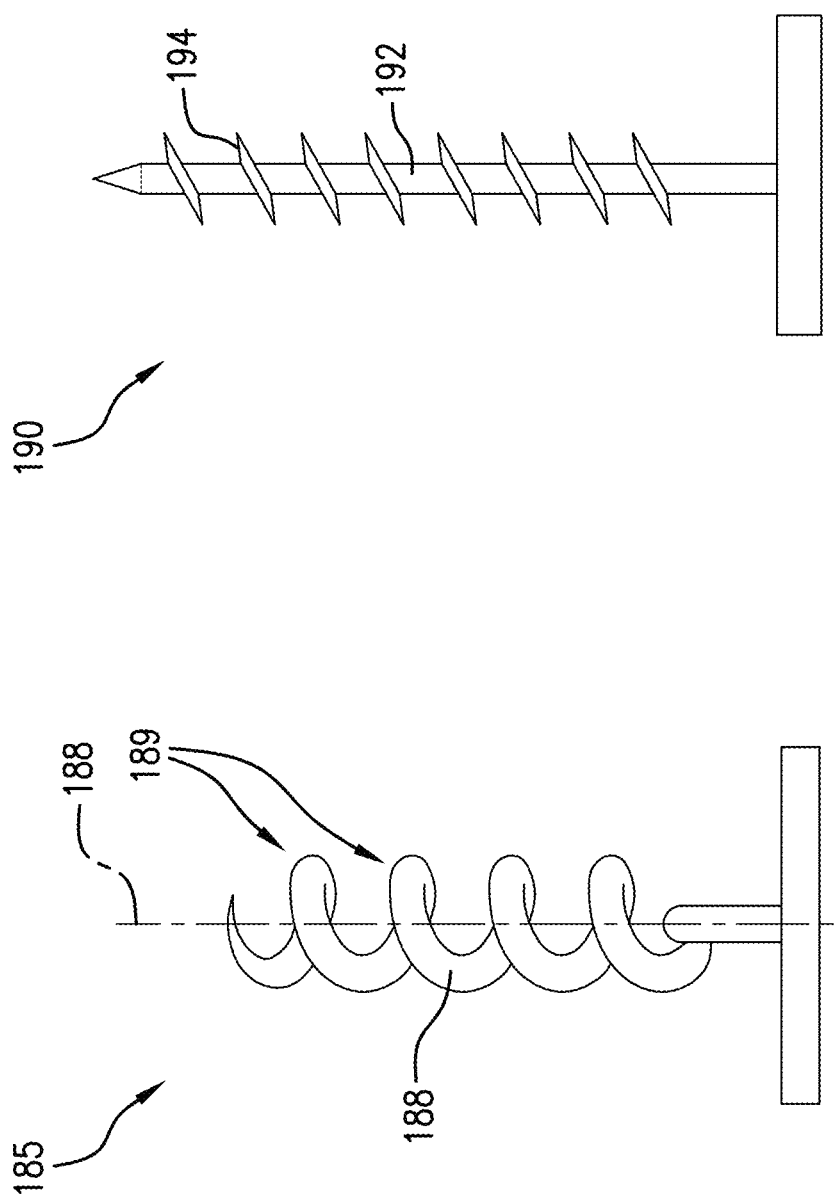
FIG. 48A shows a side elevation of a fastener having a corkscrew-like configuration according to an alternate embodiment disclosed herein.
FIG. 48B shows a side elevation of a fastener having a screw-like configuration according to an alternate embodiment disclosed herein.

It is to be noted that the barbs 42 or other elements suitable for grabbing, catching, or engaging a retainer may be formed as any structure that protrudes outwardly and is thus so capable of catching, grabbing, or otherwise engaging with a retainer, such as the retainer 44 (which elements are collectively referred to as barbs). For example, in the embodiment of FIG. 48A, a fastener 185 is formed with a helical or spiraled shank or leg 186. The helical leg 186 is formed with respect to an axis 188. Since the leg 186 has a thickness that is much less than the width of the helical shape made by the leg 186 about the axis 188, the leg 186 is able to pass through relatively small openings (e.g., the interstices 48) while being rotated during forward advancement. In this way, pulling back against the fastener 185, but without rotation (e.g., such as would occur due to the force exerted by the towers 30), will cause each turn 189 of the fastener 185 to act as a barb and grab, catch, or engage with a retainer or retaining elements (e.g., the strands 46 of the retainer 44). Another embodiment is illustrated in FIG. 48B. In this embodiment, a fastener 190 includes a leg 192. A flange 194 extends from the leg 192. The flange 194 may be a continuous flange, e.g., helically or spirally formed about the leg 192, or formed as discrete elements. Similar to the fastener 186 in FIG. 48A, the leg 192 can be advanced through a relatively small opening (e.g., the interstices 48) by advancing the fastener 190 toward the opening and rotating the fastener 190. However, when the fastener 190 is pulled back in the opposite direction without rotation, the flange 194 will act as a barb and catch, grab, or engage with a retainer or retaining elements (e.g., the strands 46 of the retainer 44). Although the fasteners of FIGS. 48A and 48B are shown with one leg, two or more legs can extend from the base (body).

Embodiments of the present disclosure are further directed to an apparatus and method for delivering and implanting one or more surgical implants, such as any of the previously described embodiments for or related to the surgical implant 10, or other fasteners, clamps, clips or other closure or sealing devices. That is, embodiments of the current invention are directed to various alternative and improved devices, apparatus, systems and methods for implanting a surgical implant to, for example, close a tissue structure of a patient which include but are not limited to blood vessels, parenchyma, bronchi, atrial appendages and the like. Tools and implants according to the present invention can be configured and dimensioned to seal and transect large vessels and bulk tissue up to about 5 mm compressed thickness and may have a configuration and size sufficient to fit through a port, such as a port 20 mm in diameter or less to allow for minimally invasive surgical procedures, and flexible enough to maneuver to an intended surgical target. The surgical implant applicator and system may be designed to well tolerate thickness variations of the tissue to be closed along a length of a surgical implant. The surgical implant applicator of the present invention may advantageously also use smaller, less expensive closing mechanisms than those used in currently known apparatus, as the surgical implant to be implanted by the apparatus do not require the amount of precision for alignment and closing that is required of currently known apparatus. Additionally, the surgical implant applicator can be provided to mount two surgical implants (or a bisectable single surgical implant) and with a cutting element to sever tissue (and the closure device when a single bisectable device is employed) between two locations where the tissue has been closed by the closure device(s). Still further alternatively, the surgical implant applicator can be provided to mount one closure device for implantation in sealing off a location with the single device.

The applicator described below moves, mounts, and/or applies two implants side by side extending generally linearly. It is also contemplated that alternatively, the implant can be arranged non-linearly, including a circular or arcuate arrangement as discussed above. Although the applicator described is for endoscopic or minimally invasive surgical products, it is also contemplated that the implants described herein can be utilized in "open" procedures. Also, the illustrated applicator is shown to have a rigid shaft, but flexible shafts and instruments can also be utilized for use in certain endoscopic procedures. Additionally, applicators without a shaft (i.e., such as a configuration that is "scissor-like" or otherwise resembles the gross structure of a long-nose pliers, with two pivoting grips, each grip operably engaged with either a top or bottom half of the implant to move the halves to and from each other), may be utilized.

Figure 50:
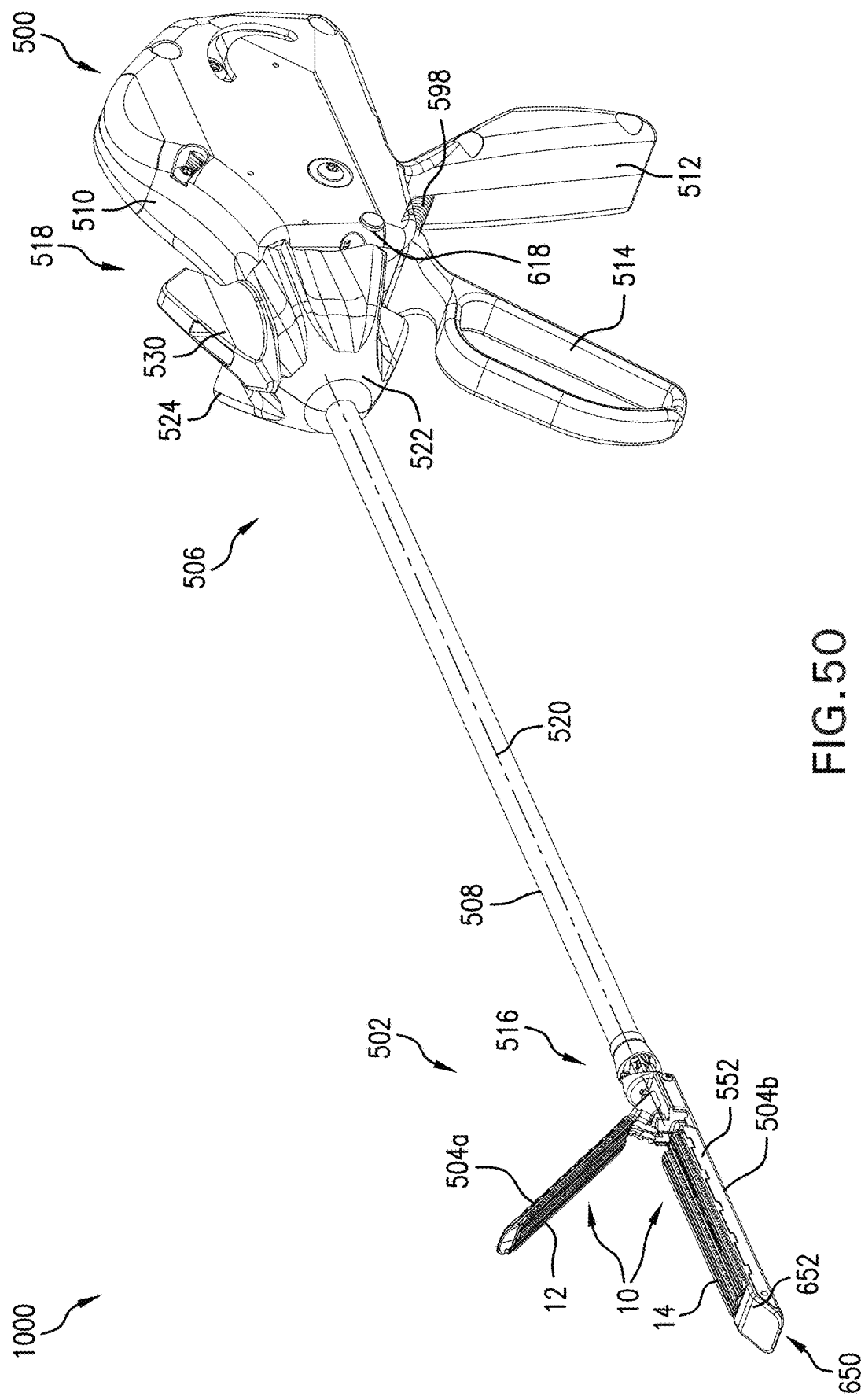
FIG. 50 is an isometric view of a system having an implant and an applicator, according to an embodiment of the present disclosure.

Referring now to FIG. 50, an isometric view of one embodiment of a system 1000 for installing surgical implants according to embodiments disclosed herein, e.g., the implant 10, is illustrated. As discussed above, surgical implants disclosed herein, such as the implant 10, can be useful for closing, sealing, or securing together one or more surgical structures during a medical procedure performed on a patient. As shown, the system 1000 includes the surgical implant 10 and a surgical implant applicator 500, which may also be referred to as a tool, device, instrument, or the like. It is to be appreciated that the implant 10 may be installed using devices other than the applicator 500, and likewise, that the applicator 500 may be used to install surgical implants other than the implant 10. Furthermore, it is noted that aspects of the applicator 500 may be useful in medical procedures that do not include surgical implants, e.g., such as any requiring actuatable jaws, slidable actuation of mechanisms along an end effector, articulation or rotation of an end effector, etc., as will be better appreciated below with respect to the various components and assemblies of the applicator 500.

In FIG. 50, the implant 10 is illustrated as mounted on an end effector 502 configured as a distal portion of the surgical implant applicator 500. Again, it is to be appreciated that the applicator 500 may be used for implanting surgical implants other than the implant 10, e.g., including the various embodiments discussed herein, and that the implant 10 is given as a representative example only. Accordingly, it is noted that any reference to the implant 10 with respect to the applicator 500 is for the purpose of assisting in describing various modes of operating the applicator 500.

The end effector assembly 502 of the applicator 500 includes a set of jaws designated with a jaw 504a and a jaw 504b (collectively, "the jaws 504"). Due to the illustrated orientation of the jaws 504 throughout the Figures, the jaw 504a may be referred to herein as the upper jaw, and the jaw 504b as the lower jaw, although it is to be appreciated that this is for the sake of discussion only and that the jaw 504a does not necessary have to be "above" the jaw 504b in other embodiments (or after changing the orientation of the applicator manipulating the jaws 504, e.g., as discussed below). FIGS. 50 and 51A-51D show the surgical implant applicator 500 in an open configuration for the jaws 504, with opposing first and second portions of the surgical implant 10, namely the receiver member 12 and the deployment member 14 (e.g., or in other embodiments, others such as the halves 160, 162, 164, 166, and/or 168 of the implants described with respect to FIGS. 45-47), mounted in the upper and lower jaws 504a and 504b, respectively. The surgical implant applicator 500 includes a proximal assembly 506 that is connected to the end effector assembly 502 via an elongated shaft (elongated portion) 508 extending therebetween. In one embodiment, the shaft 508 has a diameter of about less than 10 mm, and preferably about 8 mm, although other dimensions are contemplated. The proximal assembly 506 includes a housing 510 having a handle portion including a handle 512 configured to enable a user to hold and operate the surgical implant applicator 500, e.g., with a single hand, and a movable handle or handle member in the form of a trigger 514, which may also or alternatively be referred to as a lever, movable actuator, etc. In one embodiment, the trigger 514 is arranged to be operated by the same hand holding the applicator 500 by the handle 512 to effect operation of the end effector 502, e.g., closing, cutting, and/or reset operations that are discussed in more detail below.

The end effector 502 is connected to the shaft 508 and thus the proximal assembly 506 via a joint 516 positioned proximate to a distal end of the shaft 508. A positioning assembly 518 is configured to perform articulation of the end effector 502 (that is, e.g., left and right or side-to-side angulation of the end effector 502 relative to a longitudinal axis 520 of the shaft 508). For example, FIGS. 52A-52D show the end effector 502 having been angled to the left with respect to the axis 520 and the orientation of that Figure. Additionally, the positioning assembly 518 is configured to control rotation of the end effector 502 about the longitudinal axis 520 of the shaft 516, relative to the proximal assembly 506. While the end effector 502 is shown to be non-removably attached to the shaft 508, alternatively, it can be removable with respect to the shaft 508 and replaced by a new end effector (having a new set of jaws) containing a new implant. This enables application of multiple implants in a single procedure. Also, while the shaft may preferably be rigid and straight, in alternative embodiments it may be flexible and non-rigid.

In one embodiment, the positioning assembly 518 may include a rotation actuator 522 that is mounted to proximal assembly 506, but rotatable with respect thereto. The rotation actuator 522 may include a plurality of ribs or ridges 524 that facilitate gripping thereof by a user. The rotation actuator 522 may be non-rotatably mounted with respect to the shaft 508, with the shaft 508 also rotatably mounted to the housing 510, and the end effector 502 non-rotatably mounted to the shaft 508. In this way, rotation of the actuator 522, e.g., via a user gripping the actuator 522 at the ribs 524 and turning the actuation 522 with respect to the housing 510, causes rotation of the shaft 508 and the attached end effector 502 about the axis 520. In one embodiment, the rotation actuator 522 enables more than about 90° and preferably about 180" of rotation about the axis 520 in either direction.

As noted above, the end effector 502 (also referenced to as the end effector assembly 502) is pivotally mounted relative to the shaft 508 via the joint 516. For example, the joint 516 may be configured to enable rotation or articulation of the end effector 502 about an axis 526 (FIG. 51B), which is transverse, e.g., perpendicular, to the axis 520. A mechanism can be provided so the end effector 502 is rotatable about its axis relative to the shaft 520 which remains stationary. The jaws 504 may be arranged together with the end effector assembly 502 so that the jaws 504 of the end effector 502 can be articulated, e.g., pivoted left or right or side-to-side about the axis 526, in unison relative to the shaft 508. As shown, there is one stationary jaw and one movable jaw (i.e., movable with respect to the stationary jaw) to transition the jaws between an open and closed configuration (position), but alternatively both jaws can be movable to transition the jaws between an open and closed configuration. Thus, movement of at least one jaw to transition the jaws between open and closed configurations includes movement of only one jaw or movement of both jaws. In one embodiment, the end effector 502 can be articulated by at least about 30° to 45° from the axis 520, and preferably about 60° from the axis 520 to either side with respect to the axis 520. As noted above, in alternative embodiments the shaft can be flexible instead of rigid as shown. The positioning assembly 518 may include an articulation actuator 528 (FIG. 51C) that is configured to cause the above-described articulation of the end effector 502 when the articulation actuator 528 is rotated. A knob 530 may be included and non-rotatably mounted to the actuator 528 in order to enable a user to rotate the articulation actuator 528 via rotation of the knob 530. Rotation of the articulation actuator 528 in a first direction (such as counterclockwise in the embodiment of FIGS. 52A-52C) may be arranged to cause the end effector assembly 502, along with the jaws 504, to correspondingly angle in the first direction (e.g., to the left relative to the axis 520 by an amount represented by an angle α in the embodiment of FIGS. 52A-52C). Rotation of the articulation actuator 528 in a second direction opposite to the first direction (such as clockwise in the embodiment of FIGS. 52A-52C) causes end effector 502 and/or the jaws 504 to correspondingly angle in the second direction (e.g., to the right relative to the axis 520 in the embodiment of FIG. 52A-52C). The further the articulation actuator 528 is rotated, the greater the angle of deviation of the end effector 502 and the jaws 504 from the longitudinal axis 520 of the shaft 508. The articulation movement of the end effector 502 and/or the jaws 504 may be in or with respect to a plane, but it is noted that the plane of movement can vary, e.g., be rotated with respect to the axis 520, by rotation of rotation actuator 522.

Figure 52A:
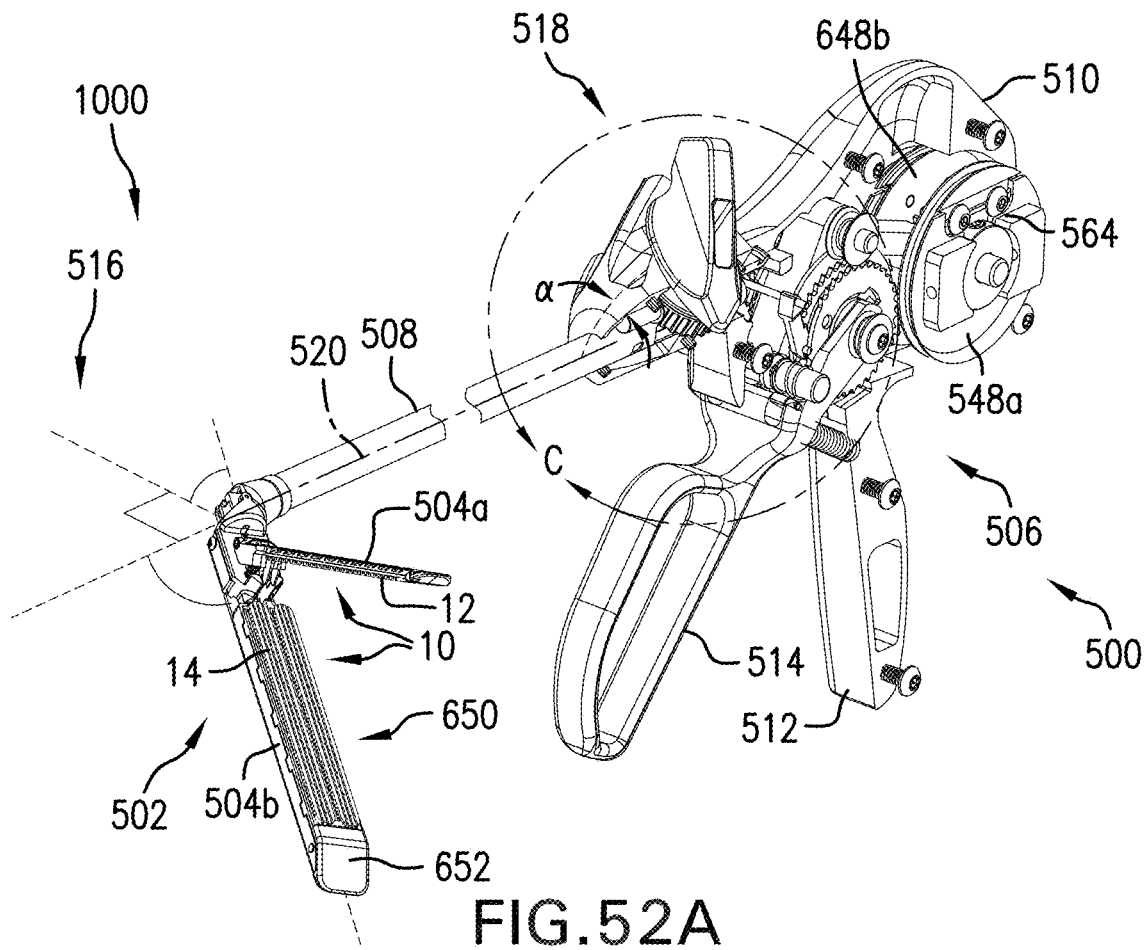
FIG. 52A is an isometric view of the system of FIG. 50, showing the jaws rotated and articulated.
Figure 52B:
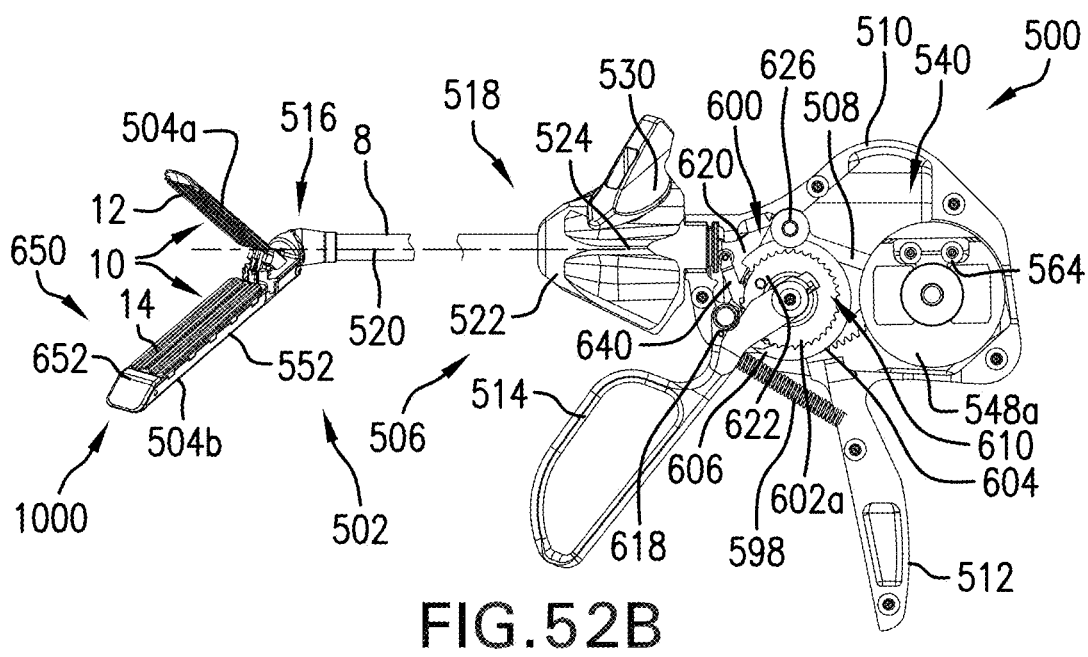
FIG. 52B is a side view of the system shown in FIG. 52A.
Figure 52C:
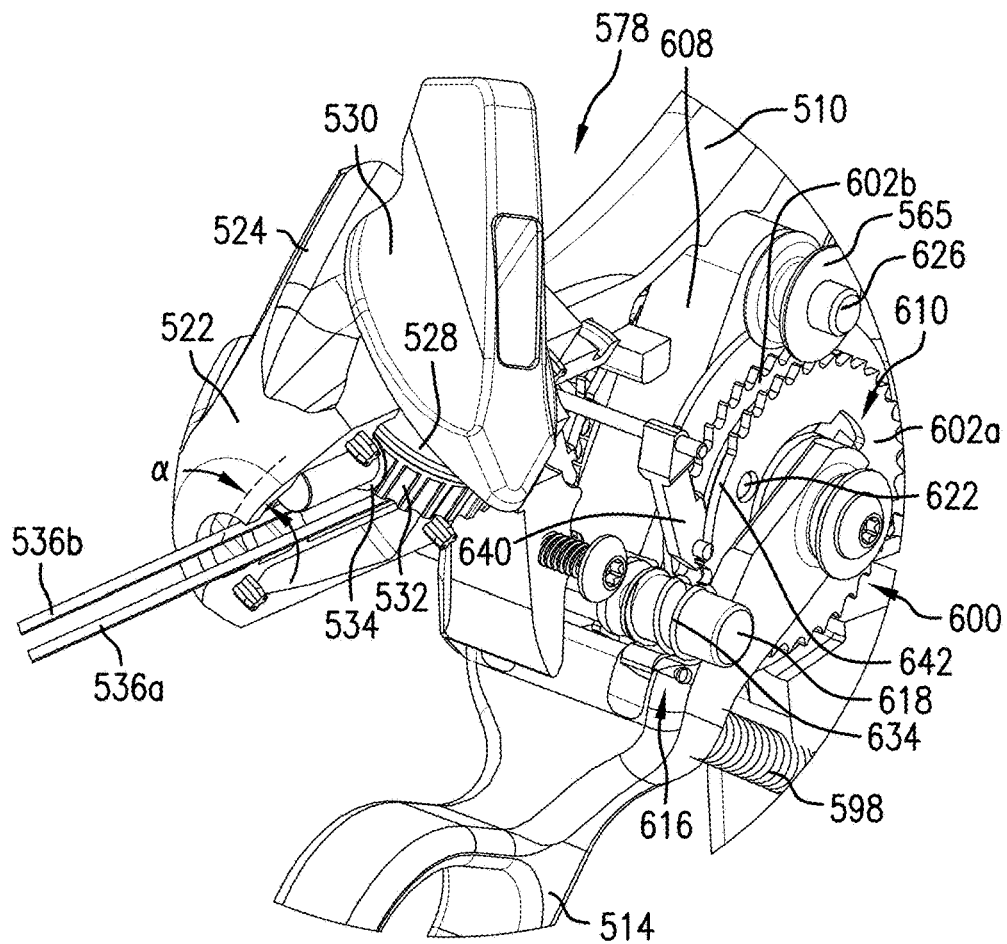
FIG. 52C is a detail view of the portion of FIG. 52A within circular border C of FIG. 52A.
Figure 52D:
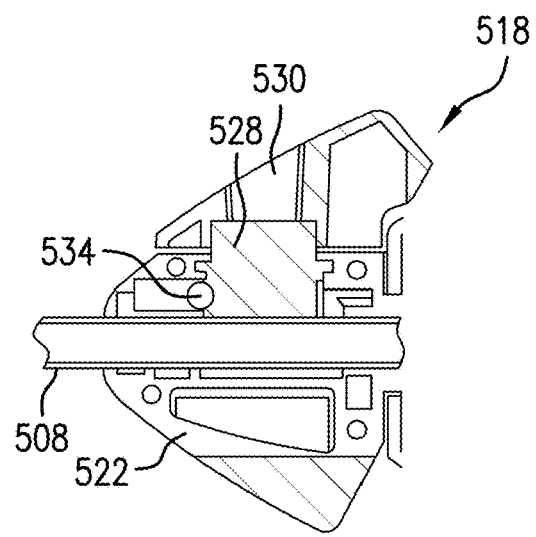
FIG. 52D is a cross-sectional view of the positioning assembly of FIG. 52A.

The articulation actuator 528 may include one or more relief features 532, such as scallops, detents, or indents, to provide a predetermined amount of frictional resistance to the articulation actuator 528 that allows it to be rotated by hand by a user, but provides sufficient friction to prevent it from counter-rotating after the user's hand is removed from the articulation actuator 528. The relief features 532 may also provide sufficient friction so that the end effector 502 maintains the desired degree of angulation until the user decides to again operate the articulation actuator 528, e.g., via the knob 530. In the embodiment shown in FIG. 52D, one or more detent balls 534 are resiliently or spring-loadedly mounted to the rotation actuator 526, or other component of the positioning assembly 518, and interact with the relief features 532 to provide the predetermined amount of friction. One or more articulation drivers may be included, e.g., two such drivers designated with the numerals 536a and 536b (collectively, "the articulation drivers 536"), which are shown in FIG. 52C mounted at their proximal ends (e.g., pivotally mounted) to the articulation actuator 528. More specifically, the articulation drivers 536 may be mounted on opposite sides of the articulation actuator 528 (i.e., the drivers 536 are eccentrically mounted to the actuator 528), such that rotation of the articulation actuator 528 pushes one of the articulation drivers 536 and pulls the other articulation driver. The distal ends of the articulation drivers 536 are pivotally mounted to opposite sides of the joint 516, designated with the numerals 538a and 538b (FIG. 54C), respectively, to translate the pushing and/or pulling actions to the end effector 502 thereby effecting angular articulation of the end effector 502. The articulation drivers 536 may preferably be flat ribbons having suitable tensile and/or compressive strength in their axial direction during the pulling and/or pushing operations. Alternatively, the articulation drivers 536 may be rigid rods or the like. In one embodiment, articulation drivers in the form of cables or wires are used, and forces for articulating the end effector 502 is transferred from the actuator 528 via tension only.

An alternate articulation mechanism is illustrated in the embodiment of FIGS. 52E-52M. This articulation mechanism provides a double articulating wrist which enables articulation in first and second opposite directions along a vertical axis, i.e., a yaw axis, and in third and fourth opposite directions along a horizontal axis, i.e. a pitch axis. Stated another way, in the orientation of FIG. 52E articulation of the end effector can be effected in the up and down direction (pitch up and pitch down) and the side to side direction (yaw right and yaw left).

Figure 52E:
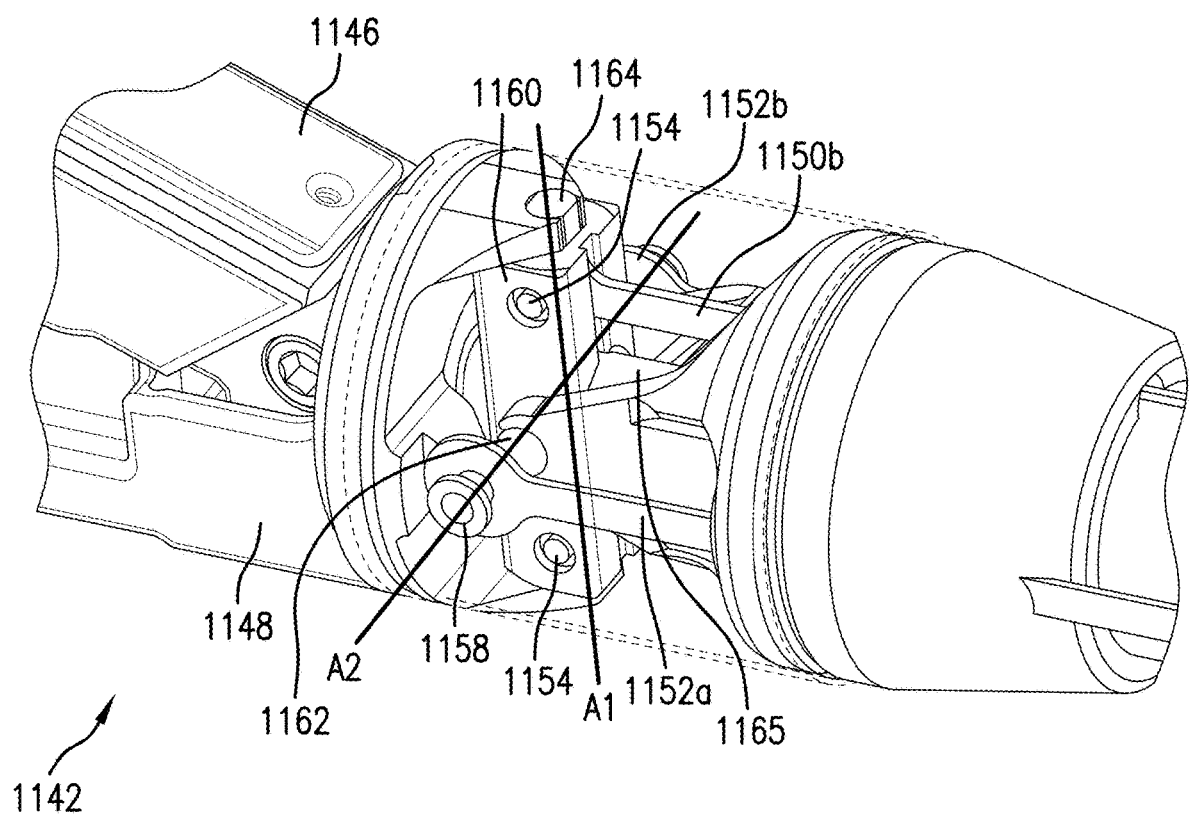
FIG. 52E is a perspective view of an alternate embodiment of an articulation mechanism of the present disclosure.
Figure 52F:
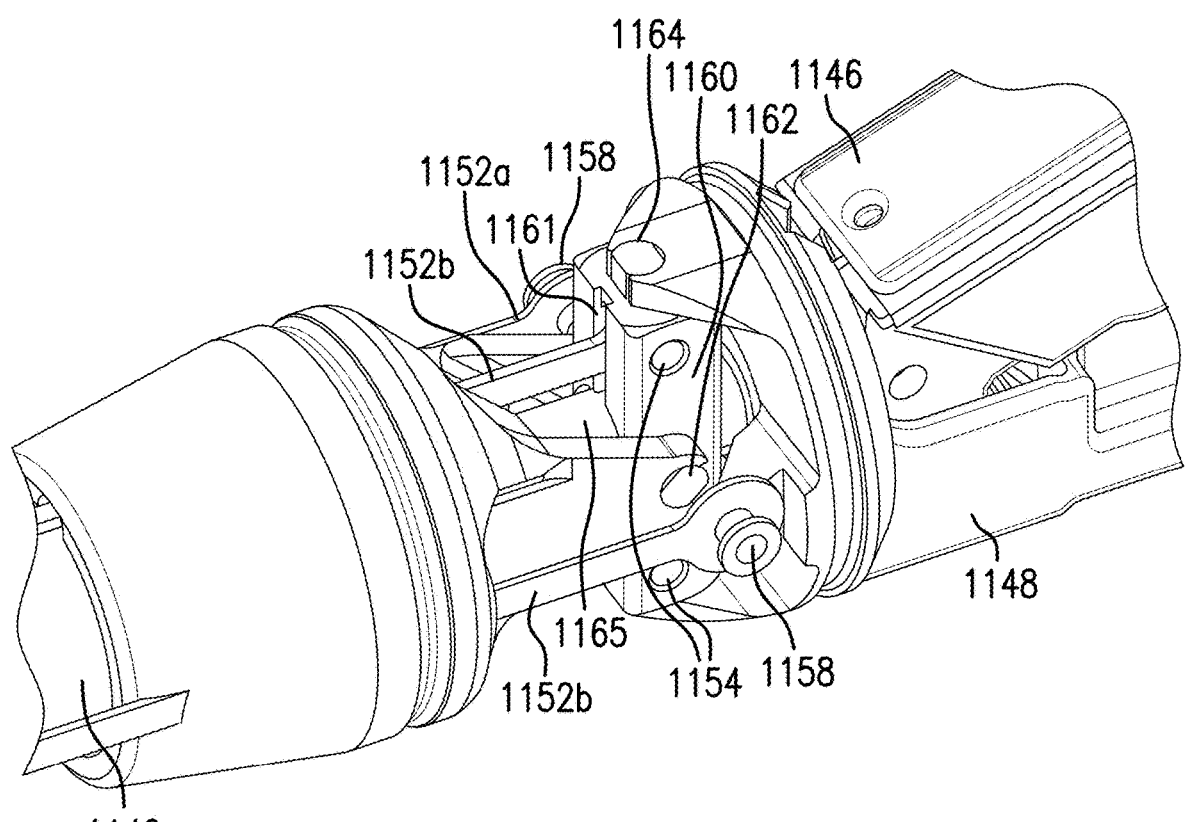
FIG. 52F is a perspective view of the other side of the articulation mechanism of FIG. 52E.

Referring initially to FIGS. 52E and 52F, the end effector 1142 of has a movable jaw 1146 and a stationary jaw 1148. The jaws 1146, 1148 can 1148 can receive any of the other implants described herein. For example, if the implant 1010 is utilized as described below, for example, the fastener supporting member (and fasteners) would be in the moving jaw 1146 and the receiver member would be in the stationary jaw 1148; if the implant such as implant 10 is used by way of another example, then the fastener supporting member would be in the stationary jaw and the receiver member would be in the movable jaw. It should also be appreciated that this double articulating wrist structure of FIGS. 52F-FIG. 52M can be utilized in other surgical applicators and other surgical devices where such articulation is beneficial, and not limited to use with applicators having implants disclosed herein.

The double articulation enables movement about the yaw axis designated by axis A1 and the pitch axis designated by axis A2. Note these two axes A1, A2 preferably intersect, and preferably intersect at a central point. Such central intersection helps to ensure the pivot joint is secure in all positions and well defined, thus keeping the articulation wrist controllable. Additionally, because of the high tensile force of firing, preferably the drive cable bundle which effects movement of the driver, e.g., driver 1147 to advance (deploy) the fasteners from the jaw, passes through the intersection of the axes A1, A2 Such placement reduces the chances of unwanted articulation, i.e., unwanted pitch and yaw movements, during advancement (firing) of the fasteners and/or retraction of the driver.

Preferably two pairs of tension ribbons are provided, the ribbons preferably only under tensile load. One advantage of using ribbons is they help keep the wrist controllable and are stiffer in comparison to cables or cords because of their lack of braiding. One pair of ribbons 1150a 1150b effect pitch movement (referred to herein collectively as pitch ribbons 1150); another pair of ribbons 1152a, 1152b effect yaw movement (referred to herein collectively as yaw ribbons 1154). When one of the pitch ribbons 1150 is pulled, it allows the other pitch ribbon 1150 to extend so the wrist pitches about the pitch axis A2. When one of the yaw ribbons 1152 is pulled, it allows the other yaw ribbon 1152 to extend so the wrist pitches about the yaw axis A1. In order to minimize the interaction of the two motions, the yaw ribbons 1154 preferably attach to the jaws via rotatable joints in line with the pitch axis A2.

Figure 52G:
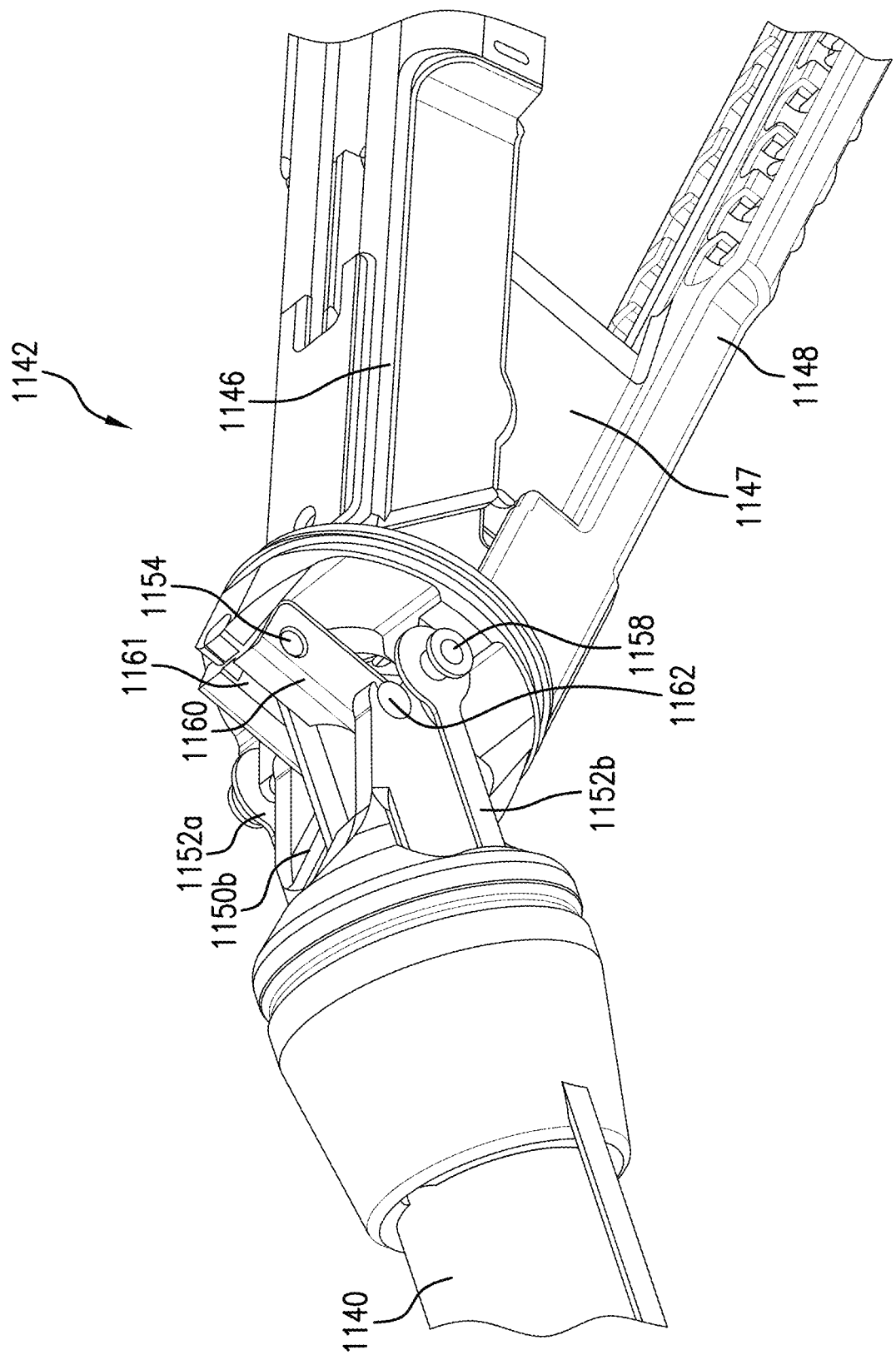
FIG. 52G is a perspective view of the articulation mechanism of FIG. 52E articulated to a pitch down position.
Figure 52H:
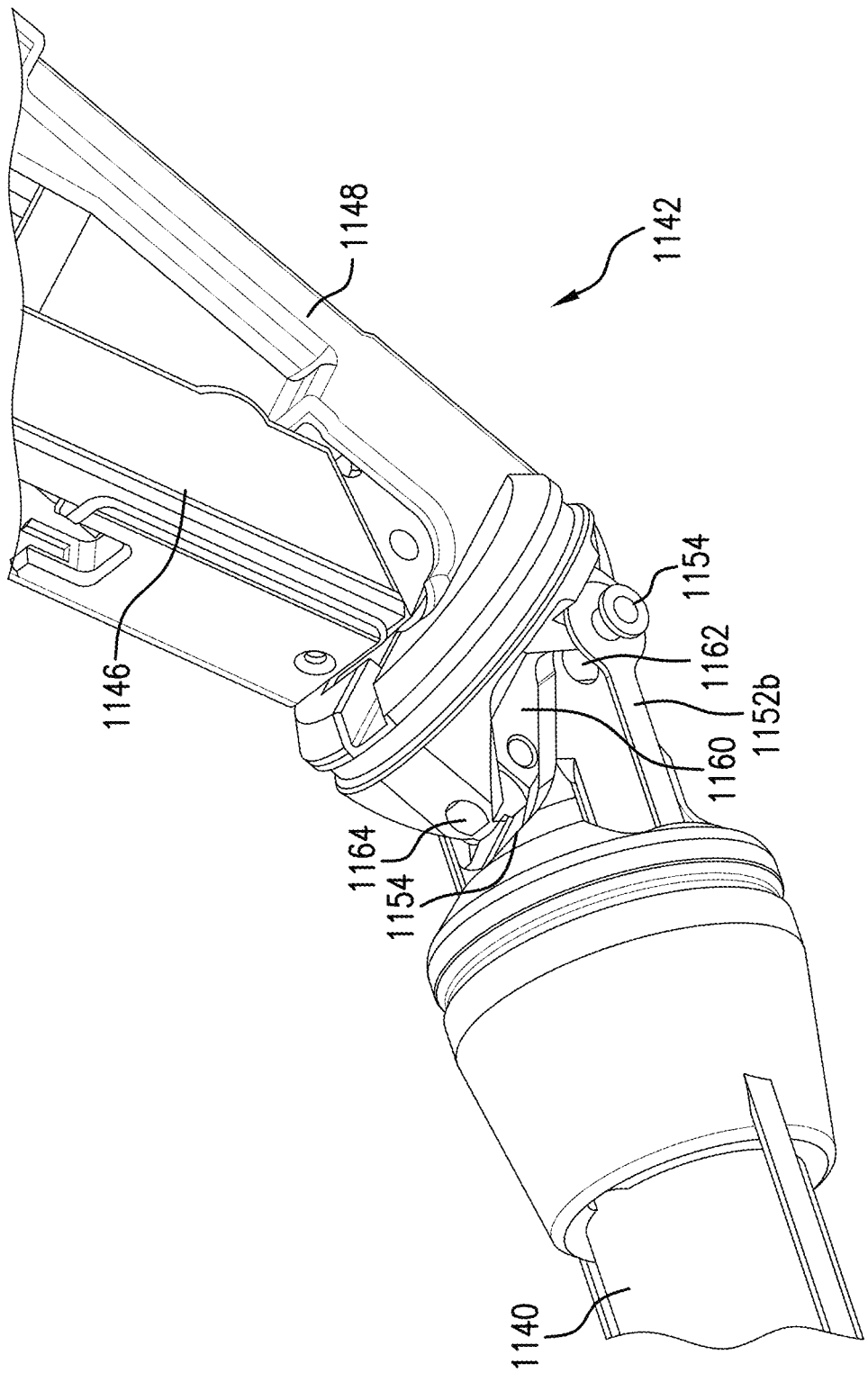
FIG. 52H is a perspective view of the articulation mechanism of FIG. 52E articulated to a pitch up position.
Figure 52I:
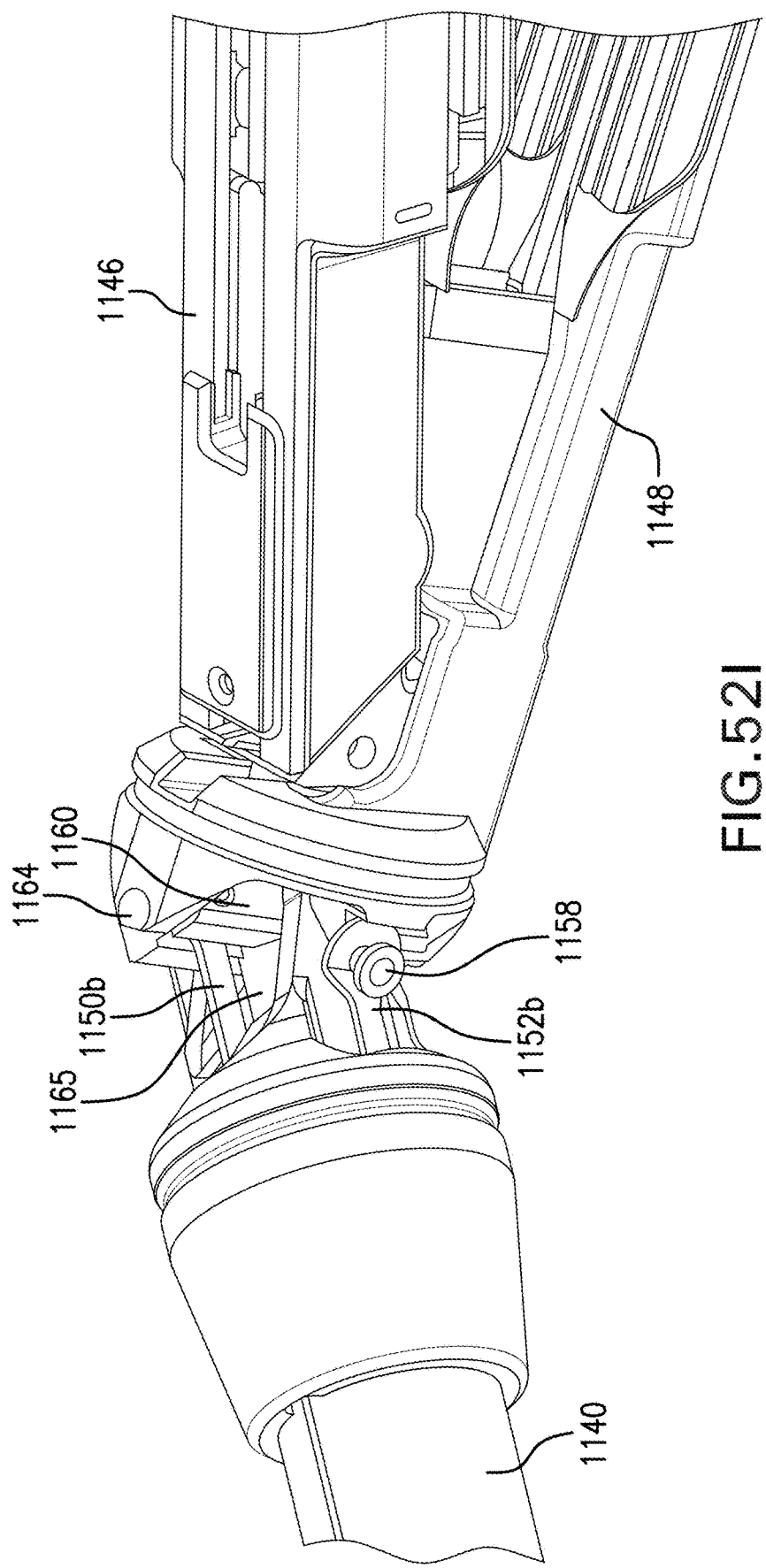
FIG. 52I is a perspective view of the articulation mechanism of FIG. 52E articulated to a yaw right position.
Figure 52J:
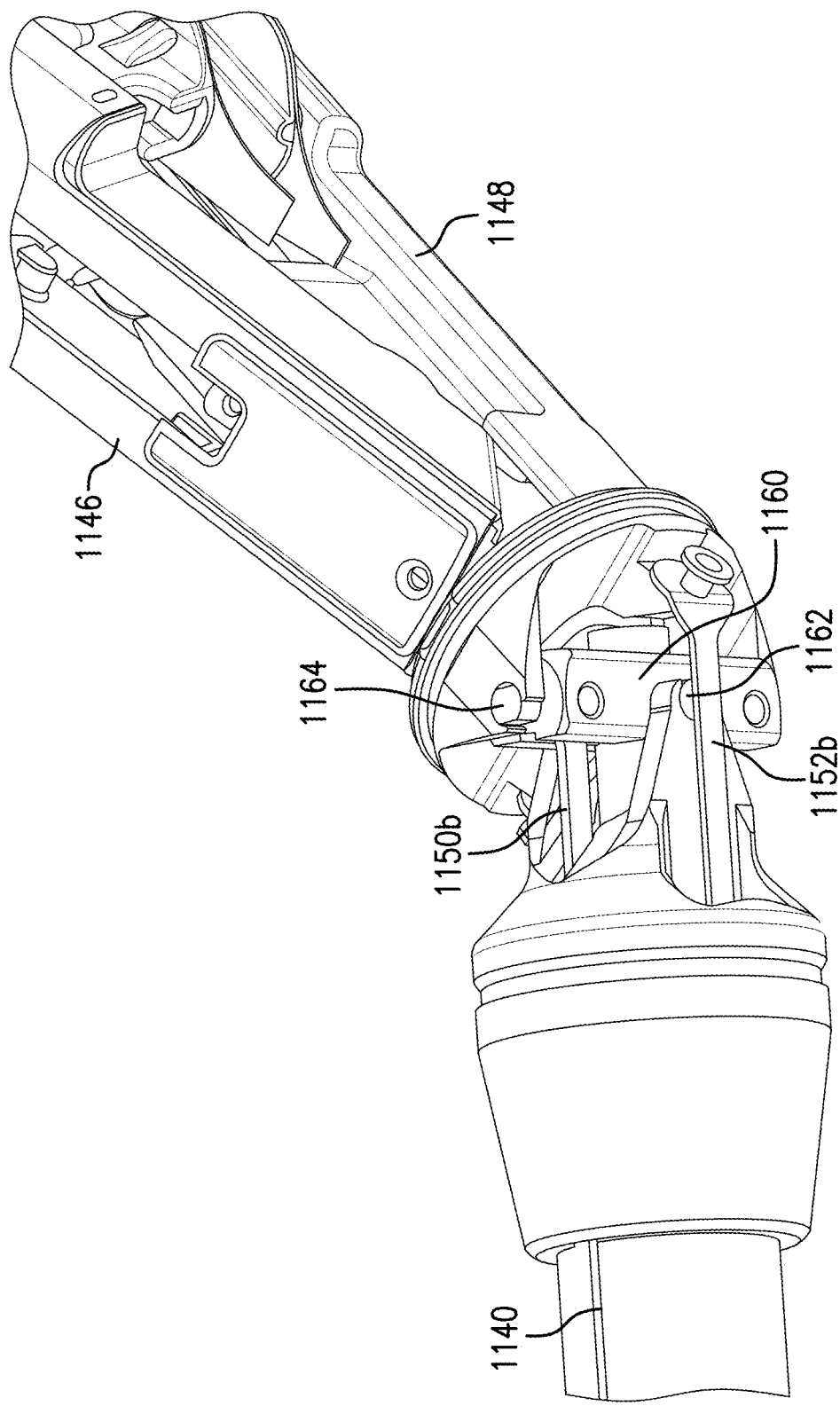
FIG. 52J is a perspective view of the articulation mechanism of FIG. 52E articulated to a yaw left position.
Figure 52K:
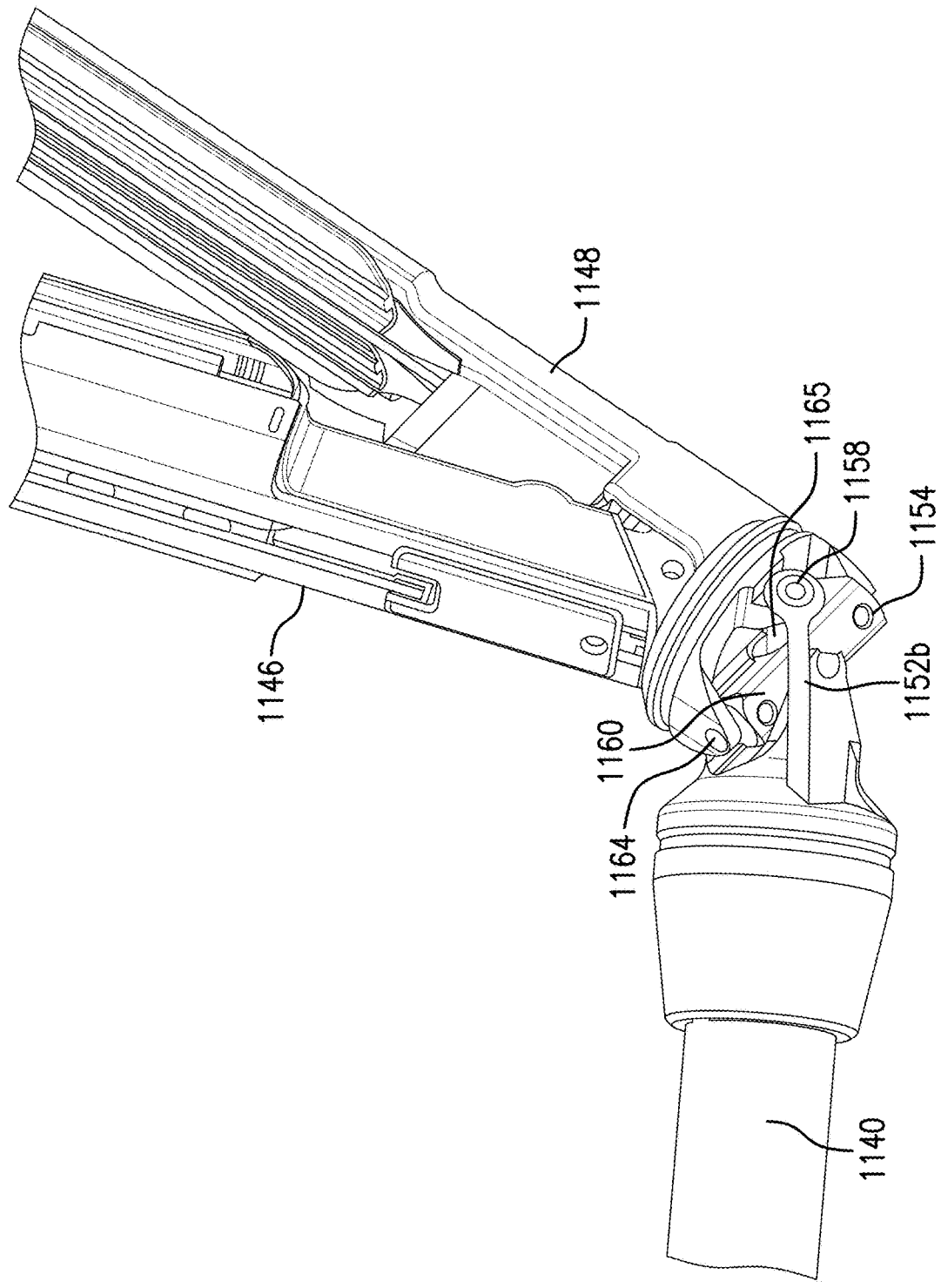
FIG. 52K is a perspective view of the articulation mechanism of FIG. 52E articulated simultaneously to a pitch up and yaw left position.
Figure 52L:
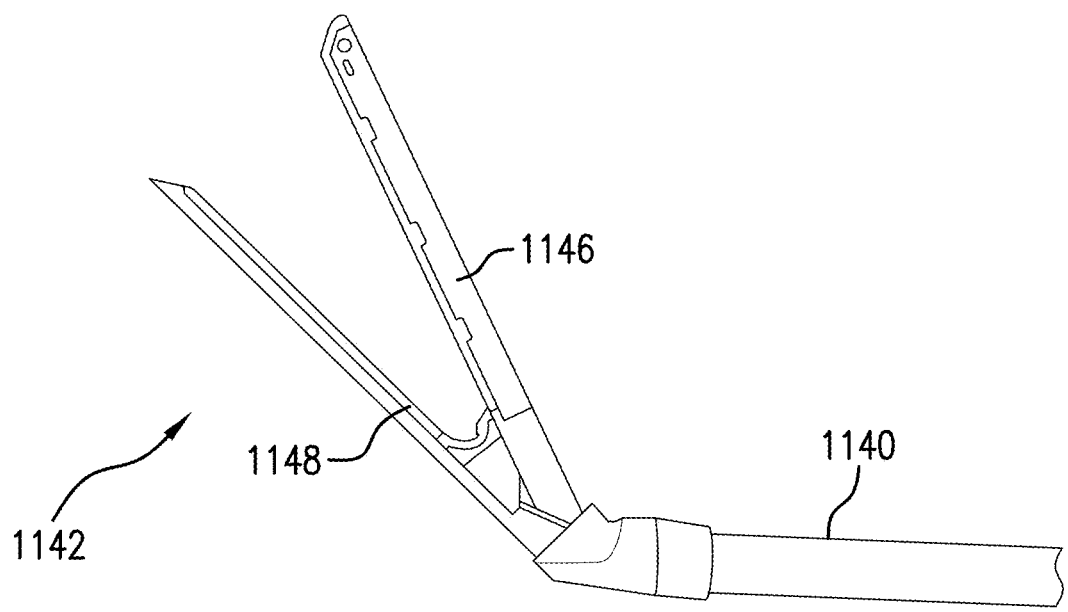
FIG. 52L is a side view showing the end effector articulated to the pitch up position corresponding to the position of FIG. 52H.
Figure 52M:
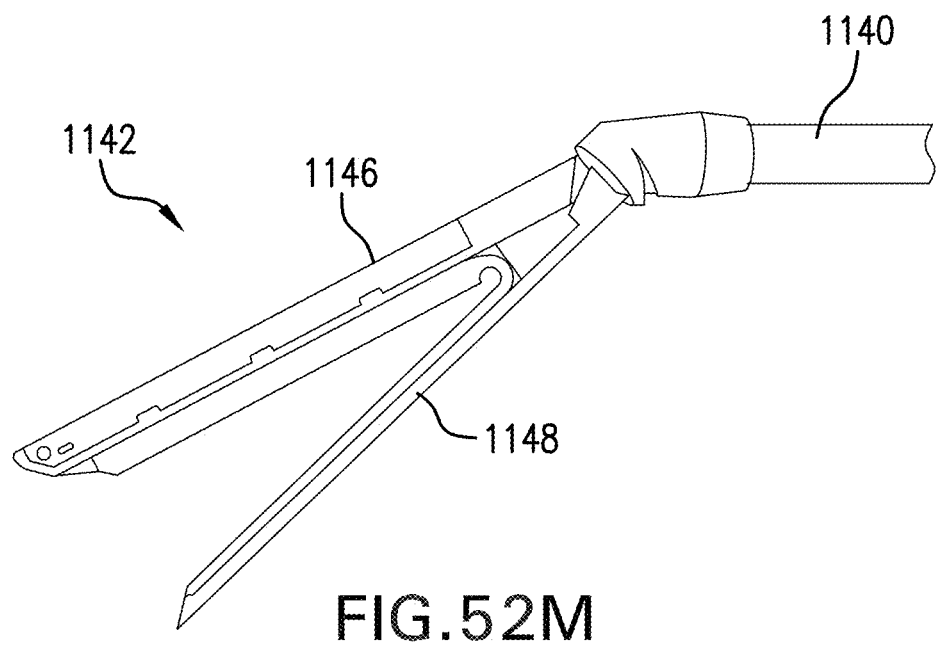
FIG. 52M is a side view showing the end effector articulated to the pitch down position corresponding to the position of FIG. 52G.

With continued reference to FIGS. 52E and 52F, the pivot 1160 is attached to the shaft yoke by fasteners 1162 and attached to the jaws 1146, 1148 by fasteners 1164. The distal ends of the pitch ribbons 1150 are attached to the pivot 1160 via pins or fasteners 1154 and as shown extend inside a slot 1161 in the pivot 1160. Note as viewed in the orientation of FIG. 52E, the pitch ribbons 1150 are spaced vertically apart, each parallel to a longitudinal axis of the shaft 1140, with one positioned above the other on each side of the longitudinal axis. In this manner, when the bottom ribbon 1150a is pulled, the pivot 1160 is pivoted (rotated) clockwise about axis A2, e.g., the bottom portion is pulled so the top portion rotates toward the distal end as shown in FIG. 52G. This can be considered a pitch down position, and the end effector is 1142 is shown in this position in FIG. 52M. Conversely, when the top ribbon 1150b is pulled, the pivot 1160 is pivoted (rotated) counterclockwise, e.g., the top portion is pulled so the bottom portion rotates toward the distal end as shown in FIG. 52H. This can be considered a pitch up position and the end effector 1142 is shown in this position in FIG. 52L. The distal end of the yaw ribbons 1152 are attached to the pivot 1160 at pins or fasteners 1154. Note as viewed in the orientation of FIG. 52E, the yaw ribbons 1152 are spaced horizontally apart, each parallel to a longitudinal axis of the shaft 1140, with one positioned on each side of the longitudinal axis. In this manner, when the ribbon 1152a is pulled, the pivot 1160 is rotated about axis A1 to the left as shown in FIG. 52J. This can be considered a yaw left position. Conversely, when the other ribbon 1152b is pulled, the pivot 1160 is rotated about axis A1 to the right as shown in FIG. 52I. This can be considered a yaw left position. It should also be appreciated that both a yaw ribbon 1152 and a pitch ribbon 1150 can be pulled simultaneously to cause the end effector 1142 to both pitch and yaw, as shown by way of example in FIG. 52K, where pitch ribbon 1150b has been pulled to effect pitch up and yaw ribbon 1152a has been pulled to effect yaw left. It should be appreciated that when one of the pair of pitch ribbons 1150 is pulled, i.e., tensioned, in a proximal direction to effect pivoting, the other of the pitch ribbons 1150 is extended. Similarly, when one of the pair of yaw ribbons 1152 is pulled, i.e., tensioned, in a proximal direction to effect pivoting, the other of the yaw ribbons is extended. Note the flexing of the pulled yaw ribbon 1152 shown in FIGS. 52I-52K. Note that up, down, top, bottom, etc. are used herein is with reference to the orientation of FIGS. 52F-52M—if the orientation of the applicator changes, then these references would change accordingly.

As noted above, the drive cable bundle for effecting movement of the driver, e.g., the drive cables 544, 546 discussed above are contained within a flexible tubing 1165, composed for example of PTFE, although other materials are also contemplated. As discussed above the drive cable bundle passes through the intersection of the yaw and pitch axes A1, A2. The tubing 1165 helps to reduce friction at large jaw and/or large pitches while keeping the bundle passing through the intersection of axes A1 and A2.

In addition to rotation and articulation of the end effector 502, the surgical implant applicator 500 may be configured to perform additional functions, such as transitioning the jaws between opened and closed configurations, actuating fasteners of an implant (e.g., the fasteners 32 of the implant 10) disposed within the jaws 504, cutting surgical structures positioned between the jaws 504 proximate to the implant 10 (e.g., cutting along the channel 124 of the implant 10 discussed above), etc. In one embodiment, the trigger 514 may be arranged with, or as part of, an end effector driving assembly or mechanism 540 to enable one or more of the above functions of the end effector 502 to occur.

Figure 53A:
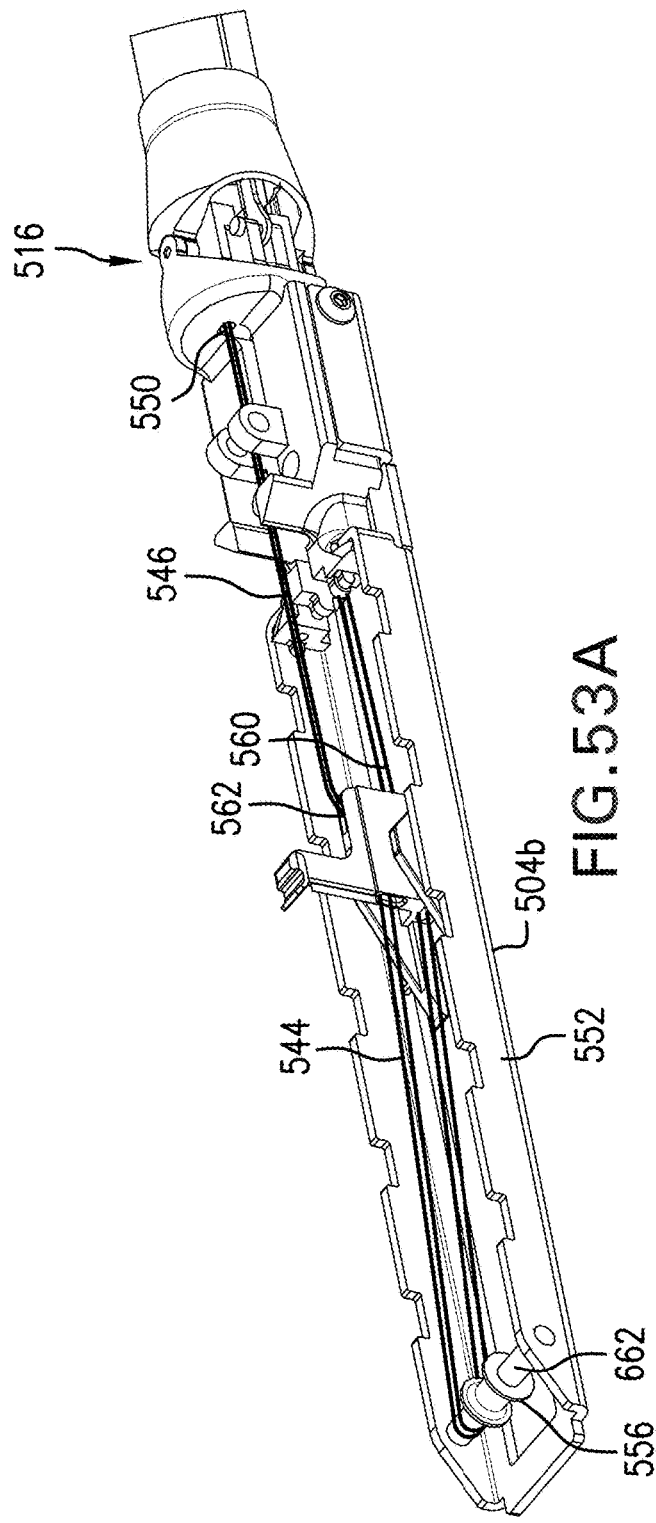
FIG. 53A is a perspective view of a lower jaw and a joint of the system of FIG. 50.
Figure 53B:
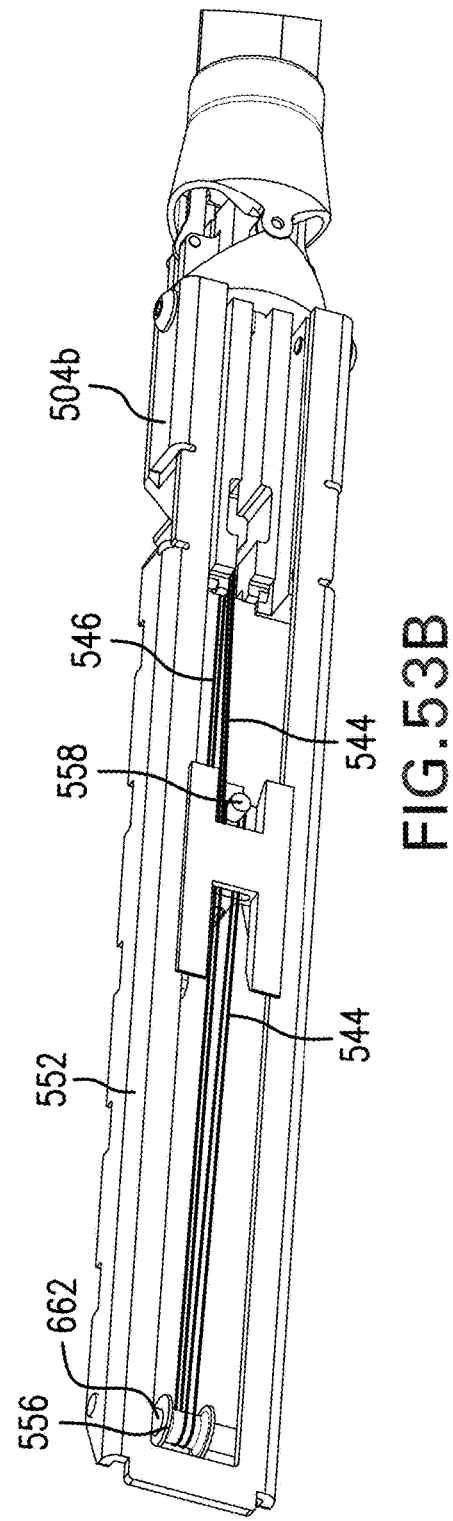
FIG. 53B is a view of a bottom of the lower jaw of FIG. 53A.

In one embodiment, the mechanism 540 may be arranged to cause actuation of a driver 542 of a drive assembly along the length of the jaws 504. A first tensioning member in the form of a first drive cable 544 and/or a second tensioning member in the form of a second return cable 546 (FIGS. 53A and 53B) may be connected to and transmit force from the end effector driving mechanism 540 to the driver 542 (FIG. 53B). The cables 544 and 546 may be any suitable wire, strand, string, rope, or other element capable of transferring tensile actuation forces. In other embodiments, the cables 544 and/or 546, or other tensile elements, may be connected to the upper jaw 504, the lower jaw 506 or other components of the end effector 502. The cables 544 and 546 in the illustrated embodiment are both connected between the mechanism 540 and the driver 542 to enable movement of the driver 542 relative to the end effector 502. Specifically in this embodiment, the drive cable 544 is arranged to pull the driver 542 in the distal direction, while the return cable 546 is arranged to pull the driver 542 proximally back to its initial position.

According to the illustrated embodiment, each of the cables 544 and 546 extends from a different one of a pair of drive spools 548a and 548b (collectively, "the drive spools 548") of the mechanism 540 (positioned within housing 510) through the shaft 508, distally past the joint 516 to the end effector 502 through a slot or opening 550 (FIG. 54B) in a distal end portion of the joint 516. The drive cable 544 continues along and through a frame 552 of the jaw 504b, through an opening, slot, or passage 554 in the driver 542 (e.g., see the view in FIG. 54C) around a pulley 556 (e.g., FIG. 55A) located adjacent the distal end of the jaw 504b, around a post 558 (e.g., see the bottom view in FIG. 53B) of the distal driver 542, back around the pulley 556, back through the passage 554 in the driver 542, and back through the opening 550 and the shaft 508 to the drive spools 548a. The return cable 546 is looped or threaded around a post 560 extending between a pair of flanges 562 of the driver 542 and back through the opening 550 and the shaft 508 to the spool 548b. Since each of the cables 544 and 546 in the illustrated embodiment forms a loop that starts and terminates at one of the spools 548, it is noted that each of the cables 544 and 546 in this embodiment may be arranged alternatively as a continuous belt or ribbon that does not have ends. One or more cable guides may be included in the housing 510, e.g., a pair of cable guides 565 in the illustrated embodiment (FIG. 52C), to direct the cables 544 and/or 546 toward the driver 542 and/or to keep the cables 544 and/or 546 away from the moving parts of the mechanism 540. It is noted that the cables 544 and 546 are shown only in portion or not at all in some of the Figures for clarity of the other components of the applicator 500.

Figure 51A:
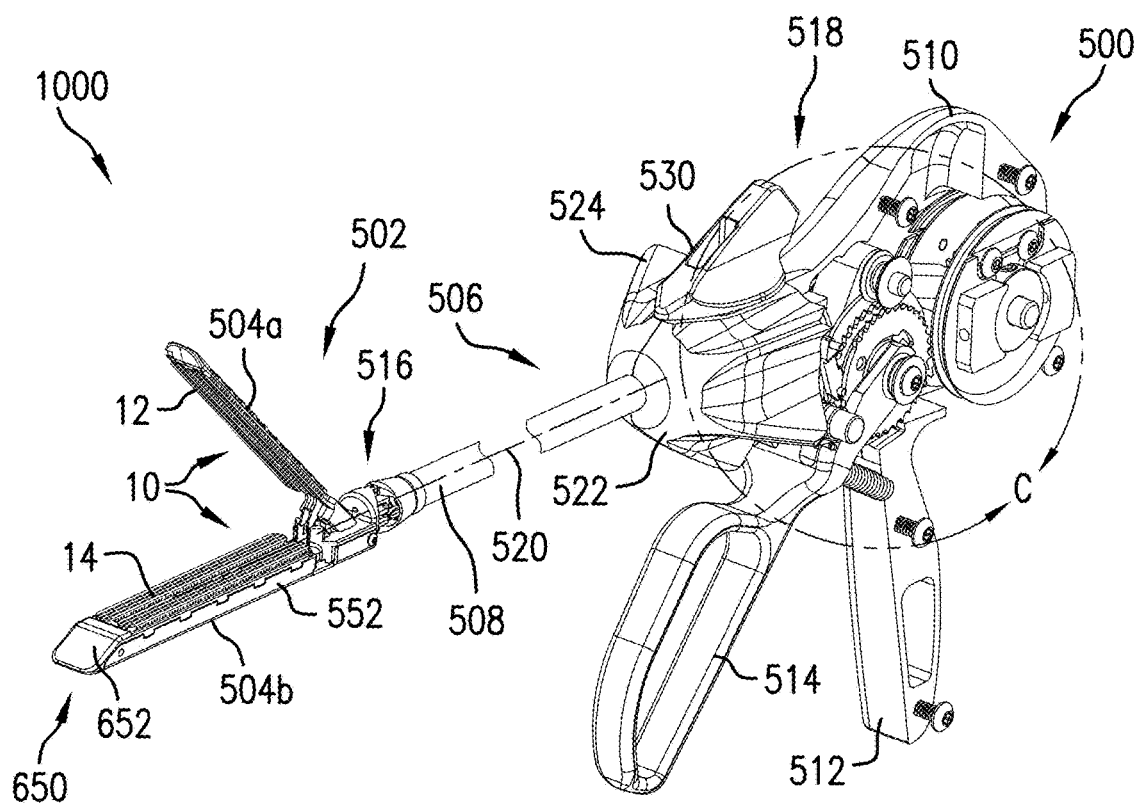
FIG. 51A is an isometric view of the system of FIG. 50 having a portion of a housing removed to illustrate components of a driving assembly in an initial position, the applicator jaws shown in open configuration.
Figure 51B:
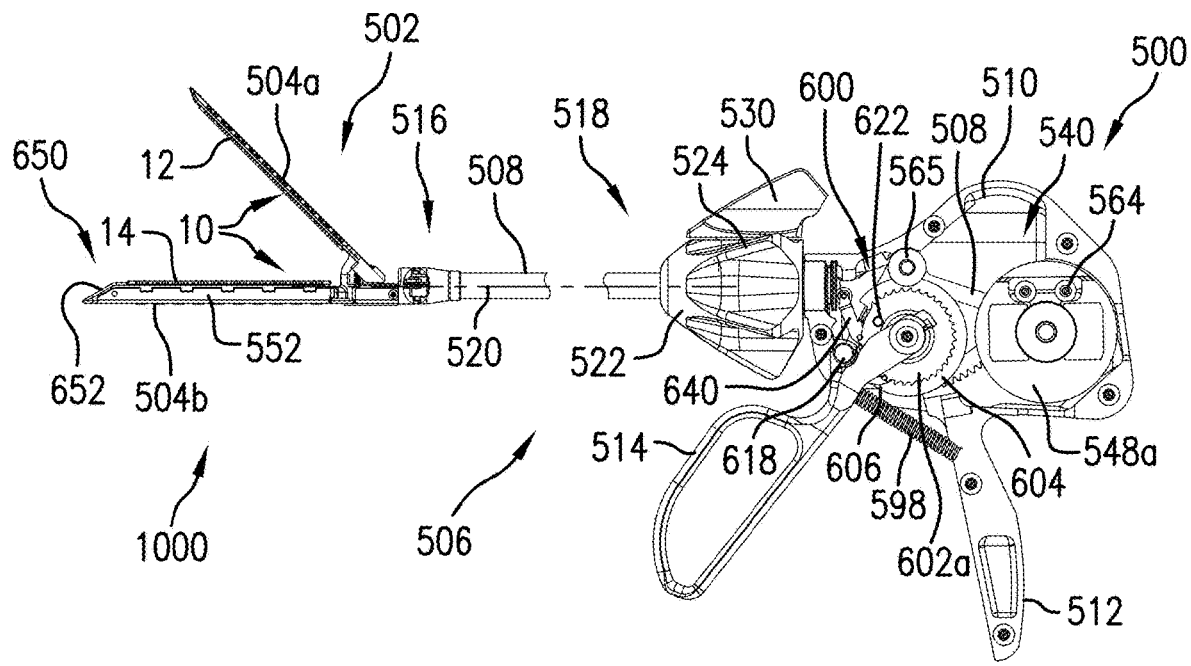
FIG. 51B is a side view of the system shown in FIG. 51A.
Figure 51C:
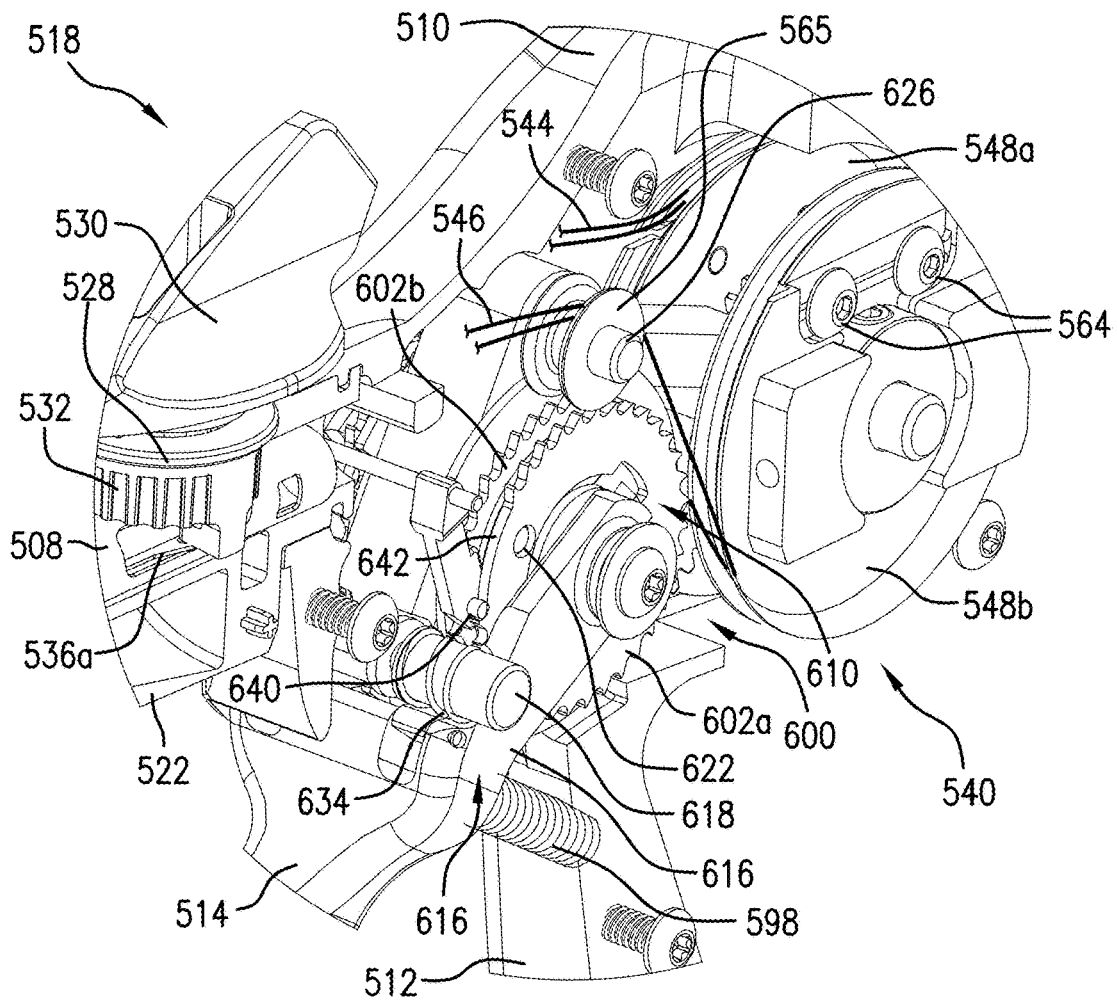
FIG. 51C is a detail view of the portion of FIG. 51A within circular border C of FIG. 51A.
Figure 51D:
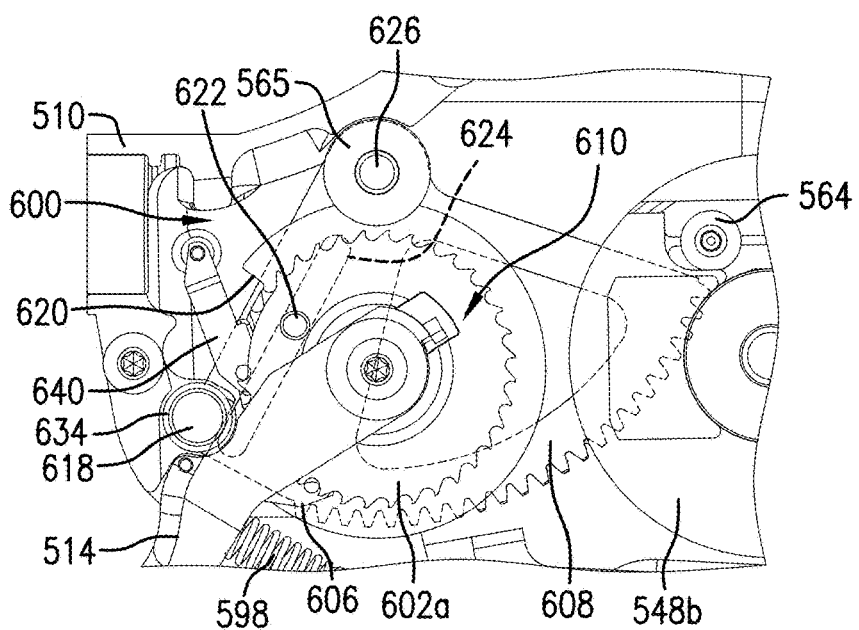
FIG. 51D is a partial side view of a portion of the system of FIG. 51C.

In the illustrated embodiment, the cables 544 and 546 are fastened to their respective one of the drive spools 548 via one or more fasteners 564 (FIG. 51D). That is, for example, the fasteners 564 each have a head or flange that is arranged to pinch or clamp the cables 544 and/or 546 to the spools 548. The fasteners 564 may be any suitable bolt, screw, clamp, clasp, etc. In one embodiment, the cables 544 and/or 546 may be arranged with a knot, bulge, or protuberance that is locked to one of the spools 548. Alternatively or additionally, the cables 544 and/or 546 may be formed similarly to a lasso (or double-sided lasso), with only the terminal end or ends of the cables 544 and/or 546 forming a loop for engagement with a post or fastener. It is to be appreciated that the cables 544 and/or 546 may be anchored, pinned, or otherwise secured to the driver 542 without looping about the posts 560 and 562, such that one end of each of the cables 544 and/or 546 terminates at the driver 542 and an opposite end of each of the cables 544 and/or 546 terminates at the corresponding one of the spools 548. For example, the posts 560 and 562 may in one embodiment be replaced with fasteners similar to the fasteners 564. It is noted that each or either of the cables 544 and/or 546 may be a multi-strand cable, either metallic or non-metallic, a single fiber or wire, belt, or other equivalent elongated, flexible member having sufficient tensile strength and dimensions to perform the functions described.

As will be discussed in more detail below, the cables 544 and 546 can be arranged with the spools 548 such that rotation of the spools 548 in one direction (e.g., counter-clockwise with respect to the embodiment illustrated in the Figures) causes tension on the drive cable 544, and rotation of the spools 548 in the opposite direction causes tension of the return cable 546. For example, the drive cable 544 can be wrapped clockwise about the spool 548a, such that counter-clockwise rotation of the spools 548 tightens the cable 544, and the return cable 546 can be wrapped counter-clockwise about the spool 548b, such that clockwise rotation of the spools 548 tightens the cable 546. Due to the inclusion of the pulley 556, tension in the drive cable 544 urges or pulls the driver 542 in the distal direction, while tension in the return cable 546 oppositely urges or pulls the driver 542 in the proximal direction. In this way, rotation of the spool 548 in one direction causes the driver 542 to travel distally along the jaws 504, while rotation of the spool 548 in the opposite direction cause the driver 542 to travel proximally along the jaws 504.

As noted above, the distal driver 542 is configured to perform multiple functions, including closing and opening jaws 504, cutting surgical structures located between the jaws 504 when the jaws 504 are in the closed configuration, installing implants, e.g., the implant 10, disposed with the jaws 504, etc. In order to provide these functions, the device driver 542 may be movably or slidably mounted along a length of the end effector 502. For example, the device driver 542, as shown in FIGS. 54C and 55A, may include a bottom, lower, or first body portion 568 that engages a lower surface of lower jaw frame 552 of the jaw 504b and a top, upper, or second body portion 570 that engages an upper surface of the upper jaw 504a In this embodiment, a rigid intermediate third body portion 572 may extend between and connect the first and second body portions 568 and 570.

Figure 54A:
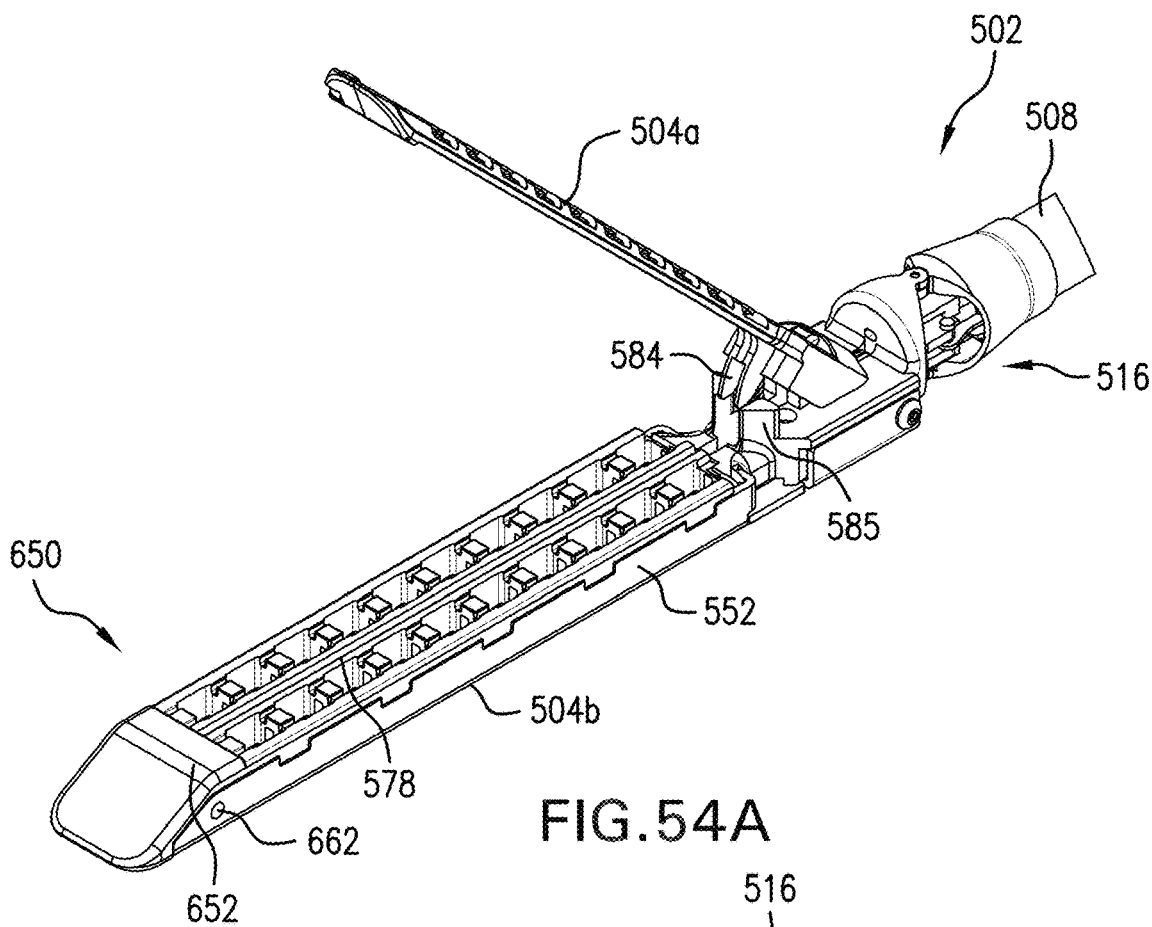
FIG. 54A is a perspective view of a set of jaws of the applicator of the system of FIG. 50 in an open configuration.
Figure 54B:
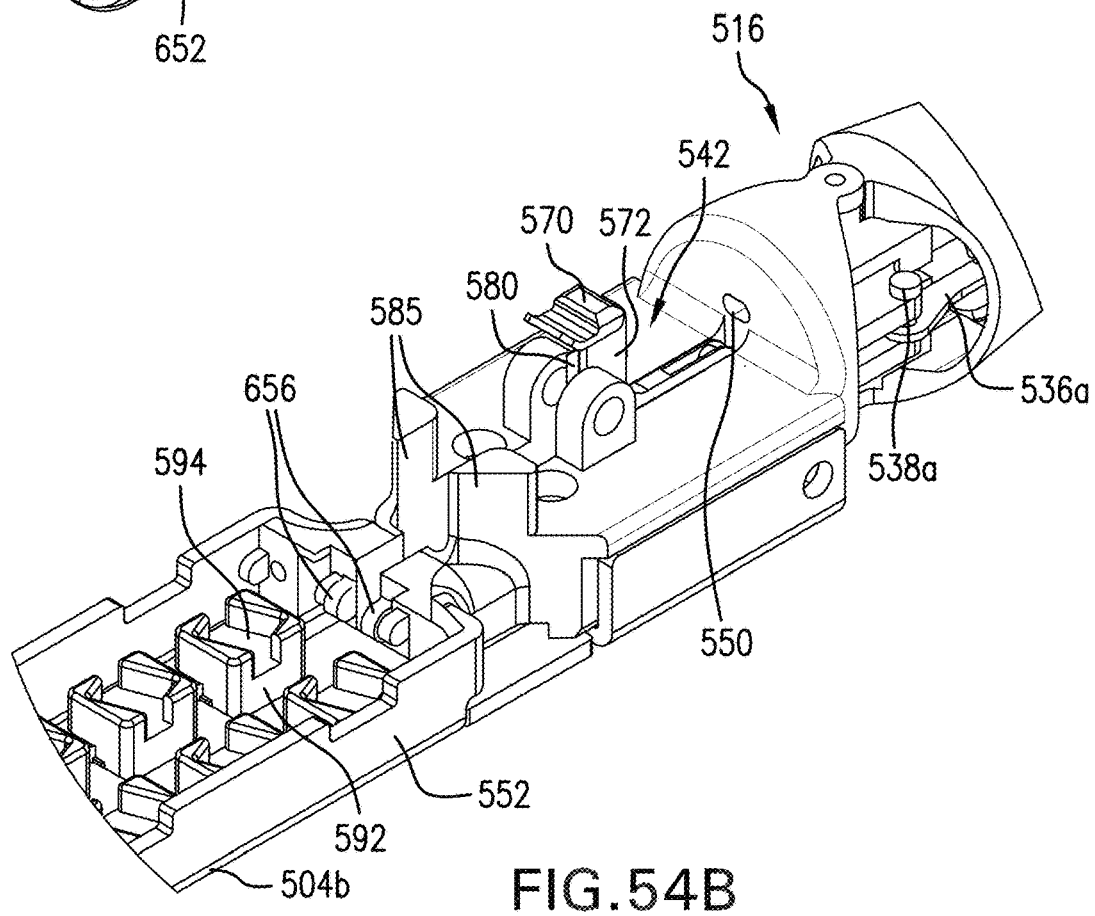
FIG. 54B is a partial, enlarged view of a proximal portion of the stationary jaw of FIG. 54A.
Figure 54C:
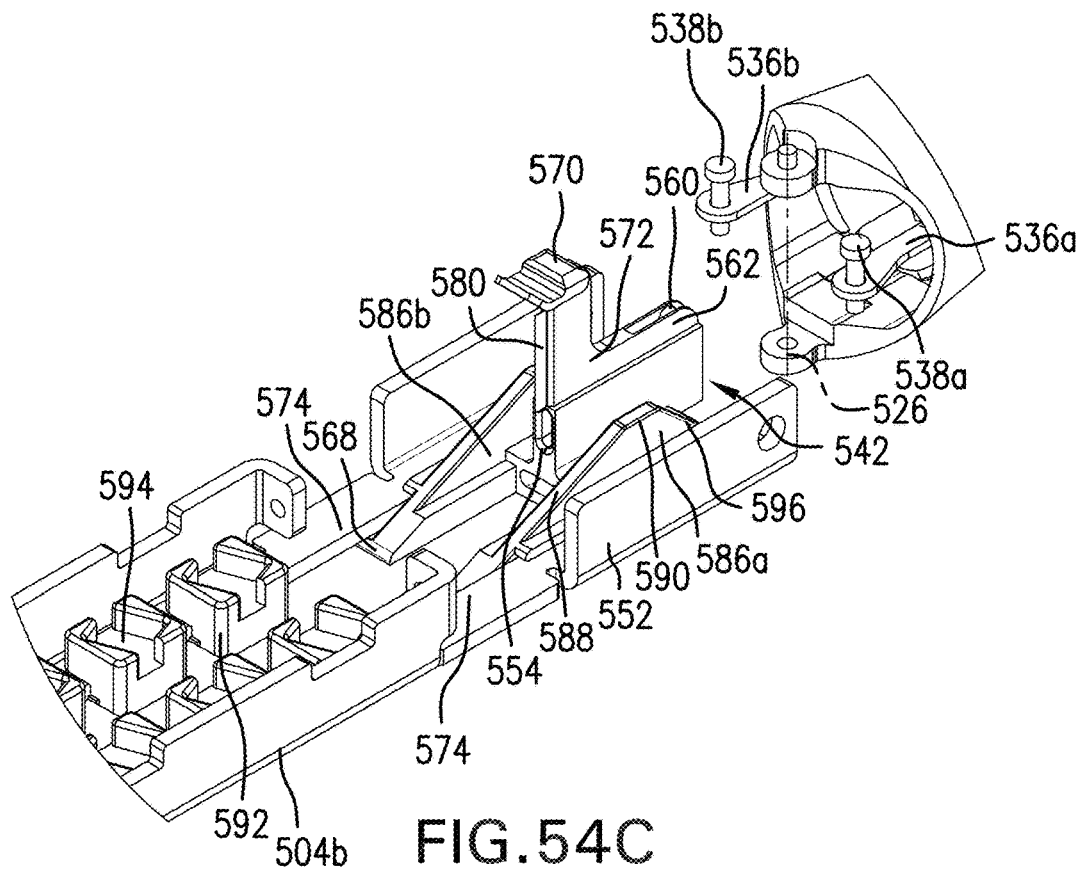
FIG. 54C is a partial, enlarged view of a proximal portion of the stationary jaw of FIG. 54A.
Figure 55A:
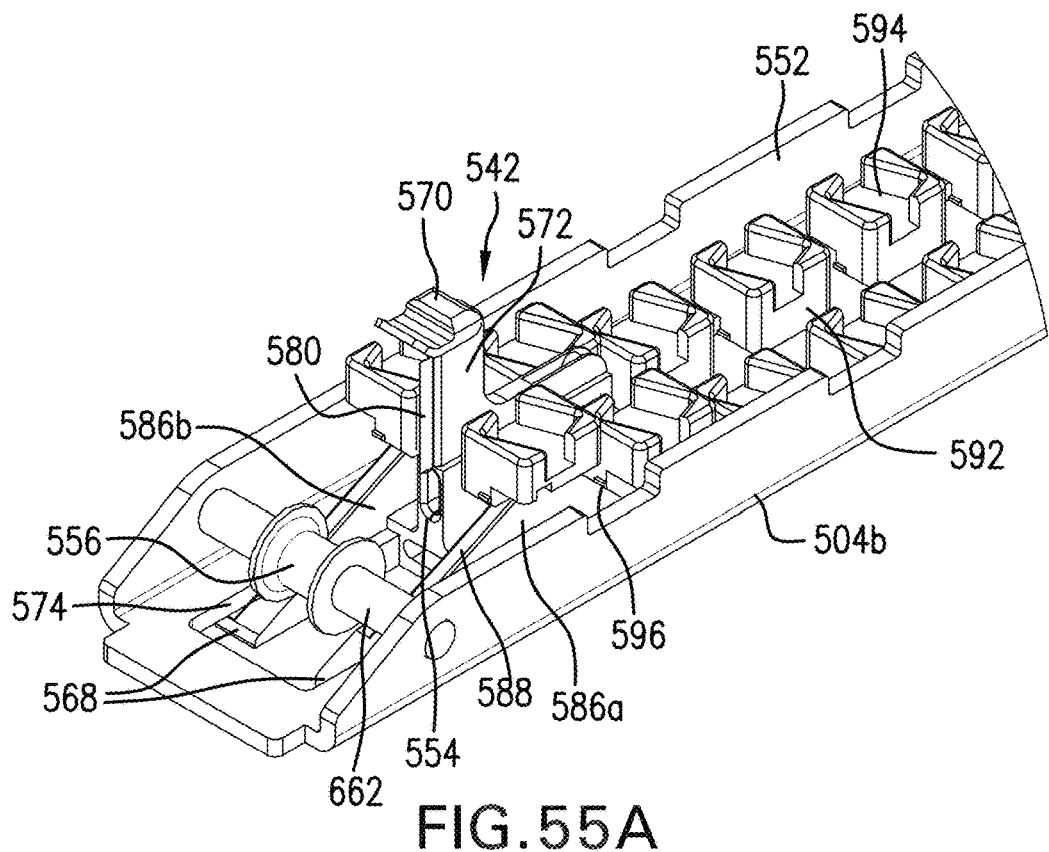
FIG. 55A is a partial, enlarged view of a distal portion of the jaw of FIG. 54A.

For example, the first, second and third body portions 568, 570, and 572 may give the device driver 542 a shape that resembles an I-beam configuration, as shown best in FIG. 54C. The bottom body portion 568 of driver 542 may be slidably mounted on a set of rails 574 of the lower jaw 504b so that the driver 542 can be driven back and forth, e.g., via the cables 544 and 546, reciprocally between a proximal end location, e.g., shown in FIGS. 54A-54C, and a distal end location adjacent the pulley 556, and proximal thereof, e.g., shown in FIGS. 55A-55C. The top body portion 570 of the driver 542 is located on the top surface of upper jaw 504a when assembled (e.g., with respect to FIGS. 54A-55C, and can best be seen in FIG. 55B) opposite the lower body portion 568 having flanges or portions located above and/or below the rails 574. For example, as shown in FIG. 55A a transverse region at the bottom body portion 568 is positioned below rail 574 on both sides to assist in retaining the clamped jaws together as the driver 542 is advanced. The first and second portions 568 and 570 may be, for example, one or more tabs, flanges, or other features dimensioned to prevent disengagement of the jaws 504 from between the first and second body portions 568 and 570. A pair of slots 576 and 578 may be included in the upper jaw 504a and the lower jaw 504b, respectively, through which the intermediate body portion 572 extends and along which the intermediate body portion 572 of distal driver 542 slides or travels as the distal driver 542 is translated distally and proximally relative to the jaws 504.

A blade, knife, cutter, or cutting implement 580 may be connected to, formed on, integral with, or otherwise form a part of a distal surface of third body portion 572 for purposes of severing tissue, implants such as the surgical implant 10, and/or other surgical structures positioned between the jaws 504 and along the length of the slot 578. For example, cutting of surgical structures can be performed via the cutter 580. For example, as discussed above, if the surgical implant includes two or more rows, e.g., the rows 35, of fastening subassemblies of implant 10 along a length of end effector 502, the cutting implement 580 may be positioned between the rows, such that the cutting operation with the driver 542 acts to sever the installed surgical implant, and the corresponding surgical structure on which the implant is installed, into two portions, one on each side of the cut made by the cutting implement 580 of the driver 542. In one embodiment, with specific reference to the implant 10 being used with the applicator 500, the cutting implement 580 severs the bridge 37, while in other embodiments the cutting implement 580 does not travel down the entire length of the jaws 504, such that the bridge 37 at the distal end of the implant (see e.g., FIG. 1) or other connecting element between rows of the implant is not cut, leaving the two rows attached at their distal portions. In one embodiment, for example, the implant 10 has a length of about 60 mm, while the cutting implement 580 travels about 55 mm of this length.

Figure 55B:
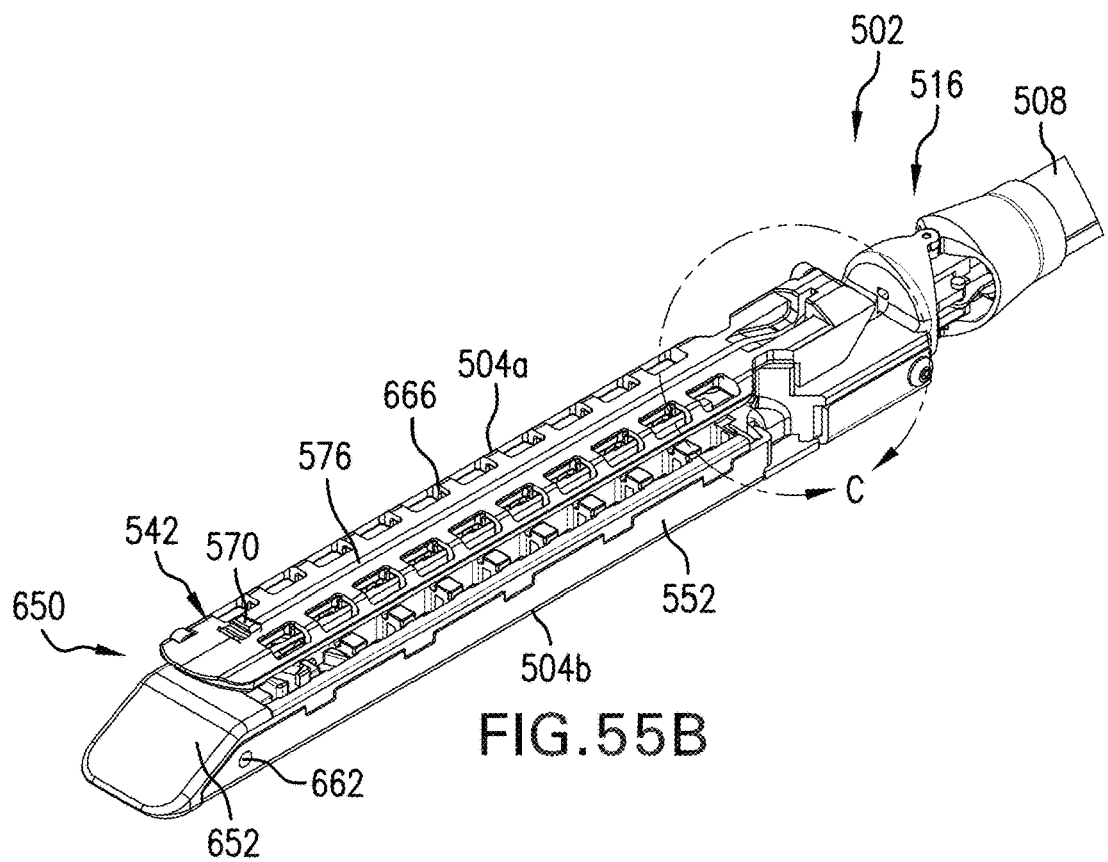
FIG. 55B is a perspective view of the jaws of FIG. 54A in a closed configuration.
Figure 55C:
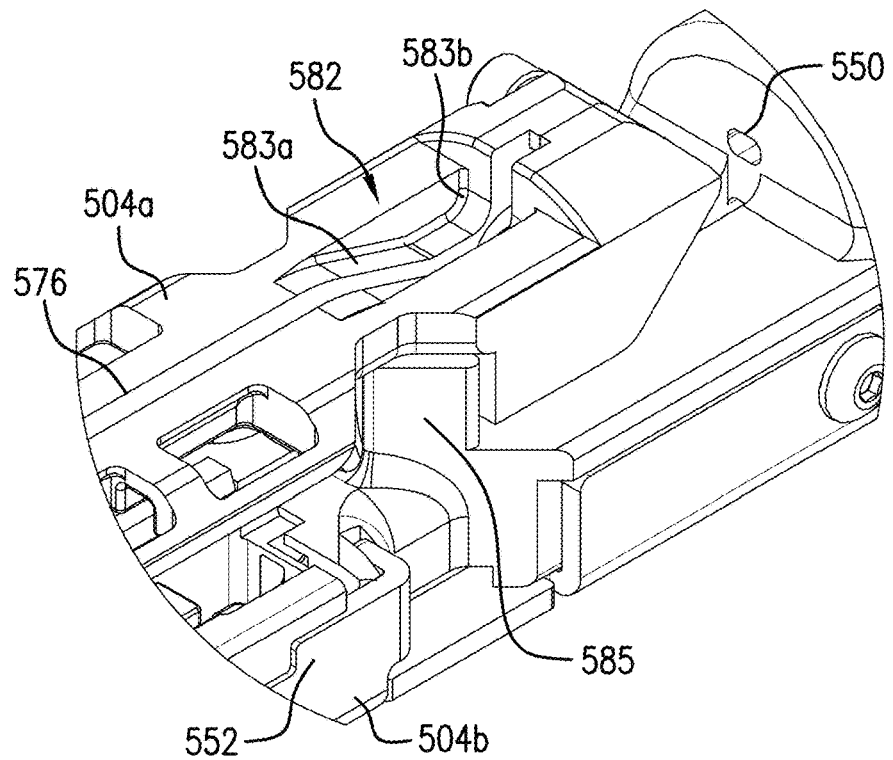
FIG. 55C is a detail view of the portion of FIG. 55B within the circular border C of FIG. 55B.

It is noted that before cutting occurs, initial distal advancement of the driver 542 from the proximal end of the jaws 504 initially toward the distal end, e.g., by drawing on the cable 544 (e.g., spooling onto the spool 548a while allowing cable 546 to lengthen (e.g., unspooling from the spool 548b), causes the jaws 504 to close, as shown in FIG. 55B-55C. More specifically, the driver 542 draws the top jaw 504a toward the bottom jaw 504b by squeezing the jaws 504 between the top body portion 570 and the flange of the bottom body portion 568 as the driver 542 is distally advanced.

Figure 56A:
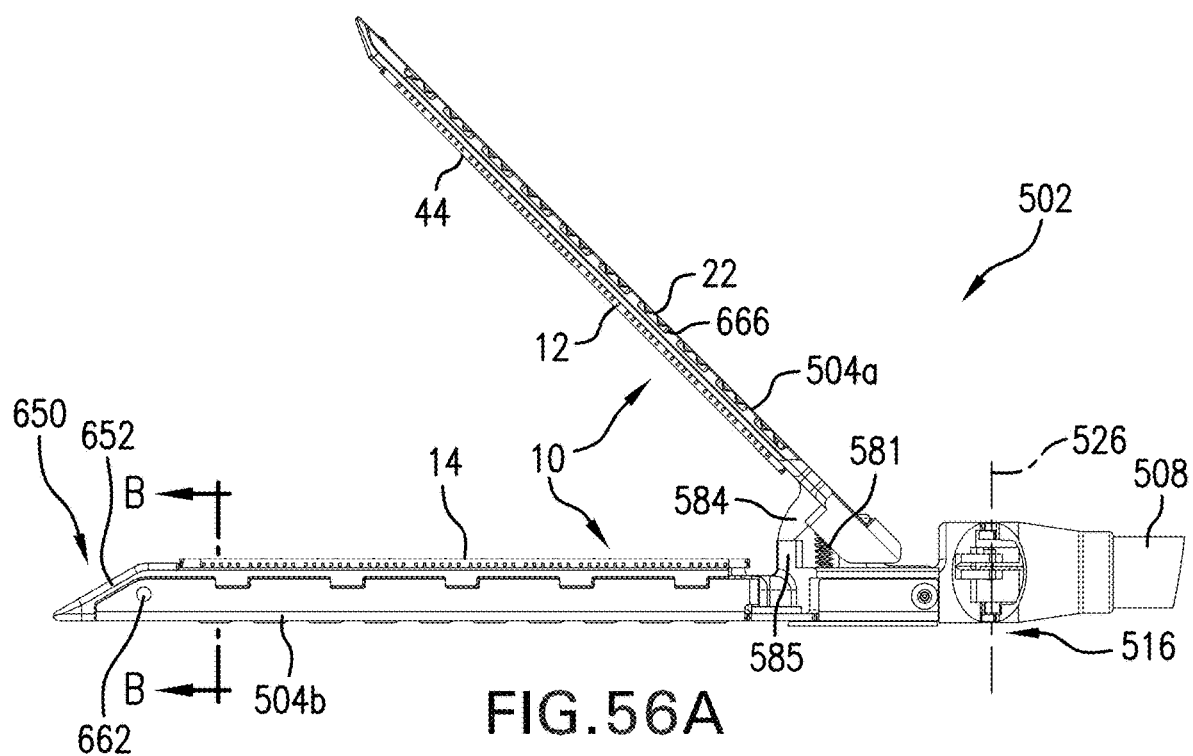
FIG. 56A is a side view of the jaws of FIG. 54a in the open configuration.

For example, as shown best in FIGS. 55B-55C, the top body portion 570 is initially located in a curved or angled recess 582 of the jaw 504a when the driver 542 is in its proximal position. The recess 582 includes a distal sloped surface 583a and a proximal sloped surface 583b. As the top body portion 570 is moved distally against the distal sloped surface 583a (e.g., during initial movement of the driver 542 via the cable 544), the top body portion 570 will press against the surface 583a, forcing the jaw 504a to rotate toward the opposite jaw 504b, thereby closing the jaws 504. Oppositely, moving the top body portion 570 proximally against the proximal sloped surface 583b (e.g., during return movement of the driver 542 back to its initial position with the cable 546), the top body portion 570 will press against the surface 583b, forcing the jaw 504a to rotate away from the opposite jaw 504b, thereby opening the jaws 504. Additionally or alternatively to the surface 583b being pressed, a spring or biasing element 581 as shown in FIG. 56A may be included to urge the jaws 504 into their open configuration when the driver 542 is aligned with the recess 582. In this way, the jaws 504 can be transitioned between their opened and closed configurations by moving the top body portion 570 of the driver distally and proximally within the recess 582. In one embodiment, the jaws 504 are opened at an angle of about 30° to about 60°, and preferably about 45°.

One or more shields 584 and/or 585 may be located on the upper and lower jaws 504a and/or 504b, respectively. The shields 584 prevent any tissue or surgical structures from being positioned too deeply into the jaws 504, thereby ensuring that the cutter 580 of the distal driver 542 does not encounter or cut tissue or other surgical structures until after the surgical implant, e.g., the implant 10, is installed via the applicator 500. The cutting implement 580 does not travel past the shields 584 and/or 585 until the jaws have been fully closed by distal travel of the driver 542.

In order to connect the halves of the surgical implant disposed with the jaws 504, e.g., the portion of the implant 10 supported in receiver member 12 and in deployment member 14, the driver 542 may include a driving ramp for each row of fastener subassemblies included by the implant. For example, in the illustrated embodiment, the device driver 542 has a pair of ramps 586a and 586b (collectively, "the ramps 586"), as shown in FIGS. 54C and 55A, corresponding to the rows 35a and 35b of the implant 10. It is noted that only one ramp is needed in embodiments in which the implant has only a single row of fasteners. The ramps 586 each include a sloped distal engagement surface 588, which is ramped up to a peak 590, which may take the form of a flattened or non-sloped section. During distal travel of the driver 542 along the jaws 504, the surfaces 588 of the ramps 586 engage against one or more pushers 592, corresponding to the number of fasteners of the implant being installed by the applicator 500 to sequentially advance the pushers and fasteners. For example, in the illustrated embodiment, the pushers 592 are arranged in two rows of ten pushers, corresponding to the two rows 35 of ten fasteners 32 of the implant 10. Again, it is noted that other numbers of pushers may be used in embodiments having an implant with a greater or lesser number of fasteners. Also, the pushers can be configured to engage and advance more than one fastener at a time so fewer pushers can be provided.

Figure 56B:
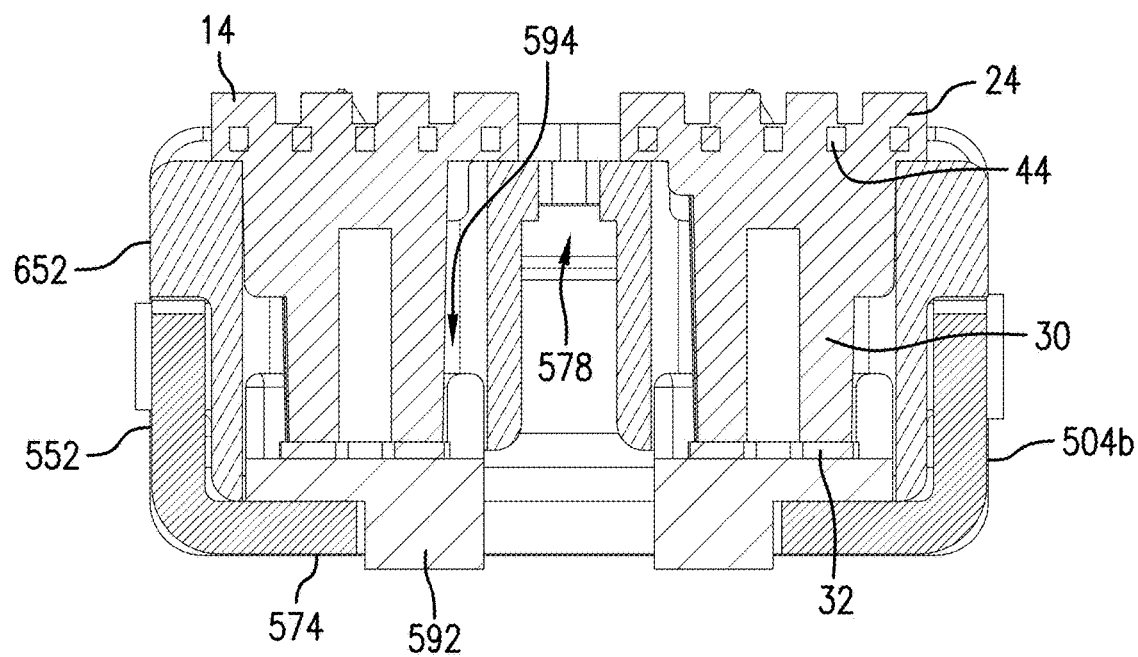
FIG. 56B is a cross-sectional view of the jaws taken generally along sectional line B-B of FIG. 56A.

The pushers are arranged to engage and/or receive each fastener and/or compressible tower of the deployment segments of the implant being implanted by the applicator 500. For example, the pushers 592 of the applicator 500 include pockets 594 configured to receive the fasteners 32 and the towers 30 of the deployment segments 28 of the deployment member 14 of the implant 10 therein, and preferably receive the base of the fastener 32 and the base of the tower 30. FIG. 56B is a longitudinal sectional view taken along line B-B in FIG. 56A and illustrates the pushers 592, each being aligned with one of the towers 30 of the surgical implant 10. In this way, distal movement of the driver 542 causes the pushers 592 to first engage, and then climb, the surfaces 588 of the ramps 586. This causes the pushers 592 to push the fasteners 32 toward the opposite jaw, e.g., the jaw 504a, which is carrying the receiver member 12 and/or receiving segments, such as the segments 20. The dimensions of the peak 590, the pushers 592, the towers 30, the legs 36 of the fasteners 32, the distance between the jaws 504 when in the closed configuration, etc. can be set with respect to each other such that when the pushers 592 reach the peak 590 of the distally advancing driver 542, the pushers 592 displace the fasteners 32 (which compresses the towers 30, as described above, a sufficient distance to cause or ensure that the barbs 42 at the ends of the tips 40 of the legs 36 of the fasteners 32 engage with the retainer 44 in the receiving member 12 and/or the receiving segments, e.g., the segments 20, held by the jaw 504a opposite thereto. The ramps 586 may include a proximal engagement surface 596, sloping opposite to that of surface 588, which gradually returns the pushers 592 to their initial positions and enables the driver 542 to be returned past the pushers 592 when the driver 542 is moved proximally back to its initial position.

In one embodiment, the distal ramp surface 588 may rise at a smaller angle than the angle at which the proximal ramp surface 596 falls. Thus, during operation, the distal surface 588 drives each of the pushers 592 at a more gradual rate than the rate at which the ramp 586 enables the pushers 592 to return to their initial positions via the proximal surfaces 596. This may provide a more controlled driving of the fasteners 32 by the pushers 592 through the tissue or other surgical structure and into the opposite member, e.g., the receiving member 12 of the surgical implant 10, while more rapidly enabling the pushers 592 to move away from the surgical implant 10 as the driver 542 is moved proximally. The peak 590 may be arranged as a substantially horizontal (non-sloped) surface that briefly sustains a maximum driving force of the driver 542 and the pushers 592 against the surgical implant 10. It is additionally noted in some embodiments that the proximal surface 596 upon retraction will cause the pushers 592 to again be driven toward the opposite jaw, thereby potentially reapplying the actuation force to the fasteners 32, the towers 30, etc., which reapplication of force may assist in creating a better seal or more secure connection with the implant, and/or to provide a second opportunity to correctly fire any misfired fasteners (e.g., to re-actuate any of the fasteners 32 which did not engage with the retainer 44 into engagement with the retainer 44).

In view of the foregoing, it is to be appreciated that in one example of operating the applicator 500, once the jaws 504 have been located in a desired surgical target area and closed on the surgical target, the distal driver 542 can be advanced distally along the length of the jaws 504 by drawing on or shortening the cable 544 (e.g., spooling the cable 544 about the spool 548a) while simultaneously allowing cable 546 to be pulled and lengthened (e.g., unspooling the cable 546 from the spool 548b). The distal movement of the driver 542 will simultaneously install the surgical implant 10, e.g., due to the pushers 592 engaging and climbing the ramps 586, and cut the tissue or surgical structure clamped between the jaws 504, due to travel of the cutting implement 580 along the length of the jaws 504, in a single operation.

After completion of the connection of the implant halves (e.g., the members 12 and 14 of the implant 10) together through the tissue or surgical structure, thereby closing, securing, and/or sealing the surgical structure with the implant, and cutting the surgical structure, the distal driver 542 may be returned proximally back along the jaws 504 to its initial position at the proximal end of the jaws 504. The return of the distal driver 542 may be driven by shortening the cable 546 (e.g., by spooling the cable 546 about the spool 548b) to cause pulling of the driver 542 in the proximal direction, while at the same time allowing the cable 544 to be pulled and lengthened (e.g., by unspooling the cable 544 from the spool 548a) to enable the return of the driver 542 to its initial position.

In the alternate embodiment of FIG. 55D-55K, fastener pushers 592 are not provided so the cam surface (ramp) 588' of the driver 542' of the drive assembly contact the fasteners directly. That is, instead of the intermediate pushers 592 as in the above described embodiment wherein the driver 542 contacts the pushers 592 which then contact the base of the fastener 32 to advance (deploy) the fasteners 32, the driver 542' directly engages the bend of the fasteners to advance the fasteners toward the receiver member 12. This embodiment without the pushers 592 is suited for example for use with the fasteners 800 of FIG. 44A and such fasteners are illustrated in these Figures. By elimination of the intermediate pushers, which are used to redirect the driver's distal motion into transverse fastener motion towards tissue, the manufacturing costs (parts and assembly time) are reduced and the risk of the pushers falling out of the cartridge is eliminated.

Figure 55D:
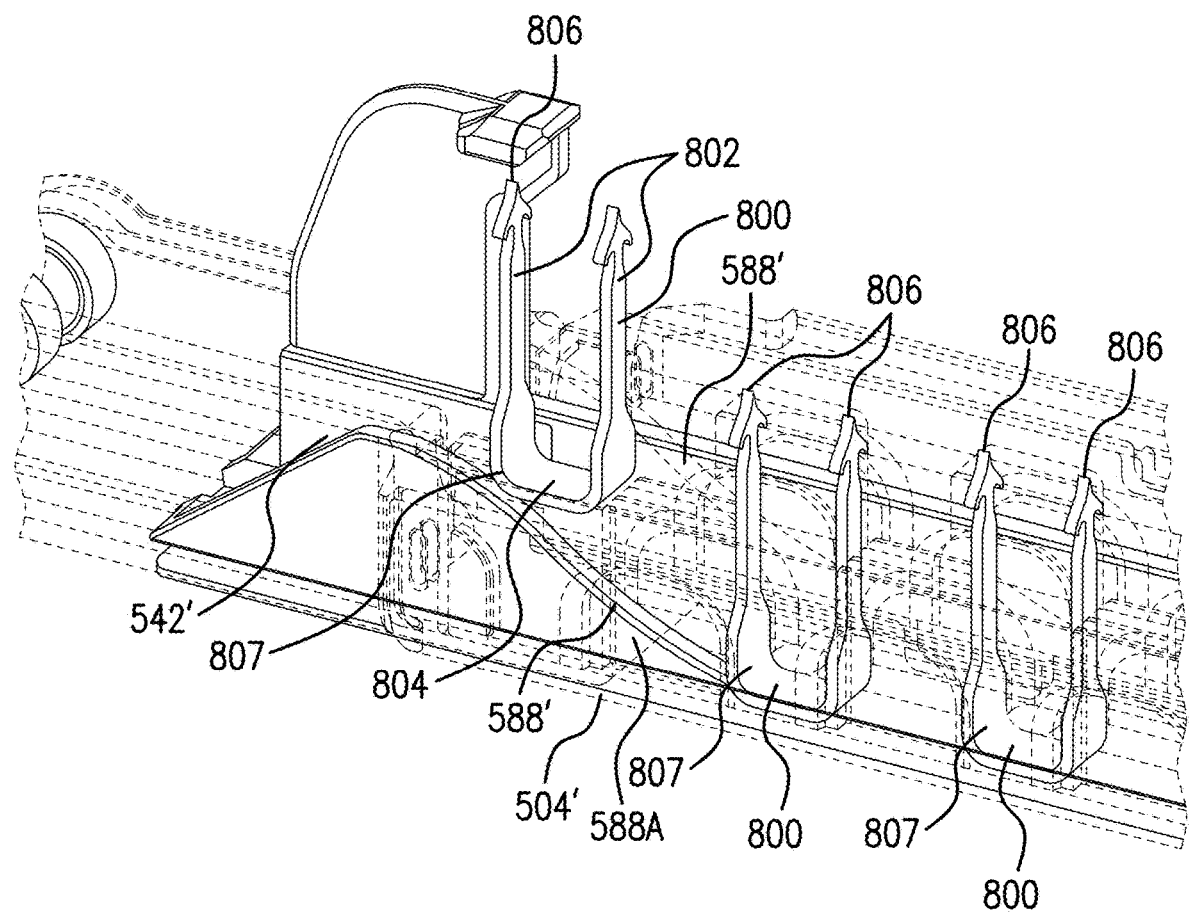
FIG. 55D is a partial, enlarged view of a proximal portion of an alternate embodiment of the stationary jaw.
Figure 55E:
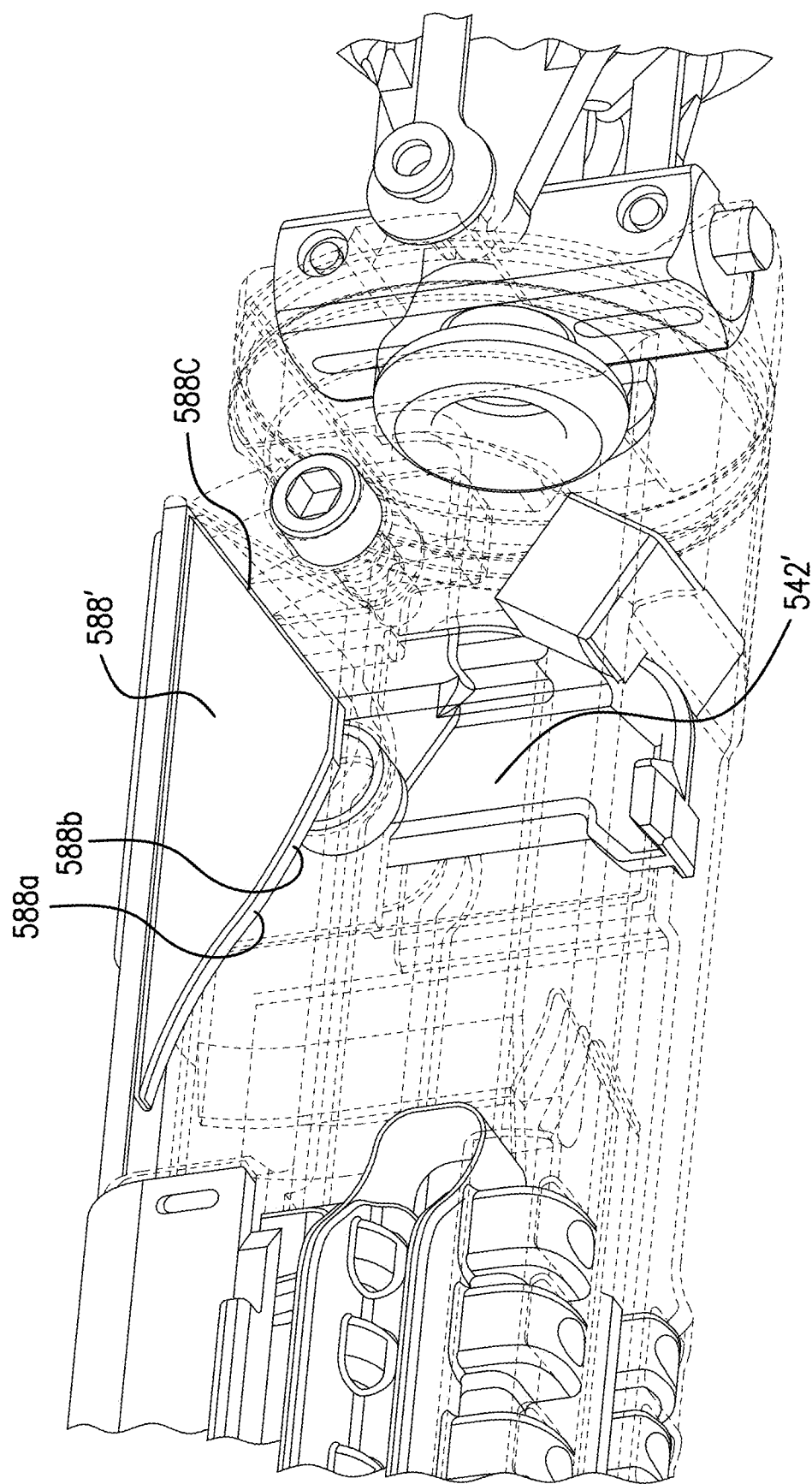
FIG. 55E is a partial, enlarged view of the stationary and movable jaws shown in the opposite orientation of FIG. 55D.

As shown in FIG. 55D which illustrates an enlarged view of a portion of the stationary jaw, fasteners 800 are positioned so that the base 804 is aligned, i.e. parallel, to the longitudinal axis of the jaw 504'. Stated another away, because the fastener bends 807 are perpendicular to the driver cam surfaces 588', the pushers 592 need not be provided. For ease of explanation, one of the fasteners 800 is shown in the advanced position; the other fasteners are shown in the pre-fired (pre-advanced) position. The curved surface or bend (radius) 807 is directly engaged by the cam surface 588' as the driver 542' is advanced distally to advance the fastener 800. The opposing bend 807 is also directly engaged by the opposing ramp (cam surface) when the driver 542' is retracted in the proximal direction. The driver 542' can move in the same fashion as driver 542, e.g., controlled by cables such as cable 544, 546, for distal and proximal movement.

Cam surface 588' of driver 542' is composed of a compound curve. The first curve 588a on the distal surface reduces the force to start the motion, i.e., advancement, of the fastener 800, and the second curve 588b reduces the firing force during the final drive distance of the fastener 800. The initial and final fastener motion require the highest force so the compound curve reduces the peak forces and thus reduces the overall force to fire the fasteners. The proximal surface of the driver 542' has a camming surface 588c which contacts the fastener 800 on the proximal return of the driver 542' after completion of its distal movement, thereby further driving the fastener 800 a greater distance from the jaw 504'.

Figure 55F:
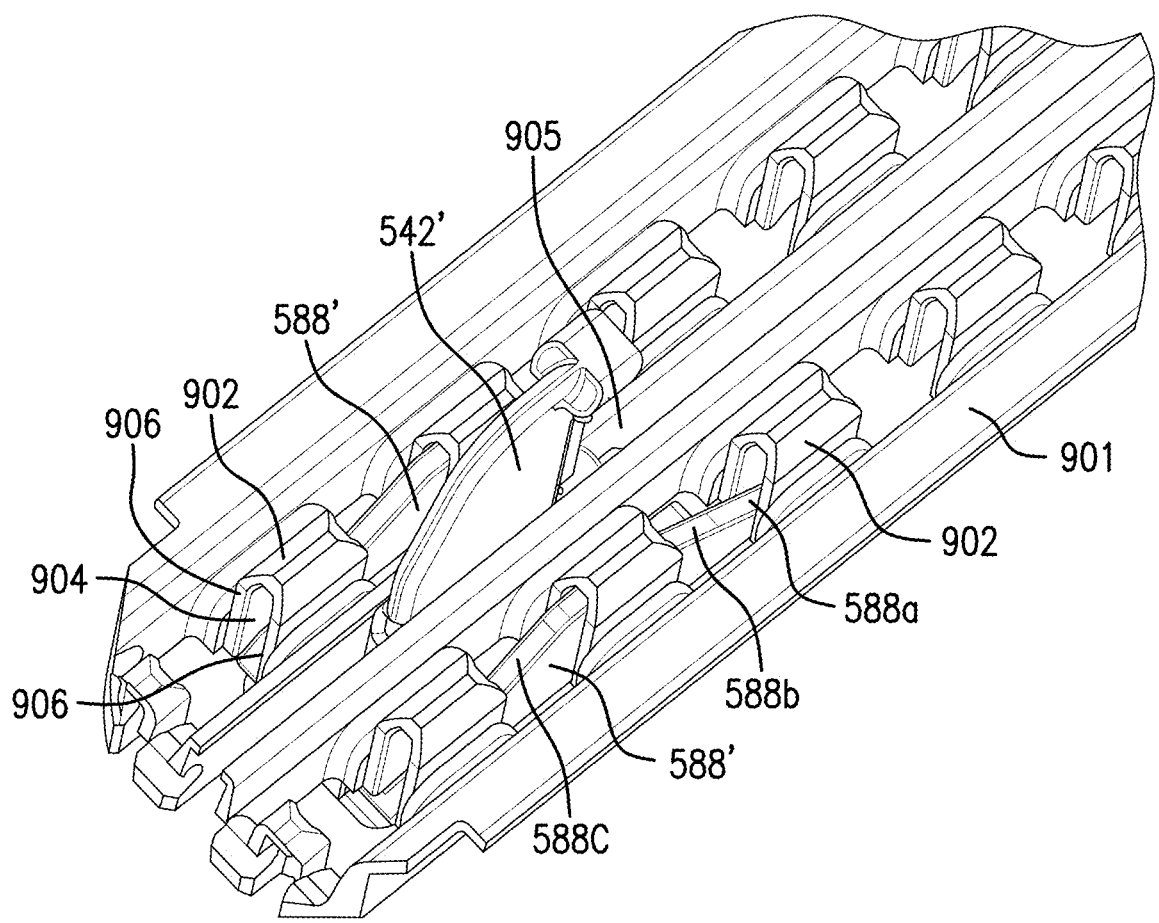
FIG. 55F is an enlarged view of a portion of the stationary jaw of FIG. 55D showing the driver and the channels for the driver.
Figure 55G:
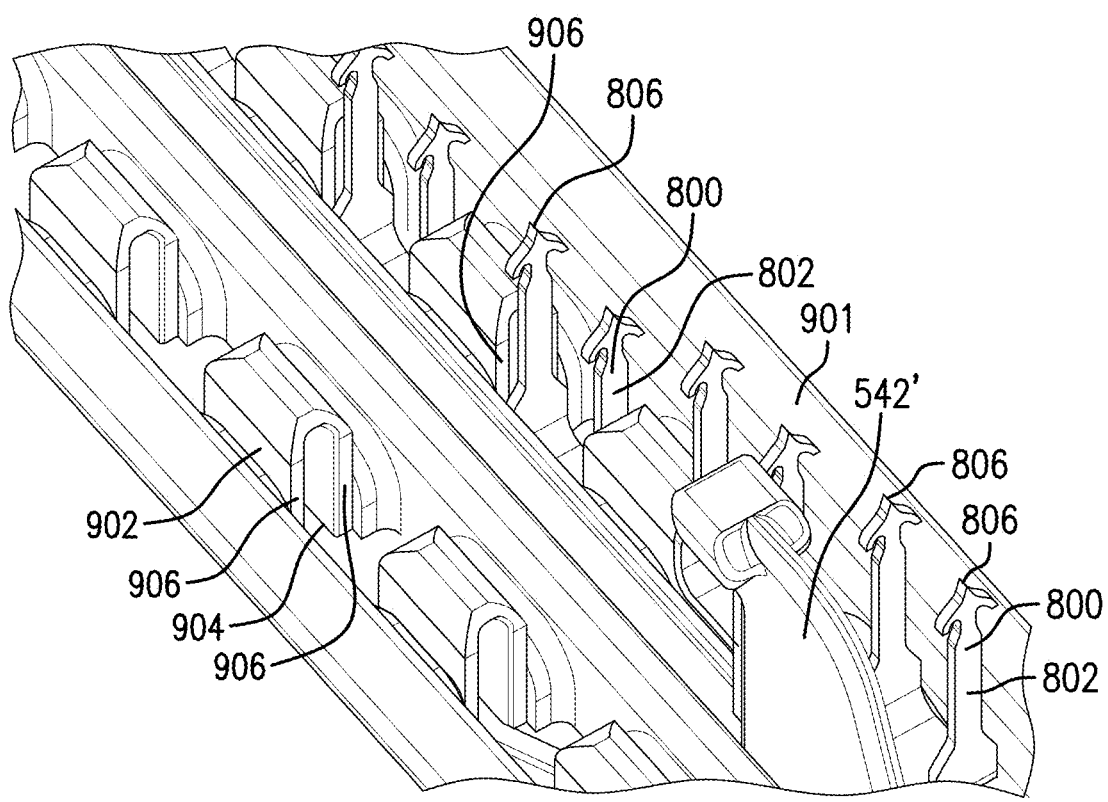
FIG. 55G is an enlarged view of a portion of the stationary jaw of FIG. 55D showing the driver, channels for the driver, and some of the fasteners.
Figure 55H:
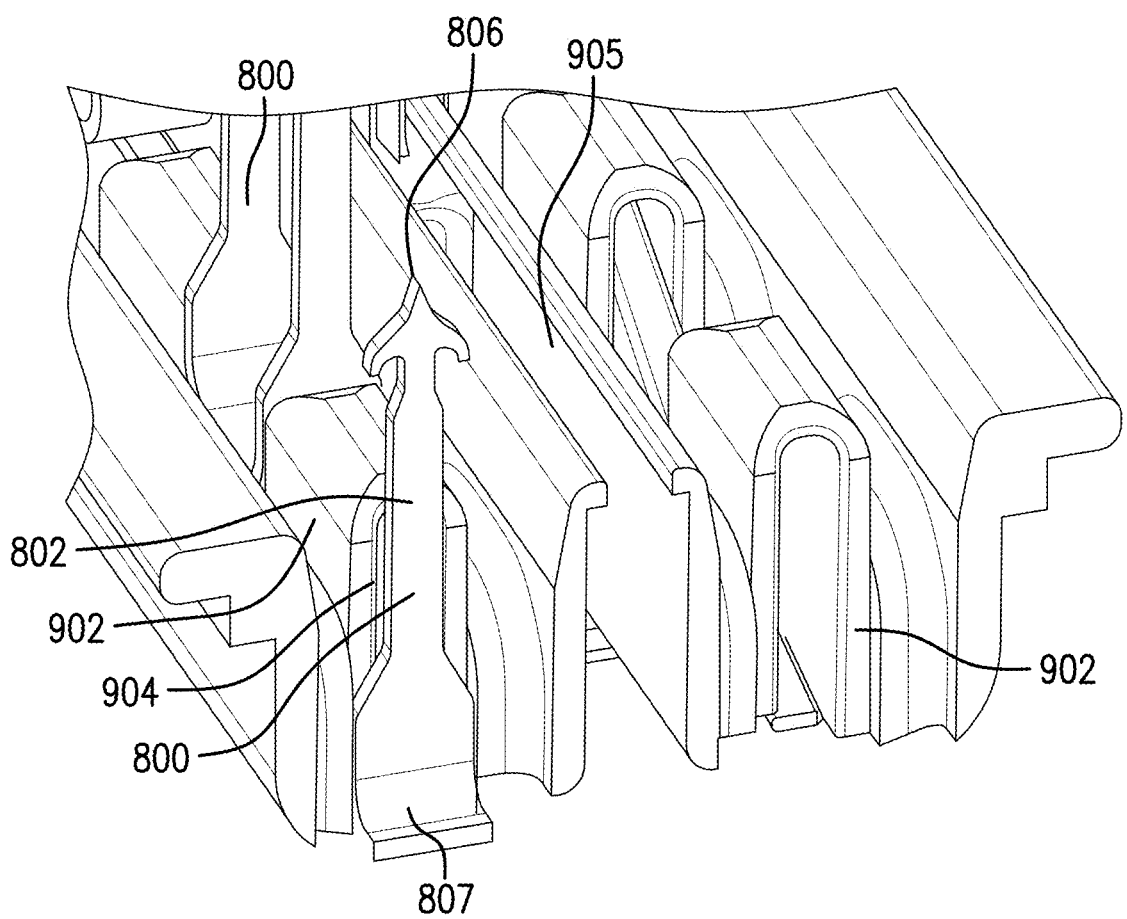
FIG. 55H is an enlarged cut away view showing the channels for the driver and some of the fasteners of FIG. 55G.
Figure 55I:
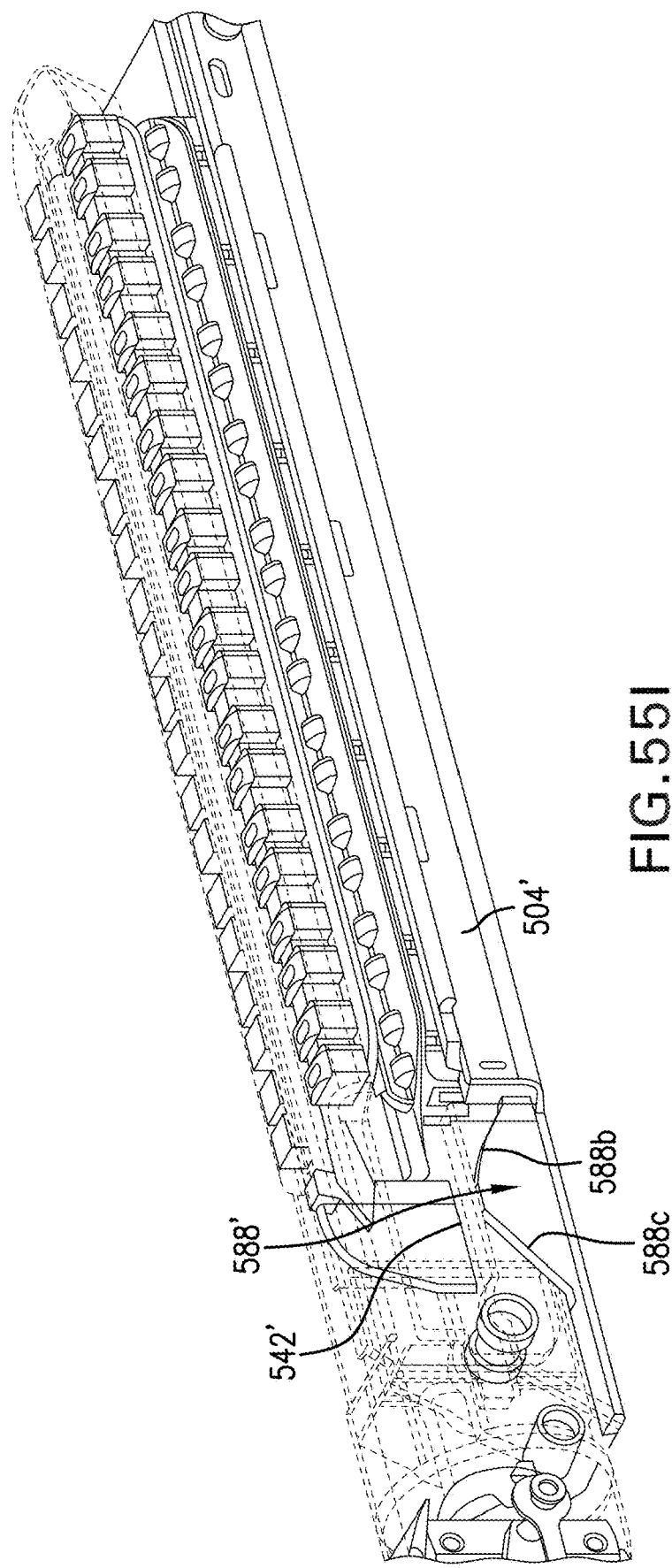
FIG. 55I is a perspective view of the movable jaw and stationary jaw having the driver of FIG. 55D, the jaws shown in the closed configuration.

Higher forces to push the fasteners through tissue or other structure require larger components to handle the higher stress and require the user to apply more force to fire the fasteners. The configuration of the camming surfaces 588a, 588b help reduce the force required to drive the fasteners. The surfaces can have different curves than that shown to further adjust the firing forces. To further reduce the firing force, the fasteners 800, compressible members (e.g., towers 32) and/or the cartridge 902 supporting the fasteners can be coated with low friction coatings such as PTFE. Such coating on the fasteners 800 and/or compressible members can for example reduce the friction between the compressible members, e.g., towers 30, and the fasteners 800. The cartridge material could also be varied and can include for example acetal, polycarbonate, nylon or other polymers with sufficient strength. The cartridge 901, supported in the deployment member, e.g. deployment member 14, can also include fastener guide features to help reduce the firing forces. As shown in FIGS. 55F and 55G, the cartridge 901 includes U-shaped channels 904 formed in guides 902. As the driver 542' is advanced distally and retracted proximally, the camming surfaces 588a, 588b and 588c slide within the channels 904. Guide features 906 on the outer surface of the guides 904 abut the fasteners 800. As the driver 542' is advanced distally, and the cam surfaces 588a, 588b apply a force to the bend 807 on one side of the fastener 800, the opposite side of the fastener 800 slides against the cartridge guides 904, converting the driver force into fastener transverse, e.g., downward, motion. Thus, the bend 807 of the fastener 800 provides the fastener 800 with sufficient strength not to buckle from the driver cam surface 588' on one side and the cartridge guide surfaces 906 which contact (abut) the fastener 800 help prevent buckling on the other side. The bends 807 of the fasteners 800 also have sufficient strength to keep the fastener 800 from skewing and/or rotating in the cartridge guides and jamming. Such strengthening can be enhanced by making the bends wider and taller. Note the bend 807 on the opposite side of the fastener 800 is contacted by camming surface 588c on the reverse (proximal) travel of the driver 542'.

The movement of the driver 542' to advance the fasteners 800 can best be appreciated in FIGS. 55J and 55K. These Figures show two of the fasteners 800 advanced (fired), one fastener 800 partially advanced and one fastener 800 not yet fired, i.e., in the pre-fired or pre-advanced position. The two proximal fasteners 800 in FIGS. 55J and 55K have been advanced (deployed) by the distal advancement of the driver 542' as they are shown advanced from the cartridge 901 (and jaw 504') as the camming surface 588' has passed beyond their curve (bend) 807 and base 804. The third fastener 800 has already been contacted by the camming surface 588a and is shown engaged directly by the camming surface 588b, which continues to directly engage the curve (bend) 807 in fastener 800. Thus, this fastener 800 is not yet fully advanced by the camming surface 588'. (Note the relative positions of the fastener tips 806 of the various fasteners 800). The distalmost fastener in FIGS. 55J and 55K is in the initial position and not yet contacted by the camming surface 588'. When the driver 542' is further advanced (not shown), camming surface 588a will contact bend 807 of this distal fastener 800, followed by contact of camming surface 588b to further advance the fastener 800. After full distal advancement of driver 542' to advance all the fasteners 800, the motion of the driver 542' is reversed in the manner described herein with regard to driver 542 so that camming surface 588c can further advance the fasteners 800 into engagement with the receiver member, e.g., the retainer member 44 within the receiver member (e.g., receiver member 12). Note the advancement of the fasteners 800 will compress the towers (not shown) in the manner described herein and the extent of advancement can be dependent on tissue thickness. Further note that only a few of the fasteners are shown in FIGS. 55J and 55K for ease of explanation. In FIGS. 55D-55K, two parallel rows of the fasteners 800 are provided with a central channel 905 between the rows to accommodate passage of the driver and optional knife, however, in alternate embodiments, a single row or a greater number of rows of fasteners can be provided. Thus, in the illustrated embodiment of FIGS. 55D-55K, two drivers 542' are provided on each side of the driver assembly, each with camming surfaces on the distal and proximal sides, i.e., camming surfaces 588a, 588b and 588c. As can be appreciated, if a different number of rows of fasteners are provided, a corresponding number of drivers (and camming surfaces 588') would be provided.

Referring back to FIGS. 51A-51D, the cables 544 and 546 pass into the housing 510 of the surgical implant applicator 500 and connect to the spools 548 of the driving mechanism 540, as described above. The driving mechanism 540 is operatively connected to the movable trigger 514 to enable a user to perform opening and closing operations of the jaws 504, installation of one or more surgical implants (e.g., the implant 10), cutting of tissue or surgical structures located between the jaws 504, etc., via manipulation of the trigger 514. The trigger 514 may be biased to its initial position shown in FIGS. 51A-51D, e.g., via a spring or biasing element 598, so that the trigger 514 returns to its initial position after each pull of the trigger 514 toward handle 512 and subsequent release of the pulling force.

Figure 57A:
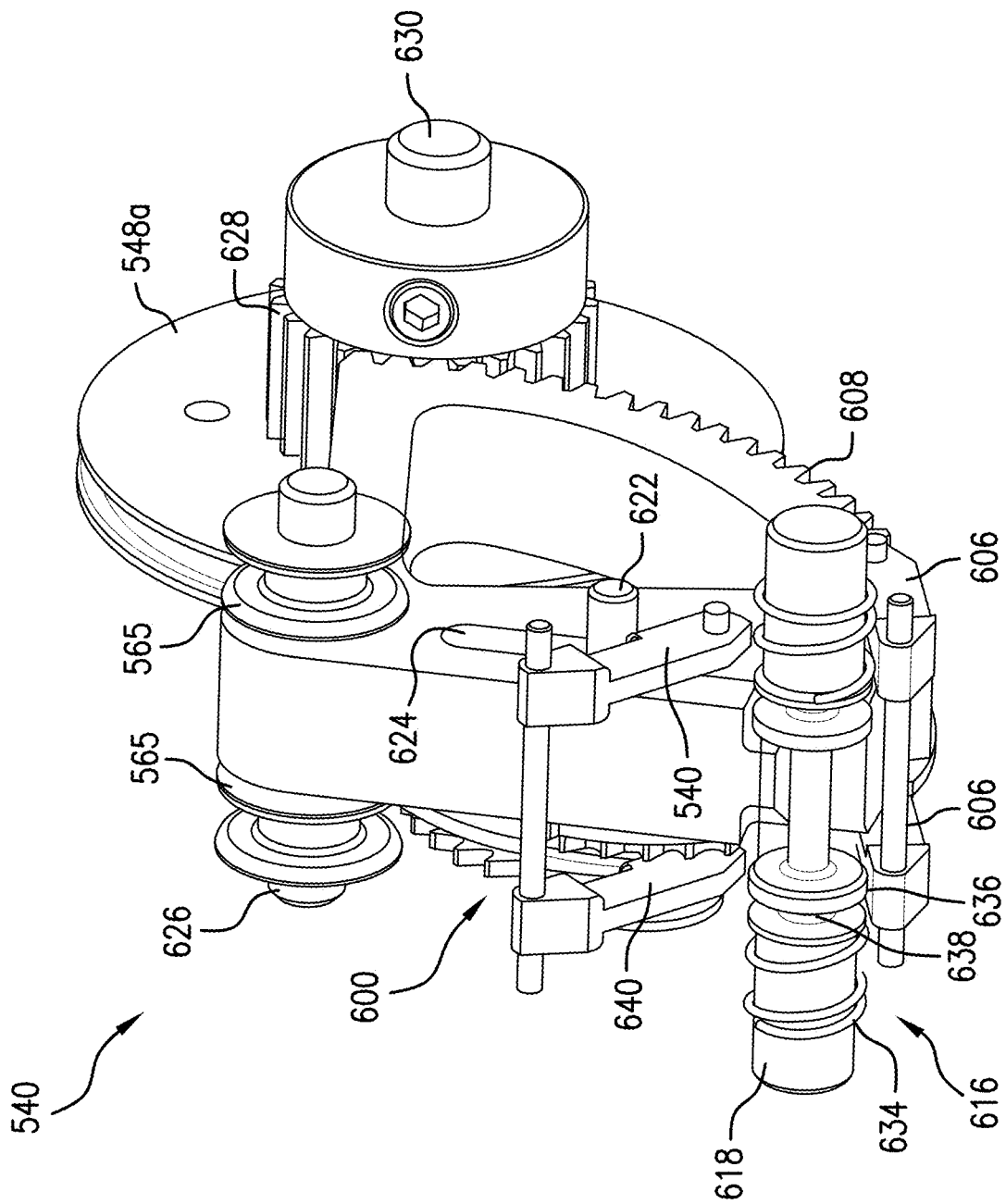
FIG. 57A is a perspective view of a driving mechanism for the applicator of FIG. 50 according to an embodiment disclosed herein.

The driving mechanism 540 includes one or more ratchet assemblies 600, each having a pair of ratchet gears or wheels 602a and 602b (collectively, "the ratchet wheels 602") and a lock wheel 604. The wheels 602 and 604 may be secured, fixed, locked, or integrally formed together such that they rotate in unison together. The trigger 514 includes one or more drive pawls 606 rotatably mounted thereto that are engageable with the teeth of both of the ratchet wheels 602. As the trigger 514 is pulled, the pawl 606 engages the teeth on both of the ratchet wheels 602 in order to drive the ratchet wheels 602. That is, for example, the teeth of the ratchet wheels 600 are angled to permit movement of the pawls 606 relative to the teeth in one direction, while rotating the wheels 600 due to movement of the pawl 606 in the other direction. In the illustrated embodiment, pulling the trigger 514 toward the handle 512 causes the pawls 606 to grab the teeth of the wheels 602, rotating the wheels 602 (and the lock wheel 604) in the counterclockwise direction with respect to the orientation shown in FIGS. 51A-51D. It is noted that the driving mechanism 540 may include a second one of the assemblies 600 and of the pawls 606 located on the opposite side of a follower gear 608 (discussed below) that are arranged as mirror images to the assembly 600 and the pawl 606, and which function in essentially the same manner described above, thereby providing redundancy and balance to operation of the mechanism 540. The mechanism 540 is shown in FIG. 57A with one of the assemblies 600 and with the drive spool 548b removed for clarity of the components of the mechanism 540 that may be hidden in the other Figures.

Figure 57C:
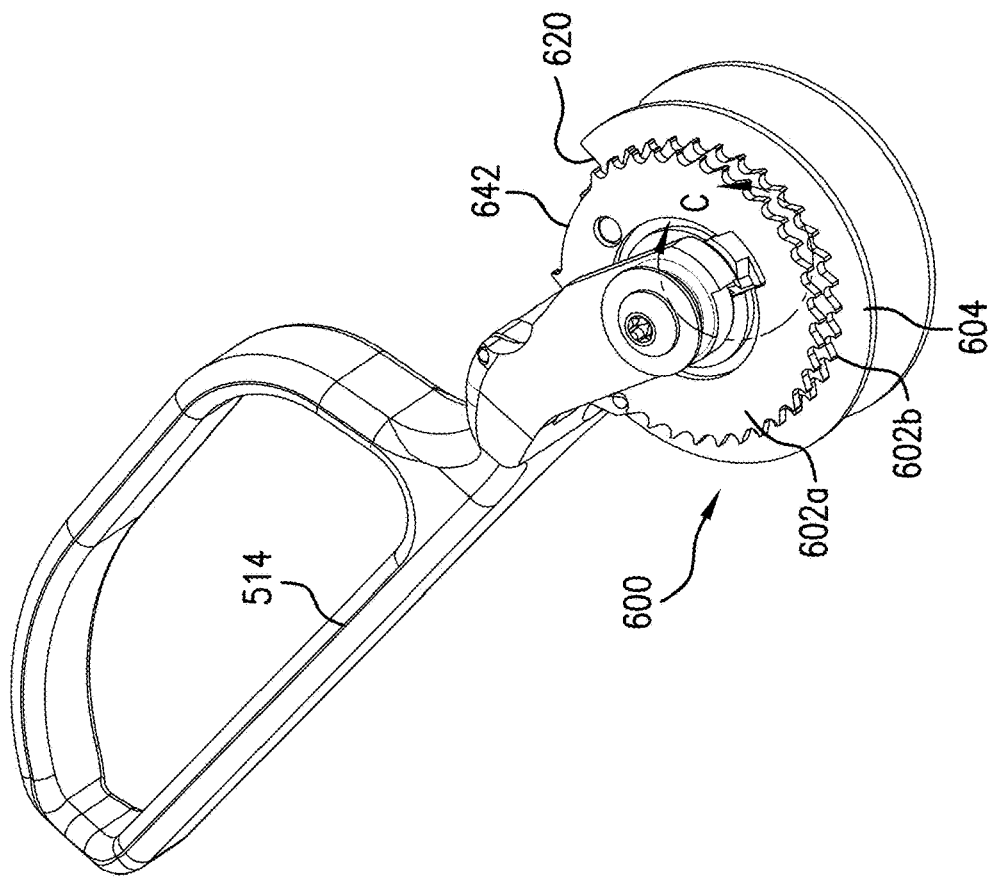
FIG. 57C is an enlarged view of the trigger and ratchet assemblies portion of FIG. 57A within the circle C.
Figure 57B:
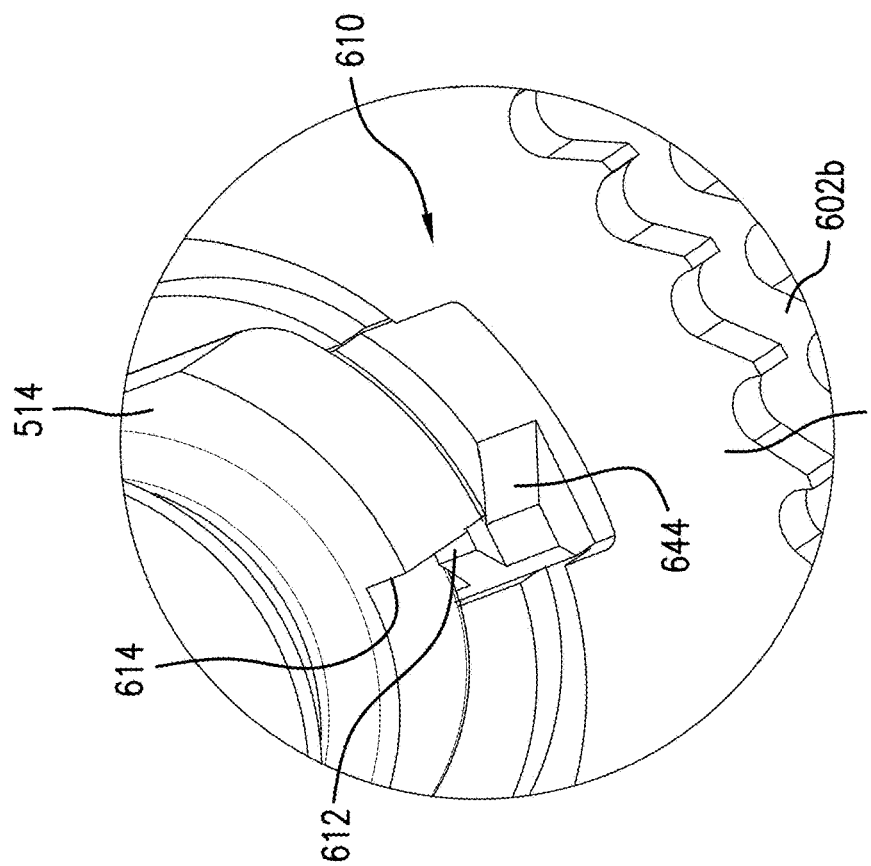
FIG. 57B is a perspective view of a trigger and a pair of ratchet assemblies for the applicator of FIG. 50 according to an embodiment disclosed herein.

The assembly 600 may include an interlock 610, shown best in FIGS. 57B-57C, which has a protrusion 612 that engages or catches a lip or shoulder 614 of the trigger 514 to lock trigger 514 relative to ratchet wheels 602. The interlock 610 in combination with the pawl 606 causes the trigger 514 and the ratchet wheels 602 to move in unison in both directions of movement of the trigger 514, until the interlock 610 is released. For example, as discussed in more detail below, the interlock 610 may be spring-loaded such that it can be pushed away from the trigger 514, removing the interference between the lip 614 of the trigger 514 and the protrusion 612 of the interlock 610.

The trigger 514 is shown in its initial position in FIGS. 51A-51D and in a first or intermediate actuation position in FIGS. 58A-58D. The drive mechanism 540 may include a safety mechanism 616 that includes a pin, shaft, or rod 618 extending laterally into or through the housing 510 that is arranged to encounter a shoulder 620 of the lock wheel 604 in order to block or prevent the trigger 514 from rotating further toward and closer to the handle 512. For example, the lock wheel 604 may include a scalloped portion to create the shoulder 620, or the shoulder 620 may be formed as a protrusion extending radially outwardly therefrom. Moving the trigger 514 between its initial (e.g., FIGS. 51A-51D) and first actuation positions (e.g., FIGS. 58A-58D), causes rotation of the wheels 602 and 604, as described above, and due to the pawl 606 and the interlock 610, the ratchet assembly 600 moves in unison with the trigger 514 as it travels back and forth between its initial position and the first actuation position.

Rotation of the assemblies 600 causes corresponding rotation of the follower gear 608. For example, the follower gear 608, located between the pair of the assemblies 600 in the illustrated embodiment, may be in operable communication with the assemblies 600 via a dowel 622 that extends between the assemblies 600. Namely, a portion of dowel 622 may extend through and be translatable along a cam slot 624 formed in the follower gear 608. For clarity, the outline of the follower gear 608, including the slot 624, is highlighted in FIGS. 51D, 58D, 59D, and 60D to show the relative location of the dowel 622 in the slot 624 as the applicator 500 is operated through its various stages. By use of the slot 624 and the dowel 622, as the trigger 514 is moved toward the handle 612 and the ratchet wheels 602 are correspondingly rotated due to the engagement of the pawl 606 with the teeth of the wheels 602 (e.g., rotated in the counterclockwise direction, with respect to the orientation shown in FIGS. 51A-51D and 58A-58D), the dowel 622 draws against the slot 624 and drives the follower gear 608 to rotate about a pin 626 connected to the housing 510 (e.g., also in the counterclockwise direction, as shown in FIGS. 51A-51D and 58A-58D).

The follower gear 608 includes teeth that mesh with corresponding teeth of a gear 628. The gear 628 is fixed relative to the spools 548 to cause the spools 548 to rotate about a pin or axle 630. As noted above, rotation of the spools 548 causes the cables 544 and 546 to be spooled and/or unspooled therefrom in order to move the driver 542 along the length of the jaws 504. The rotation of trigger 514 thereby causes the assemblies 600 to rotate, which in turn causes rotation of the follower gear 608, which drives the spools 548 to spool and unspool the cables 544 and 546, and ultimately controls movement of the driver 542 along the jaws 504. In one embodiment, the initial position of the trigger 514 may accordingly be set to position the driver 542 in its initial position at the proximal end of the jaws 504, with the top body portion 570 located in the recess 582. Accordingly, moving the trigger 514 to its first actuation position may cause the driver to be moved a limited distance distally and drive the top body portion 570 against the surface 583a, such that the first actuation position of the trigger 514 corresponds to the closed configuration of the jaws 504. Similarly, releasing actuation force on the trigger 514 and permitting the trigger 514 to return to its initial position (e.g., under the force of the biasing member 598), may cause the driver 542 to be moved proximally back to the initial position, causing the top portion 570 to encounter the surface 583b, thereby reopening the jaws 504. In short, moving the trigger 514 between its initial position and its first actuation position may be used in the illustrated embodiment to open and close the jaws 504.

As noted above, the safety mechanism 616 is provided to establish a first actuation position for the trigger 514 and prevent the trigger 514 from moving further toward the handle 512 from the first actuation position. In this way, before the safety mechanism 616 is released or unlocked, the safety mechanism 616 enables the operator to easily and repeatedly close and open the jaws 504, e.g., for purposes of locating the desired surgical target location prior to implanting the surgical implant 10 and cutting tissue or other surgical structures, as discussed above, without risk of prematurely fully actuating the driver 542. That is, for example, the safety mechanism 616 can prevent the driver 542 from being distally moved to a location at which the ramp 586 engages the pushers 592 and/or at which the cutting implement 580 is moved distally beyond the shields 584 and/or 585, until implant installation and/or cutting operations are desired.

The rod 618 extends through and protrudes out of both sides of the housing 510 of proximal assembly 506, thereby enabling the rod 618 to be actuated from either side of the applicator 500. The safety mechanism 616 can be switched off, disabled, unlocked, or released by pushing in the rod 618 into the housing 510 from either side of the housing 510. The rod 618 may be biased toward its initial, locked, or safety position by one or more biasing members 634, such as springs, such that the safety position is the default. The rod 618 includes larger diameter portions 636 and smaller diameter portions 638 (FIG. 57A) Actuation of the rod 618 out of the safety position causes the smaller diameter portions 638 to become aligned with each of the shoulders 620 (FIG. 57C) of the lock wheels 604.

The lock wheel 604 may be fixed relative to ratchet wheels 602, which are fixed relative to each other. In the safety mode, the larger diameter portions 636 are aligned with the shoulders 620, so that the shoulders 620 contact and abut against the portions 636 to limit rotation of the lock wheels 604 and therefore the entirety of the assemblies 600 as noted above. By moving the rod 618 in order to turn the safety off, the smaller diameter portions 638 are aligned with the shoulders 620, enabling the shoulders to rotate past the rod 618, thereby enabling the assemblies 600 to be fully rotated. As noted above, in the safety mode, the trigger 514 can advance the ratchet gears 602 only so far as the point where shoulder 620 contacts the larger diameter portion 636 of the rod 618 of the safety mechanism 616, which limits the amount of take-up and let-out of the cables 544 and 546, consequently limiting the possible travel distance of driver 542.

When the shoulders 620 are aligned with the smaller diameter portions 638, the trigger 514 is permitted to be pulled slightly closer to the handle 512, into a second actuation position, which may also be referred to as the fully actuated position. The applicator 500 is illustrated with the trigger 514 in the fully actuated position in FIGS. 59A-59D. As the trigger 514 is pulled closer to the handle 512, the wheels 602 are further rotated as the shoulders 620 pass the smaller diameter portions 638. Additionally, the relatively larger diameter of the shoulder 620 becomes positioned between the larger diameter portions 636 of the safety rod 618, preventing the springs 634 from being able to return the rod 618 to the safety position, thereby locking the rod 618 in position to allow firing (installation of the implant and cutting).

Once the jaws 504 have been positioned as desired, and the safety mechanism 616 is released, the operator of the applicator 500 can direct further operations of the end effector 502 using the trigger 514. For example, once the jaws 504 have been positioned as desired and closed over the surgical target area, the operator can further operate the surgical implant applicator 500 to install the surgical implant(s) 10 and/or cut tissue or other surgical structures. That is, for example, continued rotation of the trigger 514 can be used to actuate the mechanism 540 and spool and unspool the cables 544 and 546 from the spools 548, which causes the driver 542 to traverse along the length of the jaws 504 and provides the implant installation and cutting functions described above.

The drive mechanism 540 may include one or more pawls 640 rotatably mounted to the housing 510 of the proximal assembly 506. Each of the pawls 640 is arranged, unlike the pawl 606, to engage only the ratchet wheel 602a (and thus, not the wheel 602b) of the corresponding assembly 600. The pawls 640 are configured to prevent reverse rotation of the ratchet wheels 602 after the wheels 602 are rotated by the trigger 514. However, the wheel 602a includes a cutout 642 (FIG. 51C), where no gear teeth are present. As can be seen by comparing FIG. 51C (in which the trigger 514 is in its initial position) and FIG. 58C (in which the trigger 514 is in its intermediate actuation position), the pawl 640 remains aligned with the cutout 642 during movement of the trigger 514 between its initial and intermediate actuation positions. That is, the pawls 640 slide along the cutouts 642 during both forward and reverse rotation of the ratchet wheels 602 when the trigger 514 is between its initial and intermediate positions, so that the trigger 514 can be operated to repeatedly open and close the jaws 504 without the pawls 640 interfering.

After the safety mechanism 616 has been released, e.g., by pushing the rod 618 toward the housing 510, further actuation of the trigger 514 to its fully actuated position will cause the wheels 602 to rotate such that the pawl 640 exits the cutout 642 and can engage with the teeth of the wheel 602a. That is, the teeth of the wheel 602a and the pawl 640 are arranged to permit movement of the teeth relative to the pawl 640 in one direction (e.g., counter-clockwise due to actuation by the trigger 514), but such that the pawl 640 will lockingly engage the teeth of the wheel 602 in the opposite direction. The engagement of the pawls 640 between teeth of the ratchet wheel 602a thereby prevents reverse rotation of the ratchet wheels 602. In this way, repeated release and pulling of the trigger 514 to the fully actuated position incrementally rotates the assemblies 600 as the pawl 640 engages with new teeth of the wheel 602a. It is noted that instead of pulling and releasing the trigger 514 multiple times, actuating the trigger 514 to its fully actuated position may in one embodiment activate a motor to drive the spools 548.

Figure 57D:
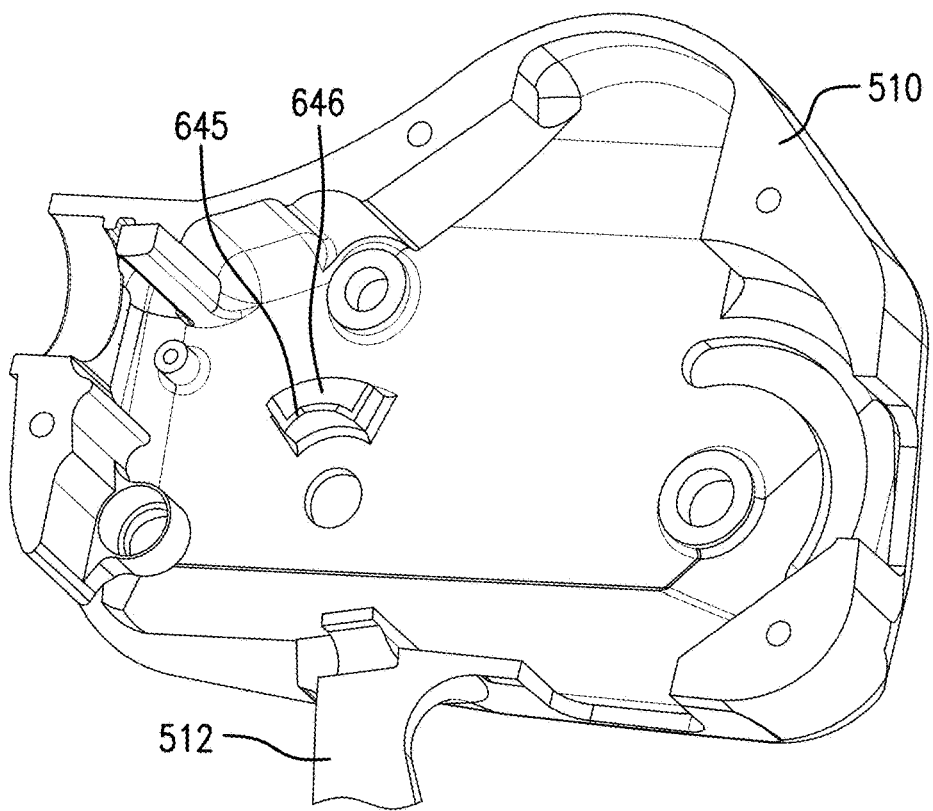
FIG. 57D is a side view of an internal portion of a housing of the applicator of FIG. 50.
Figure 57E:
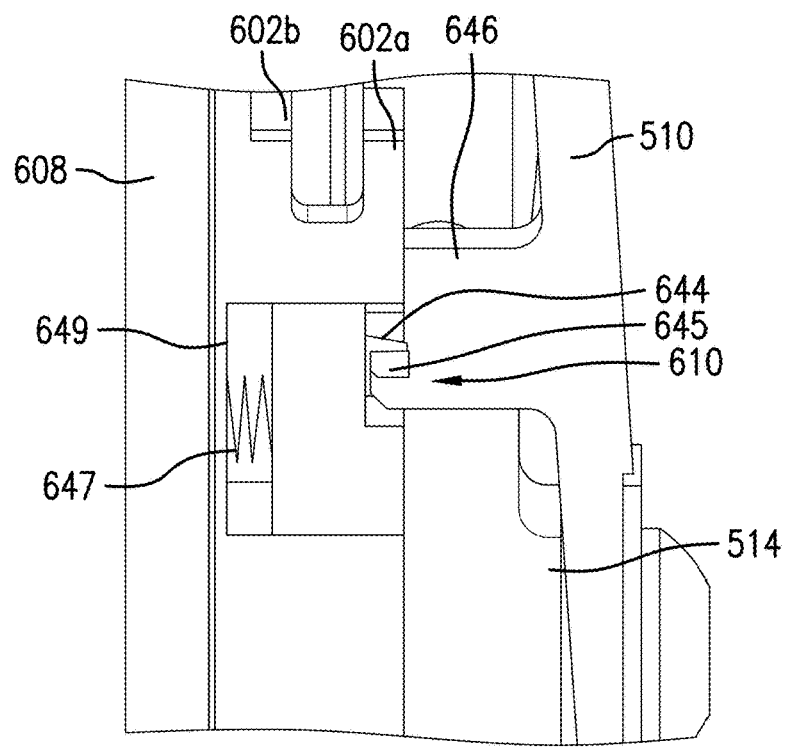
FIG. 57E is a partial, cross-sectional view taken though the housing and a portion of the driving mechanism of the applicator of FIG. 50.
Figure 58A:
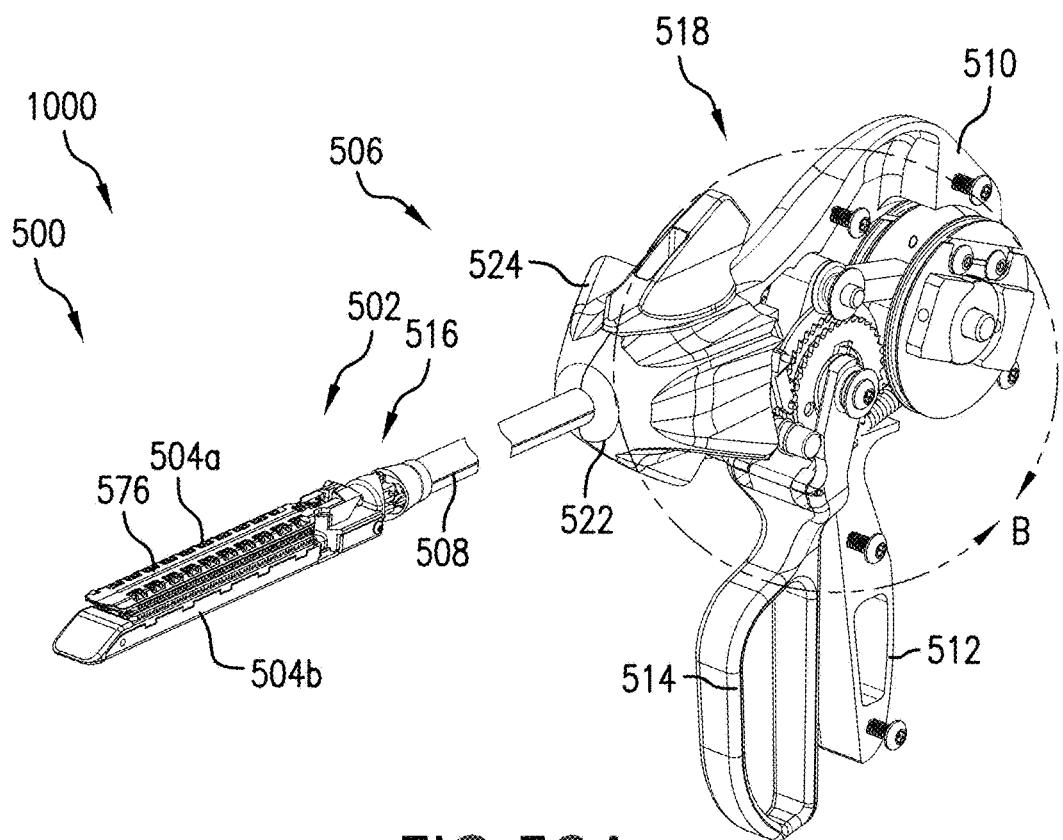
FIG. 58A is an isometric view of the system of FIG. 50 having a portion of a housing removed to illustrate components of the driving assembly, the applicator shown in an intermediate position to move the jaws to the closed configuration.
Figure 58B:
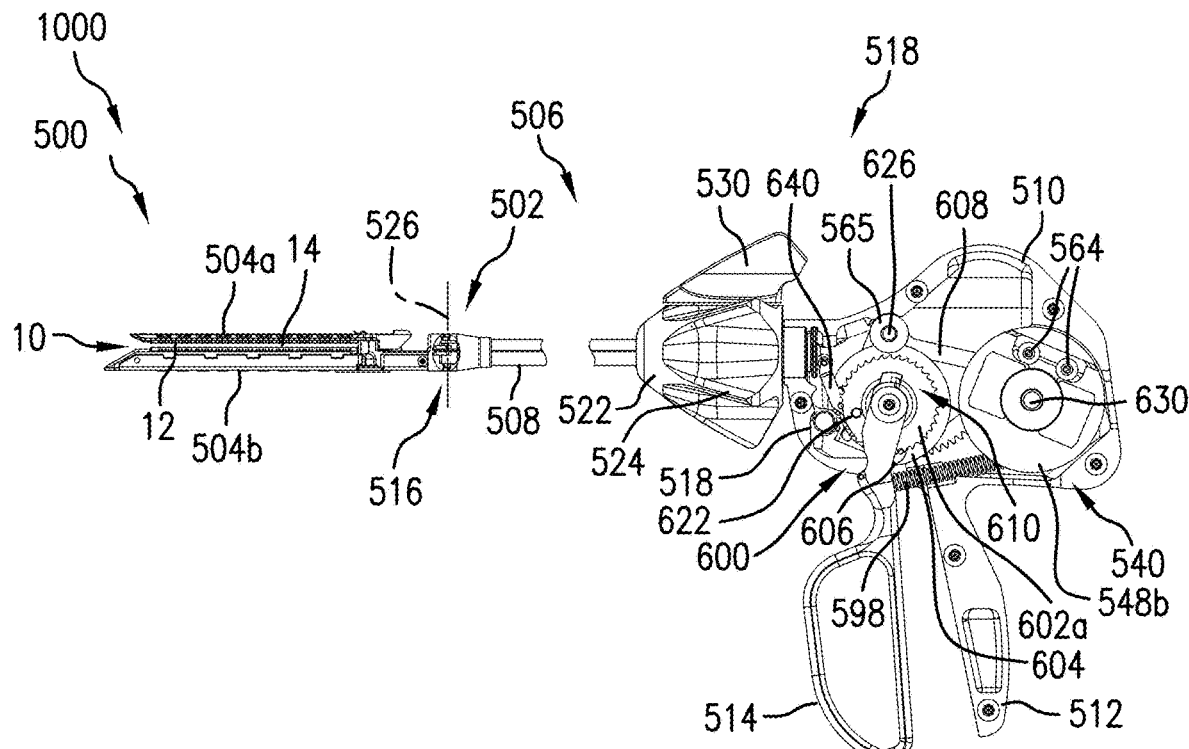
FIG. 58B is a side view of the system shown in FIG. 58A.
Figure 58C:
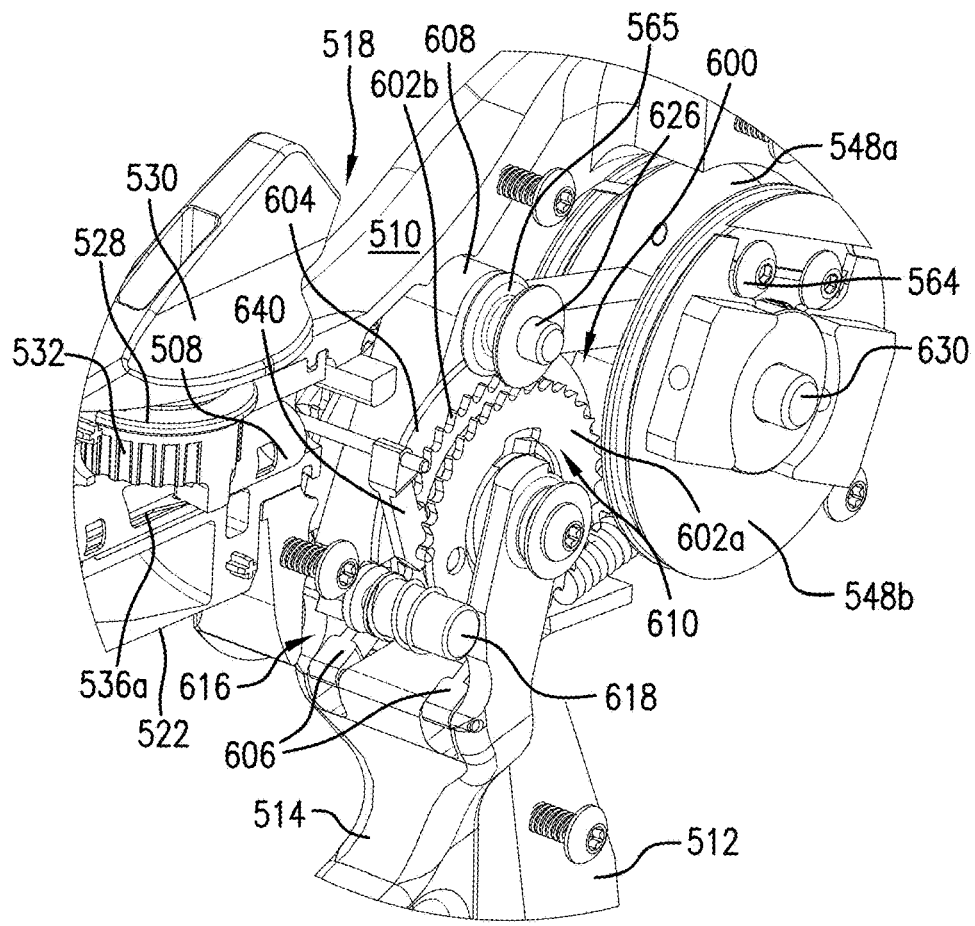
FIG. 58C is a detail view of the portion of FIG. 58A within circular border B of FIG. 58A.
Figure 58D:
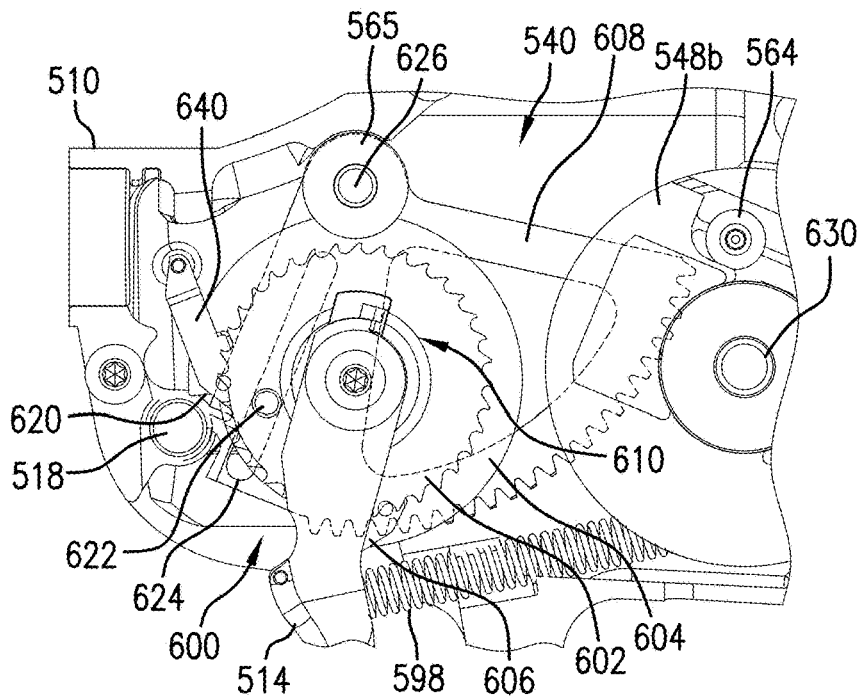
FIG. 58D is a partial side view of a portion of the system of FIG. 58C.
Figure 59A:
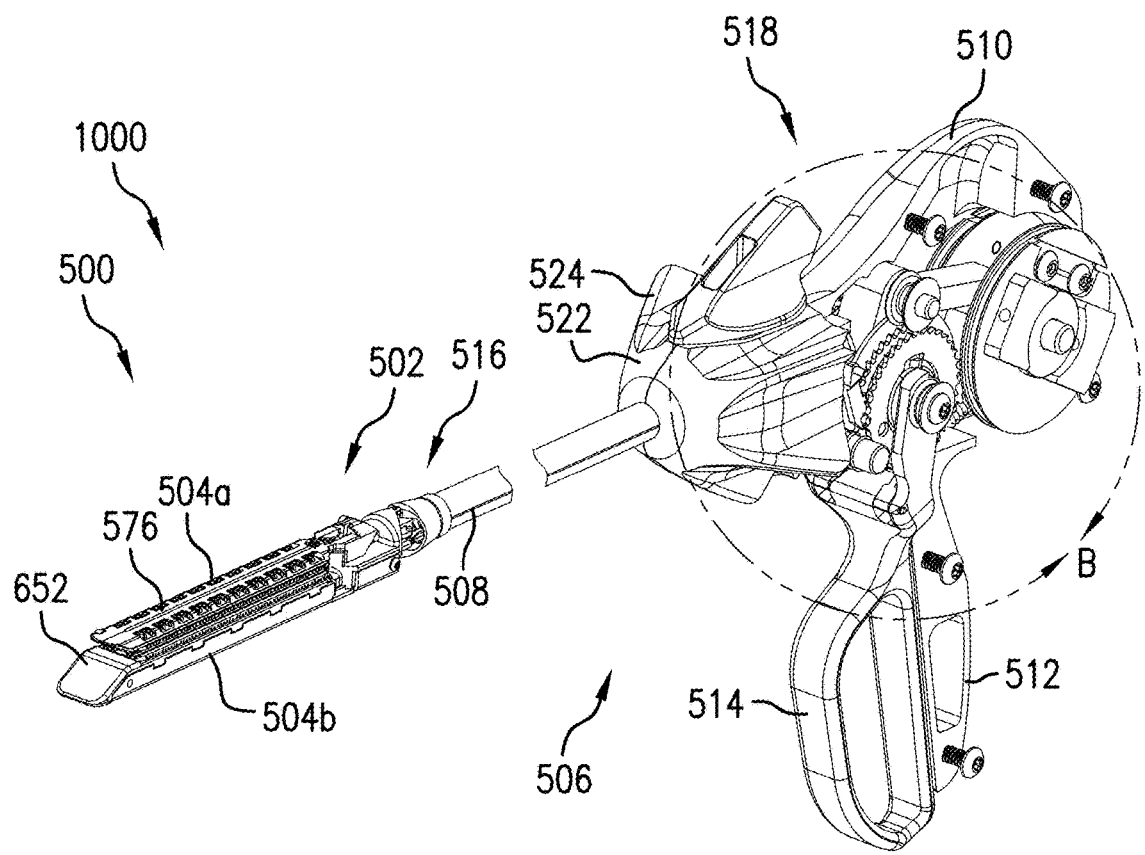
FIG. 59A is an isometric view of the system of FIG. 50 having a portion of a housing removed to illustrate components of the driving assembly, the applicator shown in the fully actuated position to advance the fasteners from the jaws.
Figure 59B:
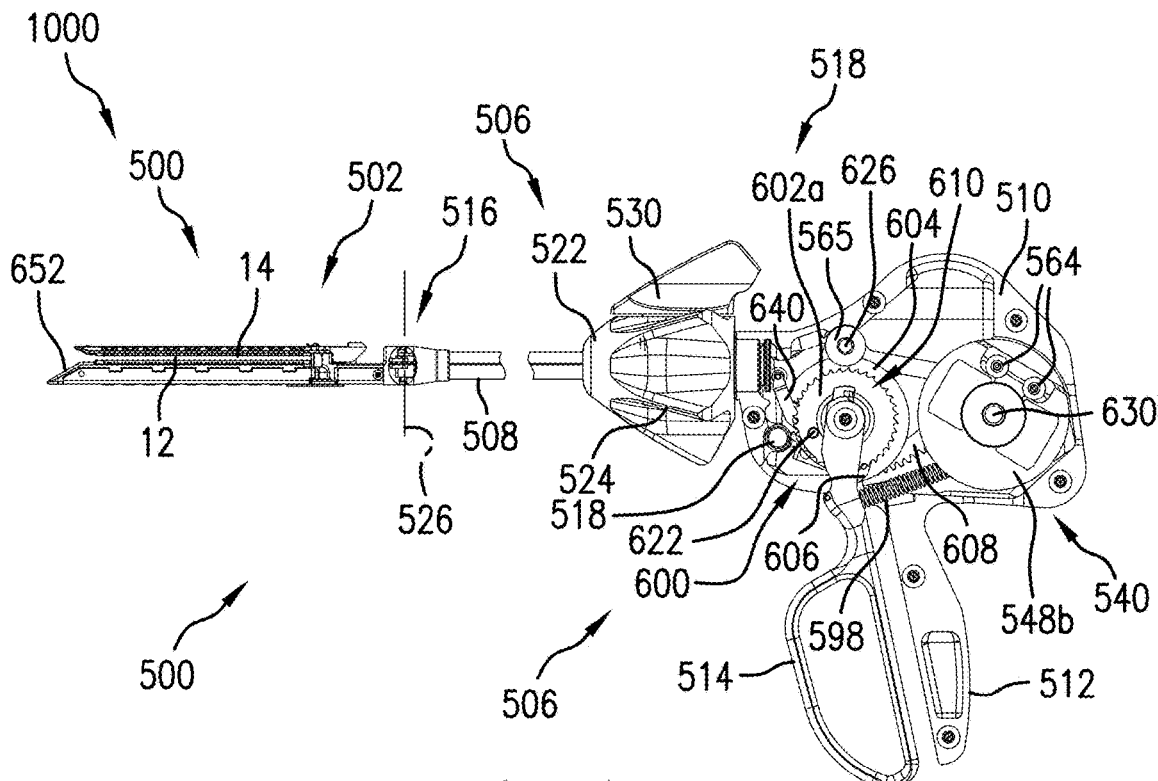
FIG. 59B is a side view of the system shown in FIG. 59A.
Figure 59C:
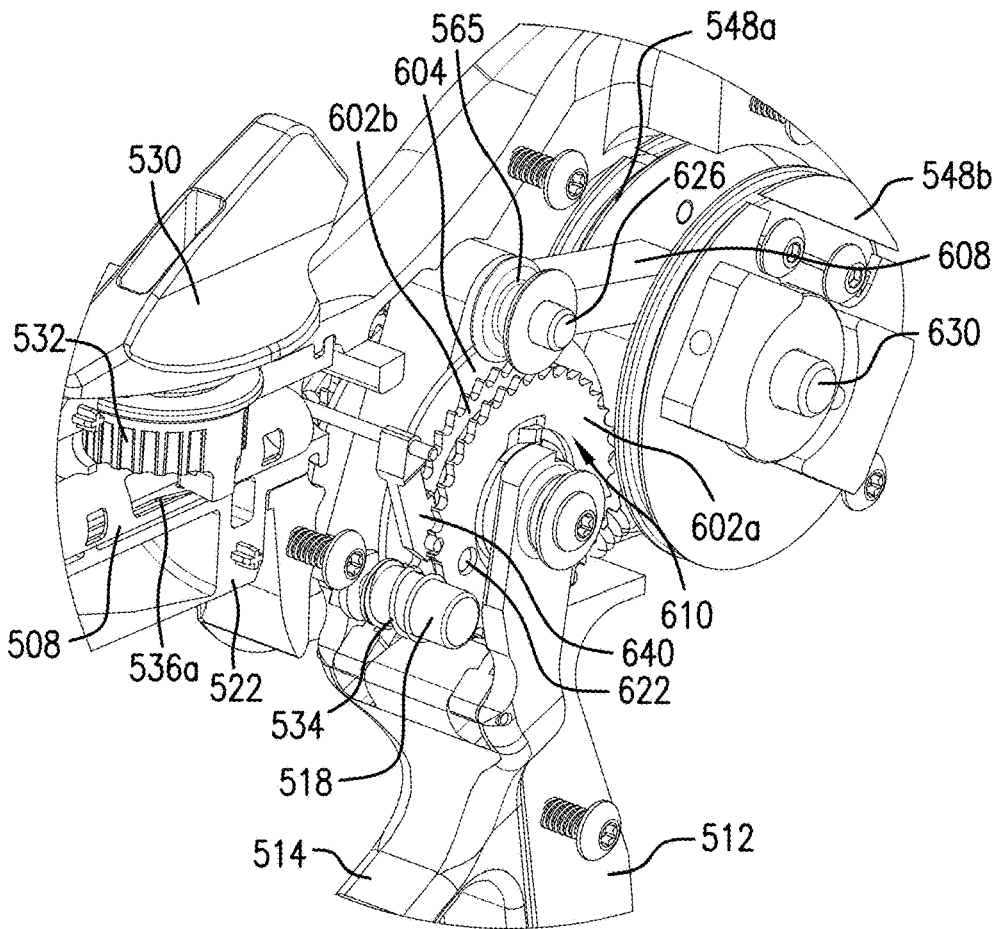
FIG. 59C is a detail view of the portion of FIG. 59A within circular border B of FIG. 59A.
Figure 59D:
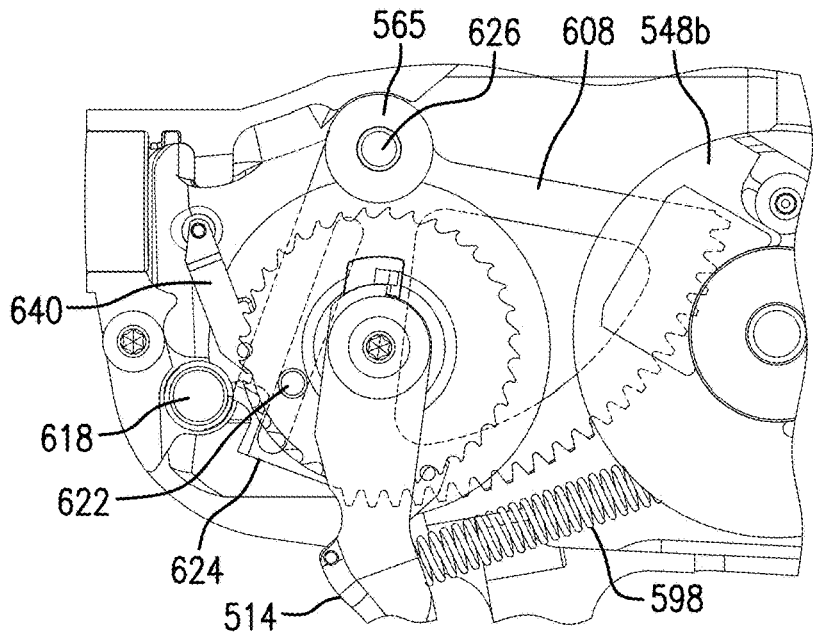
FIG. 59D is a partial side view of a portion of the system of FIG. 59C.

As noted above, the mechanism 540 may include the interlock 610. The interlock 610 may be configured such that when the operator pulls the trigger 514 further toward the handle 512 from the intermediate actuation position, a ramped portion 644 of the interlock 610 is driven against a protrusion 645 of a raised portion 646 on the housing 510 or some other component to which the wheels 602 are mounted (e.g., see FIGS. 57B-57C, FIG. 57D, which illustrates one half of the housing 510, and FIG. 57E, which is a cross-section taken laterally through the housing 510, the protrusion 645 of the raised portion 646, the interlock 610, the assembly 600, and part of the follower gear 608). As the interlock 610 is rotated so that the ramped portion 644 encounters the raised portion 646, the ramped portion 644 presses the interlock 610 toward or into the assembly 600, thereby releasing the interlock 610 by removing the interference or engagement of the protrusion 612 of the interlock 610 with the lip 614 of trigger 514. For example, in FIG. 57E, it can be seen that the interlock 610 includes a spring or biasing member 647 in a cavity 649, which enables the aforementioned release of the interlock 610. In this way, releasing the interlock 610 enables the trigger 514 to rotate back toward its initial position, while the assemblies 600 are prevented from doing so due to the pawl 640.

At this stage, repeated pulling and releasing of the trigger 514 relative to the handle 514 drives the ratchet wheels 602 in the counterclockwise direction with respect to the orientation of FIGS. 59A-59D. Continued actuation of the wheels 602 causes the follower gear 608 to rotate due to the dowel 622 driving against the cam slot 624 of the follower gear 608. During a complete rotation of the wheels 602 (e.g., incremental/partial rotation caused by a plurality of repeated pulls and releases of the trigger 514), the follower gear 608 is first driven in the counterclockwise direction so that it drives the spools 548 to take up the cable 544 and let out the cable 546. This drives the driver 542 from its initial or proximal location (e.g., see FIGS. 54A-54C) to its distal position (e.g., see FIGS. 55A-55C). During distal travel of the driver 542, as described above, the driver 542 progressively actuates the pushers 592 the fasteners 32 to pierce through the tissue and/or other surgical structures located between the jaws 504, and secure the halves, e.g., the receiver member 12 and the deployment member 14, of the implant together. Simultaneously, as also described above, the cutter 580 progressively cuts through the tissue and/or other surgical structures.

FIGS. 60A-60D show the orientation of the mechanism 540 after the trigger 514 has been pulled a sufficient number of times to fully actuate the driver 542 distally and position the driver 542 at the distal end of the jaws 504. When in the configuration of FIGS. 60A-60D, the dowel 622 has just crossed a mid-point of the slot 624. When the rotation of the ratchet wheels 602 reaches the orientation where dowel 622 reaches approximately the mid-point of the slot 624, continued rotation of the ratchet wheels 602 causes the dowel 622 to drive the follower gear 608 in an opposite direction, e.g., clockwise with respect to the orientation of FIGS. 60A-60D. By driving the follower gear 608 in the opposite direction, the direction of rotation of the spools 548 is reversed so that the cable 544 is taken up by or spooled onto the spool 548a and the cable 546 is let out or unspooled from the spool 548b. This drives the distal driver 542 back to its initial position and causes the jaws 504 to reopen, e.g., by the top body portion 570 pressing against the sloped surface 583b of the recess 582.

In one embodiment, it takes six pulls of the trigger 514 to drive the driver 542 from the initial position of FIGS. 51A-51D and 54A-54C to the distal position of FIGS. 55A-55C and 60A-60D. In one embodiment, it takes two more pulls of the trigger 514 to drive the driver 542 back to the initial position from the distal position. A different number of trigger pulls for advancing and/or retracting the driver are also contemplated. Also contemplated is a single pull of the trigger to advance the driver its full distal distance. As the shoulders 620 of the lock wheels 604 come out of alignment with the rod 618, the interference between the shoulders 620 and the rod portions 636 is removed, and the springs 598 are able to return the rod 618 back to the safety position, thereby resetting the safety mechanism 616 and preventing the trigger 514 from being moved beyond the intermediate actuation position until the safety mechanism 616 is again released. Likewise, when driver 542 is returned to its initial proximal position, the wheels 602 are orientated such that the housing pawls 640 are aligned again with the cutouts 642. Also, the angular position of the assembly 600, in the fully returned position, causes the interlock 610 to be out of alignment with the raised portion 646 and therefore no longer held in a depressed position. Thus, the interlock 610 is able to spring or move back out to cause engagement of the protrusion 612 with the lip 614 of the trigger 514. In this configuration, the surgical implant applicator 500 is fully reset and ready to be loaded with another surgical implant 10 if desired. The applicator can be designed for single use where it is utilized for a single firing of the implant into the tissue or other structure. Alternatively, it can be designed for multiple firings in a single patient with fresh implants inserted into the jaws and applied to the tissue or other structures.

FIGS. 60E-60L illustrate a handle release mechanism or handle release system that can be utilized with the handle/actuator mechanisms disclosed herein. The handle release mechanism allows the jaws to be repeatedly open and closed to repeatedly clamp and unclamp tissue or other structure before transitioning to the fastener applying mode (cycle), where the jaws cannot be opened until the fastener applying (firing) cycle is completed. The release mechanism also provides a safety to prevent unintentional firing of the fasteners. The foregoing is achieved with an easy to use and easily accessible safety on the handle.

The handle release system of FIGS. 60E-60L is configured to work with the above described pull/pull systems and therefore the cables, pulley, ratchet wheels, spools, etc. are not described herein again. The system is also designed to work with the applicator (device), e.g. applicator 500, and jaws, e.g. jaws 504, for applying the various implants, e.g. implant 10, described herein and therefore the jaws and implant are not discussed again or shown in the drawings. However, it should also be appreciated that the handle release system of this embodiment can be used with applicators designed to apply fasteners or components other than the implants described herein.

Figure 60A:
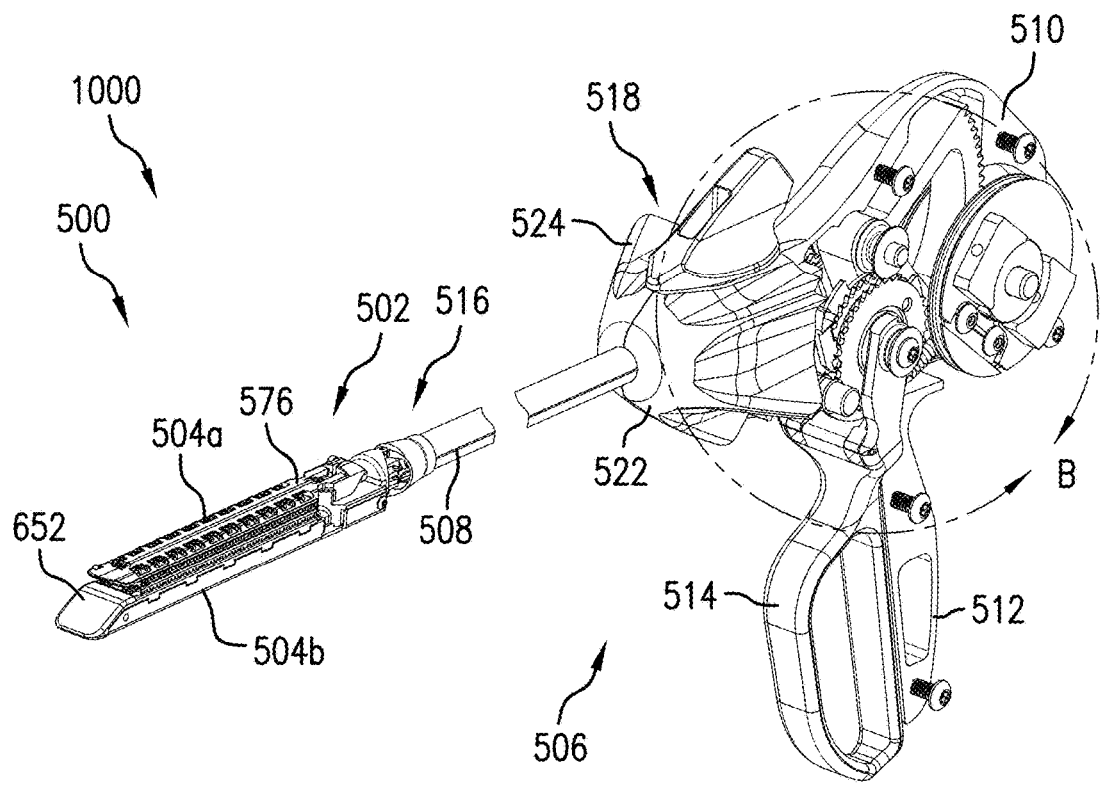
FIG. 60A is an isometric view of the system of FIG. 50 having a portion of a housing removed to illustrate components of a driving assembly.
Figure 60B:
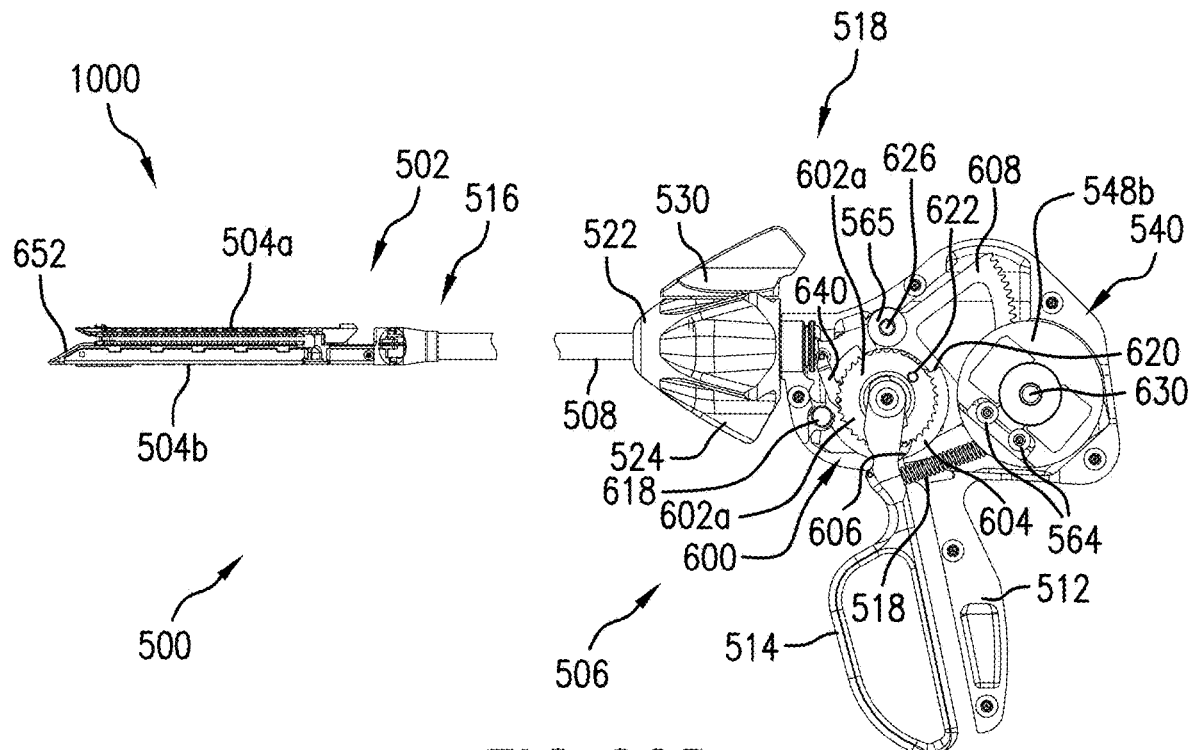
FIG. 60B is a side view of the system shown in FIG. 60A.
Figure 60C:
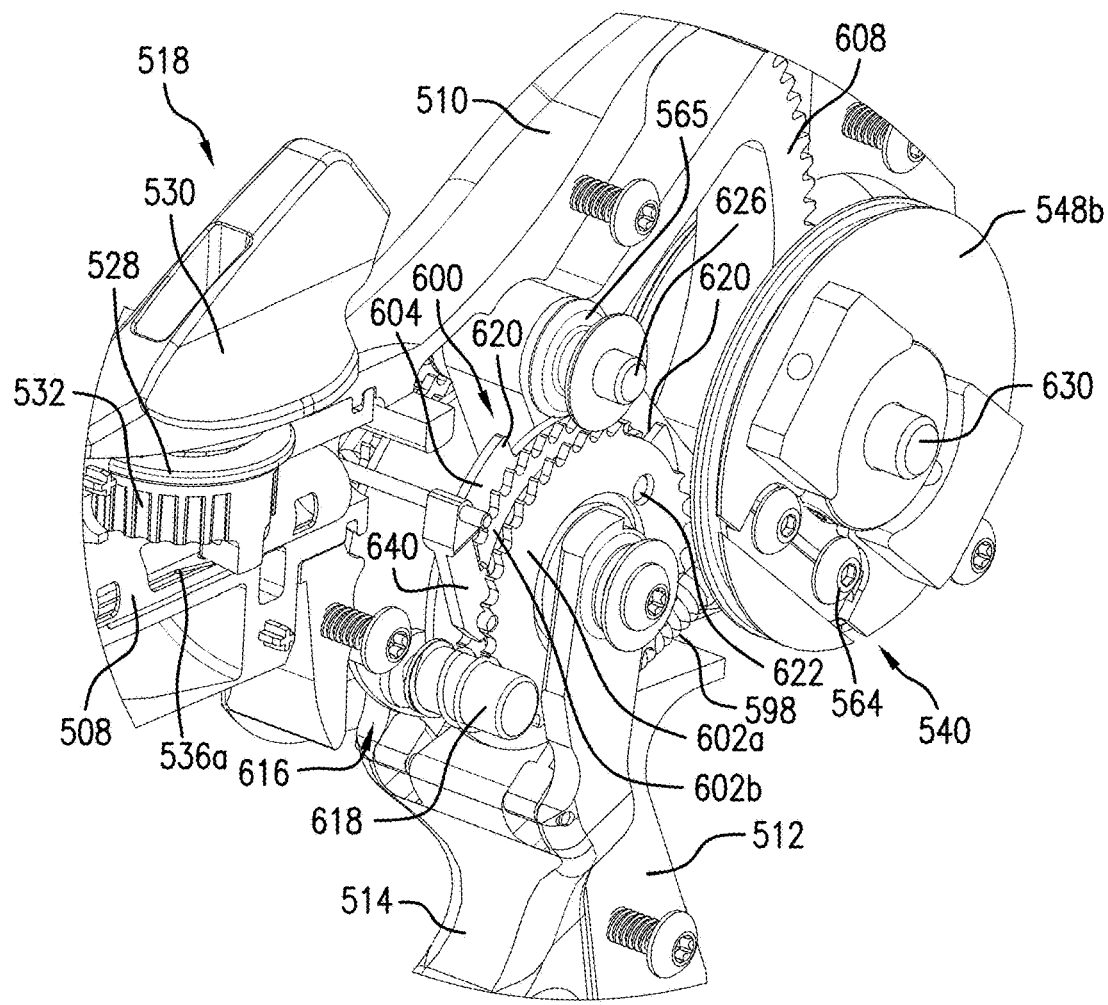
FIG. 60C is an enlarged view of the portion of FIG. 60A within circle C.
Figure 60D:
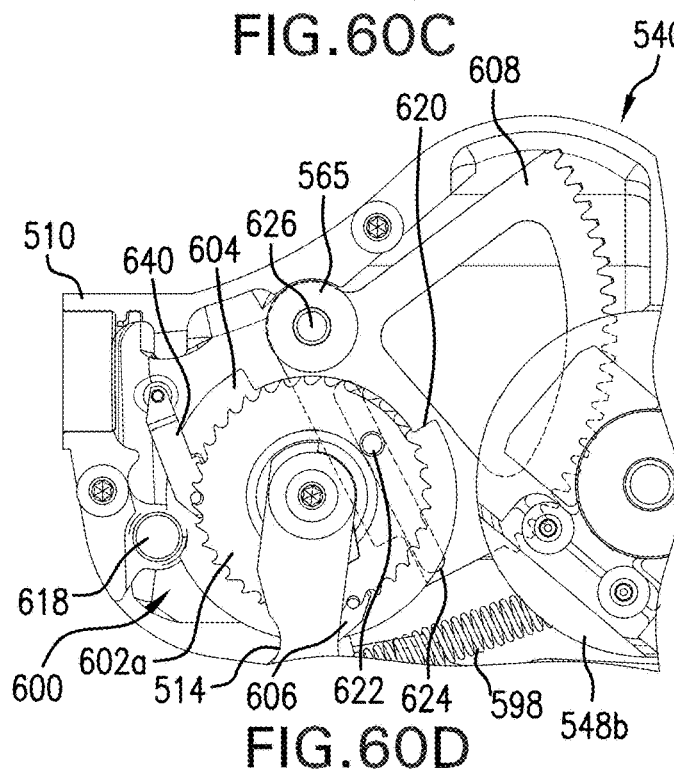
FIG. 60D is a partial side view of a portion of the system of FIG. 60C.
Figure 60E:
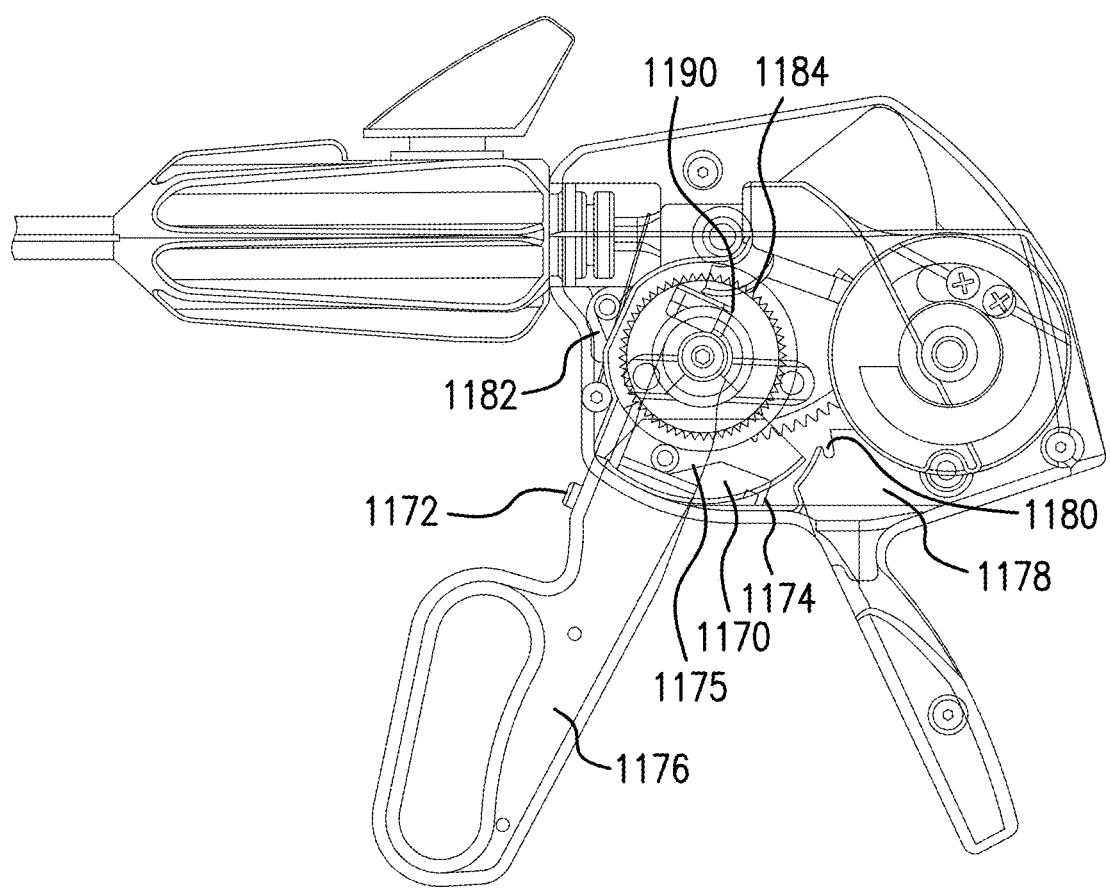
FIG. 60E is a side view of a handle portion having a handle release mechanism in accordance with another embodiment, the handle shown in the initial jaws open position.
Figure 60F:
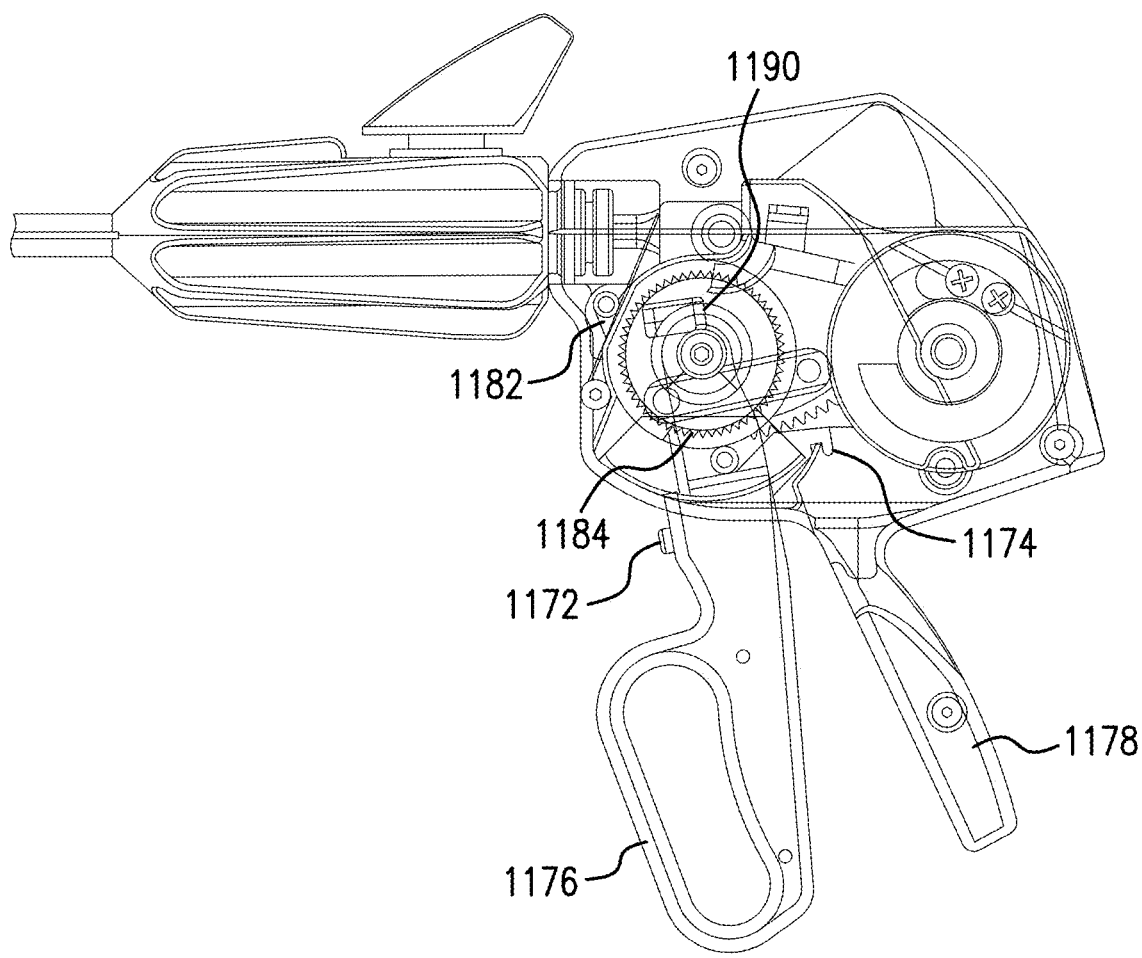
FIG. 60F is a side view similar to FIG. 60E showing the movable handle in the jaws closed position.
Figure 60G:
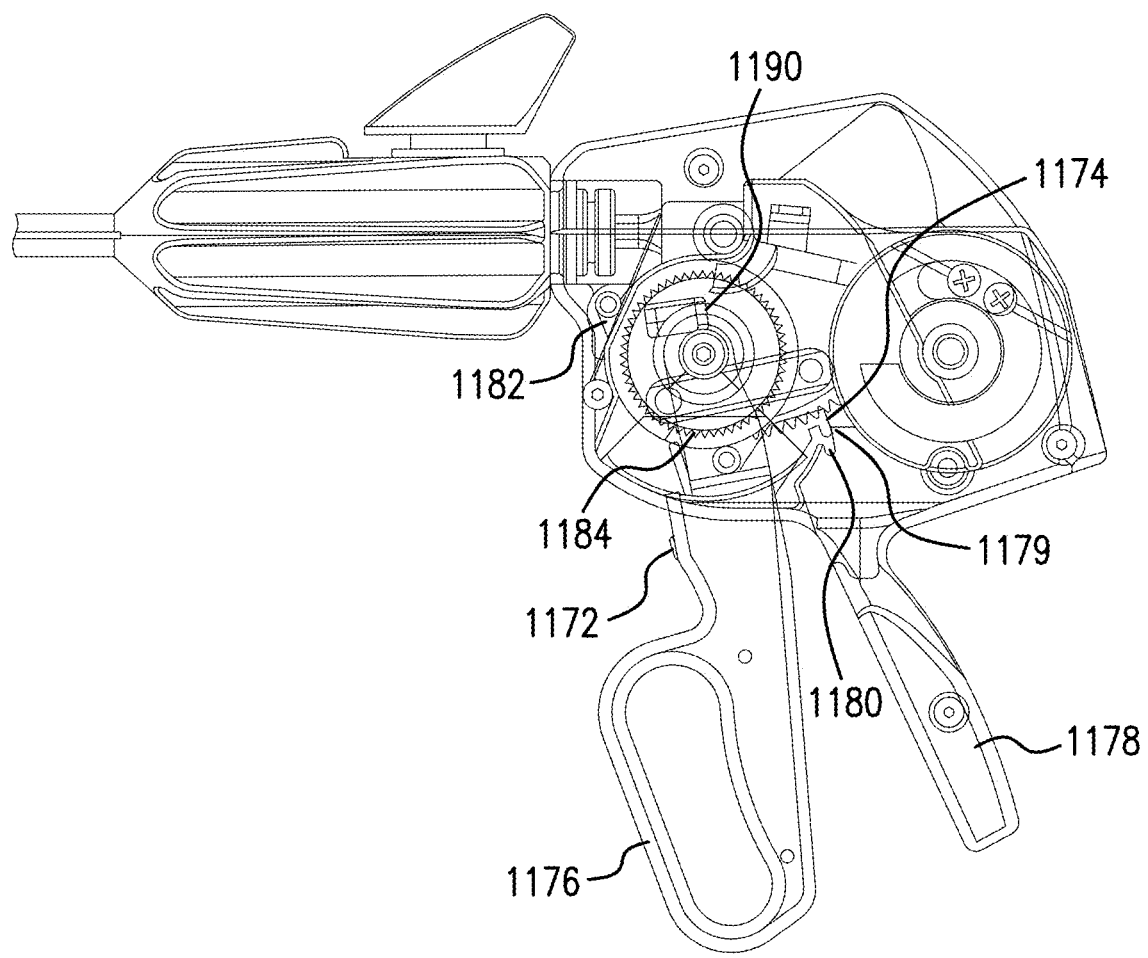
FIG. 60G is a side view similar to FIG. 60F showing the movable handle in the jaws closed position and the safety button partially pressed.

Turning initially to FIG. 60E, the safety (or release) of the handle release mechanism (system) is designated generally by reference numeral 1170. Safety 1170 is positioned on movable handle (or trigger) 1176 and operatively associated therewith. The movable handle 1176 is movable toward and away from stationary handle 1178 and is biased in a clockwise direction. Safety 1170 has a hook or latch 1174 engageable with a hook receiving member illustratively in the form of a recess 1180 in stationary handle 1178. Safety 1170 further has a safety button 1172, positioned on the movable handle 1176, e.g., under the index finger of the user when the handle is grasped, for ease of access, which is selectively movable (pressible) by the user to an intermediate position, e.g., partially pressed or half pressed, as in FIG. 60G, and to a fully pressed position as in FIG. 60H. In the engaged position of the hook 1174 and recess 1180 as illustrated in FIG. 60F, the hook 1174 catches the handle 1178 and holds the movable handle 1176 in this position with the jaws closed such that the movable handle 1176 cannot be opened, i.e., returned to its initial position, and therefore the jaws cannot be opened. Thus, the jaws are held closed until the safety button 1172 is pressed. When the safety button 1170 is partially pressed to a first release (intermediate) position, it pivots the hook 1174 out of engagement with the recess 1180 as shown in FIG. 60G to enable the handle 1176 to be returned to the initial position of FIG. 60E to reopen the jaws. However, in this partially pressed position, the movable handle 1176 cannot be actuated, i.e., further squeezed, to initiate the fastener firing (advancement) due to the abutment surface 1179 blocking an outer portion of the hook 1174. When the safety button 1172 is fully pressed (to a second release position), the hook 1174 moves away from the wall 1179 (FIG. 60K), releasing the movable handle 1176 for further movement to actuate the drive assembly to fire (advance) the plurality of fasteners. The safety button 1172 is preferably biased clockwise by a compression spring to an extended (non-pressed) position. Note the movable handle 1176 is preferably biased distally by a tension spring (not shown) to the position of FIG. 60E. A handle ratchet 1182 is biased in a counterclockwise direction into engagement with the ratchet wheel 1184. In the position of FIG. 60E, handle (trigger) catch 1175 is locked to ratchet wheel 1184 for forward driving and ratchet wheel snap 1190 is locked to the movable handle 1176 for reverse driving. With the movable handle 1176 in the closed position of FIG. 60F, the handle ratchet 1182 is disengaged from the ratchet wheel 1184 to allow reverse movement of the movable handle 1176 to allow jaw opening if needed. With the safety button fully pressed, the handle ratchet 1182 reengages the ratchet wheel 1184 and disables the reversing ratchet wheel and a protrusion 1189 (FIG. 60K) on the inside of the handle presses the ratchet wheel snap 1190 inwardly to disengage the ratchet wheel 1184 from the movable handle 1176 to disable reverse driving. When the handle ratchet 1182 is engaged with the ratchet wheel 1184, then the movable handle 1176 can effect firing of the fasteners. Note the outer wall 1188 of the ratchet wheel 1184 (FIG. 60L) keeps the safety button 1172 depressed until the firing cycle is completed. The safety button 1170 is advantageously solidly positioned between movable handle 1176 and the stationary handle 1178 so as to be sufficiently strong to tolerate full hand strength.

Figure 60H:
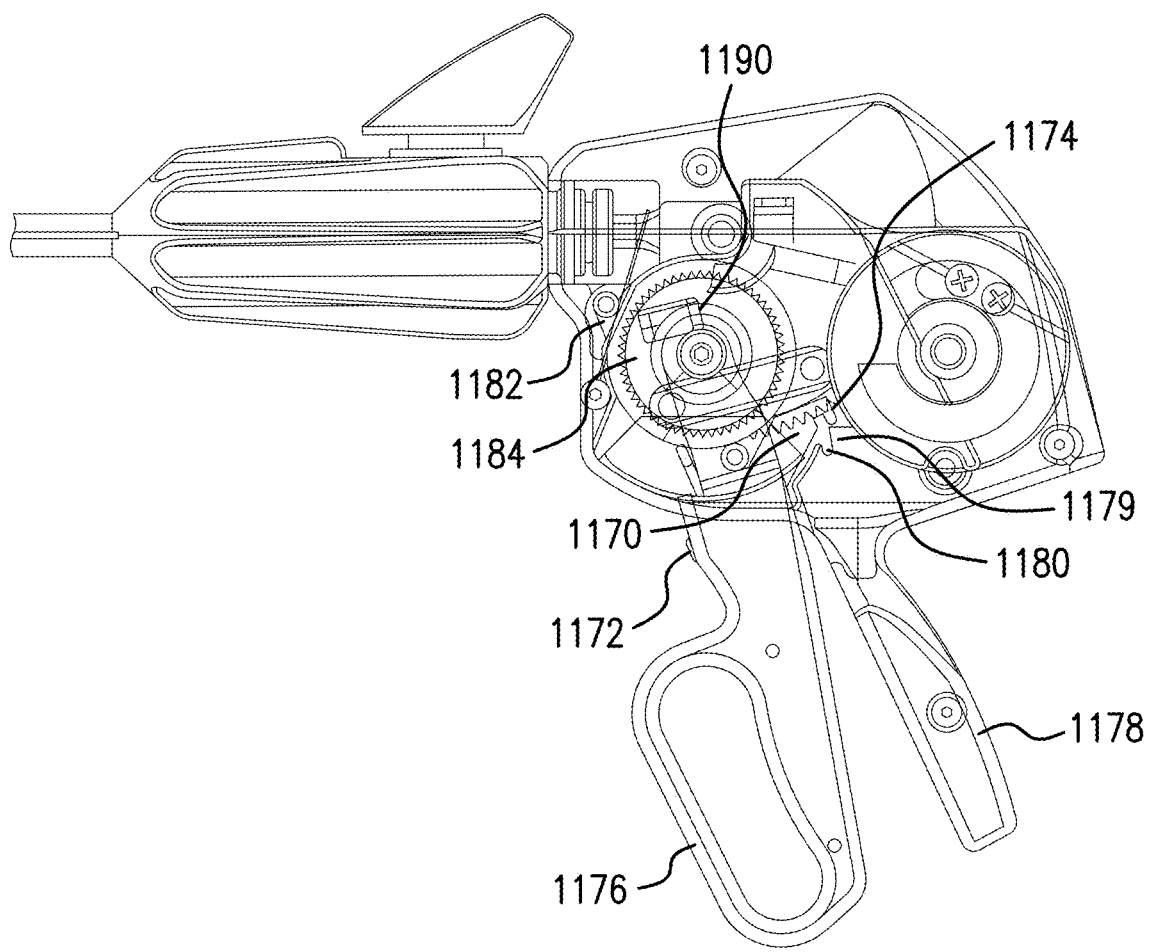
Figure 60I:
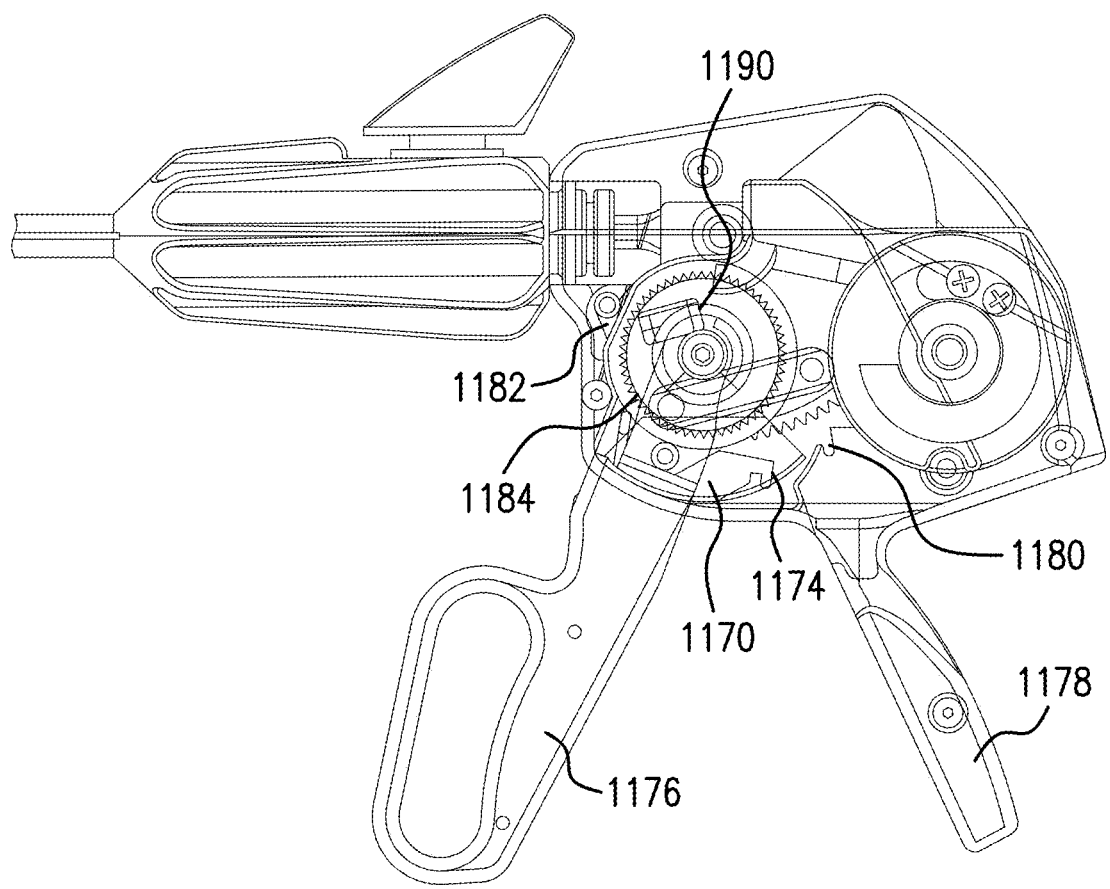
Figure 60J:
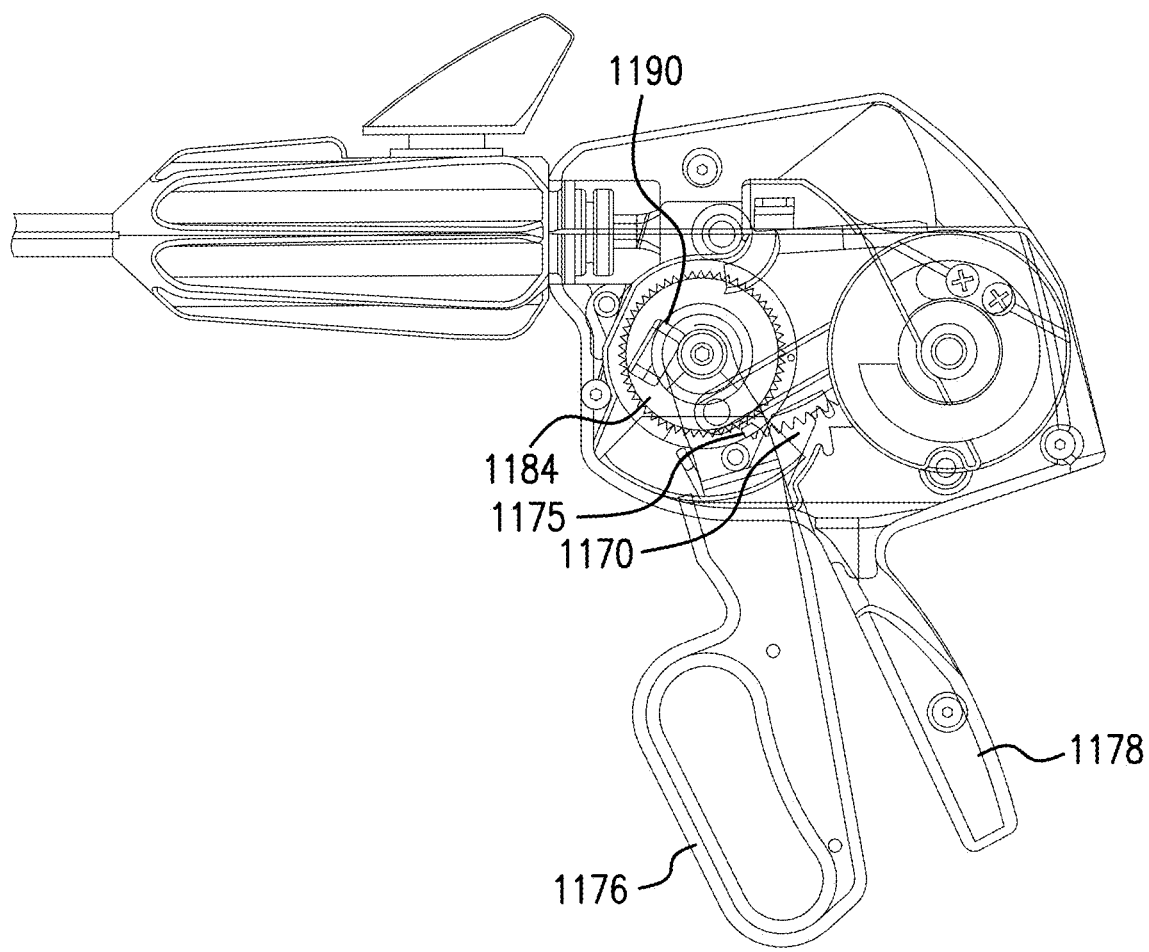
Figure 60K:
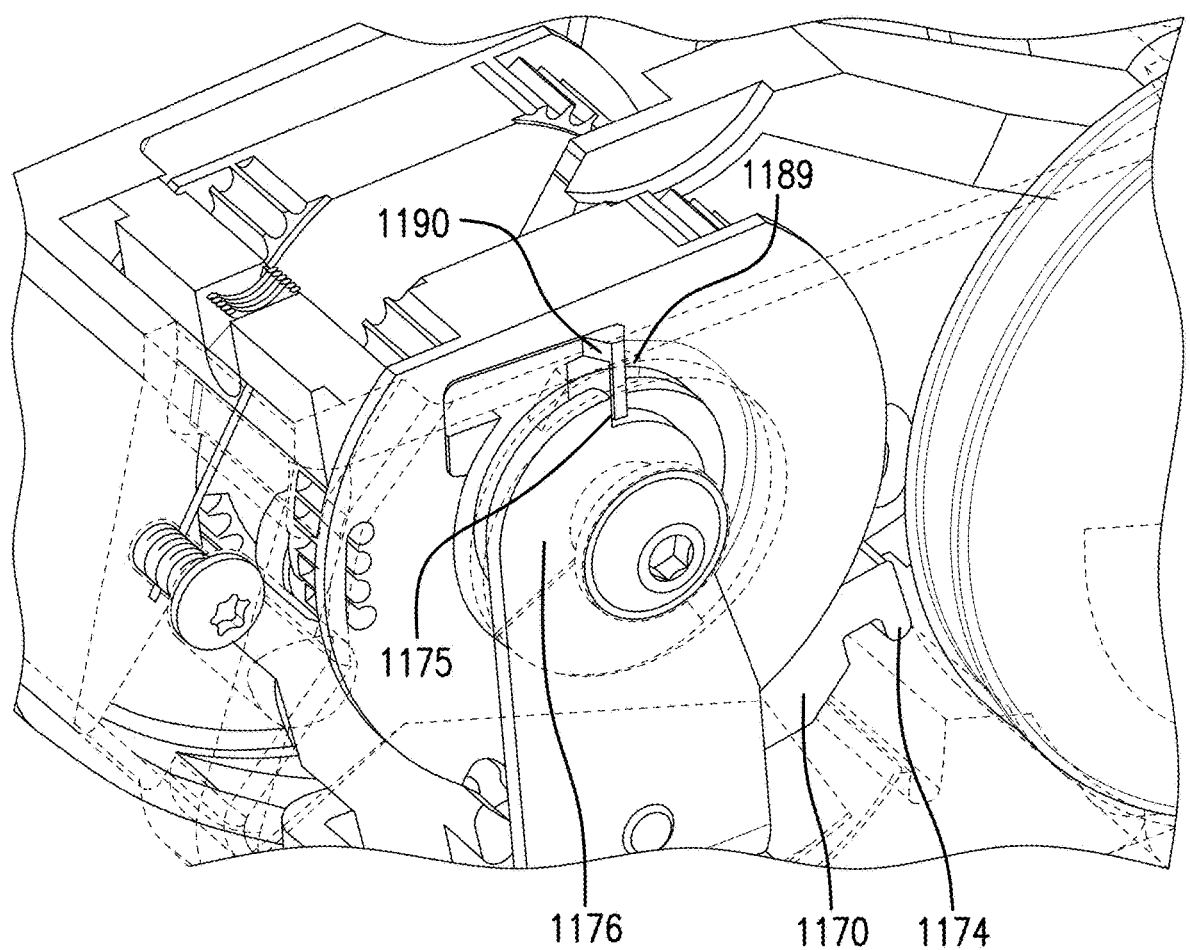
Figure 60L:
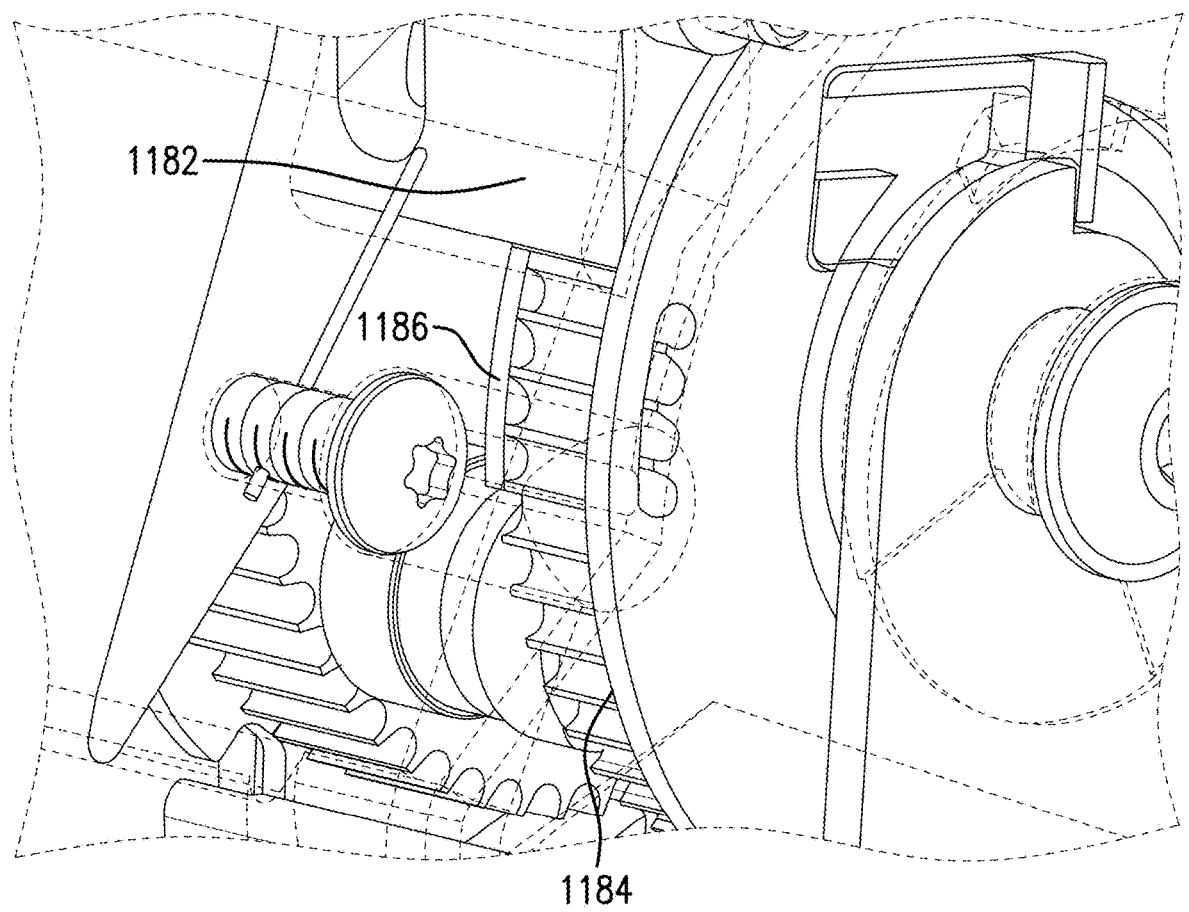

Turning now to the use of the release mechanism, in the open position of FIG. 60E, movable handle 1176 is spaced from stationary handle 1178 and the instrument jaws are in the open position as in the aforedescribed embodiments. In this open position of the movable handle 1176, release button 1172 is in the extended (non-pressed) position, biased clockwise by a compression spring, and hook 1174 of safety 1170 is out of engagement with recess 1180 of stationary handle 1178. As noted above, movable handle 1176 is biased to the open position by a tension spring. Also, in this position, handle ratchet 1182 is engaged with ratchet wheel 1184, handle catch 1175 is locked to the ratchet wheel 1184 for forward driving and the ratchet wheel snap 1190 is locked to the movable handle 1176 for reverse driving. When the movable handle 1176 is moved from its initial position toward stationary handle 1178 to the closed position (FIG. 60F) to transition the jaws to the closed position, the handle ratchet 1182 is disengaged from the ratchet wheel 1184 to allow reversing to reopen the jaws, i.e., movement of the movable handle 1176 back to the open position of FIG. 60E, if the user desires to reclamp the tissue or other structure. Note the hook 1174 of safety button 1170 engages the recess 1180 of the stationary handle 1178 to catch and lock the movable handle 1176, and thus the jaws, in the closed position. If the user wants to reopen the jaws to change the position of the instrument and/or reclamp, safety button 1172 of safety 1170 is pressed partially inwardly, i.e., into the movable handle 1176, to an intermediate position. This releases the hook 1174 as shown in FIG. 60G so the movable handle 1176 can be pivoted distally (clockwise) back to its at rest position of FIG. 60E. However, movable handle 1174 cannot be moved proximally in a fastener deploying motion to initiate the fastener applying (firing) cycle because the hook 1174 is in abutment with wall 1179 of the stationary handle 1178. If the user does not wish to reopen the jaws, then the user can proceed with the steps for deploying the fasteners. Once the jaws are closed to the position of FIG. 60F, to begin the fastener firing cycle, the safety button 1172 is fully depressed as shown in FIG. 60H, moving the hook 1174 out of engagement with wall 1179, thereby freeing movable handle 1176 for proximal movement. The handle ratchet 1182 reengages the ratchet wheel 1184, disabling reversing of the ratchet wheel 1184. The protrusion 1189 on the inside of the handle (FIG. 60K) presses the ratchet wheel snap 1190 inwardly, disengaging the ratchet wheel 1184 from the movable handle 1176, disabling reverse driving. The jaws cannot be open once this fastener deploying movement has commenced. Movable handle 1176 springs forward as the handle catch 1175 skips over the teeth of the ratchet wheel 1184 as the ratcheting cycle starts (FIG. 60I), with outer wall 1188 of ratchet wheel 1184 keeping the safety button 1182 depressed. Note the handle ratchet 1182 remains engaged to the ratchet wheel 1184 to prevent reverse motion. The movable handle 1176 is squeezed, i.e., moved proximally, as shown in FIG. 60J to begin the cycle to deploy (fire the fasteners). Note the trigger catch 1175 engages the ratchet wheel 1184 add drives the ratchet wheel 1184 counterclockwise to fire the fasteners. Also the ridge 1188 of the ratchet wheel 1184 holds the safety button 1172 retracted until the firing cycle is complete. The pull and release of the movable handle 1174 is repeated until the ratchet 1182 has made a complete rotation, firing the fasteners.

Figure 61A:
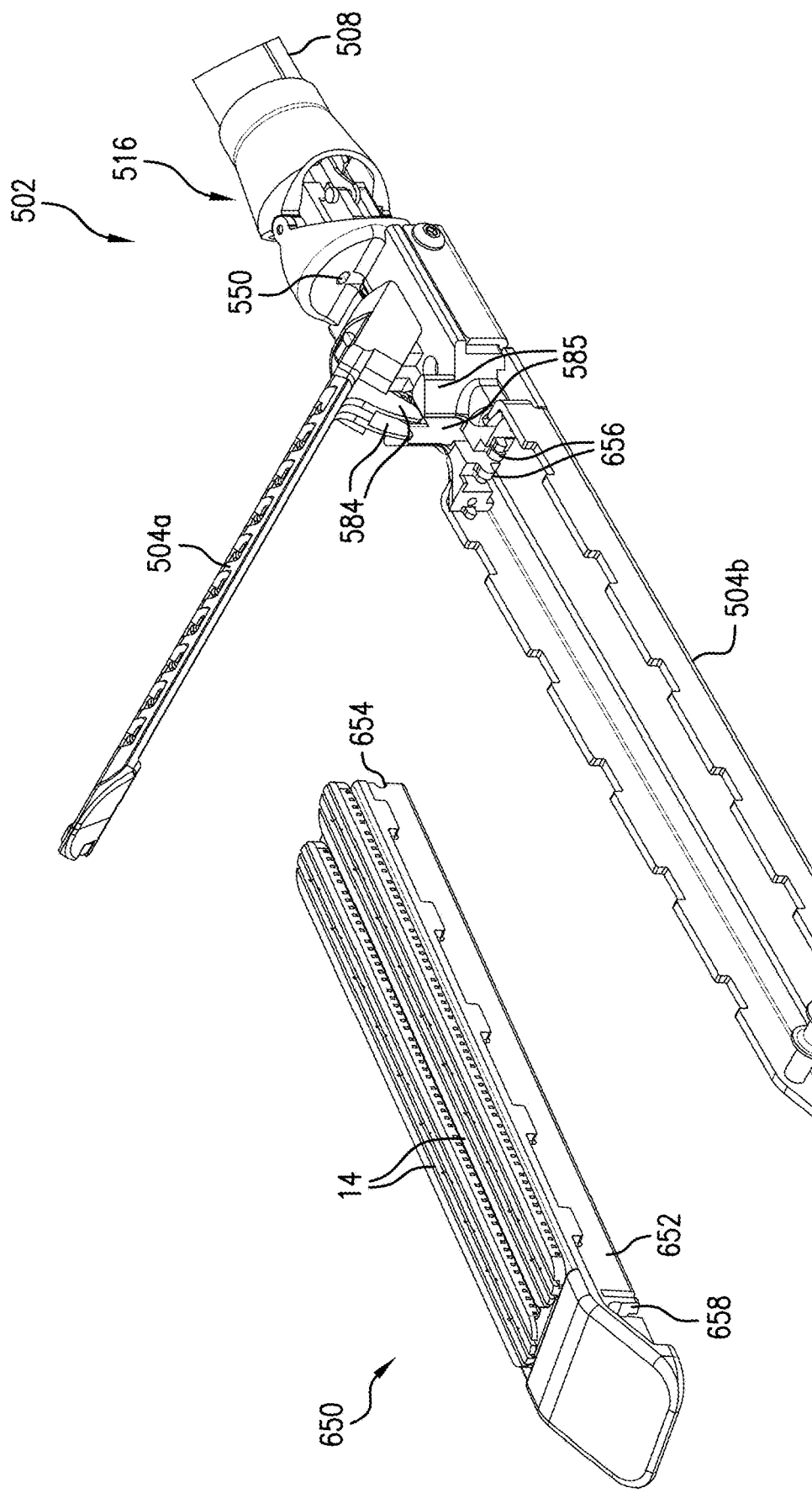

In one embodiment, the halves of the implant (e.g., the receiving member 12 and the deployment member 14 of the implant 10) are directly loaded into the jaws of an applicator (e.g., the jaws 504 of the applicator 500) and supported (mounted) within the jaws. In one embodiment, one or more of the halves are pre-loaded into a loading assembly or loader, which is then loaded into and supported by the jaws. For example, FIGS. 61A-61C illustrate the deployment member 14 of the surgical implant 10 preloaded into a loader or loading assembly 650 before the loading assembly 650 is loaded into the jaw 504b. In the embodiment of FIGS. 61A-61C, the loading assembly 650 comprises a carrier 652 and the deployment member 14 of surgical implant 10. Carrier 652 may be made of polycarbonate, acrylonitrile butadiene styrene (ABS) plastic, or other sufficiently strong polymer, for example. The pushers 592 may optionally be included in the loading assembly 650, or alternatively carried by the jaw 504b. It is noted that other implant halves besides the deployment member 14, e.g., the receiver member 12, may be loaded into loading assemblies according to other embodiments of the present invention. Additionally, if practical, the entire implant, e.g., a hinged implant 1010 in FIG. 77 having the members 12 and 14 connected by a hinge 1012, but which otherwise resembles the implant 10 discussed above, may be so loaded.

The loading assembly 650 may be loaded into the jaw 504b by inserting proximal end portions 654 of the carrier 652 beneath a corresponding set of holding features 656, such as hinges, hooks, shoulders, ledges, projections, or the like, provided in the frame 552 of the jaw 504b (e.g., see FIGS. 54B and 61A). Near its distal end, the carrier 652 includes a pair of slots 658 and a recess 660 (FIG. 61B), which are complementarily arranged to receive a shaft 662 of the pulley 556 and the pulley 556, respectively. After engaging the proximal end portions 654 of the loading assembly 65 with the holding features 656 of the jaw 504b, the distal end of the carrier 652 is attached to jaw 504b with a snap fit of shaft 662 into the slots 658 by pressing the distal end portion of the loading assembly 700 against the jaw 504b. During installation of the loading assembly 650, the carrier 652 may initially be positioned with the end portions 654 located beneath the holding features 656 and with the carrier 652 at an angle relative to the jaw 504b (e.g., preferably an angle of about 15° to 30°, but the angle could be smaller than 15° or larger than 30°), such that the engagement of the end portions 654 and the holding features 656 acts like a hinge to rotate the carrier 652 about the holding features 656 when pressing down on the proximal end of the carrier 652 in order to secure the carrier 652 to the jaw 504*b*.

Ribs or webbing of the implant held by the jaws 504 of the applicator 500, e.g., the ribs 23 and/or 29 of the implant 10, (see FIGS. 1 and 2) may facilitate alignment of the implant with the jaws 504, and form a friction fit between the surgical implant and the jaws 504, etc., to help retain the implant in the jaws against the force of gravity. For example, upon installation of the receiver member 12 of the surgical implant 10 into the upper jaw 504*a*, ribs may be aligned and/or form a compression or friction fit with corresponding grooves 664 (FIG. 62D) formed in upper jaw 504*a*. Likewise, the ribs 29 may be aligned and/or form a compression or friction fit with corresponding grooves 665 in the lower jaw 504*b*. The jaw 504*a* may additionally or alternatively include openings suitably arranged to align with and/or frictionally engage the shields 22 of the receiver member 12 of the implant 10. For example, the jaw 504*a* in the illustrated embodiment includes a plurality of openings 666 sized and spaced to align with and receive the shields 22 upon installation of the receiver member 12 with the jaw 504*a*. A compression fit formed between the members 12 and/or 14 and the jaws 504 may be sufficiently strong to retain the halves of the surgical implant 10 in the jaws 504 during the installation process, or other manners of releasable connection are possible, including adhesives, mechanical fasteners, components, e.g., flanges or rails. The retention is sufficient so jaws 504 initially support the halves e.g., members 12 and 14, of the implant and then allow release from the jaws 504 due to the passage of the driver 542 as discussed above.

The surgical implant applicator 500 is configured for the ability to install a sequence of two or more surgical implants 10 in a head-to-tail arrangement (e.g., a proximal end of a second one of the surgical implants 10 adjacent to a distal end of a first of the surgical implants 10), if needed or desired. For example, in a situation where a target surgical site to be sealed and cut is longer than the length of the implant, two or more of the implants can be installed in a head-to-tail arrangement in order to extend the length of the seal and cut resulting therefrom FIGS. 62A-62D show portions of the jaws 504 and FIGS. 63A-63E illustrate one example of a procedure wherein a first surgical implant 10' and a second surgical implant 10" have been installed in a target structure 700. The implants 10' and 10" may exactly resemble the implant 10 (or any of the aforedescribed alternate embodiments of the implant) discussed above, and are given prime and double prime symbols for the sake of clarity in discussion.

Figures 63A, 63B, 63C:
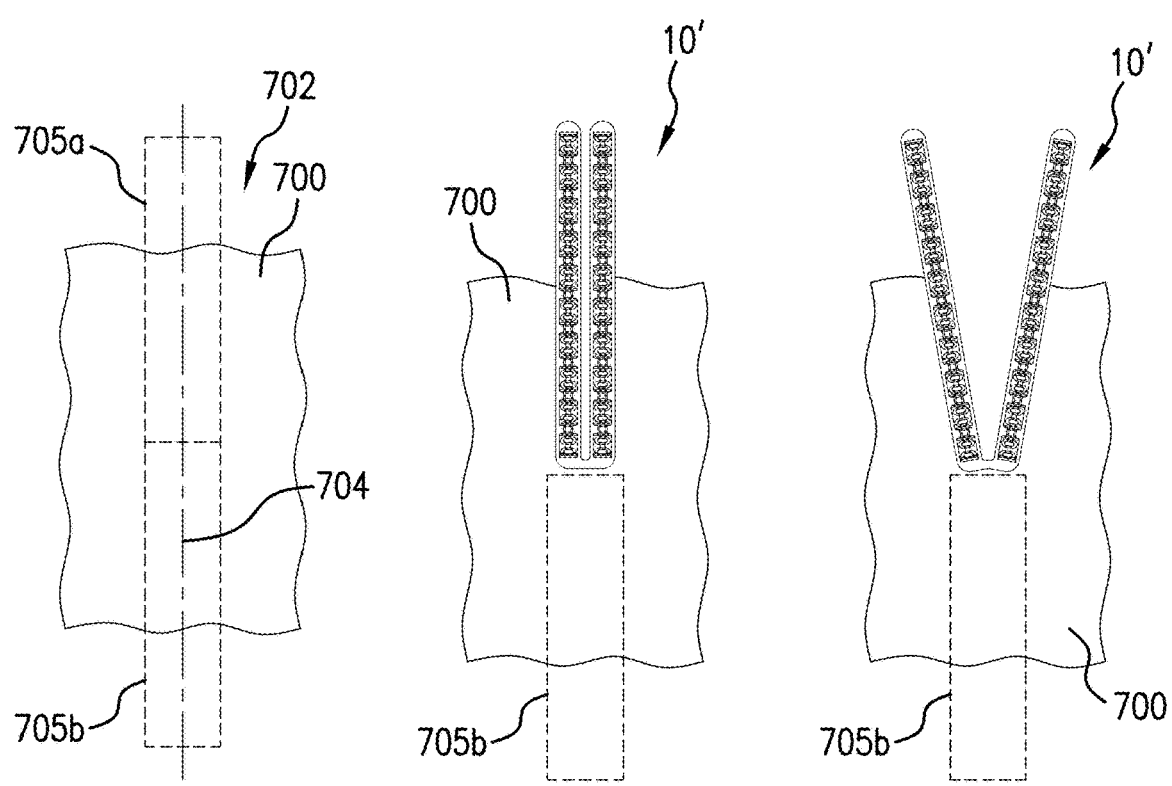
Figures 63D, 63E:
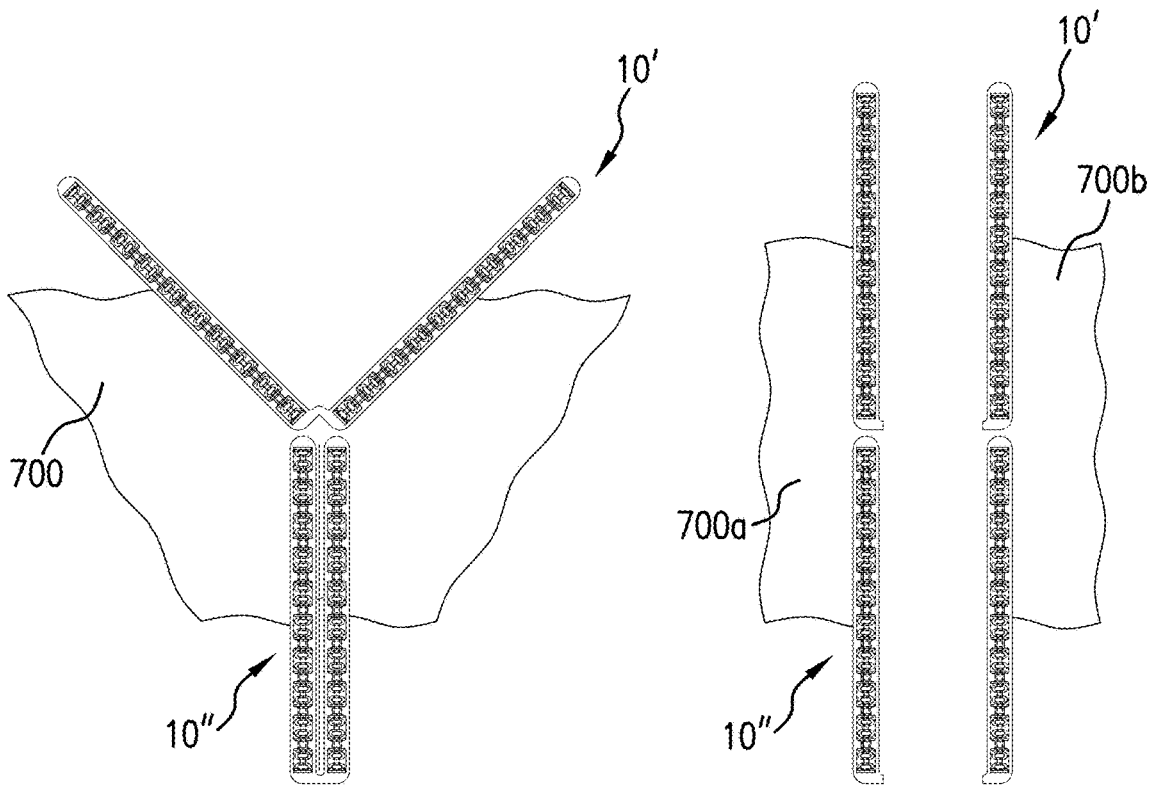

According to the method outlined in FIGS. 63A-63E, and with reference also to FIGS. 62A-62D, a target surgical site 702 is first determined for establishing a seal or connection with the implants 10' and 10" and establishing a location for a cut as indicated by a dashed line 704. Since the length of the target site 702 is longer than that of the implants 10' and 10", the site is broken down into multiple sub-sites 705*a* and 705*b*, equal to or less than the length of the implants 10' and 10". FIGS. 63B and 63C illustrate the structure 700 after the first implant 10' has been installed at the target sub-site 705*a* and the tissue structure 700 has been cut between the rows of the implant 10', enabling the cut and sealed portions of the structure 700 to separate from each other as shown in FIGS. 63C and 63D.

Next, as illustrated in FIG. 63D, the first implant 10', after cutting, may be spread wide by the jaws 504 to part the cut portions of the structure 700 away from each other. For example, as can be appreciated in view of FIGS. 62A-62D, the shields 585 are sharply or acutely angled with respect to the axis 520 of the jaws 504. As can be seen in FIG. 62B, a gap 668 may be formed between the shields 585 and the next implant to be installed (e.g., the implant 10"). As shown in FIG. 62A, the distal end of the already installed implant 10' may be positioned in the gap 668 and the jaws 504 closed over the distal end of the implant 10' after the second implant 10" is installed in the jaws 504. The angle of shields 585 causes the already installed implant 10' to spread from a first angle to a second angle larger than the first, and the portions of the cut tissue or other structure to widen, as illustrated in FIG. 63D. After positioning the implant 10' in the gap 668 and closing the jaws 504 and firing the driver 542 with the implant 10" located at the target sub-site 705*b*, the structure 700 is again sealed and cut to separate the structure 700 into discrete halves 700*a* and 700*b*, as illustrated in FIG. 63E. Cutting of the connected vertex of implant 10' may occur during the cutting of implant 10" (as suggested by FIGS. 63A-63E), but may alternatively occur during the cutting of implant 10', or as an entirely separate step occurring prior to, after, or intermediate the cutting of implant 10' and implant 10".

In view of the above, it is to be appreciated that the present disclosure is directed to novel systems and methods for sealing and/or connecting tissue and non-tissue structures using the surgical implant 10 and other implants described herein, the applicator 500 and other applicators described herein, and the system 1000 and other systems described herein. In one exemplary method, the implant 10 is installed with the surgical implant applicator 500. The method involves securing together one or more tissue portions via a surgical implant (e.g., the surgical implant 10) such that thickness variations in the tissue as well as wide tissue thickness ranges can be accommodated. Each half of the implant is brought into opposition through an applied clamping pressure generated by resilient and/or compressible members (e.g., the towers 30), which results in a relatively constant and/or more uniform pressure distribution across the tissue contacting surfaces of the implant, regardless of variations in tissue thickness, than would be experienced by other types of fastening mechanisms, such as staples. The system can be used to form a hemostatic seal of various types of tissue and tissues of varying thicknesses. That is, the application of the implant forms a hemostatic seal without inducing an unacceptable degree of necrosis of the clamped or adjoining tissue. By way of example, the system may be used to seal pulmonary parenchyma, or also used to seal the pulmonary artery. In an exemplary embodiment, the method involves loading the implant into an applicator (e.g., the applicator 500); positioning the applicator at the surgical site to join or seal one or more tissue portions or structures; actuating the applicator to deploy fasteners (e.g., the fasteners 32) and install the implant to form a hemostatic seal with or without the severing of adjoining tissue; an optional step of resizing the length of the implant as needed; and another optional step of resetting the applicator to deploy one or more additional implants. In some embodiments, the implant may already be loaded (i.e., pre-loaded) in the applicator such as in a situation in which the implant is loaded at the point of manufacture; in other embodiments, the user loads the implant in the applicator. In a method of fastening parenchyma by way of example, parenchyma is clamped between the tissue contacting (engaging) surface on the fastener supporting (deployment) member 14 and the tissue contacting (engaging) surface on the receiver member 12 and the fasteners (e.g., fasteners 32 or other fasteners disclosed herein) are advanced into the receiver member 12, compressing the compressible members (e.g., towers 30) which then apply a counterforce when the fastener supporting member 14 and receiver member 12 are coupled, by the fasteners, in the manner described above. In another example, an anastomosis between a first structure and a second structure within the body is achieved utilizing the fasteners are described herein to couple together the fastener supporting (deployment) member 14 which is positioned adjacent a first structure and the receiver member 12 which is positioned adjacent a second structure.

In one example of use, an implant (e.g., the implant 10) is fitted within and secured to an end effector (e.g., the end effector 502) of an implant applier assembly (e.g., the applicator 500) such that a deployment member (e.g., deployment member 14 including, e.g., fasteners 32 and towers 30) and a receiving member (e.g., the receiving member 12) are supported by and attached to one or both of a set of jaws (e.g., the jaws 504) and positioned for deployment. In one embodiment, each of the deployment member and the receiver member of the implant is positioned within a removable carrier (e.g., the carrier 652) of a loading assembly (e.g., the loading assembly 650) that is received within a corresponding cavity or receptacle of the jaws. In another embodiment, the receiving members and the deployment member may be directly attached to the jaws at the point of use or manufacture. In an exemplary embodiment, the applicator (e.g., the applicator 500) is inserted into the body with the jaws in the closed position using a minimally invasive procedure involving insertion of its end effector through a trocar or cannula having a diameter of about 5 to about 22 mm, more preferably, about 6 to about 16 mm, and even more preferably about 12 mm. The user may activate the articulation actuator and/or the rotation actuator to orient the end effector (e.g., via the positioning assembly 518) at the desired surgical site, preferably with the jaws in the closed position. The jaws are moved to the open position and the receiving and deployment members are positioned on opposite sides of the tissue defining a defect or other overlapping separate tissue portions such that when deployed, the tips (e.g., the tips 40) of the fasteners (e.g., the fasteners 32) are inserted through the tissue portions and a portion of the receiving member. In other embodiments, it is contemplated that the tips of the fasteners arrive at opposite sides of the tissue without piercing through the tissue, e.g., located adjacent to the tissue or through openings in the tissue.

A user can then actuate a trigger (e.g., the trigger 514) to transition the jaws from the open to the closed position (configuration). Note that in the illustrated embodiment, one of the jaws moves relative to the other jaw which is stationary jaw e.g., the jaw containing the deployment member is stationary. It is also contemplated that the jaw containing the deployment member could move relative to the jaw containing the receiver member which remains stationary. It is also contemplated that both of the jaws could move relative to each toward and away from each other between open and closed positions as discussed above. When closed, a user may then orient and move a safety mechanism (e.g., the safety mechanism 616 having the rod 618) in an unlocked position to enable a driver or actuator (e.g., the driver 542) to slide or move along the length of the end effector. As the driver slides along and over a dorsally facing surface of the jaws, the portion of jaws over which the driver slides may be further compressed together relative to the natural position of jaws in its closed state. As the driver moves over portions of the jaws loaded with the deployment member, the driver may engage and move one or more pushers (e.g., the pushers 592) towards the opposite jaw. The pushers in turn deploy the fasteners away from the deployment member, through the deployment member, through one or more tissue portions and into the one or more receiver members opposite thereto. In this manner, the fasteners are fired and deployed along the length of the implant as the driver moves from a first (e.g., proximal) end to a second (e.g., distal) end of the end effector.

The tissue secured between the deployment member and the receiving member is clamped together at a constant, uniform, normalized, or distributed pressure along the length of the implant sufficient to form a hemostatic seal that does not induce necrosis by virtue of the compliant resilient, biasing, and/or compressible members (e.g., the towers 30). As the properties of the tissue changes over time and/or changes due to different environmental conditions, such as movement of the tissue and/or a build-up of pressure within the tissue, each resilient, biasing, and/or compressible member (e.g., each of the towers 30) may independently function to adjust for and otherwise accommodate the localized pressure disturbance occurring within each fastener subassembly of the implant (e.g., the subassemblies 34). This allows for the implant to maintain a more normalized and/or substantially constant pressure for forming a hemostatic seal than otherwise would be available with other surgical fastener or stapling systems.

In one embodiment, the driver (e.g., the driver 542) includes a cutting blade (e.g., the cutting implement 580) located in a channel formed in and through the end effector. The blade, which is preferably towards the side of the driver that moves towards the clamped tissue, may be secured to a body portion of the driver that causes and/or facilitates maintaining the jaws of fixed predetermined distance apart, and further may function to sever tissue and/or any intervening portions of the implant encountered by the blade when moved along a channel along the length of the jaws.

Upon reaching a second and/or distal end of the end effector, continued actuation of the trigger induces the driver to return to the first and/or proximal end of the end effector. The subsequent return of the driver may function as a safety means for ensuring that all of the pushers and the fasteners are deployed along the entire length of the implant. Once the driver is docked at the proximal end of the end effector, the implant may be released from the jaws.

A user may then cut between the fastener subassemblies (e.g., through the ribs 23 and/or 29 of the implant 10) to remove any excess implant material or otherwise alter the size of the implant. In other words, the implant can be used on tissue lengths shorter than the implant itself. Additional implants may also be used to seal tissue sections longer than a single implant by directly adjoining the prior implant or may otherwise be connected directly to the prior implant. A series of the implants may be arranged to form a hemostatic seal as a stand-alone procedure or alternatively in conjunction with a tissue resection procedure. The aforementioned situations can allow a single or "standard" length of implant to be used on a variety of different lengths or as different length rows.

As noted above, in an alternate embodiment, the deployment member (containing the fasteners) can be positioned on the movable jaw and the receiver member positioned on the stationary jaw as an alternative to the aforedescribed positioning of the receiver member on the movable jaw and the deployment member (containing the fasteners) on the stationary jaw. This embodiment is illustrated in FIGS. 78A-81D. It should be appreciated that this embodiment differs from the above described embodiments, e.g., the embodiment of FIG. 50, in the different positioning of the deployment and receiver member of the implant and the resulting described changes as a result of this positioning. In all other respects, the implant, e.g. the retainer, the fasteners, compressible members, etc., and the applicator for applying the implant, e.g., the trigger, pulley, articulation, locking mechanisms, etc., are the same as described herein, and the various embodiments of the implant and applicator described and illustrated herein can be utilized with the embodiment of FIGS. 78A-81D. For this reason, for brevity, the details of the applicator for use with the end effector of this embodiment are not repeated herein since the function and components of applicator 500 are fully applicable to this embodiment of FIGS. 78A-81D. Consequently, only the end effector assembly of this alternate embodiment is illustrated. Additionally, the implant 10 or other implants disclosed herein can be utilized with this embodiment of FIGS. 78A-81D, so for brevity details of the implants, e.g., the fasteners, compressible members, retainer, etc., are not repeated herein. The difference regarding the implant is as noted above, the receiving part of the implant is on the stationary jaw and the deployment part (fastener receiving/fastener supporting member) is on the movable jaw.

Placing the deployment member on the movable jaw instead of the stationary jaw has advantages in certain clinical applications where additional tissue dissection is desired. In certain applications, when the user is placing the jaws of the end effector around tissue, there is limited space to place the jaw around the backside as the target tissue structure that is to be transected and sealed is connected to other tissue. Dissection of the target tissue from the other tissue can be difficult without causing collateral damage to the tissue. Therefore, dissection of tissue is often minimized. With minimal dissection, in certain clinical applications, there is little space for the jaw to slide through. Since the jaw containing the receiver member (receiver jaw) is smaller than the jaw containing the deployment member (cartridge jaw) which supports the fasteners, the receiver jaw is the preferred jaw to slide through the dissection opening. However, once this receiver jaw is in place in the dissection, the user does not want to move the jaw which could damage tissue. To keep this smaller receiver jaw stationary, the cartridge jaw would need to be the jaw that moves, e.g., pivots, towards the stationary receiver jaw for subsequent application of the fasteners. Thus, by placing the deployment member on the movable jaw, the smaller receiver jaw can fit through the minimal tissue space.

Turning now to FIGS. 78A-81D which show an embodiment of the deployment member (fastener supporting member) on the movable jaw, the end effector of the applicator, e.g. applicator 500, is designated generally by reference numeral 1002 and has a movable jaw 1004 and a stationary jaw 1006. Due to the illustrated orientation of the jaws 1004, 1006 throughout the Figures, the movable jaw 1004 may be referred to herein as the upper jaw, and the stationary jaw 1006 as the lower jaw, although it is to be appreciated that this is for the sake of discussion only and that the jaw 1004 does not necessary have to be "above" the jaw 1006, i.e., after changing the orientation of the applicator. The stationary jaw 1006 can have a width and/or height less than a width and/or height of the movable jaw to provide a lower profile. FIGS. 78A, 81A and 81C show the end effector 1002 in an open configuration, with opposing first and second portions of the surgical implant 1010, namely the receiver member 1012 and the deployment member 1014, mounted in the lower and upper jaws 1004, 1006, respectively. The end effector 1002 is at the distal portion of the surgical implant applicator, such as applicator 500, described above which includes a proximal assembly including a handle assembly that is connected to the end effector assembly 1002 via an elongated shaft (elongated portion) 1007 (only the very distal end is shown in FIG. 78A) extending therebetween. The shaft 107 can be identical to shaft 508 described above. The proximal assembly includes a handle portion like handle 512 of the aforedescribed embodiments to effect operation of the end effector 1002, e.g., closing of the jaws 1004, 1006, and advancement of the fasteners into the receiver member and cutting tissue. The jaws 1004, 1006 may each have a distal angled surface 994, 996 respectively with angles represented by curved lines 990 and 992 respectively, angled away from each other such that when the jaws 1004, 1006 are brought into approximation, an angle 998 is formed that opens towards a distal direction 988.

Lower receiver jaw 1006 has a pair of openings 1020, 1022 formed in upwardly extending ears 1024, 1026, respectively, (see e.g., FIGS. 79 and 80C) to receive bosses (protrusions) 1030, 1032 of jaw arm extensions 1034, 1036, respectively, of upper cartridge jaw 1004. (see e.g., FIG. 80B). The protrusions 1030, 1032 as shown extend inwardly toward a longitudinal axis of the movable jaw 1004 and snap over the ears 1026, 1024 of stationary jaw 1004 and into engagement with openings 1022, 1020. Screw 1038 extends through opening 1040 on stationary jaw 1004 and openings 1035 on movable jaw 1004 for attachment of the movable jaw 1004 to the stationary jaw 1006. Note that because the tension loads are resisted by the moving jaw pivot, the pivot is under high loads. The pivot is created by the protrusions 1030, 1032 engagement with the openings 1022, 1020.

FIGS. 81A-81D illustrate schematically forces required to close the jaw 1004. By placing the cartridge which supports the deployment member (which supports the fasteners) on the movable jaw 1004, the drive system has to work at a larger angle with respect to the longitudinal axis of the shaft 1007. That is, when the cartridge is on the stationary jaw, the drive system needs to work at most through the articulation angle A1 of the end effector 1002. For example, if the end effector is articulatable 60 degrees, the drive system would need to work through this 60 degree angle. However, assuming the movable jaw 1004 is open at an angle A2 to the stationary jaw 1006, when the cartridge is on the movable jaw, the drive system would need to work through an angle A1+A2. For example, if the articulation angle A1 is 60 degrees and the jaw opening angle is 30 degrees, then the drive system would have to work through an angle of 90 degrees. Additionally, by placing the cartridge on the movable jaw 1004, the pull-pull cable system described above which fires (advances) the fasteners into the receiver member also needs to open and close the movable jaw 1004. To accommodate this, the pull force that retracts the driver (and cutting blade when provided) needs to be on the opening side of the pivot of the movable jaw 1004. This pivot is designated by reference numeral 1039 and for ease of illustration is depicted as a solid black circle. The placement of the pivot 1039 creates a jaw opening moment which is shown by the line labeled 1042. Thus, the pull force that causes the driver (and optional blade) to move distally is below the moving jaw pivot 1039 so as to create a jaw closing moment during firing of the fasteners labeled as line 1043 in FIGS. 81C and 81D. Note that since the pull cables (similar to cables 544, 546) which move the driver distally and proximally need to make tight changes in direction which can cause additional friction, a PTFE O-ring and/or PTFE lubricants can be utilized to reduce friction.

The end effector assembly 1002 can in some embodiments have a relief track for the driver, as shown in the embodiment of FIGS. 82A-88C, in which the driver 1050 engages the stationary jaw 1006 to hold the movable jaw 1004 and stationary jaw 1006 closed during advancement (firing) of the fasteners, allows the jaws 1004, 1006 to open slightly after firing of the fasteners and pushes the jaws 1004, 1006 open upon retraction. The driver 1050 also resets after full retraction and is ready to repeat the cycle if another implant is loaded in the jaws 1004, 1006. The path of the driver 1050 is shown by the dashed line in FIG. 82A which as can be seen travels along one plane in one direction and moves along a second plane on its return in the other direction.

More specifically, stationary jaw 1006 has outer cam surfaces 1060a, 1060b (collectively cam surface 1060) which extends longitudinally along most of its length. The cam surface 1060 (FIG. 82B) as shown is formed on each side of the slot 1005 of the stationary jaw 1006. Cam surface 1060 terminates proximally of the distal end of slot 1005. Driver 1050 has a tab 1054 on its lower surface (as viewed in the orientation of FIG. 82A). The tab 1054 extends laterally with respect to the driver 1050 to create a wider width to engage the cam surfaces 1060a, 1060b of stationary jaw 1006. That is, the tab 1054 is in the form of protrusions extending perpendicular to the direction of movement of the driver 1050. The cam surface 1060 ends just proximal of the distal end of the jaw 106, thus creating a gap or opening 1062 (FIG. 82B) dimensioned to allow the tab 1054 to drop through. That is, the width of opening 1062 is greater than the width of tab 1054 so that when the tab 1054 reaches opening 1062 it can fit through the opening 1062. Conversely, the width spanning camming surfaces 1060a, 1060b is less than the width of the tab 1054 so the tab 1054 cannot pass through the space between the cam surface 1060a, 1060b, i.e., cannot pass through the slot 1005. Stationary jaw 1006 also has inner cam surfaces 1064a, 1064b (collectively cam surface 1064) best shown in FIG. 85F. Cam surface 1064 is engaged by the tab 1054 after the driver 1050 has completed its distal travel, has moved through the opening 1062 in slot 105 and begins its proximal travel. This engagement causes the jaws 1004, 1006 to move to an open position. Note the opposite end of the driver 1050 includes a tab 1052 which travels along an outer surface of the movable jaw 1004 to maintain the jaw 1004 in a closed position.

One advantage of the driver 1050 and relief track is that the driver 1050 does not to be fully retracted past the jaw hinge point in order for the jaws 1004, 1006 to open. In configurations where the driver must be retracted past the hinge point before the jaws can open, abrupt opening of the jaws can occur which can in certain applications cause tissue damage. In this embodiment of FIG. 82A-88C, the jaws 1004, 1006 open slightly when the driver 1050 finishes its distal travel and thus the jaws are not in the fully closed position when the driver 1050 is retracted, i.e., moved proximally, The operation of the driver 1050 is illustrated in FIGS. 83A-88C. FIGS. 83A-83C illustrate the jaws 1004, 1006 in the open position with the driver 1050 in the proximal position prior to initial advancement. Note the tab or flange 1052 on the side of the driver 1050 opposite the side having the tab 1054 engages an outer surface 1009, e.g., upper surface as viewed in the orientation of FIG. 83A, of the movable jaw 1004. As the driver 1050 moves distally past the hinge point, the movable jaw 1004 is moved to a closed position as shown in FIGS. 84A-84C. Note the driver tab 1054 is below the stationary jaw 1006 (as viewed in the orientation of FIG. 84C) and the tab 1052 of driver 1050 is above the movable jaw 1004 (as viewed in the orientation of FIG. 84C). Continued distal motion of the driver 1050 is shown in FIGS. 85A-85C, where tabs 1054 and 1052 continue moving along their respective jaws 1006, 1004, to hold the jaws 1006, 1004 closed. In FIG. 85C, driver 1050 has completed its distal travel to advance the fasteners from the cartridge within movable jaw 1004 (and transect tissue if a cutting blade is provided) and is entering opening 1062 in slot 1005 as the camming surface 1060 ends, causing the driver 1050 to move from a lower plane (FIG. 85C) to an upper plane (FIG. 86C), as viewed in the orientation of FIGS. 85C and 86C, so it no longer will be in engagement with the under (lower) surface 1013 of the stationary jaw 1006. (See also FIGS. 85D and 85E which show movement of the tab 1054 along the camming surfaces 1060 in FIG. 85D and at the distal opening 1062 in FIG. 85E). When the driver 1050 reaches this distal position, as shown in FIGS. 86A-86C, the jaws 1004, 1006 can spring open. Note the compressed tissue and implant can push the jaws 1004, 1006 apart to open slightly. The slight opening of the jaws 1004, 1006 causes the driver tab 1054 to push against the camming surfaces 1064a, 1064b (collectively camming surface 1064) which are on the opposing surface or inner surface of the stationary jaw 1006. Stated another way, the camming surface 1060 (FIG. 85E) is on the outer side of the stationary jaw 1004 to keep the jaws 1004, 1006 closed while the camming surface 1064 (FIG. 85F) is on the inner side of the stationary jaw 1006 to push the jaw 1006 open as the driver 1050 is retracted. Note as the driver 1050 retracts, it pushes the implant from the cartridge contained within the movable jaw 1004. The retraction of the driver 1050 back toward its initial proximal position is shown in FIGS. 87A-87C. As the driver 1050 approaches the proximal position, the jaws 1004, 1006 can be further opened, e.g. opened to about 25 degrees, although opening to other degrees is also contemplated, and the rubber spring 1056 is compressed. The cam surface 1064 of stationary jaw 1006 ends just distal of the proximal position of the driver 1050, and as the driver 1050 reaches its most proximal position and the cam surface 1064 ends, the jaws 1004, 1006 are slightly closed by the spring 1056. This sets the driver tabs 1054 back on the outer side of the stationary jaw 1006 to reset for another cycle if another cartridge is loaded in the movable jaw 2004. FIGS. 88A-88C show the driver 1050 reset for another cycle with the jaws 1004, 1006 in the open position.

As noted above, in certain embodiments, the surgical applicator can be loaded with a new implant and the new implant applied to the tissue or tissue structure. FIGS. 89A-96 illustrate an embodiment wherein a new (fresh) implant is loaded into the jaws of an applicator which has the deployment member in the movable jaw and the receiver member in the stationary jaw as in jaws 1004, 1006 of FIG. 78A. More specifically, with initial reference to FIGS. 89A-89C, the reload assembly (also referred to as the reload or loading assembly) is designated generally by reference numeral 1100 and has a distal portion 1108 and a proximal portion 1110 with optional recesses 1119 located on its sides that may be utilized to facilitate manual gripping. At the distal portion 1108, the reload assembly may have a distal angled surface 1117 that is at an angle (e.g., between 20 and 75 degrees) from a horizontal plane established by a top surface 1116 of the reload assembly. The reload assembly includes a housing or carrier 1109 containing (supporting) an implant 1120. Implant 1120 is identical to implant 1010 of FIG. 78A in that it as a deployment member 1124 designed for placement in the movable jaw and a receiver member 1126 designed for placement in the stationary jaw. The deployment member 1124 is identical to the deployment member 1014 of implant 1010 in that it has, e.g., a plurality of fasteners preferably arranged in at least one row parallel to the longitudinal axis of the fastener supporting member, compressible members compressible by the fasteners, etc. The receiver member 1126 is identical to receiver member 1012 of implant 1010 in that it has, e.g., a retainer, a plurality of shields, etc. Since the implant 1120 is identical to implant 1010, for brevity it is not further discussed herein since the features and components and function of the implant 1010 is fully applicable to the implant 1120. Note that although the loading assembly 1100 contains implant 1120, other implants disclosed herein can alternatively be loaded in the loading assembly 1100 to enable a user to load a desired implant and/or apply additional implants to tissue or other structure.

As shown in FIGS. 89A-89C, the deployment member 1124 which contains the fasteners is on one side of the loading assembly 1100 and the receiver portion 1126 is on the opposite side of the loading assembly 1100 for placement in the opposing jaws of the end effector assembly discussed below. The deployment member 1124 is mounted within a cartridge 1129 which has a tab engaging slot 1125 (FIG. 91B) to engage tab 1113 discussed below to first mount loading assembly 1100 to the movable jaw. The cartridge portion 1129 also has projections 1130 (FIGS. 93A and 93B) which form snap features to engage slots 1132 in the movable jaw 1104 to retain the cartridge portion 1129 in the movable jaw 1104, also discussed below. The receiver member 1126 frictionally engages the stationary jaw 1106 in the friction areas 1133 as shown in FIG. 95B. When the deployment member 1124 and the receiver member 1126 are engaged in the respective movable and stationary jaws 1104, 1106, the housing 1109 of the loading assembly 1100 can be removed from the deployment member 1124 and the receiver member 1126. That is, separation of the housing 1109 from the implant 1120 leaves a first portion of the implant e.g., the deployment member 1124, in the movable jaw 1104, and the second portion of the implant, e.g., the receiver member 1126, in the stationary jaw 1106 (see FIG. 96). The transfer of the first and second portions to the jaws 1104, 1106 and removal of the housing 1109 are discussed below in the method of loading the implant into the jaws of an applicator.

FIGS. 90-96 show the steps for loading the loading assembly 1100 into the end effector 1103 of the applicator. The end effector assembly 1103 has a stationary jaw 1106 and a movable jaw 1104. Movable jaw is actuable to transition the jaws 1104, 1106 between open and closed positions. The end effector assembly 1103 is connected to the handle assembly of the applicator by shaft 1107 in the same manner as shaft 1007 of end effector assembly 1002. The handle assembly (not shown) is actuable as described above to close the jaws 1104, 1106 and driver 1112, which can have a jaw camming tab 1114 as in tab 1152 of driver 1150 described above, is advanced distally in the same manner as driver 1050 described above to deploy (advance) the fasteners from the movable jaw 1104 toward the receiver member 1126 in the stationary jaw 1106. As shown in FIG. 90, the jaws 1104, 1106 are in the open position, connected at pin 1115, to provide a space to receive loading (reload) assembly 1100. The loading assembly 1100 is inserted between the jaws 1104 with the cartridge side 1121 facing the open movable jaw 1104 (the upper jaw as viewed in the orientation of FIG. 90) and the receiver side 1123 facing the stationary jaw 1106 (the lower jaw as viewed in the orientation of FIG. 90). As can be appreciated, if the orientation of the end effector assembly 1103 changes, the positioning of the upper and lower jaws will also change.

In the next step, the loading assembly 1100 is moved into engagement with the jaw tab (or tabs) 1113 of the movable jaw 1104 (FIGS. 91A and 91B) as the slotted region 1125 at the proximal end of the cartridge portion 1129 is slid under the tab 1113. When the slots 1125 engage the tab 1113, the loading assembly 1100 is rotated by the user toward the movable jaw 1104, e.g., rotated upwardly toward the jaw 1104, from the position of FIG. 90 to the position of FIG. 92. Note FIG. 91A shows the slot/tab engagement before the load assembly 1100 is rotated as in FIG. 90; FIG. 91B shows the slot/tab engagement when the load assembly 100 has been rotated as in FIG. 92. Also note in the position of FIG. 92, the load assembly envelops the movable jaw 1104 on three sides—lower side and two sides. When the reload assembly 1100 is rotated to the position of FIG. 92, the projections 1130, extending outwardly from opposing sides of the cartridge portion 1129, are snapped into the elongated slots 1132 on opposing sides of the movable 1104 as shown in FIGS. 93A and 93B. This retains the cartridge portion 1129 in the movable jaw 1104. Subsequently, the handle trigger (not shown) is actuated to move the jaws 1004, 1006 to the closed position of FIG. 94, i.e., to move the jaw 1104 toward jaw 1106. The snap feature engagement of projections 1130 and slots 1132 holds the deployment member 1124 in the movable jaw 1104 and the receiver member 1126 is frictionally engaged in the stationary jaw 1106 at regions 1133 of FIG. 95B. Thus both portions of the implant 120 are retained in the jaws 1104, 106. With the jaws 1104, 1106 held in the closed position, the housing 1109 of the loading assembly 1100 is slid out from the jaws 1104, 1106 in a distal direction as shown in FIG. 95A. After removal of the housing 1109, the trigger is released to move the jaw 1104 to the open position as shown in FIG. 96 with the deployment member 1124 of implant 1120 held in the movable jaw 1104 and the receiver member 1126 of implant 1120 held in the stationary jaw 1106. The applicator is now ready for actuation to close the jaws around tissue or other structure and advance the fasteners from the movable jaw 1104 into the receiver member 1126 in the manner described above, including, if provided, the driver movement and relief track of FIGS. 82A-82C. Other mechanisms to close the jaws and advance the fasteners are also contemplated It should be appreciated that this method of loading and/or reloading an applicator of FIGS. 90-96 can be used to load other implants. Thus, the concept of inserting a housing containing an implant between the jaws of an applicator (instrument/device), closing the jaws to transfer the implant to one or both of the jaws and free the housing for separation from the implant, and removal of the housing from the implant to leave the implant in one or both of the jaws can be utilized to load or reload various types of implants, fasteners, etc.

It should further be appreciated that one or more loading assemblies 1100 may be presented for storage and eventual use in a one or more sterile configurations, including for instance: (i) individual package(s) 982 as sterile with a sterile barrier 981 encapsulating a loading assembly 1100 (see FIG. 97A), (ii) a plural package 983 of loading assemblies 1100 in a single sterile barrier (see FIG. 97B), or (iii) a packaging band or strip 984, which may include one or both of individual packages (e.g., 982) or plural packages (e.g., 983) that are interconnected. The band or strip may be able to be separated along predetermined separation lines 980, which may be constructed for instance as perforations to provide a predetermined tear line or region. Sterility may be for example greater than or equal to 10^(−6) or 10^(−3) SAL. As packaged, the loading assemblies may be pre-loaded with the implants as taught for example throughout the present disclosure. Additionally, any of the aforementioned packages 982, 983, 984 may be pre-packaged in one or more boxes 985 (see FIG. 97D), which may be configured according to implant size, desired maximum or preferred implant tissue thickness, and/or implant length.

Referring now to FIGS. 64-66 and 69, an implant 200 according to an alternate embodiment of the present invention is shown. The implant 200 includes a deployment member 202 and a receiver member 204. The deployment member 202 and receiver member 204 are of substantially the same length and are configured and dimensioned to be connected in substantial alignment to one another, on opposite sides of surgical structure to be closed, tacked, secured, or sealed by compressing the surgical structure therebetween. The members 202 and 204 are configured so that installation of the implant 200 on different thicknesses of surgical structures can be accomplished within the same implant 200, as will be described in greater detail and generally akin to the implant 10 discussed above. In the example shown, the implant 200 is being applied to a vessel 205, e.g., a large pulmonary vessel of a patient, so as to transversely and completely seal off the vessel 205.

The base of deployment member 202, similar to the base 24 of the deployment member 14, may in some embodiments be made of a soft, flexible material, preferably silicone rubber, but could, alternatively or additionally be composed of one or more of other soft, biocompatible material suitable for implantation, such as, but not limited to polyurethane, thermoplastic elastomer (TPE), natural rubber, latex, bio-absorbable polymers, etc. Deployment member 202 further includes clips, fasteners, or anchors 206, including those of the type described above, that are actuatable to be driven out of deployment member 202, through the tissue 205 and into a receiver or anchor base 208 in receiver member 204. The anchor base 208 includes a retainer 210, generally resembling the retainer 44 (or its variants) discussed above. For example, the retainer 210 in the illustrated embodiment may include a layer of mesh or woven material embedded or molded in the anchor base 208 of the receiver member 204, or is otherwise fixed to the main body of the receiver member 204. Similar to the retainer 44, the retainer 210 may optionally be made of polyethylene terephthalate (PET), polyetheretherketone (PEEK), nylon, or other polymers, cotton, or other fibrous materials, etc. A retainer similar to retainer 210 could also be provided in the deployment member 202 in a similar fashion to some of the embodiments discussed above.

The anchor 206 may include fasteners in the form of one or more legs, shanks, or pins 212 arranged to be actuated through a surgical structure or tissue positioned between the deployment member 202 and the receiver member 204. The pins 212 may be made of stainless steel, titanium or other biocompatible metals, metal alloys, and/or rigid, biocompatible polymers. The pins 212 may extend from a base body 213. Each pin 212 is provided with a series of barbs 214 that are spaced apart along a length of the pin 212. Optionally, the pins 212 and/or the barbs 214 may be over-molded by the material of the deployment member 202, e.g., silicone or other soft polymer. As each pin 212 is driven toward the surgical structure e.g., tissue 205 and into the anchor base 208, each pin 212 passes through one of the mesh openings 216 (see FIG. 65) and is driven along a distance determined by a predetermined driving force and the thickness of the tissue 205 that exists between the deployment member 202 and receiver member 204 at the location of that anchor 206. Implant 200 can be applied using the applicators described herein.

FIGS. 67-68 show alternate embodiments in which an anchor 218 and an anchor 219 comprise a pair of substantially parallel pins 220 and 221, respectively, each pair of pins having alternating barbs 222 that extend respectively from a base 223 and a base 224 against which a driving or actuation force may applied to drive the anchor members 218 and/or 219. In this case, the two pins 220 and/or 221, when deployed pass through two of the openings 216 in the anchor base 208. The barbs 222 alternate from side-to-side of the pins 220 and 221 so that no barb 222 is transversely aligned (along or parallel to a transverse axis 225 of the pins 220 and/or 221) with another barb 222 on the same pin. Note that in FIG. 67, the transverse axis 225 is aligned with a plane 226, but in FIG. 68, the transverse axis 225 is normal to the plane 226. As a result, all barbs 222 are substantially in or parallel to the plane 226 in FIG. 67, but in FIG. 68, the barbs 222 lie in planes normal to the plane 226. The use of two pins 220 and/or 221 may be beneficial in these embodiments, e.g., for ease of manufacturing and to balance the piercing pressure so that the pins 220 and/or 221 pierce through the surgical structure along generally straight paths. In the examples shown in FIGS. 67-68, the anchor 218, 219 may be stamped from stainless steel or other suitable material and the pins 220 and/or 221 are bent at an angle perpendicular to the bases 223 and/or 224 of the anchors 218 and 219, respectively. Additionally, the barbs 222 of one of the pins 220 and/or 221 are in a plane that is parallel to a plane in which the barbs 222 of the other pin lie. The anchors 218, 219 form part of the implant which is otherwise the same as the aforedescribed implant of FIGS. 64-66, and can be applied in a similar manner.

Alternative forms of barbs discussed herein are also contemplated. For example, the barbs 214, 222, (and 42), etc., that may be employed include, but are not limited to, forming the barb by piercing a "V" or other generally pointed shape into a base structure and bending the "V" or other shape outward; skive barbs formed by sliding a blade, or skive, along the structure and driving the blade into the structure, such as commonly used for fishing hooks; micro barbs, e.g., barbs having a plurality of very small protrusions in the range of approximately 0.010″ or smaller, etc. Further optionally, the pins 212, 220, and/or 221 may be configured so that the free ends/distal tips 230 bend over after deployment to further secure the corresponding anchor from releasing from the retainer, e.g., the retainer 44 and/or 210. It is to be appreciated that any discussion of any component from one embodiment herein generally applies to like-components from other embodiments, whether or not the same name is used to refer to both (and in fact, with reference to some embodiments, different names are purposely used for like-components from different embodiments for the sake of clarity in discussing those particular components). For example, it is to be understood that similarly to the legs 36 of the fasteners 32, the anchors 206, 218, and/or 219 may include a single one of the pins 212, 220, and/or 221, or any number thereof. Likewise, similarly to the pins 212, 220, and/or 221, the legs 36 may be arranged to be bent over after deployment to further secure a surgical structure in place.

Referring back to FIGS. 64-66, as the pins 212 are driven to pierce the tissue 205, the distal tips pass through the tissue 205 (or other surgical structure) and the openings 216 of anchor base 208 and/or the openings of the retainer, to a depth that is dependent on the tissue (or surgical structure) thickness through which each anchor 206 passes. If the barbs 214 are alternatingly positioned along the length of the pin as described above with respect to the barbs 222, the opening 216 is not stretched as the barbs 214 pass therethrough, but is rather shifted back and forth by the alternating barbs. After the application of the driving force and the anchors 206 having been driven to full deployment, the driving force is removed and the last barb 214 having passed through the opening 216 for each pin 212 catches against the anchor base 208 material surrounding the opening 216, thereby maintaining the closure pressure initially applied by an apparatus for closing the members 202 and 204 together against the vessel 205. The apparatus can then be removed.

Preferably the main body of the deployment member 202 includes a resilient and/or compressible member, suspension, spring, biasing member to provide a biasing force similar to the towers 30 discussed above. In the embodiment of FIG. 65, a cavity or hollow 232 is provided, which enables the portions of the member 202 opposite the cavity to flex and bend, thereby acting as a spring to assist in maintaining the closing/sealing pressure on the tissue 205 held between the members 202 and 204, but avoid necrosis of the tissue 205 therebetween. Thus, the hollow 232 helps provide a similar variable function as the towers 30 of the implant 10 discussed above. Further preferably the main body of the deployment member 202 is perforated, being provided with through holes 233 that extend through the body from a face 234 contacting the tissue 205, to allow fluid communication to the tissue 205 between the members 202 and 204, further avoiding necrosis and promoting healing/scarring. Optionally, leading ends 235 and 236 of the members 202 and 204, respectively, may have a convex shape and trailing ends 237 and 238 may have a concave shape that mates with the convex shape (or vice versa) as shown in FIG. 64, to support end-to-end or head-to-tail placement with another implant 200 in circumstances where multiple implants need to be installed (similar to the head-to-tail arranged discussed above with respect to the implant 10). Of course the mating shapes are not limited to concave and convex, as virtually any other mating shapes could be employed, as well as non-mating shapes.

FIG. 65 is an enlarged view of a leading end portion of the implant 200 without showing the tissue for better visualization of the relationship between the anchors 206 and anchor base 208 upon deployment. As can be seen, the anchor base 208 can be provided as a continuous sheet that runs substantially along the full length and width of the receiver member 204, at least to an extent that extends beyond the length and width of the area occupied by the anchors 206 on the opposing deployment member 202. Because of this, multiple openings 216 are available for each distal tip of each pin 212 (or pins 220, 221) of each anchor 206 to potentially pass through. Because of this, less exact alignment is required between the anchors 206 and where they are to be anchored, so that the engineering constraints upon aligning the jaws of the apparatus for deploying the device and aligning the deployment and receiving members are significantly lessened. This leads to a potentially smaller and/or less expensive deployment apparatus. The anchor 206 does not need to be aligned with any particular opening 216, as it can pass through any opening 216 in the vicinity of where it is driven and then anchored to the base 208 upon release of driving force in a manner as described above. It is again to be appreciated that the implant 10 offered similar advantages and acceptable performance under even loose tolerances. The anchor base 208 can be molded into the receiver member 204. Alternatively, the anchor base 208 can be mounted to a face 240 of the receiver member 204 that faces the deployment member 202 and contacts the surgical structure. Similar to the deployment member 14 and the retainer 44 of the implant 10 discussed above, the deployment member 202 of the implant 200 may include a retainer, e.g. the retainer 210, disposed or embedded therein.

The deployment member 202 may include grooves 217 (preferably formed by molding, but could be machined or otherwise cut in) to hold the base bodies 213 and thus the anchor 206, prior to deployment. The material portion of the deployment member 202 between the bases 213 and the surgical structure is compliant so that it maintains the anchors 206 in tension against the retainer 210 after deployment and engagement with the retainer 210. The face 236 of the deployment member 202 to be applied to the surgical structure may be provided with ridges 244 extending along the sides, which are raised, relative to the remainder of the face 236 to concentrate sealing action away from the anchors 206 so as to minimize risks of leakage through the holes in the surgical structure formed by piercing through the surgical structure with the anchors 206. Likewise, the face 240 of the receiver member 204 that faces the deployment member 202 may be provided with longitudinally extending ridges similar to the ridges 244 along the side lengths thereof that extend lower than the remainder of the face 240 so as to minimize the risk of leakage due to the holes pierced through the surgical structure by the pins 212 on the receiver member 204 side of the surgical structure. Slots 248 may be provided in the receiver member 204 that may extend from the face 240 of the receiver member 204, and into shields or protrusions 250 extending dorsally from of the receiver member 204. Protrusions 250 are provided to ensure that the pins 212 of the anchors 206 do not extend out of the receiver member 204 after deployment (so the tips do not extend beyond the dorsal surface of receiver member 204). Protrusions 250 are provided with a height sufficient to ensure that the pins 212 cannot extend out of the receiver member 204 after deployment, even if there is no surgical structure provided between the deployment member 202 and the receiver member 204. The protrusions can be solid, or alternatively can form a cavity like a shell.

FIG. 69 is an illustration of a working end portion (distal end portion) of a tool, device, or instrument 300 used to deploy the implants 200 described above with regard to FIGS. 64-68. In the embodiment shown, the instrument 300 and implants 200 may be configured and dimensioned to seal off a vessel, e.g., the vessel 205, or otherwise be used to secure, close, clamp, tack, etc., various tissue and non-tissue surgical structures. In one embodiment, the vessel 205 has an outside diameter of about 25 mm, and a compressed thickness (between the members 202 and 204) of about 0 to about 3 mm, although vessels of other sizes may be sealed by use of the instrument 300 and the implant 200. Similar to the implant 10, suitable surgical structures include vessels, parenchyma, gastrointestinal structures, meshes, grafts, etc.

In the illustrated embodiment, the instrument 300 includes a set of jaws 302a and 302b (collectively, "the jaws 302") arranged to receive and engage the members 202 and 204. In one embodiment, the jaws 302 and the members 202 and 204 are together configured and dimensioned to provide about a 57 mm sealing length. As already noted, this configuration is not limiting, as the instrument 300 and implant 200 may be configured and dimensioned to provide a sealing length that is less than or greater than 57 mm. As shown, two implants 200 are releasably mounted in the jaws 302 for delivery and deployment thereof. It is to be appreciated that in some embodiments two of the implants 200 may be secured by a bridge, e.g., resembling the bridge 37 of FIG. 1, to form a double-rowed implant resembling two of the implants 200. In other embodiments, a single implant row, or more than two implant rows can be secured to the jaws. In the illustrated embodiment, the receiver members 204 are releasably mounted, e.g., via friction, in the jaw 302a and the deployment members 202 are releasably mounted, e.g., via friction, in the jaw 302b in opposition to the receiver members 204.

The proximal end portion of the instrument is not shown, but the instrument 300 includes a shaft 318 extending from the support 306 for the jaws 302 that is connectable to any suitable handle. In one embodiment, the shaft 306 has a diameter in the range of about 5 mm to about 10 mm, preferably about 7 mm. The jaws 302 may be articulated in the manner described above. Other articulation mechanisms are also contemplated. The jaws are actuatable to close down on the tissue/vessel 205 as shown in FIG. 70, either by pivoting movement of one of the jaws toward the other jaw or by pivoting movement of both of the jaws toward each other. The jaws 302 can be closed by operation of an actuation member, such as a trigger (not illustrated) similar to the trigger of the embodiment of FIG. 50 described above, so as to close the jaws together, as illustrated in FIG. 70, a preset distance and/or with a predetermined amount of closing force in the manner described above. The jaws 302 can be re-opened and repositioned, if desired, prior to deployment of one or more of the implants 200 in the same manner as application 500 described above.

Once in the desired position, as shown in FIG. 70, implants may be deployed by advancing an actuator or driver 308 (FIGS. 71 and 72) from a proximal end of the jaw 302b to a distal end of the jaw 302b. In this embodiment, the driver 308 may comprise a ramped force applicator 310 having a ramped surface 312 that is actuated to push or force the bases 213 of the anchors 206 toward the surgical structure as the applicator 310 passes by the anchors 206 during its traversal from the proximal end to the distal end of the jaw 302b. The ramped surface 312 of the driver 308 in one embodiment may not be rigid, but instead resiliently provide a predetermined spring force so as to apply a predetermined amount of driving or actuating force to the bases 213 to actuate the anchors 206 toward the surgical structure. In one embodiment, the driver 308 applies a pressure of about 3 to about 30 g/mm^2, and preferably about 9 g/mm^2 to the anchors 206. The ramped surfaces 312 of the driver 308 are provided on both sides of the jaw 302b so as to align with both of the implants 200 held by the jaws 302. In some embodiments, in between the ramped surfaces 312, the driver 308 includes a cutting element 316, such as a sharp blade or knife configured for cutting tissue, vessels, and other surgical structures. Thus, as the actuating driver 308 is distally advanced, the surgical structure between the two implants 200 held by the jaws 302 can be cut by the cutting element 316 simultaneously with the actuation of the anchors 206 through the surgical structure and into the anchor base 208 for engagement with the retainer 210. The actuating driver 308 can be driven by various types of different force transferors 318, for example, a rigid or semi-rigid rod, cable, wire, ribbon, or the like, or in the manner of driver 542 described in detail above. The force transferors 318 can be driven in compression or tension.

FIG. 71 is an enlarged, partial view of a portion of the instrument 300, showing a proximal portion of the jaws 302 and articulation joint 320 connecting the jaws 302 to the shaft 306 that extends proximally from the jaws 302, e.g., toward a handle used by a user to manipulate the instrument 300. The articulation joint 320 in the illustrated embodiment has one degree of freedom, although it is to be appreciated that further degrees of freedom may be used, e.g., the shaft 306 may be rotatable, etc. The articulation mechanisms of the previously described applicator could also be utilized.

FIG. 72 illustrates the driver 308 in its distal position. At this stage, the driver 308 has completely severed the surgical structure between the implants 200 and all of the anchors 206 have been driven by the predetermined force to squeeze the surgical structure and secure the surgical structure between the deployment members 202 and the receiver members 204. Different thickness of the surgical structure along the sealing path result in different driving distances of the anchors 206, as all anchor members are driven up to the same predetermined driving force. For example, a relatively smaller thickness of the surgical structure requires an anchor 206 to be driven by a greater distance into the anchor base than does a relatively larger thickness of the surgical structure.

After completing the actuating and severing processes discussed with respect to FIG. 72, the jaws 302 can be opened, at which time the implants 200 detach from the jaws 302 as the jaws 302 move away from the implant 200, and the instrument 300 can be removed from the surgical site. FIG. 73 shows the deployed, implanted, or installed implants 200 that remain in the vessel 205, and a cut 322 between the implants where the vessel 205 is severed, thereby transecting the vessel 205. As discussed above with respect to the implant 10, transecting the vessel 205 may be used, for example, in a vessel harvesting operation, and that other tissue and non-tissue structures can be similarly cut by use of the implants 200.

FIG. 74 shows one half of the transected or cut vessel 205 and the corresponding one of the implants 200 in perspective. At the location of the cut 322, it can be seen that the vessel 205 has been sealed by the deployment of the implant 200. Also, it is understood that the deployment member 202 and receiver member 204 will abut against one another at locations where there is no tissue, as represented by a set of lines 326 peripheral to the vessel 205 clamped by the implant 200. In situations where excessive lengths of the implant 200 extend beyond the surgical structure, one or both end portions of the closure device can be cut off (cropped) as shown in FIG. 74. For example, FIG. 75 illustrates a vessel 255 having an outside diameter smaller than that of the vessel 205 having been transected and sealed using the implant 200 as described above. Since fewer of the anchors 206 are needed for the smaller size of the vessel 255, both ends of the implant 200 that extend beyond the width of the vessel 255 are illustrated as having been cut or cropped in FIG. 75.

The instrument 300 may be low profile and can be configured and dimensioned so as to be delivered through a port for minimally invasive procedures. FIG. 76 is a distal end view of instrument 300 with the jaws 302 in a closed configuration, illustrating the compactness of the design. A circle 328 represents a port for inserting the jaws 302 of the instrument 302 through. In one embodiment, the port represented by the circle 328 has a 12 mm diameter. The instrument 300 can include the articulation, rotation and implant firing mechanism described above with regards to FIGS. 50-60D, as well as the aforementioned alternatives.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A surgical method of sealing tissue comprising:
   providing a fastener supporting member supporting a plurality of fasteners and having a plurality of compressible members, the fastener supporting member having a first surface facing towards a first direction, the compressible members extending from the fastener supporting member in a direction generally opposite the first direction;
   providing a receiver member having a second surface facing the first surface of the fastener supporting member;
   clamping tissue between the first surface on the fastener supporting member and the second surface on the receiver member; and
   advancing the plurality of fasteners into the receiver member, the plurality of fasteners compressing the compressible members in accordance with a distance of advancement of the fasteners, the distance relating to a thickness of tissue between the first and second surfaces;
   wherein the receiver member includes a retainer positioned therein, and the step of advancing the plurality of fasteners advances the plurality of fasteners into engagement with the retainer; and
   wherein the fastener supporting member includes a further retainer positioned therein, and the step of advancing the plurality of fasteners advances the plurality of fasteners through the retainer in the fastener supporting member.

2. The method according to claim 1, wherein the step of advancing the plurality of fasteners deforms the plurality of compressible members.

3. The method according to claim 1, wherein the plurality of compressible members flex to absorb excess forces to accommodate an increase in pressure in sealed tissue.

4. The method according to claim 1, wherein the retainer in the receiver member has a plurality of openings, and barbs of the plurality of fasteners engage the retainer in the receiver member adjacent to the openings.

* * * * *